US010660901B2

(12) United States Patent
Yin et al.

(10) Patent No.: US 10,660,901 B2
(45) Date of Patent: May 26, 2020

(54) PYRROLOBENZODIAZEPINES AND CONJUGATES THEREOF

(71) Applicant: Mersana Therapeutics, Inc., Cambridge, MA (US)

(72) Inventors: Mao Yin, Needham, MA (US); Joshua D. Thomas, Natick, MA (US); Aleksandr V. Yurkovetskiy, Littleton, MA (US); Patrick R. Conlon, Wakefield, MA (US); Bingfan Du, Cambridge, MA (US); Eugene W. Kelleher, Wellesley, MA (US); Timothy B. Lowinger, Carlisle, MA (US); Shuyi Tang, Shanghai (CN)

(73) Assignee: Mersana Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/181,867

(22) Filed: Nov. 6, 2018

(65) Prior Publication Data

US 2019/0070194 A1   Mar. 7, 2019

Related U.S. Application Data

(62) Division of application No. 15/597,453, filed on May 17, 2017, now Pat. No. 10,143,695.

(60) Provisional application No. 62/338,436, filed on May 18, 2016.

(51) Int. Cl.
| | | |
|---|---|---|
| *A61K 31/551* | (2006.01) | |
| *A61K 31/407* | (2006.01) | |
| *C07D 487/04* | (2006.01) | |
| *A61K 31/55* | (2006.01) | |
| *A61P 35/00* | (2006.01) | |
| *A61K 47/68* | (2017.01) | |
| *C07D 403/14* | (2006.01) | |

(52) U.S. Cl.
CPC .......... *A61K 31/55* (2013.01); *A61K 47/6803* (2017.08); *A61K 47/6851* (2017.08); *A61P 35/00* (2018.01); *C07D 403/14* (2013.01); *C07D 487/04* (2013.01)

(58) Field of Classification Search
CPC ... A61K 31/551; A61K 31/407; C07D 487/04
See application file for complete search history.

(56) References Cited

U.S. PATENT DOCUMENTS

| 10,143,695 | B2 | 12/2018 | Yin et al. |
| 2017/0050971 | A1 | 2/2017 | Thurston et al. |

FOREIGN PATENT DOCUMENTS

| WO | WO 2000/012506 A2 | 3/2000 |
| WO | WO 2005/085177 A2 | 9/2005 |
| WO | WO 2005/085250 A1 | 9/2005 |
| WO | WO 2007/039752 A1 | 4/2007 |
| WO | WO 2008/099416 A2 | 8/2008 |
| WO | WO 2009/060208 A1 | 5/2009 |
| WO | WO 2010/091150 A1 | 8/2010 |
| WO | WO 2011/117882 A1 | 9/2011 |
| WO | WO 2011/130598 A1 | 10/2011 |
| WO | WO 2013/164592 A1 | 11/2013 |
| WO | WO 2013/164593 A1 | 11/2013 |
| WO | WO 2013/177481 A1 | 11/2013 |
| WO | WO 2014/140174 A2 | 9/2014 |
| WO | WO 2016/198869 A1 | 12/2016 |
| WO | WO 2017/032983 A1 | 3/2017 |
| WO | WO 2017/051249 A1 | 3/2017 |

OTHER PUBLICATIONS

Baraldi, P. et al. "Design, Synthesis and Biological Activity of Pyrrolo [2,1-c][1,4] Benzodiazepine (PBD)-Distanycin Hybrid", *Bioorganic & Medicinal Chemistry Letters*, 1998, vol. 8, p. 3019-3024.

Baraldi, P. et al. "Synthesis, in Vitro Antiproliferative Activity, and DNA-Binding Properties of Hybrid Molecules Containing Pyrrolo[2,1-c][1,4]benzodiazepine and Minor-Groove-Binding Oligopyrrole Carriers", *J. Med. Chem.* 1999, vol. 42, p. 5131-5141.

Basher, M. et al. "Sequence-selective binding of C8-conjugated pyrrolobenzodiazepines (PBDs) to DNA", *Biophysical Chemistry*, 2017, 9 pages.

Brucoli, F. et al. "Novel C8-linked pyrrolobenzodiazepine (PBD)—heterocycle conjugates that recognize DNA sequences containing an inverted CCAAT box", *Bioorganic & Medicinal Chemistry Letters*, 2011, vol. 21, p. 3780-3783.

Brucoli, F. et al. "An Extended Pyrrolobenzodiazepine-Polyamide Conjugate with Selectivity for a DNA Sequence Containing the ICB2 Transcription Factor Binding Site", *Journal of Medicinal Chemistry*, 2013, vol. 56, p. 6339-6351.

Damayanthi, Y. et al. "Design and Synthesis of NovelPyrrolo[2,1-c][1,4]benzodiazepine-Lexitropsin Conjugates", *J. Org. Chem.* 1999, vol. 64, p. 290-292.

Kotecha, M. et al. "Inhibition of DNA binding of the NF-Y transcription factor by the pyrrolobenzodiazepine-polyamide conjugate GWL-78", *Mol Cancer Ther* 2008, vol. 7, No. 5, p. 1319-1328.

Masterson, L. et al. "Synthesis and biological evaluation of pyrrolo[2,1c][1,4]benzodiazepine (PBD) C8 cyclic amine conjugates", *Bioorganic & Medicinal Chemistry Letters*, 2004, vol. 14, p. 901-904.

Rahman, K. et al. "GC-Targeted C8-linked Pyrrolobenzodiazepine (PBD)-Biaryl Conjugates with Femtomolar In Vitro Cytotoxicity and In Vivo Antitumour Activity in Mouse Models", *Journal of Medicinal Chemistry*, 2013, vol. 56, p. 2911-2935.

Rahman, K. et al. "Antistaphylococcal activity of DNA-interactive pyrrolobenzodiazepine (PBD) dimers and PBD-biaryl conjugates", *J. Antimicrob. Chemother.* 2012, vol. 67, p. 1683-1696.

(Continued)

*Primary Examiner* — Brenda L Coleman
(74) *Attorney, Agent, or Firm* — Cooley LLP; Heidi A. Erlacher; Xixi Sun

(57) ABSTRACT

The present disclosure relates generally to derivatives of pyrrolobenzodiazepines and antibody-drug conjugates thereof and to methods of using these conjugates as therapeutics and/or diagnostics.

25 Claims, 1 Drawing Sheet

(56) References Cited

OTHER PUBLICATIONS

Wells, G. et al. "Design, Synthesis, and Biophysical and Biological Evaluation of a Series of Pyrrolobenzodiazepine-Poly(N-methylpyrrole) Conjugates", *J. Med. Chem.* 2006, vol. 49, p. 5442-5461.

Reddy B. et al. "Design, synthesis and in vitro cytotoxicity studies of novel pyrrolo[2,1-c][1,4]benzodiazepine (PBD)—polymade conjugates and 2,2'-PBD Dimers", Anti-Cancer Drug Design, vol. 15, No. 3, 2000, p. 225-238.

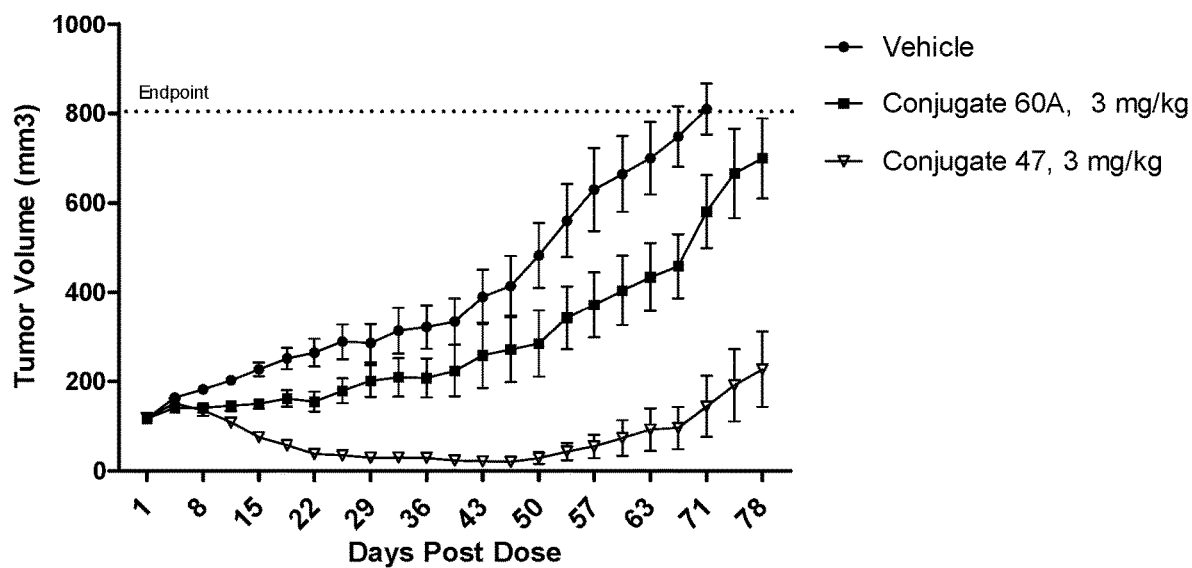

PYRROLOBENZODIAZEPINES AND CONJUGATES THEREOF

RELATED APPLICATIONS

This application is a divisional application of U.S. application Ser. No. 15/597,453, filed on May 17, 2017 (now allowed), which claims priority to, and the benefit of, U.S. provisional application No. 62/338,436, filed May 18, 2016, under 35 USC § 119(e). The content of these applications are hereby incorporated by reference in their entireties.

BACKGROUND

The pyrrolo[2, 1-c][1, 4]benzodiazepines (PBDs) are a family of naturally occurring, monofunctional DNA alkylating antitumor antibiotics, which includes anthramycin, DC-81, tomaymycin, and sibiromycin. These compounds bind exclusively to the exocyclic N2 of guanine in the minor groove and span 3 base pairs in a sequence specific manner (5'PuGPu). The first PBD antitumor antibiotic, anthramycin, was discovered in 1965 (Leimgruber et al., 1965 *J. Am. Chem. Soc.*, 87, 5793-5795; and Leimgruber et al., 1965 *J. Am. Chem. Soc.*, 87, 5791-5793). Since then, a number of naturally occurring PBDs and variety of analogues have been reported.

PBDs have the general structure:

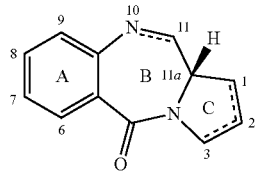

The PBDs differ in the number, type and position of substituents, in both their aromatic A rings and pyrrolo C rings, and in the degree of saturation of the C ring. In the B-ring there is either an imine (N=C), a carbinolamine (NH—CH(OH)) or a carbinolamine methyl ether (NH—CH(OMe)) at the N10-C11 position which is the electrophilic center responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, 1975 In *Antibiotics III.* Springer-Verlag, New York, pp. 3-11; and Hurley and Needham-VanDevanter, 1986 *Acc. Chem. Res.*, 19, 230-237). Their ability to form an adduct in the minor groove enables them to interfere with DNA processing, hence their use as antitumor agents.

The first PBD to enter the clinic, SJG-136 (NSC 694501) is a potent cytotoxic agent that causes DNA inter-strand crosslinks (S. G Gregson et al., 2001, J. Med. Chem., 44: 737-748; M. C. Alley et al., 2004, Cancer Res., 64: 6700-6706; J. A. Hartley et al., 2004, Cancer Res., 64: 6693-6699; C. Martin et al., 2005, Biochemistry., 44: 4135-4147; S. Arnould et al., 2006, Mol. Cancer Ther., 5: 1602-1509). Results from a Phase I clinical evaluation of SJG-136 revealed that this drug was toxic at extremely low doses (maximum tolerated dose of 45 μg/m², and several adverse effects were noted, including vascular leak syndrome, peripheral edema, liver toxicity and fatigue. DNA damage was noted at all doses in circulating lymphocytes.

Accordingly, there exists a need for more selective and efficacious drugs that can deliver critical DNA damage with minimal side effects continues.

SUMMARY

In one aspect the present disclosure features a compound of Formula (I),

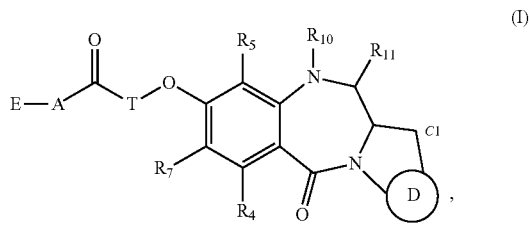

or a tautomer thereof, or a pharmaceutically acceptable salt or solvate of the compound or the tautomer.

In Formula (I) above,

D is D1, D2 or D3:

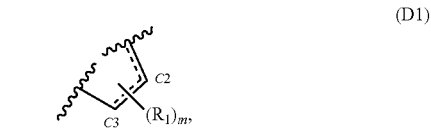

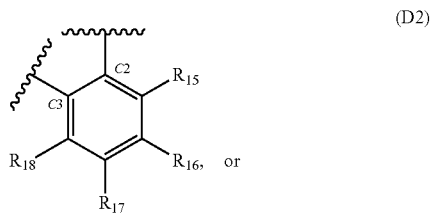

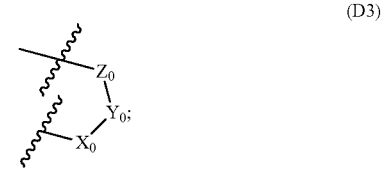

wherein the dotted line between C2 and C3 or between C2 and C1 in D1 indicates the presence of a single or double bond; and m is 0, 1 or 2;

when D is D1, the dotted line between C2 and C3 is a double bond, and m is 1, then $R_1$ is:

(i) $C_{6-10}$ aryl group, optionally substituted by one or more substituents selected from —OH, halo, —NO$_2$, —CN, —N$_3$, —OR$_2$, —COOH, —COOR$_2$, —COR$_2$, —OCONR$_{13}$R$_{14}$, $C_{1-10}$ alkyl, $C_{3-10}$ cycloalkyl, $C_{2-10}$ alkenyl, $C_{2-10}$ alkynyl, a polyethylene glycol unit —(OCH$_2$CH$_2$)$_r$—OR$_a$, 3- to 14-membered heterocycloalkyl, 5- to 12-membered heteroaryl, bis-oxy-$C_{1-3}$ alkylene, —NR$_{13}$R$_{14}$, —S(=O)$_2$R$_{12}$, —S(=O)$_2$NR$_{13}$R$_{14}$, —SR$_{12}$, —SO$_x$M, —OSO$_x$M, —NR$_9$COR$_{19}$, —NH(C=NH)NH$_2$;

(ii) $C_{1-5}$ alkyl;

(iii) $C_{3-6}$ cycloalkyl;

(iv)

[structure with $R_{31}$, $R_{32}$, $R_{33}$]

(vi)

[structure with $R_{34}$ alkyne]

(vii)

[structure with $R_{35a}$, $R_{35b}$]

(vii)

[structure with $R_{36a}$, $R_{36b}$, $R_{36c}$, $R_{36d}$]

(viii) halo;

when D is D1, the dotted line between C2 and C3 is a single bond, and m is 1, then $R_1$ is:

(i) —OH, =O, =CH$_2$, —CN, —R$_2$, —OR$_2$, halo, =CH—R$_6$, =C(R$_6$)$_2$, —O—SO$_2$R$_2$, —CO$_2$R$_2$, —COR$_2$, —CHO, or —COOH; or (ii)

[structure with $R_{37a}$, $R_{37b}$]

when D is D1 and m is 2, then each $R_1$ independently is halo and either both $R_1$ are attached to the same carbon atom or one is attached to C2 and the other is attached to C3;

T is $C_{1-10}$ alkylene linker;

A is

[structure with $X_1$, $Y_1$, $Z_1$, NH, C=O, subscript s]

wherein the —NH group of A is connected to the —C(O)-T-moiety of Formula (I) and the C=O moiety of A is connected to E; and each

[ring structure with $X_1$, $Y_1$, $Z_1$]

independently is

[four heterocyclic ring structures with $X_1$, $Y_1$, $Z_1$, N], or ;

E is —OH, —NH—($C_{1-6}$ alkylene)-$R_{13a}$, E1, E2, E3, or E4:

(E1)

[indazole structure with ($R_8$)$_t$, $X_2$, $X_3$, N]

(E2)

[isoindoline structure with ($R_8$)$_t$, $X_3$, N]

(E3)

[structure with ($R_8$)$_t$, $X_3$, NH]

or (E4)

[bicyclic structure with $X_3$, $X_4$, ($R_8$)$_t$, NH]

wherein the dotted line in E1 or E4 indicates the presence of a single or double bond;

each occurrence of $R_2$ and $R_3$ independently is an optionally substituted $C_{1-8}$ alkyl, optionally substituted $C_{2-8}$ alkenyl, optionally substituted $C_{2-8}$ alkynyl, optionally substituted $C_{3-8}$ cycloalkyl, optionally substituted 3- to 20-membered heterocycloalkyl, optionally substituted $C_{6-20}$ aryl or optionally substituted 5- to 20-membered heteroaryl, and, optionally in relation to the group $NR_2R_3$, $R_2$ and $R_3$ together with the nitrogen atom to which they are attached form an optionally substituted 4-, 5-, 6- or 7-membered heterocycloalkyl or an optionally substituted 5- or 6-membered heteroaryl;

$R_4$, $R_5$ and $R_7$ are each independently —H, —$R_2$, —OH, —$OR_2$, —SH, —$SR_2$, —$NH_2$, —$NHR_2$, —$NR_2R_3$, —$NO_2$, —$SnMe_3$, halo or a polyethylene glycol unit —$(OCH_2CH_2)_r$—$OR_a$; or $R_4$ and $R_7$ together form bis-oxy-$C_{1-3}$ alkylene;

each $R_6$ independently is —H, —$R_2$, —$CO_2R_2$, —$COR_2$, —CHO, —$CO_2H$, or halo;

each $R_8$ independently is —OH, halo, —$NO_2$, —CN, —$N_3$, —$OR_2$, —COOH, —$COOR_2$, —$COR_2$, —$OCONR_{13}R_{14}$, —$CONR_{13}R_{14}$, —CO—NH—($C_{1-6}$ alkylene)-$R_{13a}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3- to 14-membered heterocycloalkyl, 5- to 12-membered heteroaryl, —$S(=O)_2R_{12}$, —$S(=O)_2NR_{13}R_{14}$, —$SR_{12}$, —$SO_xM$, —$OSO_xM$, —$NR_9COR_{19}$, —$NH(C=NH)NH_2$ or —$R_{20}$—$R_{21}$—$NR_{13}R_{14}$;

each $R_9$ independently is $C_{1-10}$ alkyl, $C_{3-10}$ cycloalkyl, $C_{2-10}$ alkenyl or $C_{2-10}$ alkynyl;

$R^{10}$ is —H or a nitrogen protecting group;

$R^{11}$ is -$QR^Q$ or —$SO_xM$;

or $R^{10}$ and $R^{11}$ taken together with the nitrogen atom and carbon atom to which they are respectively attached, form a N=C double bond;

each $R_{12}$ independently is $C_{1-7}$ alkyl, 3- to 20-membered heterocycloalkyl, 5- to 20-membered heteroaryl, or $C_{6-20}$ aryl;

each occurrence of $R_{13}$ and $R_{14}$ are each independently H, $C_{1-10}$ alkyl, 3- to 20-membered heterocycloalkyl, 5- to 20-membered heteroaryl, or $C_{6-20}$ aryl;

each $R_{13a}$ independently is —OH or —$NR_{13}R_{14}$;

$R_{15}$, $R_{16}$, $R_{17}$ and $R_{18}$ are each independently —H, —OH, halo, —$NO_2$, —CN, —$N_3$, —$OR_2$, —COOH, —$COOR_2$, —$COR_2$, —$OCONR_{13}R_{14}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3-14 membered heterocycloalkyl, 5- to 12-membered heteroaryl, —$NR_{13}R_{14}$, —$S(=O)_2R_{12}$, —$S(=O)_2NR_{13}R_{14}$, —$SR_{12}$, —$SO_xM$, —$OSO_xM$, —$NR_9COR_{19}$ or —$NH(C=NH)NH_2$;

each $R_{19}$ independently is $C_{1-10}$ alkyl, $C_{3-10}$ cycloalkyl, $C_{2-10}$ alkenyl or $C_{2-10}$ alkynyl;

each $R_{20}$ independently is a bond, $C_{6-10}$ arylene, 3-14 membered heterocycloalkylene or 5-to 12-membered heteroarylene;

each $R_{21}$ independently is a bond or $C_{1-10}$ alkylene;

$R_{31}$, $R_{32}$ and $R_{33}$ are each independently —H, $C_{1-3}$ alkyl, $C_{2-3}$ alkenyl, $C_{2-3}$ alkynyl or cyclopropyl, where the total number of carbon atoms in the $R_1$ group is no more than 5;

$R_{34}$ is —H, $C_{1-3}$ alkyl, $C_{2-3}$ alkenyl, $C_{2-3}$ alkynyl, cyclopropyl, or phenyl wherein the phenyl is optionally substituted by one or more of halo, methyl, methoxy, pyridyl or thiophenyl;

one of $R_{35a}$ and $R_{35b}$ is —H and the other is a phenyl group optionally substituted with one or more of halo, methyl, methoxy, pyridyl or thiophenyl;

$R_{36a}$, $R_{36b}$, $R_{36c}$ are each independently —H or $C_{1-2}$ alkyl;

$R_{36d}$ is —OH, —SH, —COOH, —C(O)H, —N=C=O, —$NHNH_2$, —$CONHNH_2$,

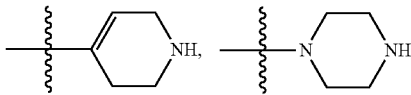

or $NHR^N$, where $R^N$ is —H or $C_{1-4}$ alkyl;

$R_{37a}$ and $R_{37b}$ are each independently is —H, —F, $C_{1-4}$ alkyl, $C_{2-3}$ alkenyl, wherein the alkyl and alkenyl groups are optionally substituted by $C_{1-4}$ alkyl amido or $C_{1-4}$ alkyl ester; or when one of $R_{37a}$ and $R_{37b}$ is —H, the other is —CN or a $C_{1-4}$ alkyl ester;

$X_0$ is $CH_2$, $NR_6$, C=O, BH, SO or $SO_2$;

$Y_0$ is O, $CH_2$, $NR_6$ or S;

$Z_0$ is absent or $(CH_2)_n$;

each $X_1$ independently is $CR_b$, or N;

each $Y_1$ independently is $NR_a$, O or S;

each $Z_1$ independently is $NR_a$, O or S;

each $R_a$ independently is H or $C_{1-4}$ alkyl;

each $R_b$ independently is H, OH, $C_{1-4}$ alkyl, or $C_{1-4}$ alkoxyl;

$X_2$ is CH, $CH_2$ or N;

$X_3$ is CH or N;

$X_4$ is NH, O or S;

Q is O, S or NH;

when Q is S or NH, then $R^Q$ is —H or optionally substituted $C_{1-7}$ alkyl; or when Q is O, then $R^Q$ is —H or optionally substituted $C_{1-7}$ alkyl, or —$SO_xM$;

each M independently is H or a monovalent pharmaceutically acceptable cation;

n is 1, 2 or 3;

each r independently is an integer from 1 to 200;

s is 1, 2, 3, 4, 5 or 6;

t is 0, 1, or 2; and each x independently is 2 or 3.

In certain embodiments, when E is E4, the dotted line indicates the presence of a double bond, $X_3$ is CH, and $X_4$ is O or S, then s is 2, 3, 4, 5 or 6, for example, s is 2, s is 3, s is 4, s is 5 or s is 6.

In certain embodiments, when $X_4$ is O or S, then s is 2, 3, 4, 5 or 6, for example, s is 2, s is 3, s is 4, s is 5 or s is 6.

Subsets of compounds of Formula (I) include those of Formula (II), (II-1) or (II-2):

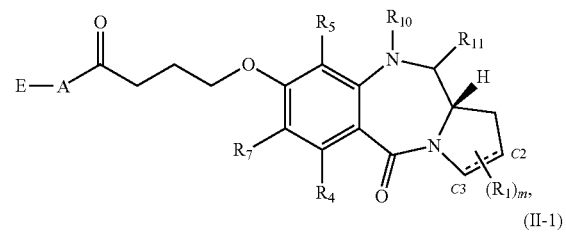

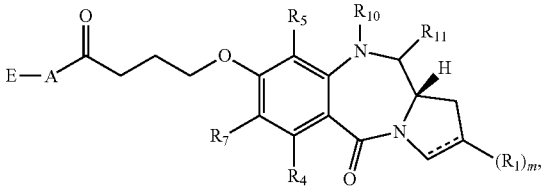

-continued

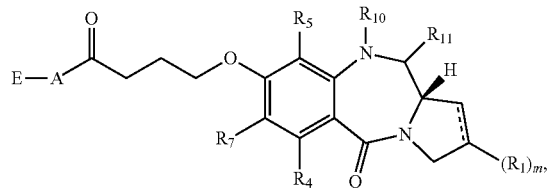

or a tautomer thereof, or a pharmaceutically acceptable salt or solvate of the compound or the tautomer.

Another subset of compounds of Formula (I) includes those of Formula (III):

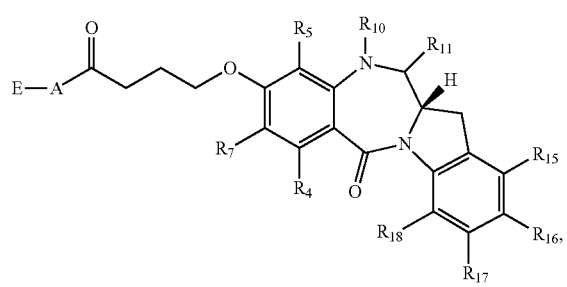

or a tautomer thereof, or a pharmaceutically acceptable salt or solvate of the compound or the tautomer.

Yet another subset of compounds of Formula (I) includes those of Formula (IV):

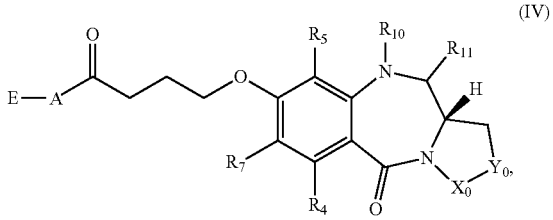

or a tautomer thereof, or a pharmaceutically acceptable salt or solvate of the compound or the tautomer.

Still other subsets of compounds of Formula (I) include those of Formula (II-a)-(II-p):

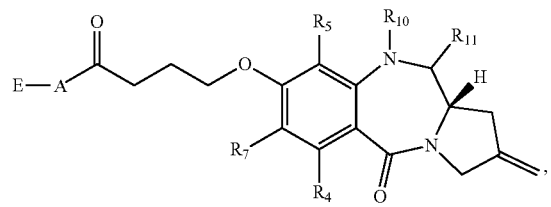
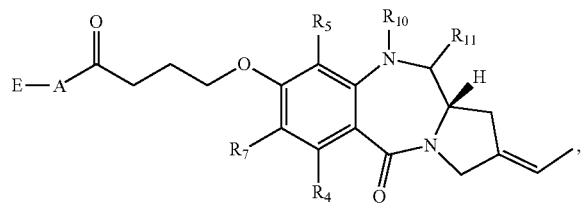
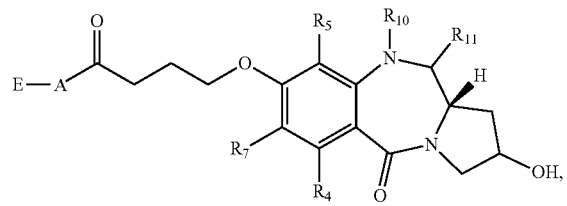
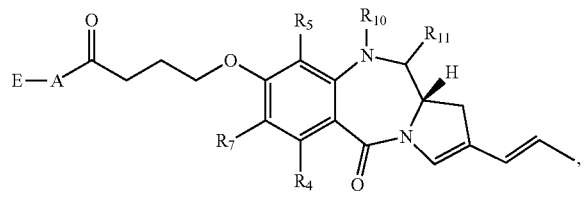
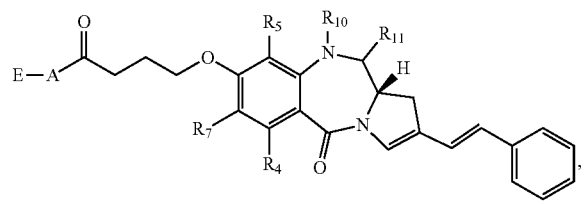
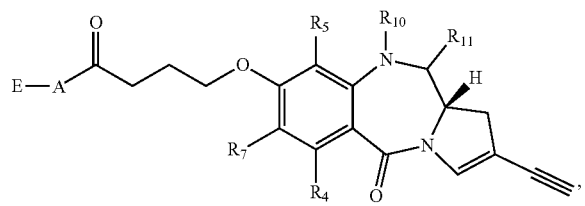

-continued
(II-g)
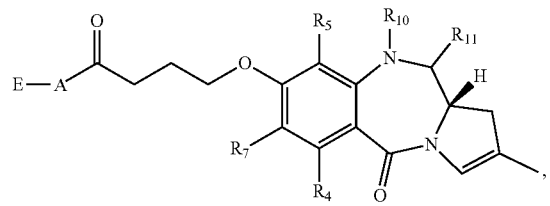
(II-h)
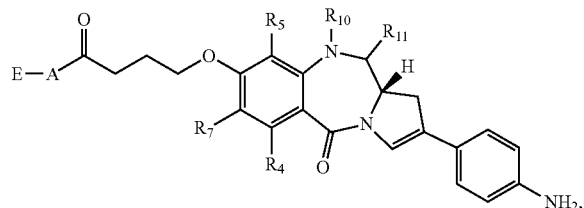
(II-i)
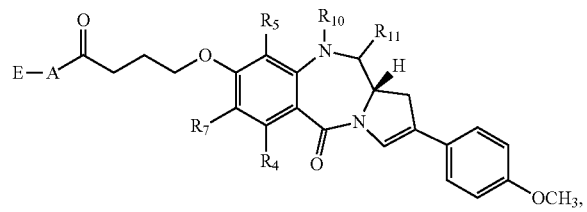
(II-j)
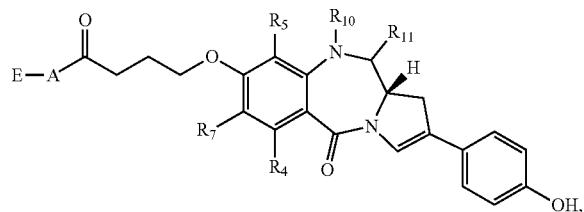
(II-k)
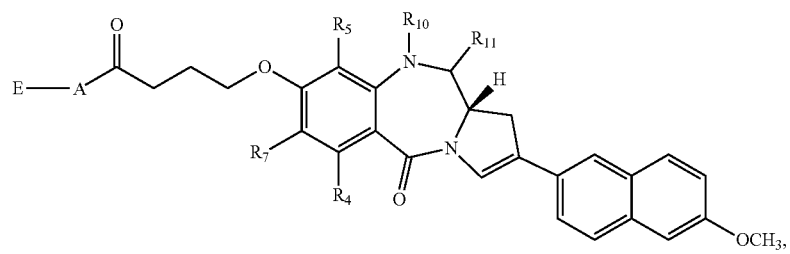
(II-l)
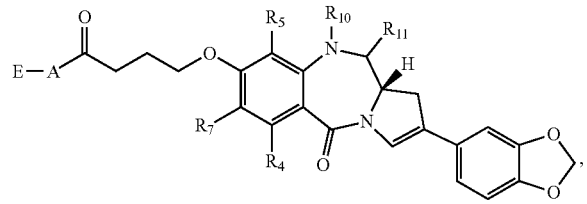
(II-m)
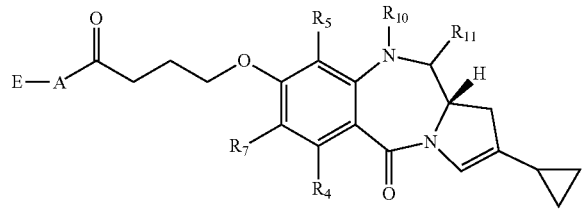
(II-n)
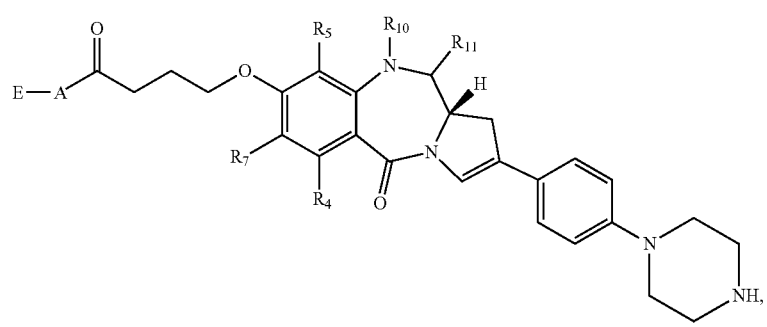
(II-o)
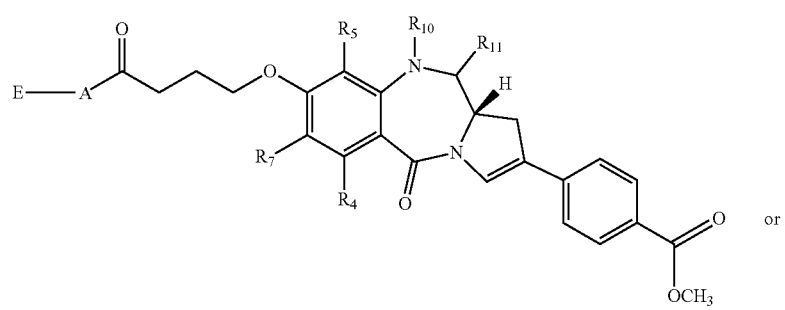
or

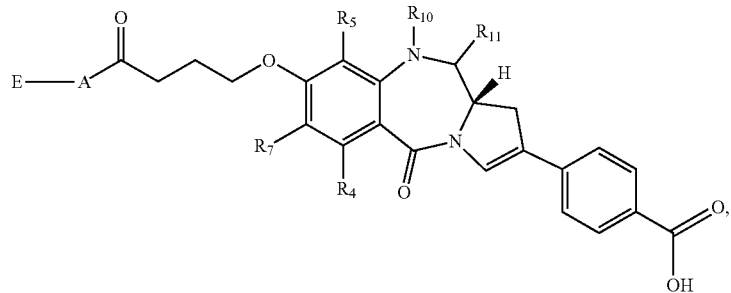

or a tautomer thereof, or a pharmaceutically acceptable salt or solvate of the compound or the tautomer.

Other subsets of compounds of Formula (I) include those of any of Formulae (III-a), (III-b) or (III-c):

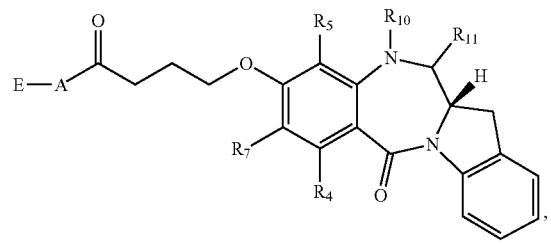

(III-a)

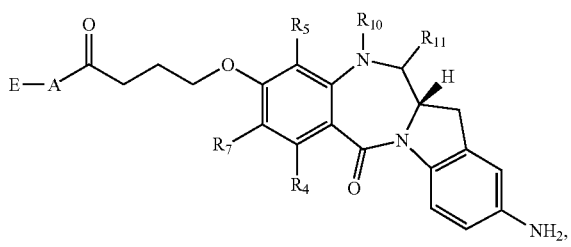

(III-b)

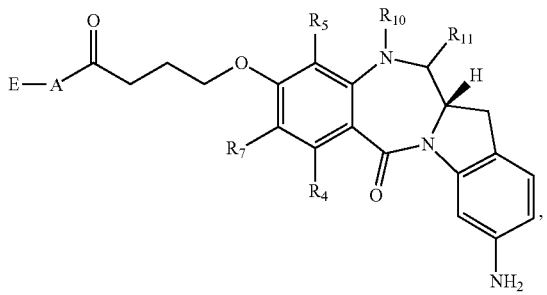

(III-c)

or a tautomer thereof, or a pharmaceutically acceptable salt or solvate of the compound or the tautomer.

Still another subset of compounds of Formula (I) includes those of the following formula:

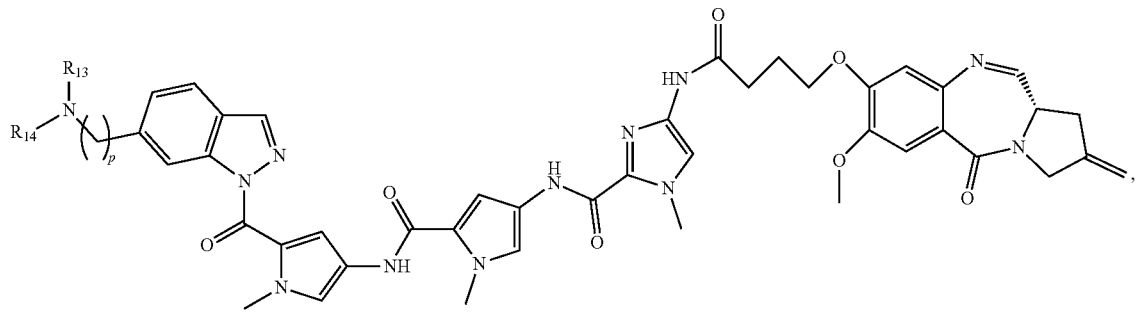

or a tautomer thereof, or a pharmaceutically acceptable salt or solvate of the compound or the tautomer.

In another aspect, the present disclosure features a conjugate of a compound of Formula (I), wherein the conjugate comprising an antibody or antibody fragment directly or indirectly connected to the compound.

In yet another aspect, the present disclosure features a conjugate of a compound of Formula (I), wherein the conjugate comprising an antibody or antibody fragment indirectly connected to the compound, wherein the compound is connected to the antibody or antibody fragment via one or more polymeric scaffold. In one embodiment, the one or more polymeric scaffold comprises poly(1-hydroxymethylethylene hydroxymethyl-formal) (PHF). In one embodiment, the PHF has a molecular weight ranging from about 2 kDa to about 40 kDa. In another embodiment, the PHF has a molecular weight ranging from about 20 kDa to about 300 kDa.

In certain embodiments, upon conjugation with the antibody or antibody fragment, the conjugate is of Formula (VI),

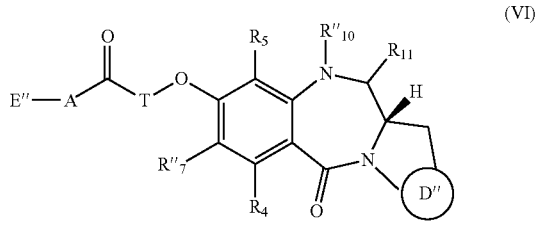

(VI)

or a tautomer thereof, or a pharmaceutically acceptable salt or solvate of the compound or the tautomer, wherein:
the antibody or antibody fragment is directly or indirectly linked to the compound at the position of one of E", D", R"$_7$ or R"$_{10}$; and the remaining of E", D", R"$_7$ or R"$_{10}$ are respectively E, D, R$_7$, or R$_{10}$;
wherein:
E" is E or $$E\text{—}\underset{\xi}{\overset{\xi}{\big|}}\text{—}$$

in which $$\text{—}\underset{\xi}{\overset{\xi}{\big|}}\text{—}$$

denotes direct or indirect linkage to the antibody or antibody fragment via a functional group of E;
D" is D or $$D\text{—}\underset{\xi}{\overset{\xi}{\big|}}\text{—};$$

in which $$\text{—}\underset{\xi}{\overset{\xi}{\big|}}\text{—}$$

denotes direct or indirect linkage to the antibody or antibody fragment via a functional group of D;
R"$_7$ is R$_7$ or $$R_7\text{—}\underset{\xi}{\overset{\xi}{\big|}}\text{—};$$

in which $$\text{—}\underset{\xi}{\overset{\xi}{\big|}}\text{—}$$

denotes direct or indirect linkage to the antibody or antibody fragment via a functional group of R$_7$; and
R"$_{10}$ is R$_{10}$ or $$R_{10}\text{—}\underset{\xi}{\overset{\xi}{\big|}}\text{—};$$

in which $$\text{—}\underset{\xi}{\overset{\xi}{\big|}}\text{—}$$

denotes direct or indirect linkage to the antibody or antibody fragment via a functional group of R$_{10}$.

Also provided herein are pharmaceutical compositions comprising a compound for Formula (I) or a conjugate thereof and a pharmaceutically acceptable carrier.

In still another aspect, the present disclosure features a compound for Formula (I) or a conjugate thereof for use in a method for medical treatment, e.g., for treating cancer.

In one aspect the present disclosure features a method for treating cancer comprising administering an effective amount of a compound for Formula (I) or a conjugate of Formula (VI) to a subject in need thereof.

Unless otherwise stated, any description of a method of treatment includes use of the compounds to provide such treatment or prophylaxis as is described herein, as well as use of the compounds to prepare a medicament to treat or prevent such condition. The treatment includes treatment of human or non-human animals including rodents and other disease models.

Further, the compounds or methods described herein can be used for research and other non-therapeutic purposes.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTION OF THE FIGURE

The FIGURE is a plot of tumor volume vs. time, showing the tumor response in mice inoculated subcutaneously with NCI-N$_{87}$ cells (n=10 for each group) after IV administration as a single dose on day 1 of vehicle or trastuzumab-PBD conjugates, i.e., Conjugates 47 and 60A, at 3 mg/kg.

DETAILED DESCRIPTION

The present disclosure features a compound of Formula (I),

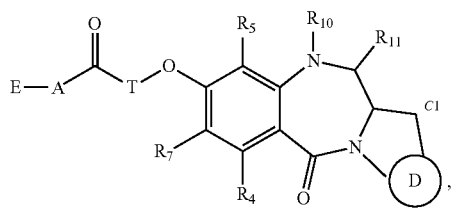
(I)

or a tautomer thereof, or a pharmaceutically acceptable salt or solvate of the compound or the tautomer.

In the compound of formula (I) above,

D is D1, D2 or D3:

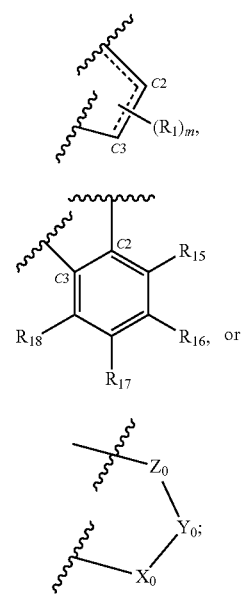

wherein the dotted line between C2 and C3 or between C2 and C1 in D1 indicates the presence of a single or double bond; and m is 0, 1 or 2;

when D is D1, the dotted line between C2 and C3 is a double bond, and m is 1, then $R_1$ is:

(i) $C_{6-10}$ aryl group, optionally substituted by one or more substituents selected from —OH, halo, —NO$_2$, —CN, —N$_3$, —OR$_2$, —COOH, —COOR$_2$, —COR$_2$, —OCONR$_{13}$R$_{14}$, $C_{1-10}$ alkyl, $C_{3-10}$ cycloalkyl, $C_{2-10}$ alkenyl, $C_{2-10}$ alkynyl, a polyethylene glycol unit —(OCH$_2$CH$_2$)$_r$—OR$_a$, 3- to 14-membered heterocloalkyl, 5- to 12-membered heteroaryl, bis-oxy-$C_{1-3}$ alkylene, —NR$_{13}$R$_{14}$, —S(=O)$_2$R$_{12}$, —S(=O)$_2$NR$_{13}$R$_{14}$, —SR$_{12}$, —SO$_x$M, —OSO$_x$M, —NR$_9$COR$_{19}$, —NH(C=NH)NH$_2$;

(ii) $C_{1-5}$ alkyl;

(iii) $C_{3-6}$ cycloalkyl;

(iv)

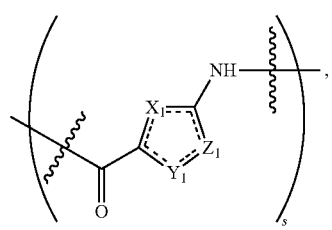

(vi)

(vii)

(vii)

(viii) halo;

when D is D1, the dotted line between C$_2$ and C$_3$ is a single bond, and m is 1, then $R_1$ is:

(i) —OH, =O, =CH$_2$, —CN, —R$_2$, —OR$_2$, halo, =CH—R$_6$, =C(R$_6$)$_2$, —O—SO$_2$R$_2$, —CO$_2$R$_2$, —COR$_2$, —CHO, or —COOH; or (ii)

when D is D1 and m is 2, then each $R_1$ independently is halo and either both $R_1$ are attached to the same carbon atom or one is attached to $C_2$ and the other is attached to $C_3$;

T is $C_{1-10}$ alkylene linker;

A is wherein the —NH group of A is connected to the —C(O)-T-moiety of Formula (I) and the C=O moiety of A is connected to E; and each

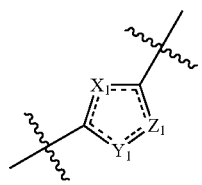

independently is

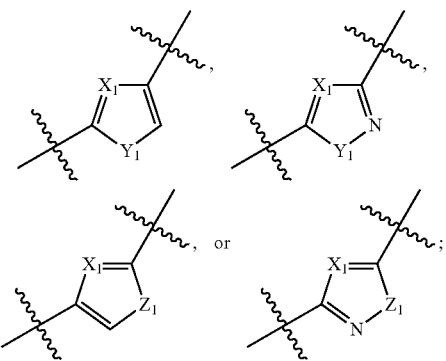

E is —OH, —NH—($C_{1-6}$ alkylene)-$R_{13a}$, E1, E2, E3 or E4:

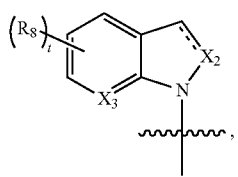
(E1)

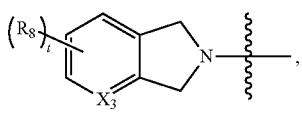
(E2)

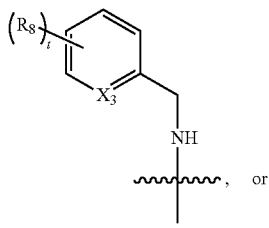
(E3)

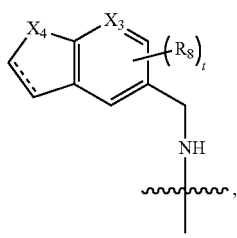
(E4)

wherein the dotted line in E1 or E4 indicates the presence of a single or double bond;

each occurrence of $R_2$ and $R_3$ independently is an optionally substituted $C_{1-8}$ alkyl, optionally substituted $C_{2-8}$ alkenyl, optionally substituted $C_{2-8}$ alkynyl, optionally substituted $C_{3-8}$ cycloalkyl, optionally substituted 3- to 20-membered heterocycloalkyl, optionally substituted $C_{6-20}$ aryl or optionally substituted 5- to 20-membered heteroaryl, and, optionally in relation to the group $NR_2R_3$, $R_2$ and $R_3$ together with the nitrogen atom to which they are attached form an optionally substituted 4-, 5-, 6- or 7-membered heterocycloalkyl or an optionally substituted 5- or 6-membered heteroaryl;

$R_4$, $R_5$ and $R_7$ are each independently —H, —$R_2$, —OH, —$OR_2$, —SH, —$SR_2$, —$NH_2$, —$NHR_2$, —$NR_2R_3$, —$NO_2$, —$SnMe_3$, halo or a polyethylene glycol unit —$(OCH_2CH_2)_r$—$OR_a$; or $R_4$ and $R_7$ together form bis-oxy-$C_{1-3}$ alkylene;

each $R_6$ independently is —H, —$R_2$, —$CO_2R_2$, —$COR_2$, —CHO, —$CO_2H$, or halo;

each $R_8$ independently is —OH, halo, —$NO_2$, —CN, —$N_3$, —$OR_2$, —COOH, —$COOR_2$, —$COR_2$, —$OCONR_{13}R_{14}$, —$CONR_{13}R_{14}$, —CO—NH—($C_{1-6}$ alkylene)-$R_{13a}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3- to 14-membered heterocycloalkyl, 5- to 12-membered heteroaryl, —$S(=O)_2R_{12}$, —$S(=O)_2NR_{13}R_{14}$, —$SR_{12}$, —$SO_xM$, —$OSO_xM$, —$NR_9COR_{19}$, —$NH(C=NH)NH_2$ or —$R_{20}$—$R_{21}$—$NR_{13}R_{14}$;

each $R_9$ independently is $C_{1-10}$ alkyl, $C_{3-10}$ cycloalkyl, $C_{2-10}$ alkenyl or $C_{2-10}$ alkynyl;

$R^{10}$ is —H or a nitrogen protecting group;

$R^{11}$ is -$QR^Q$ or —$SO_xM$;

or $R^{10}$ and $R^{11}$ taken together with the nitrogen atom and carbon atom to which they are respectively attached, form a N=C double bond;

each $R_{12}$ independently is $C_{1-7}$ alkyl, 3- to 20-membered heterocycloalkyl, 5- to 20-membered heteroaryl, or $C_{6-20}$ aryl;

each occurrence of $R_{13}$ and $R_{14}$ are each independently H, $C_{1-10}$ alkyl, 3- to 20-membered heterocycloalkyl, 5- to 20-membered heteroaryl, or $C_{6-20}$ aryl;

each $R_{13a}$ independently is —OH or —$NR_{13}R_{14}$;

$R_{15}$, $R_{16}$, $R_{17}$ and $R_{18}$ are each independently —H, —OH, halo, —$NO_2$, —CN, —$N_3$, —$OR_2$, —COOH, —$COOR_2$, —$COR_2$, —$OCONR_{13}R_{14}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3-14 membered heterocycloalkyl, 5- to 12-membered heteroaryl, —$NR_{13}R_{14}$, —$S(=O)_2R_{12}$, —$S(=O)_2NR_{13}R_{14}$, —$SR_{12}$, —$SO_xM$, —$OSO_xM$, —$NR_9COR_{19}$ or —$NH(C=NH)NH_2$;

each $R_{19}$ independently is $C_{1-10}$ alkyl, $C_{3-10}$ cycloalkyl, $C_{2-10}$ alkenyl or $C_{2-10}$ alkynyl;

each $R_{20}$ independently is a bond, $C_{6-10}$ arylene, 3-14 membered heterocycloalkylene or 5-to 12-membered heteroarylene;

each $R_{21}$ independently is a bond or $C_{1-10}$ alkylene;

$R_{31}$, $R_{32}$ and $R_{33}$ are each independently —H, $C_{1-3}$ alkyl, $C_{2-3}$ alkenyl, $C_{2-3}$ alkynyl or cyclopropyl, where the total number of carbon atoms in the $R_1$ group is no more than 5;

$R_{34}$ is —H, $C_{1-3}$ alkyl, $C_{2-3}$ alkenyl, $C_{2-3}$ alkynyl, cyclopropyl, or phenyl wherein the phenyl is optionally substituted by one or more of halo, methyl, methoxy, pyridyl or thiophenyl;

one of $R_{35a}$ and $R_{35b}$ is —H and the other is a phenyl group optionally substituted with one or more of halo, methyl, methoxy, pyridyl or thiophenyl;

$R_{36a}$, $R_{36b}$, $R_{36c}$ are each independently —H or $C_{1-2}$ alkyl;

$R_{36d}$ is —OH, —SH, —COOH, —C(O)H, —N=C=O, —$NHNH_2$, —$CONHNH_2$,

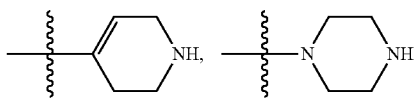

or NHR$^N$, where R$^N$ is —H or C$_{1-4}$ alkyl;

R$_{37a}$ and R$_{37b}$ are each independently is —H, —F, C$_{1-4}$ alkyl, C$_{2-3}$ alkenyl, wherein the alkyl and alkenyl groups are optionally substituted by C$_{1-4}$ alkyl amido or C$_{1-4}$ alkyl ester; or when one of R$_{37a}$ and R$_{37b}$ is —H, the other is —CN or a C$_{1-4}$ alkyl ester;

X$_0$ is CH$_2$, NR$_6$, C=O, BH, SO or SO$_2$;

Y$_0$ is O, CH$_2$, NR$_6$ or S;

Z$_0$ is absent or (CH$_2$)$_n$;

each X$_1$ independently is CR$_b$, or N;

each Y$_1$ independently is NR$_a$, O or S;

each Z$_1$ independently is NR$_a$, O or S;

each R$_a$ independently is H or C$_{1-4}$ alkyl;

each R$_b$ independently is H, OH, C$_{1-4}$ alkyl, or C$_{1-4}$ alkoxyl;

X$_2$ is CH, CH$_2$ or N;

X$_3$ is CH or N;

X$_4$ is NH, O or S;

Q is O, S or NH;

when Q is S or NH, then R$^Q$ is —H or optionally substituted C$_{1-7}$ alkyl; or when Q is O, then R$^Q$ is —H or optionally substituted C$_{1-7}$ alkyl, or —SO$_x$M;

each M independently is H or a monovalent pharmaceutically acceptable cation;

n is 1, 2 or 3;

each r independently is an integer from 1 to 200;

s is 1, 2, 3, 4, 5 or 6;

t is 0, 1, or 2; and each x independently is 2 or 3.

The compounds of Formula (I) can have one or more of the following features when applicable:

For example, the compounds of Formula (I) include those of Formula (I-a),

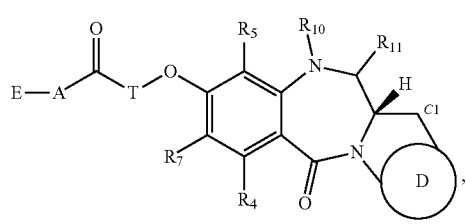

or a tautomer thereof, or a pharmaceutically acceptable salt or solvate of the compound or the tautomer.

For example, D is D1.

For example, D is D2.

For example, D is D3.

For example, the compounds of Formula (I) include those of Formula (II), (II-1) or (II-2):

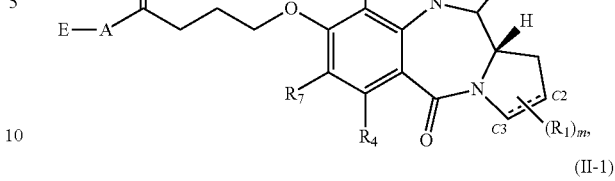

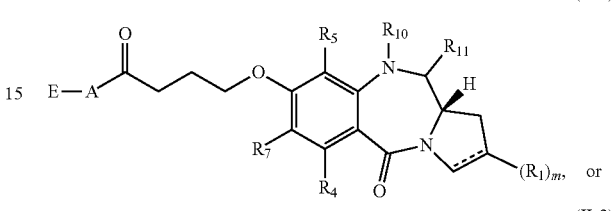

or a tautomer thereof, or a pharmaceutically acceptable salt or solvate of the compound or the tautomer.

For example, the compounds of Formula (I) include those of Formula (III):

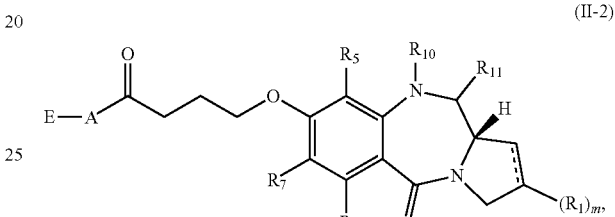

or a tautomer thereof, or a pharmaceutically acceptable salt or solvate of the compound or the tautomer.

For example, the compounds of Formula (I) include those of Formula (IV):

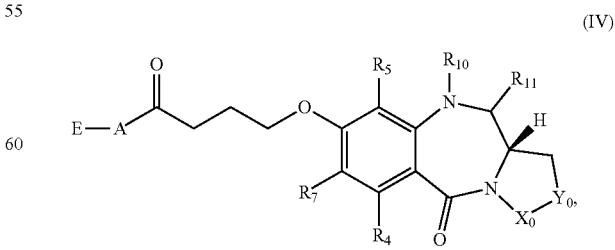

or a tautomer thereof, or a pharmaceutically acceptable salt or solvate of the compound or the tautomer.

For example, when D is D1, the dotted line between C₂ and C₃ is a double bond, and m is 1, then R₁ is C₆₋₁₀ aryl group, optionally substituted by one or more substituents selected from —OH, halo, —NO₂, —CN, —N₃, —OR₂, —COOH, —COOR₂, —COR₂, —OCONR₁₃R₁₄, C₁₋₁₀ alkyl, C₃₋₁₀ cycloalkyl, C₂₋₁₀ alkenyl, C₂₋₁₀ alkynyl, a polyethylene glycol unit —(OCH₂CH₂)ᵣ—ORₐ, 3- to 14-membered heterocycloalkyl, 5- to 12-membered heteroaryl, bis-oxy-C₁₋₃ alkylene, —NR₁₃R₁₄, —S(=O)₂R₁₂, —S(=O)₂NR₁₃R₁₄, —SR₁₂, —SOₓM, —OSOₓM, —NR₉COR₁₉, and —NH(C=NH)NH₂.

For example, when D is D1, the dotted line between C₂ and C₃ is a double bond, and m is 1, then R₁ is C₆₋₁₀ aryl group, optionally substituted by one or more substituents selected from —OH, halo, —NO₂, —CN, —N₃, —OR₂, —COOH, —COOR₂, —COR₂, —OCONR₁₃R₁₄, C₁₋₁₀ alkyl, C₃₋₁₀ cycloalkyl, C₂₋₁₀ alkenyl, C₂₋₁₀ alkynyl, a polyethylene glycol unit —(OCH₂CH₂)ᵣ—ORₐ, 3- to 14-membered heterocycloalkyl, 5- to 12-membered heteroaryl, —NR₁₃R₁₄, —S(=O)₂R₁₂, —S(=O)₂NR₁₃R₁₄, —SR₁₂, —NR₉COR₁₉, and —NH(C=NH)NH₂.

For example, when D is D1, the dotted line between C₂ and C₃ is a double bond, and m is 1, then R₁ is C₆₋₁₀ aryl group, optionally substituted by one or more substituents selected from —OH, halo, —OR₂, —COOH, —COOR₂, —COR₂, 3- to 14-membered heterocycloalkyl, and —NR₁₃R₁₄.

For example, when D is D1, the dotted line between C₂ and C₃ is a double bond, and m is 1, then R₁ is C₆₋₁₀ aryl group, substituted by one or more substituents selected from —OH, halo, —OR₂, —COOH, —COOR₂, —COR₂, 3- to 14-membered heterocycloalkyl, and —NR₁₃R₁₄.

For example, when D is D1, the dotted line between C₂ and C₃ is a double bond, and m is 1, then R₁ is C₆₋₁₀ aryl group, substituted by one substituent selected from —OH, halo, —OR₂, —COOH, —COOR₂, —COR₂, 3- to 14-membered heterocycloalkyl, and —NR₁₃R₁₄.

For example, when D is D1, the dotted line between C₂ and C₃ is a double bond, and m is 1, then R₁ is C₆₋₁₀ aryl group, substituted by one substituent selected from —OH, —OR₂, —COOH, —COOR₂, 3- to 14-membered heterocycloalkyl, and —NR₁₃R₁₄.

For example, when D is D1, the dotted line between C₂ and C₃ is a double bond, and m is 1, then R₁ is C₆₋₁₀ aryl group, substituted by one substituent selected from —OH, and —COOH.

For example, when D is D1, the dotted line between C₂ and C₃ is a double bond, and m is 1, then R₁ is C₆₋₁₀ aryl group, substituted by one substituent selected from —OR₂— and —COOR₂.

For example, when D is D1, the dotted line between C₂ and C₃ is a double bond, and m is 1, then R₁ is C₆₋₁₀ aryl group, substituted by one 3- to 14-membered heterocycloalkyl.

For example, when D is D1, the dotted line between C₂ and C₃ is a double bond, and m is 1, then R₁ is C₆₋₁₀ aryl group, substituted by one —NR₁₃R₁₄.

For example, when D is D1, the dotted line between C₂ and C₃ is a double bond, and m is 1, then R₁ is C₁₋₅ alkyl.

For example, when D is D1, the dotted line between C₂ and C₃ is a double bond, and m is 1, then R₁ is C₃₋₆ cycloalkyl.

For example, when D is D1, the dotted line between C₂ and C₃ is a double bond, and m is 1, then R₁ is cyclopropyl.

For example, when D is D1, the dotted line between C₂ and C₃ is a double bond, and m is 1, then R₁ is

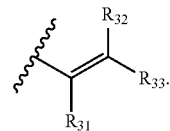

For example, when D is D1, the dotted line between C₂ and C₃ is a double bond, and m is 1, then R₁ is

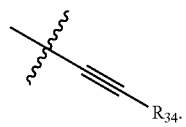

For example, when D is D1, the dotted line between C₂ and C₃ is a double bond, and m is 1, then R₁ is

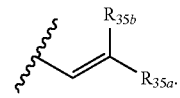

For example, when D is D1, the dotted line between C₂ and C₃ is a double bond, and m is 1, then R₁ is

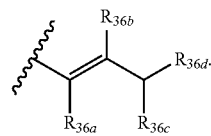

For example, when D is D1, the dotted line between C₂ and C₃ is a double bond, and m is 1, then R₁ is halo.

For example, when D is D1, the dotted line between C₂ and C₃ is a single bond, and m is 1, then R₁ is: —OH, =O, =CH₂, —CN, —R₂, —OR₂, halo, =CH—R₆, =C(R₆)₂, —O—SO₂R₂, —C₀₂R₂, —COR₂, —CHO, or —COOH.

For example, when D is D1, the dotted line between C₂ and C₃ is a single bond, and m is 1, then R₁ is: =CH₂, =CH—R₆ or =C(R₆)₂.

For example, when D is D1 and m is 2, then each R₁ independently is halo and either both R₁ are attached to the same carbon atom or one is attached to C₂ and the other is attached to C₃.

For example, T is C₂₋₆ alkylene linker.
For example, T is C₂₋₄ alkylene linker.
For example, T is butylene.
For example, T is propylene
For example, T is n-propylene.
For example, T is ethylene.
For example, each

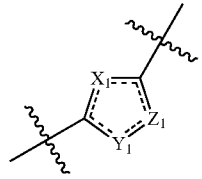

independently is

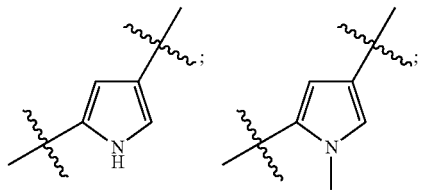

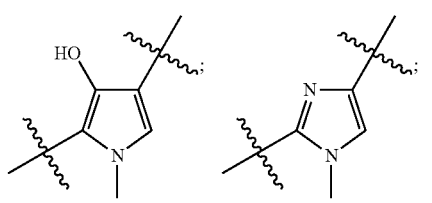

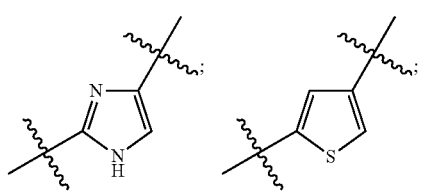

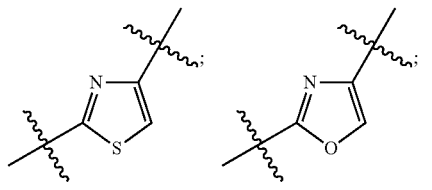

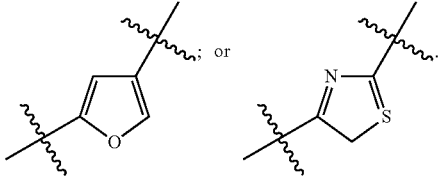 or

For example, each

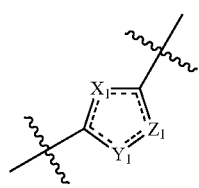

independently is

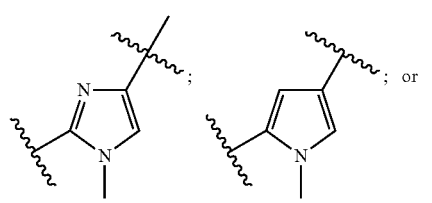

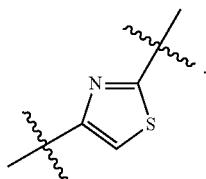

For example, s is 1, 2, 3, 4 or 5.
For example, s is 2, 3, 4, 5 or 6.
For example, s is 1, 2, 3 or 4.
For example, s is 2, 3, 4 or 5.
For example, s is 3, 4, 5 or 6.
For example, s is 1, 2 or 3.
For example, s is 2, 3 or 4.
For example, s is 3, 4 or 5.
For example, s is 4, 5 or 6.
For example, s is 1 or 2.
For example, s is 2 or 3.
For example, s is 3 or 4.
For example, s is 4 or 5.
For example, s is 5 or 6.
For example, s is 1.
For example, s is 2.
For example, s is 3.
For example, s is 4.
For example, s is 5.
For example, s is 6.
For example, A is

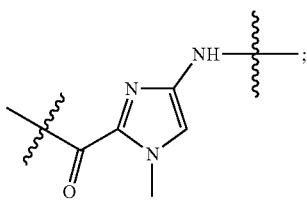

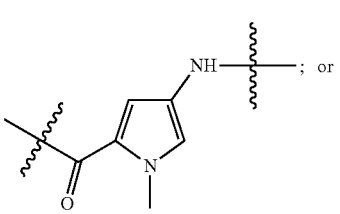 or

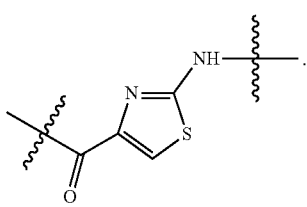

For example, A is
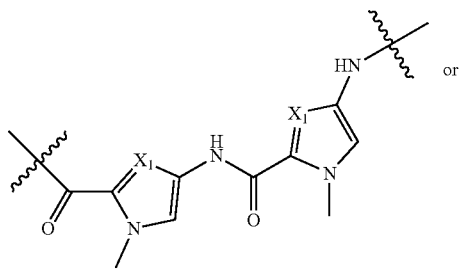 or
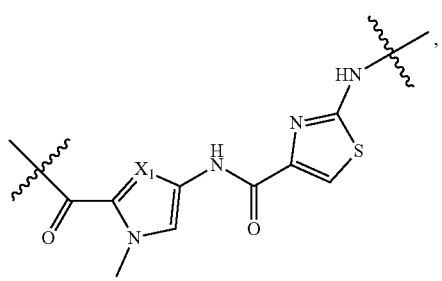,
wherein each $X_1$ independently is CH or N.
For example, A is
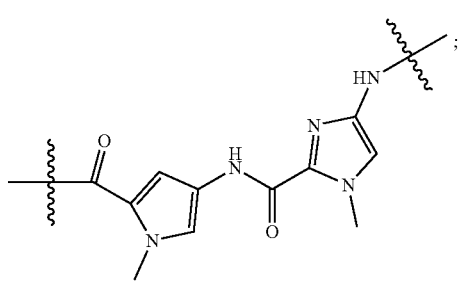;
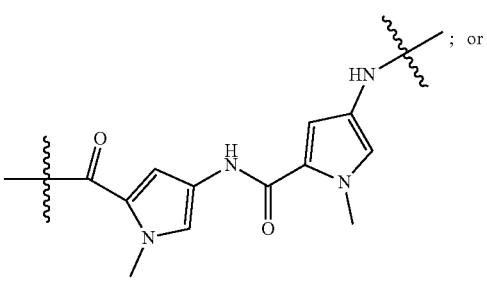; or
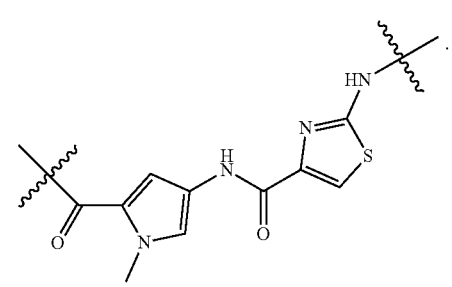.
For example, A is
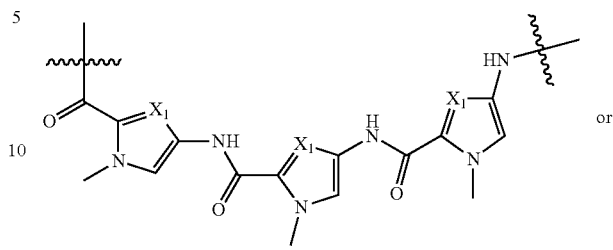 or
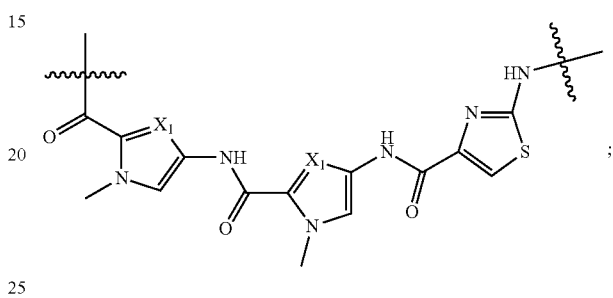;
wherein each $X_1$ independently is CH or N.
For example, A is:
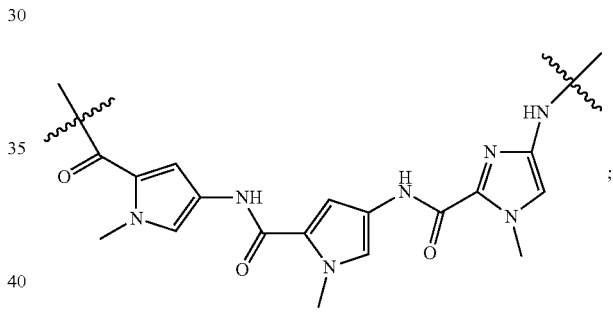;
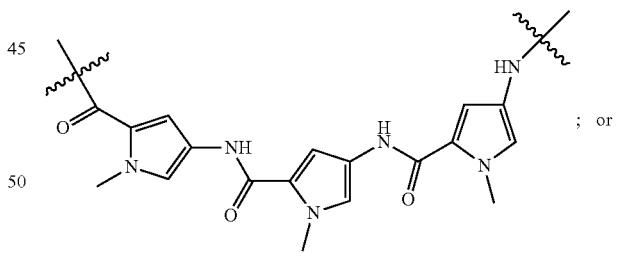; or
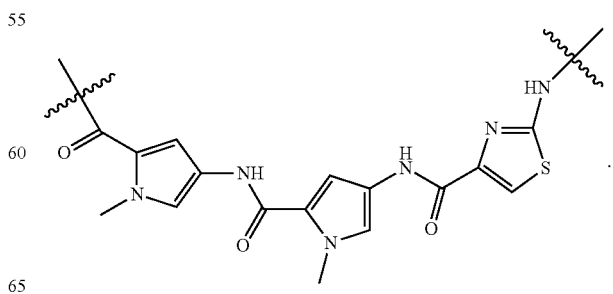.

For example, A is:
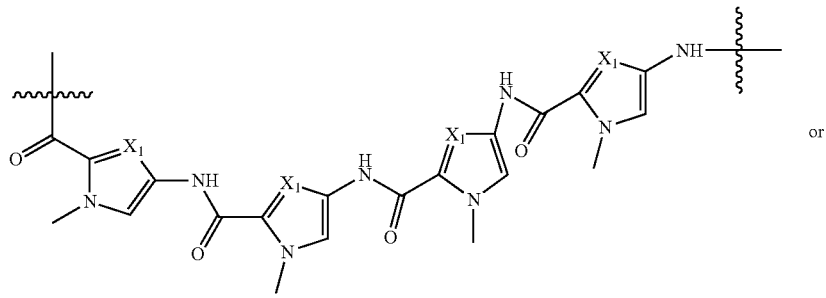
or
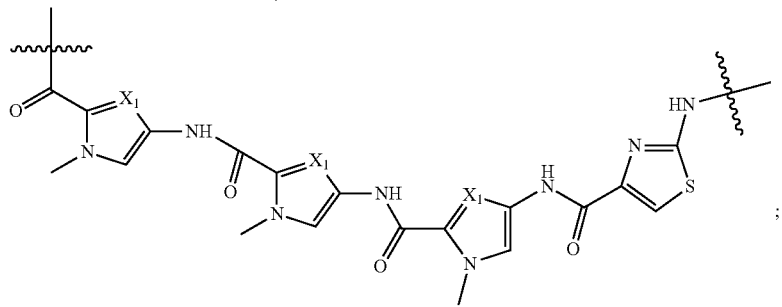
;
wherein each $X_1$ independently is CH or N.
For example, A is:
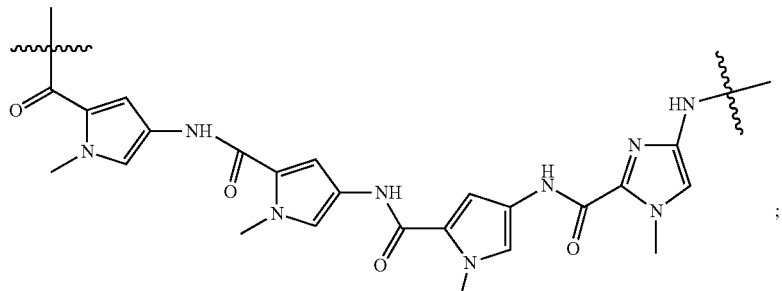
;
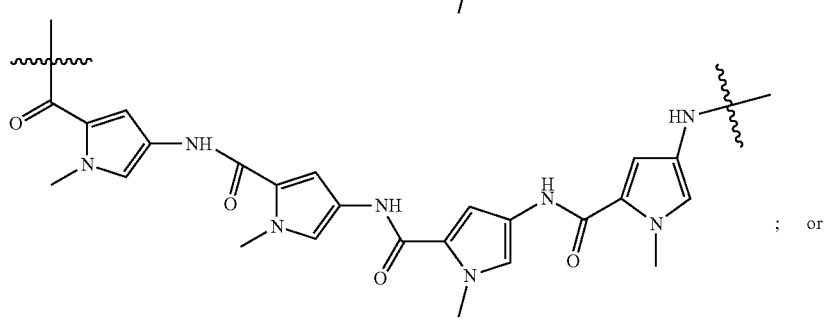
; or
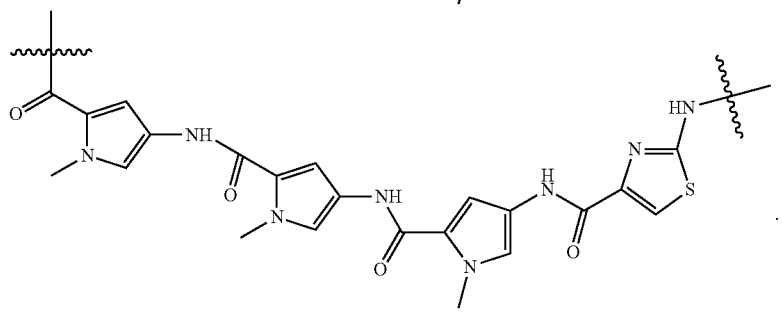
.

For example, t is 0.
For example, t is 1.
For example, t is 2.
For example, E is

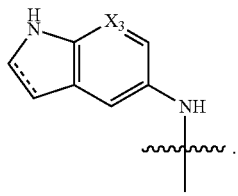

For example, E is

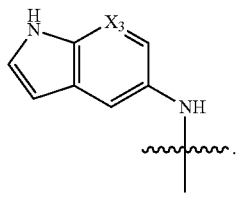

For example, $X_3$ is CH. For example, $X_3$ is N.
For example, when E is

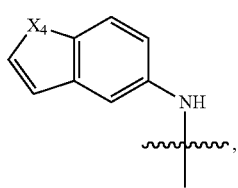

then s is 2, 3, 4, 5 or 6, for example, s is 2, s is 3, s is 4, s is 5 or s is 6.

For example, when $X_4$ is O or S, then s is 2, 3, 4, 5 or 6, for example, s is 2, s is 3, s is 4, s is 5 or s is 6.

For example, E is

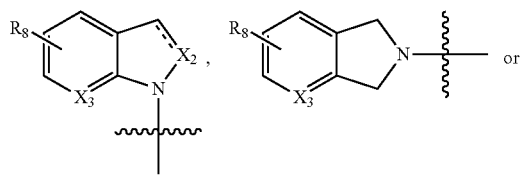

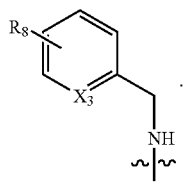

For example, E is —OH.
For example, E is —NH—($C_{1-6}$ alkylene)-OH, wherein $C_{1-6}$ alkylene is a linear or branched alkylene.
For example, E is —NH—$(CH_2)_u$—OH, in which u is 1, 2, 3, 4, 5, or 6.
For example, E is —NH—$(CH_2)_3$—OH.

For example, E is

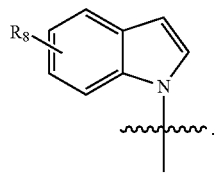

For example, E is

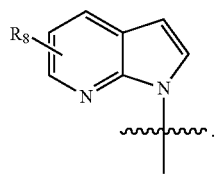

For example, E is

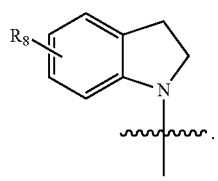

For example, E is

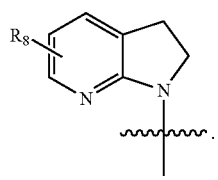

For example, E is

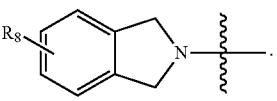

For example, E is N

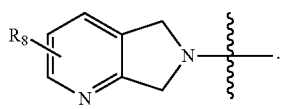

For example, E is

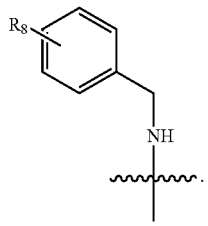

For example, E is

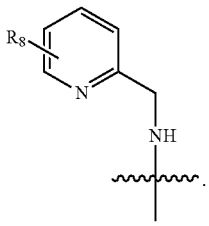

For example, each $R_8$ independently is —OH, —OR$_2$, —COOH, —COOR$_2$, —COR$_2$, —OCONR$_{13}$R$_{14}$, —CONR$_{13}$R$_{14}$, —CO—NH—(C$_{1-6}$ alkylene)-R$_{13a}$, a polyethylene glycol unit —(OCH$_2$CH$_2$)$_r$—OR$_a$, 3- to 7-membered heterocycloalkyl, 5- to 6-membered heteroaryl, —S(=O)$_2$R$_{12}$, —S(=O)$_2$NR$_{13}$R$_{14}$, —SR$_{12}$ or —R$_{20}$—R$_{21}$—NR$_{13}$R$_{14}$;

wherein $R_{13}$ and $R_{14}$ are each independently —H or C$_{1-10}$ alkyl;

each $R_{20}$ is phenylene; and each $R_{21}$ independently is C$_{1-4}$ alkylene.

For example, each $R_8$ independently is —OH, —OR$_2$, —COOH, —COOR$_2$, —COR$_2$, —S(=O)$_2$R$_{12}$, —SR$_{12}$ or —R$_{20}$—R$_{21}$—NR$_{13}$R$_{14}$.

For example, each $R_8$ independently is —OH or —OR$_2$.

For example, each $R_8$ independently is —COOH, —COOR$_2$, or —COR$_2$.

For example, each $R_8$ independently is —S(=O)$_2$R$_{12}$ or —SR$_{12}$.

For example, each $R_8$ independently is —CONR$_{13}$R$_{14}$ or —CO—NH—(C$_{1-6}$ alkylene)-R$_{13a}$.

For example, each $R_8$ independently is —R$_{20}$—R$_{21}$—NR$_{13}$R$_{14}$. For example, $R_8$ is —NH$_2$.

For example $R_8$ is —CH$_2$NH$_2$. For example $R_8$ is —CH$_2$CH$_2$NH$_2$. For example $R_8$ is —CH$_2$CH$_2$CH$_2$NH$_2$.

For example, each $R_{13a}$ independently is OH or NHR$_{13}$.

For example, each occurrence of $R_{13}$ is independently H or C$_{1-10}$ alkyl (e.g., C$_{1-6}$ alkyl).

For example, each occurrence of $R_{14}$ is independently H or C$_{1-10}$ alkyl (e.g., C$_{1-6}$ alkyl).

For example, each occurrence of $R_{13}$ is independently 3- to 20-membered (e.g., 4- to 14-membered) heterocycloalkyl or 5- to 20-membered (e.g., 5- to 10-membered) heteroaryl.

For example, each occurrence of $R_{14}$ is independently 3- to 20-membered (e.g., 4- to 14-membered) heterocycloalkyl or 5- to 20-membered (e.g., 5- to 10-membered) heteroaryl.

For example, $R_4$, $R_5$ and $R_7$ are each independently —H, —R$_2$, —OH, —OR$_2$, —SH, —SR$_2$, —NH$_2$, —NHR$_2$, —NR$_2$R$_3$, —NO$_2$, halo or a polyethylene glycol unit —(OCH$_2$CH$_2$)$_r$—OR$_a$.

For example, at least one of $R_4$, $R_5$ and $R_7$ is —OR$_2$.

For example, at least one of $R_4$, $R_5$ and $R_7$ is a polyethylene glycol unit —(OCH$_2$CH$_2$)$_r$—OR$_a$.

For example, at least two of $R_4$, $R_5$ and $R_7$ are —H.

For example, two of $R_4$, $R_5$ and $R_7$ are —H, and the other is —OR$_2$.

For example, two of $R_4$, $R_5$ and $R_7$ are —H, and the other is —OCH$_3$.

For example, $R_4$ and $R_5$ are each —H, and $R_7$ is —OCH$_3$.

For example, $R_4$ and $R_5$ are each —H, and $R_7$ is —(OCH$_2$CH$_2$)$_r$—OR$_a$.

For example, $R_4$ and $R_7$ together form bis-oxy-C$_{1-3}$ alkylene.

For example, each of $R_{20}$ and $R_{21}$ is a bond.

For example, one of $R_{20}$ and $R_{21}$ is a bond and the other is not a bond.

For example, $R_{20}$ is a bond and $R_{21}$ is not a bond.

For example, $R_{20}$ is a bond and $R_{21}$ is C$_{1-10}$ alkylene.

For example, $R_{21}$ is a bond and $R_{20}$ is not a bond.

For example, $R_{21}$ is a bond and $R_{20}$ is C$_{6-10}$ arylene, 3-14 membered heterocycloalkylene or 5- to 12-membered heteroarylene.

For example, $R^{10}$ and $R^{11}$ taken together with the nitrogen atom and carbon atom to which they are respectively attached, form a N=C double bond.

For example, $R^{10}$ is —H or a nitrogen protecting group, and $R^{11}$ is -QR$^Q$.

For example, $R^{10}$ is —H and $R^{11}$ is -QR$^Q$.

For example, $R^{10}$ is a nitrogen protecting group and $R^{11}$ is -QR$^Q$, wherein the nitrogen protecting group is allyloxycarbonyl (alloc), carbobenzyloxy (Cbz), p-methoxybenzyl carbonyl (Moz or MeOZ), acetyl (Ac), benzoyl (Bz), benzyl (Bn), trichloroethoxycarbonyl (Troc), t-butoxycarbonyl (BOC) or 9-fluorenylmethylenoxycarbonyl (Fmoc).

For example, $R^{11}$ is -OSO$_x$M.

For example, $R^{11}$ is —SO$_x$M.

For example, $R_{15}$, $R_{16}$, $R_{17}$ and $R_{18}$ are each independently —H, —OH, halo, —NO$_2$, —CN, —N$_3$, —OR$_2$, —COOH, —COOR$_2$, —COR$_2$, —OCONR$_{13}$R$_{14}$, C$_{1-10}$ alkyl, C$_{3-10}$ cycloalkyl, C$_{2-10}$ alkenyl, C$_{2-10}$ alkynyl, a polyethylene glycol unit —(OCH$_2$CH$_2$)$_r$—OR$_a$, 3-14 membered heterocycloalkyl, 5-to 12-membered heteroaryl, —NR$_{13}$R$_{14}$, —S(=O)$_2$R$_{12}$, —S(=O)$_2$NR$_{13}$R$_{14}$, —SR$_{12}$ or —NH(C=NH)NH$_2$.

For example, at least one of $R_{15}$, $R_{16}$, $R_{17}$ and $R_{18}$ is —H.

For example, at least two of $R_{15}$, $R_{16}$, $R_{17}$ and $R_{18}$ is —H.

For example, at least three of $R_{15}$, $R_{16}$, $R_{17}$ and $R_{18}$ is —H.

For example, $R_{15}$, $R_{16}$, $R_{17}$ and $R_{18}$ are each —H or —NR$_{13}$R$_{14}$.

For example, at least one of $R_{15}$, $R_{16}$, $R_{17}$ and $R_{18}$ is —NR$_{13}$R$_{14}$.

For example, at least one of $R_{15}$, $R_{16}$, $R_{17}$ and $R_{18}$ is —NH$_2$.

For example, one of $R_{15}$, $R_{16}$, $R_{17}$ and $R_{18}$ is —NR$_{13}$R$_{14}$.

For example, one of $R_{15}$, $R_{16}$, $R_{17}$ and $R_{18}$ is —NH$_2$.

For example, $R_{16}$, $R_{17}$ and $R_{18}$ are each —H; and $R_{15}$ is —NH$_2$.

For example, $R_{15}$, $R_{17}$ and $R_{18}$ are each —H; and $R_{16}$ is —NH$_2$.

For example, $R_{15}$, $R_{16}$ and $R_{18}$ are each —H; and $R_{17}$ is —NH$_2$.

For example, $R_{15}$, $R_{16}$ and $R_{17}$ are each —H; and $R_{18}$ is —NH$_2$.

For example, $X_0$ is CH$_2$, NR$_6$, or C=O.

For example, $Y_0$ is O, CH$_2$, or NR$_6$.

For example, $Z_0$ is absent.

For example, $Z_0$ is (CH$_2$)$_n$; and n is 1 or 2.

For example when Q is S or NH, then $R^Q$ is —H.

For example when Q is S or NH, then $R^Q$ is optionally substituted $C_{1-7}$ alkyl.

For example, when Q is O, then $R^Q$ is —H.

For example, when Q is O, then $R^Q$ is optionally substituted $C_{1-7}$ alkyl.

For example, when Q is O, then $R^Q$ is —$SO_xM$.

For example, the compound of Formula (I) contains at most one —$SO_xM$ or —$OSO_xM$. For example, $R^{11}$ is —$OSO_xM$ or —$SO_xM$.

For example, the compounds of Formula (I) include those of any of Formulae (II-a) through (II-p):

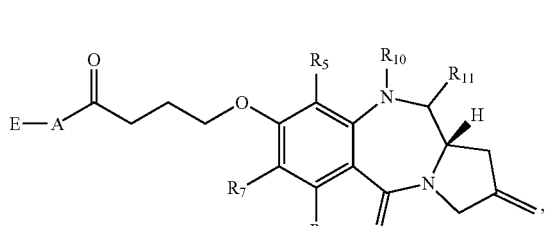
(II-a)

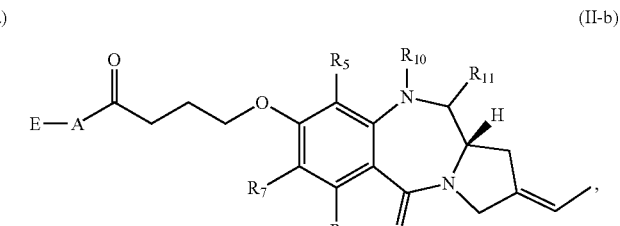
(II-b)

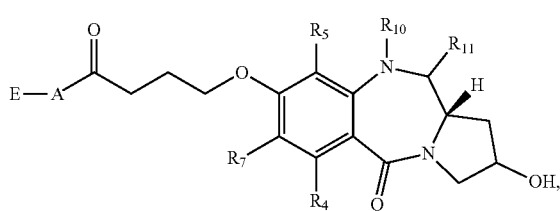
(II-c)

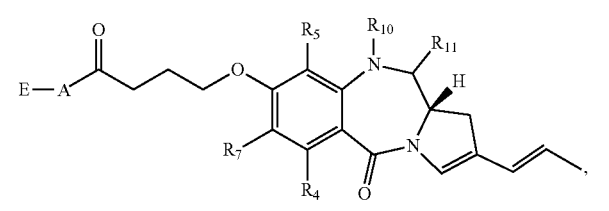
(II-d)

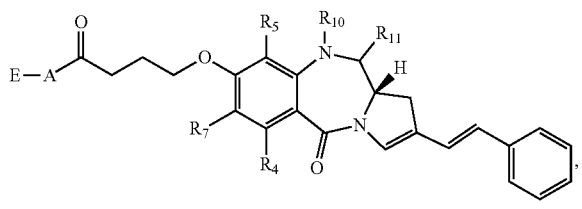
(II-e)

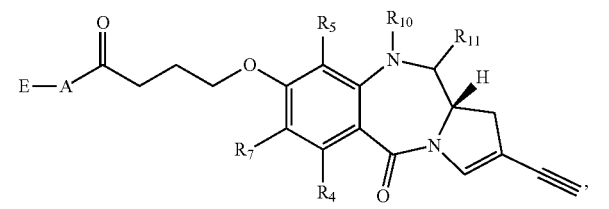
(II-f)

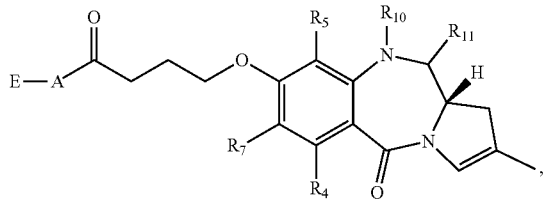
(II-g)

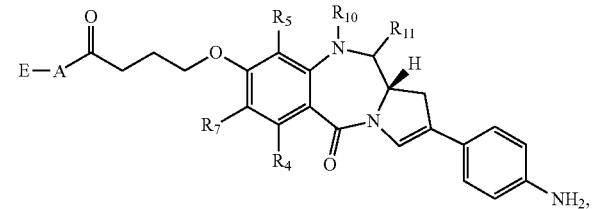
(II-h)

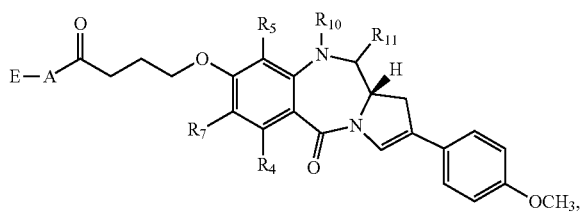
(II-i)

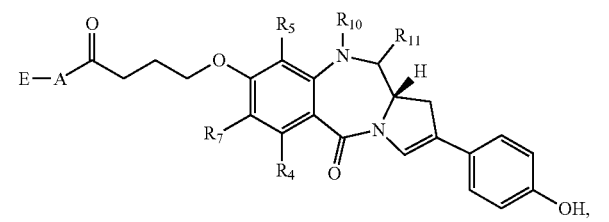
(II-j)

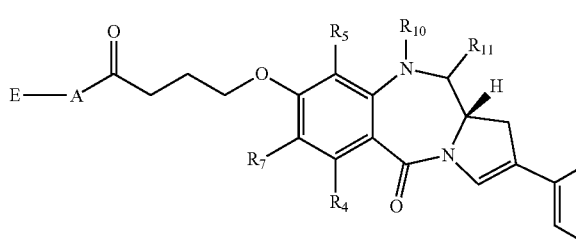
(II-k)

(II-l)
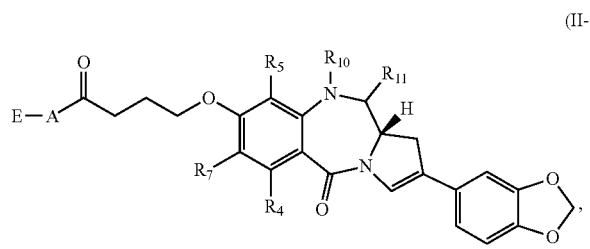
(II-m)
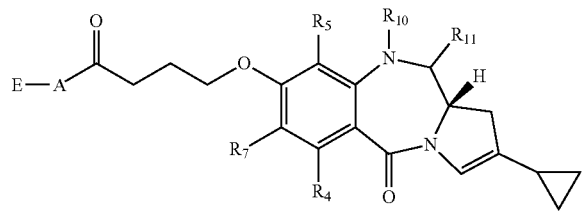
(II-n)
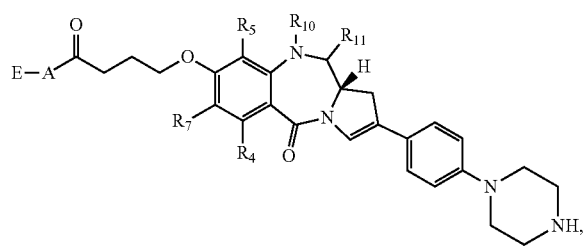
(II-o)
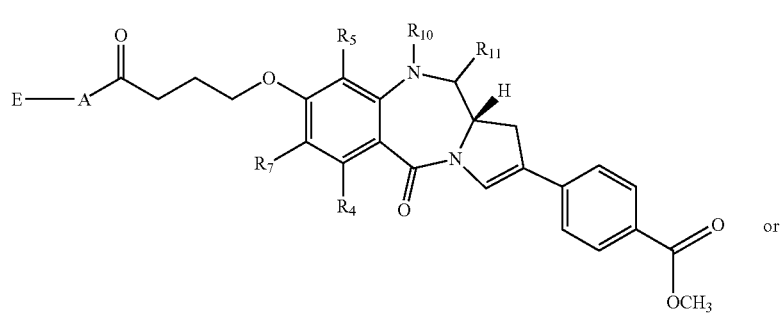
or
(II-p)
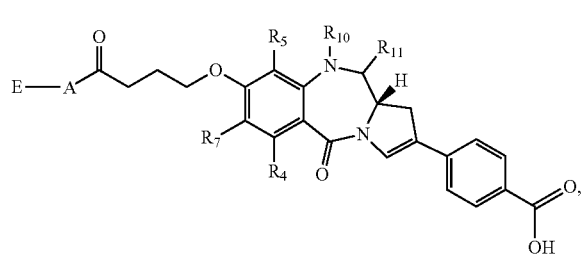
or a tautomer thereof, or a pharmaceutically acceptable salt or solvate of the compound or the tautomer.
For example, the compounds of Formula (I) include those of any of Formulae (III-a) through (III-c):
(III-a)
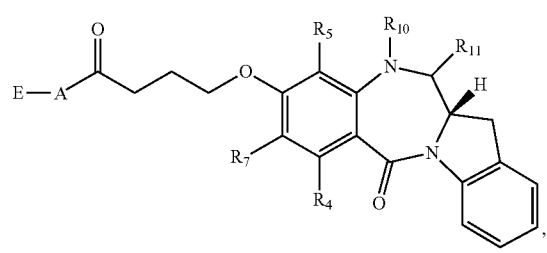
(III-b)
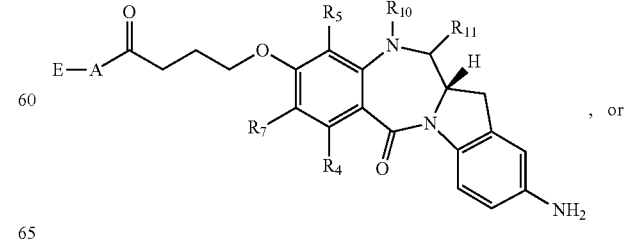
, or

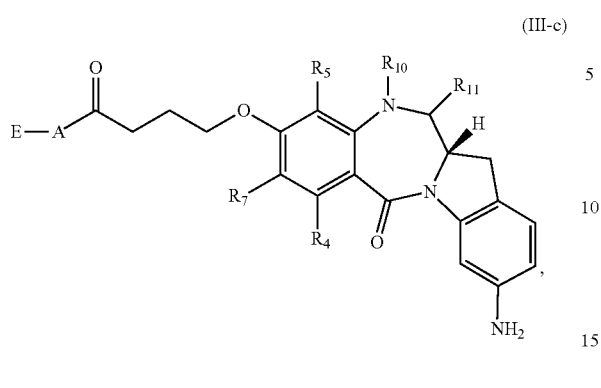

(III-c)

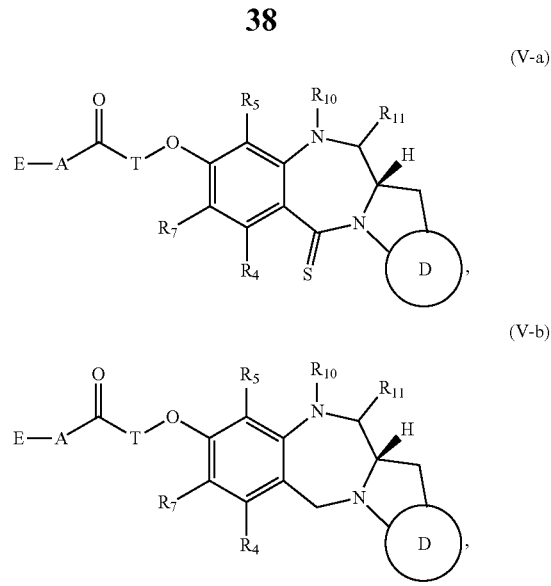

(V-a)

(V-b)

or a tautomer thereof, or a pharmaceutically acceptable salt or solvate of the compound or the tautomer.

For example, the compounds of Formula (I) include

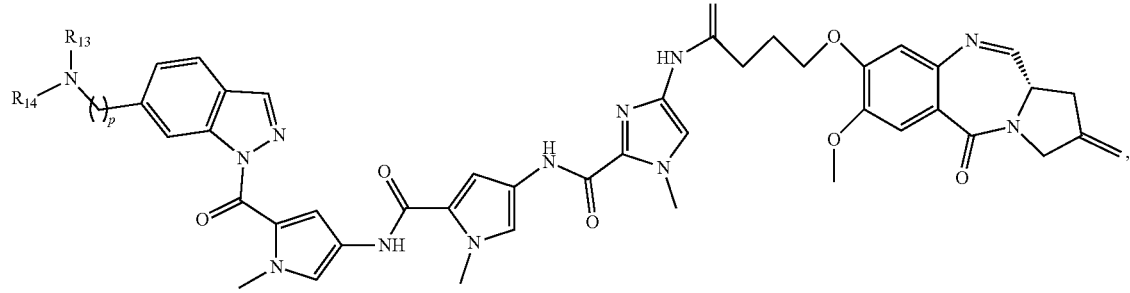

or a tautomer thereof, or a pharmaceutically acceptable salt or solvate of the compound or the tautomer, wherein:

$R_{13}$ is H;

$R_{14}$ is H or methyl; and p is 1, 2, 3 or 4.

The present disclosure also features a compound of Formula (V),

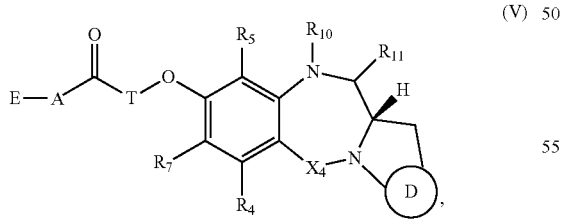

(V)

or a tautomer thereof, or a pharmaceutically acceptable salt or solvate of the compound or the tautomer.

In the compound of Formula (V) above, $X_4$ is C=S, $CH_2$, SO, $SO_2$ or BH; and E, A, T, D, $R_4$, $R_5$, $R_7$, $R_{10}$ and $R_{11}$ are as defined herein.

For example, the compounds of Formula (V) include those of any of Formulae (V-a) through (V-e):

-continued (V-c)

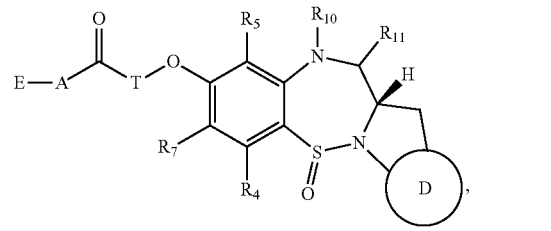

(V-d)

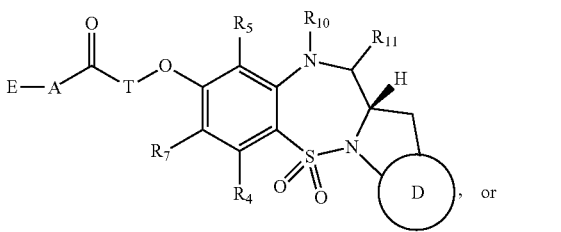

, or

-continued

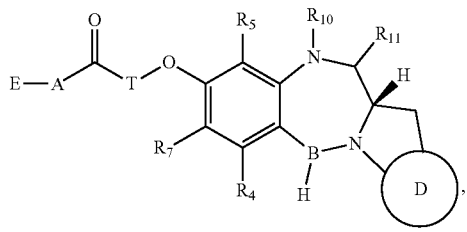

(V-e)

or a tautomer thereof, or a pharmaceutically acceptable salt or solvate of the compound or the tautomer.

For example, the compounds of Formula (I) include those where each of the moieties defined for one of D, T, E, A, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{31}$, $R_{32}$, $R_{33}$, $R_{34}$, $R_{35a}$, $R_{35b}$, $R_{36a}$, $R_{36b}$, $R_{36c}$, $R_{36d}$, $R_{37a}$, $R_{37b}$, $R_a$, $R^b$, $R^N$, $R^Q$, $X_0$, $Y_0$, $Z_0$, $X_1$, $Y_1$, $Z_1$, $X_2$, $X_3$, M, Q, m, n, r, s, t, and x, can be combined with any of the moieties defined for the others of D, T, E, A, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{31}$, $R_{32}$, $R_{33}$, $R_{34}$, $R_{35a}$, $R_{35b}$, $R_{36a}$, $R_{36b}$, $R_{36c}$, $R_{36d}$, $R_{37a}$, $R_{37b}$, $R_a$, $R^b$, $R^N$, $R^Q$, $X_0$, $Y_0$, $Z_0$, $X_1$, $Y_1$, $Z_1$, $X_2$, $X_3$, M, Q, m, n, r, s, t, and X.

Representative examples of compounds of the present disclosure include those listed in Table 1, or a tautomer thereof, or a pharmaceutically acceptable salt or solvate of the compound or the tautomer.

TABLE 1

| Compound No. | Structure |
| --- | --- |
| Compound No. 8 (Example 1) | 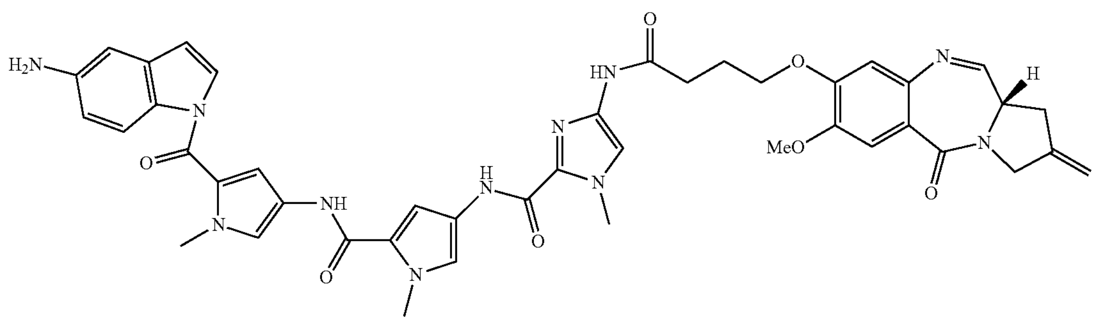 [SMILES: C=C1C[C@H]2C=Nc3cc(OCCCC(=O)Nc4cn(C)c(C(=O)Nc5cc(C(=O)Nc6cc(C(=O)n7ccc8cc(N)ccc87)n(C)c6)n(C)c5)n4)c(OC)cc3C(=O)N2C1] |
| Compound No. 12 (Example 2) | 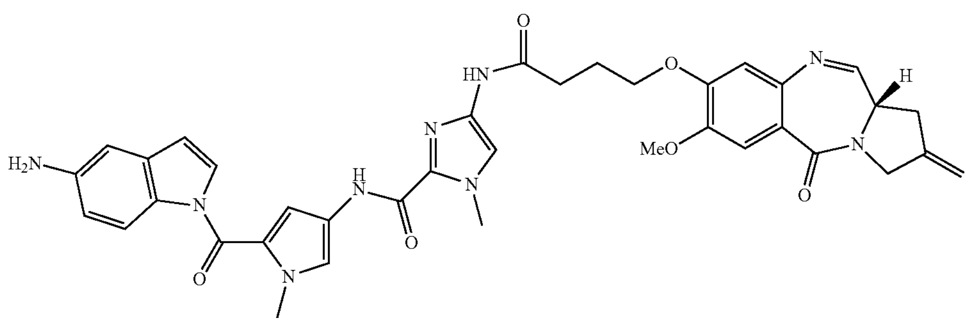 [SMILES: C=C1C[C@H]2C=Nc3cc(OCCCC(=O)Nc4cn(C)c(C(=O)Nc5cc(C(=O)n6ccc7cc(N)ccc76)n(C)c5)n4)c(OC)cc3C(=O)N2C1] |
| Compound No. 3A (Example 3) | 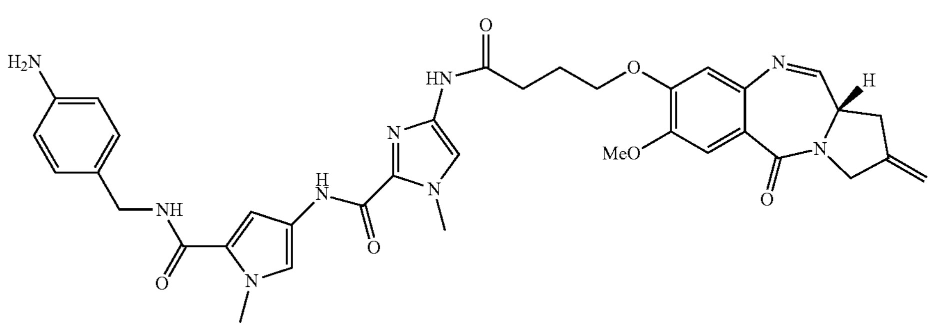 [SMILES: C=C1C[C@H]2C=Nc3cc(OCCCC(=O)Nc4cn(C)c(C(=O)Nc5cc(C(=O)NCc6ccc(N)cc6)n(C)c5)n4)c(OC)cc3C(=O)N2C1] |

TABLE 1-continued
| Compound No. | Structure |
|---|---|
| Compound No. 4A (Example 4) | 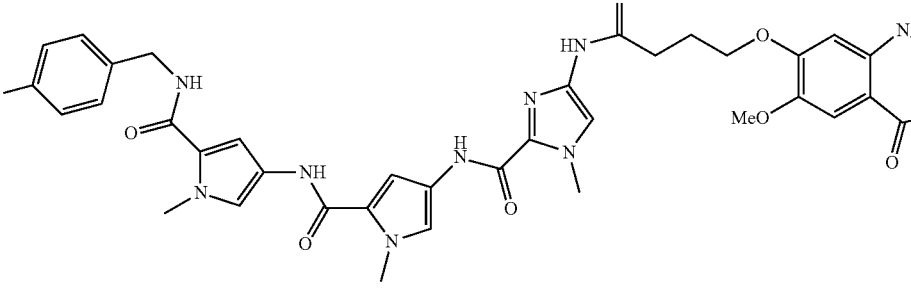 |
| Compound No. 5A (Example 5) | 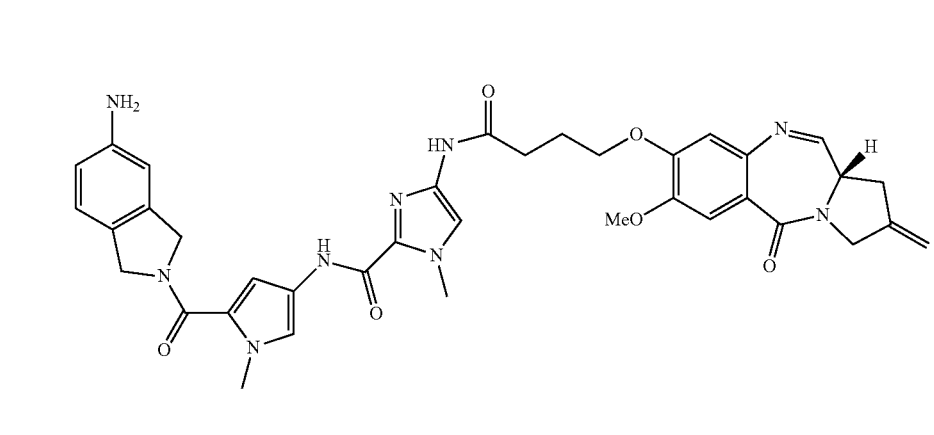 [SMILES: C=C1C[C@H]2C=Nc3cc(OCCCC(=O)Nc4cn(C)c(C(=O)Nc5cc(C(=O)N6Cc7ccc(N)cc7C6)n(C)c5)n4)c(OC)cc3C(=O)N2C1] |
| Compound No. 6A (Example 6) | 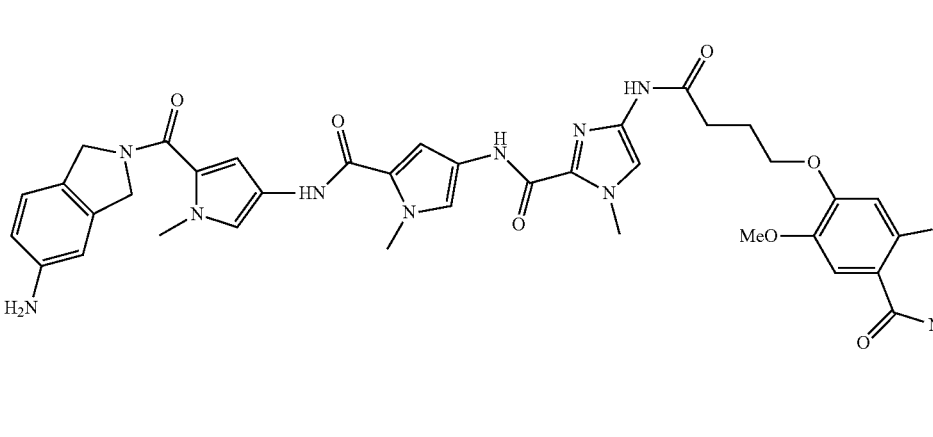 |
| Compound No. 7A (Example 7) | 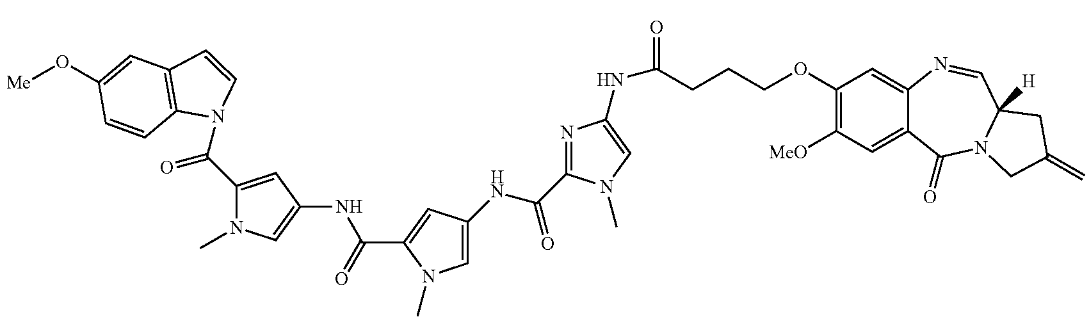 [SMILES: C=C1C[C@H]2C=Nc3cc(OCCCC(=O)Nc4cn(C)c(C(=O)Nc5cc(C(=O)Nc6cc(C(=O)n7ccc8cc(OC)ccc87)n(C)c6)n(C)c5)n4)c(OC)cc3C(=O)N2C1] |

TABLE 1-continued

| Compound No. | Structure |
|---|---|
| Compound No. 8A (Example 8) | (structure) |
| Compound No. 19 (Example 9) | (structure) |
| Compound No. 20 (Example 10) | (structure) |
| Compound No. 11A (Example 11) | (structure) |

TABLE 1-continued

| Compound No. | Structure |
|---|---|
| Compound No. 28 (Example 12) | 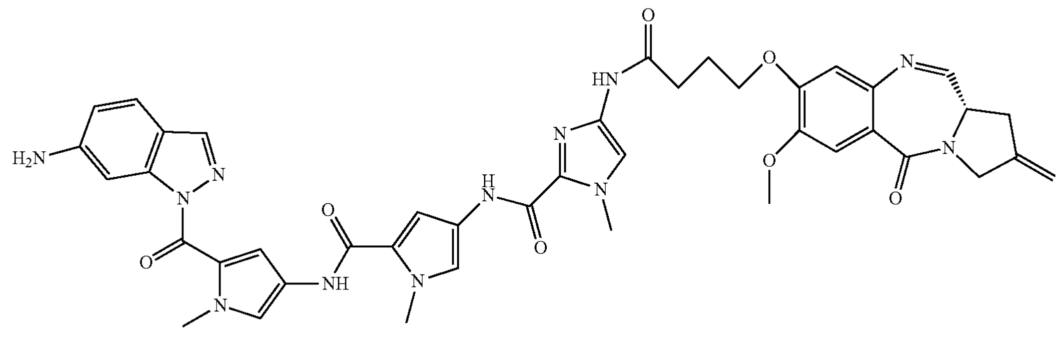 [SMILES: C=C1C[C@H]2C=Nc3cc(OCCCC(=O)Nc4cn(C)c(C(=O)Nc5cc(C(=O)Nc6cc(C(=O)n7ncc8ccc(N)cc87)n(C)c6)n(C)c5)n4)c(OC)cc3C(=O)N2C1] |
| Compound No. 13A (Example 13) | 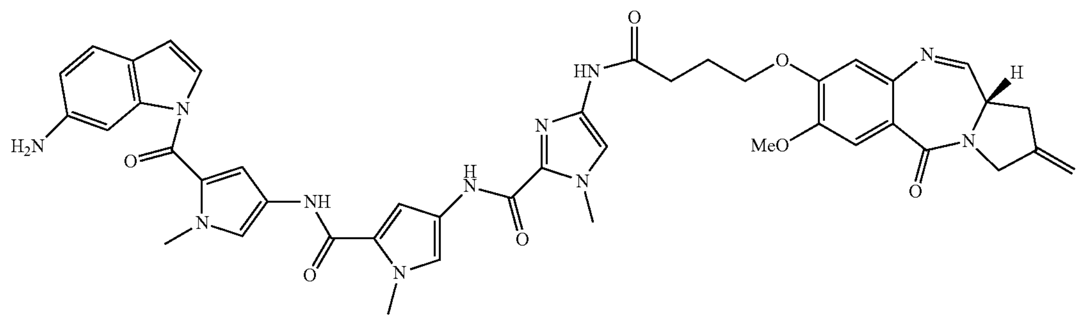 [SMILES: C=C1C[C@H]2C=Nc3cc(OCCCC(=O)Nc4cn(C)c(C(=O)Nc5cc(C(=O)Nc6cc(C(=O)n7ccc8ccc(N)cc87)n(C)c6)n(C)c5)n4)c(OC)cc3C(=O)N2C1] |
| Compound No. 101 | 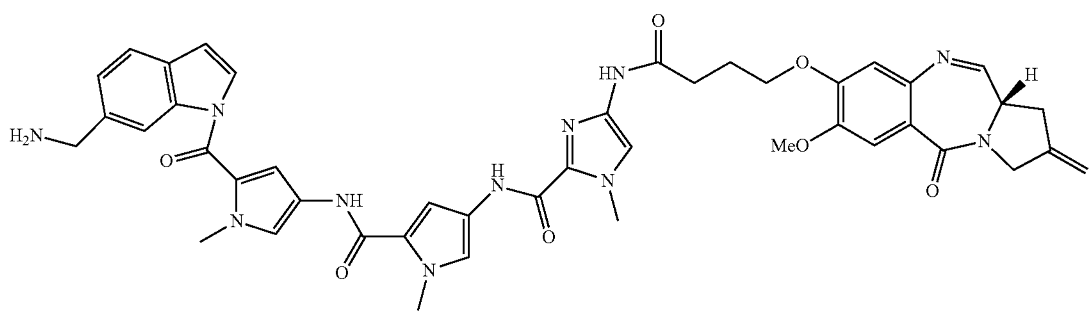 [SMILES: C=C1C[C@H]2C=Nc3cc(OCCCC(=O)Nc4cn(C)c(C(=O)Nc5cc(C(=O)Nc6cc(C(=O)n7ccc8ccc(CN)cc87)n(C)c6)n(C)c5)n4)c(OC)cc3C(=O)N2C1] |
| Compound No. 48 (Example 22) | 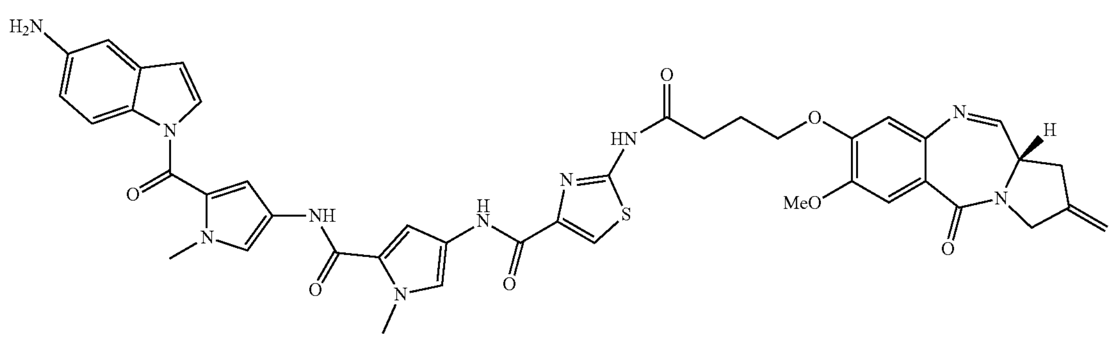 [SMILES: C=C1C[C@H]2C=Nc3cc(OCCCC(=O)Nc4nc(C(=O)Nc5cc(C(=O)Nc6cc(C(=O)n7ccc8cc(N)ccc87)n(C)c6)n(C)c5)cs4)c(OC)cc3C(=O)N2C1] |

TABLE 1-continued

| Compound No. | Structure |
| --- | --- |
| Compound No. 102 | 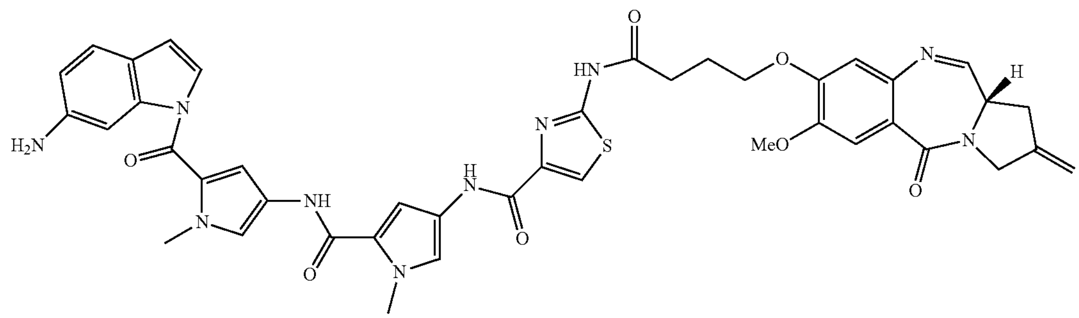 [SMILES: C=C1C[C@H]2C=Nc3cc(OCCCC(=O)Nc4nc(C(=O)Nc5cc(C(=O)Nc6cc(C(=O)n7ccc8ccc(N)cc87)n(C)c6)n(C)c5)cs4)c(OC)cc3C(=O)N2C1] |
| Compound No. 103 | 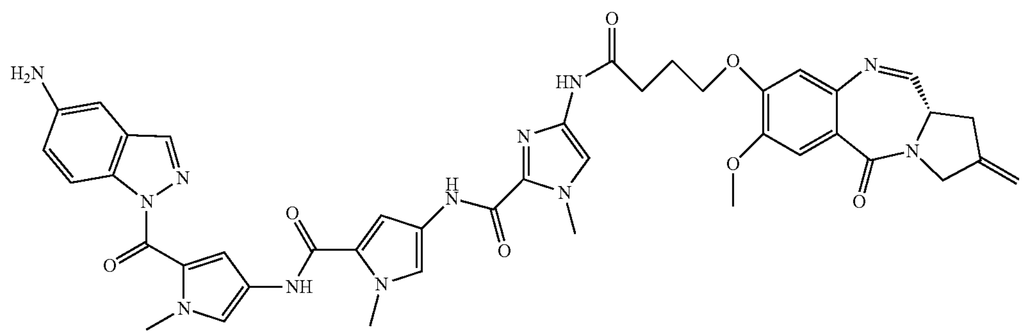 [SMILES: C=C1C[C@H]2C=Nc3cc(OCCCC(=O)Nc4cn(C)c(C(=O)Nc5cc(C(=O)Nc6cc(C(=O)n7ncc8cc(N)ccc87)n(C)c6)n(C)c5)n4)c(OC)cc3C(=O)N2C1] |
| Compound No. 104 | 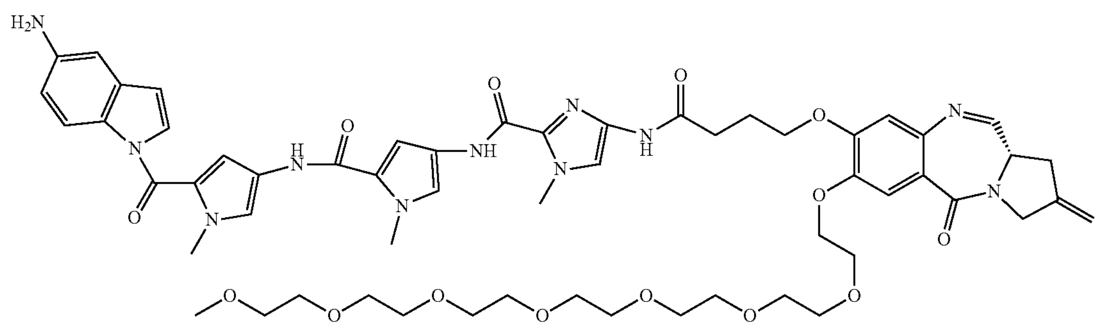 [SMILES: C=C1C[C@H]2C=Nc3cc(OCCCC(=O)Nc4cn(C)c(C(=O)Nc5cc(C(=O)Nc6cc(C(=O)n7ccc8cc(N)ccc87)n(C)c6)n(C)c5)n4)c(OCCOCCOCCOCCOCCOCCOCCOC)cc3C(=O)N2C1] |
| Compound No. 51 (Example 23) | 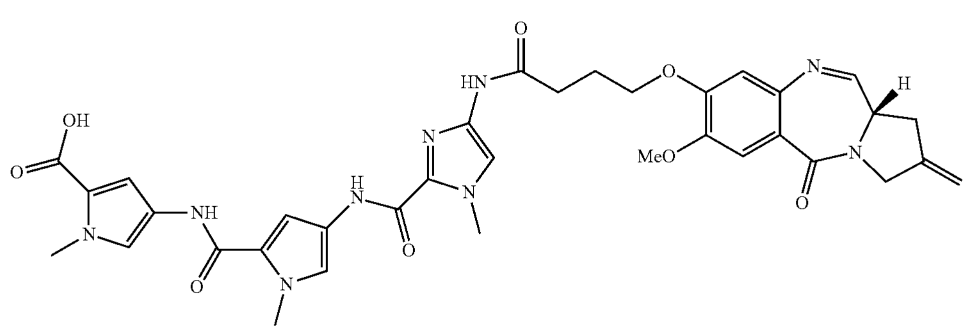 |

TABLE 1-continued

| Compound No. | Structure |
|---|---|
| Compound No. 55 (Example 24) | 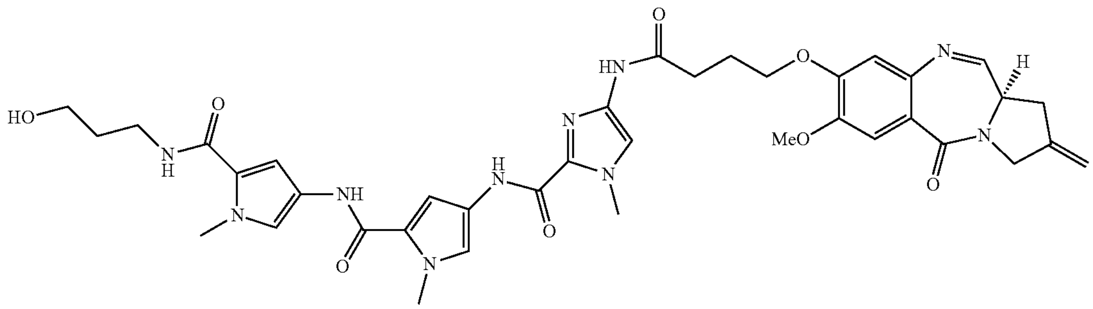 [SMILES: C=C1C[C@@H]2C=Nc3cc(OCCCC(=O)Nc4cn(C)c(C(=O)Nc5cc(C(=O)Nc6cc(C(=O)NCCCO)n(C)c6)n(C)c5)n4)c(OC)cc3C(=O)N2C1] |
| Compound No. 56 (Example 25) | 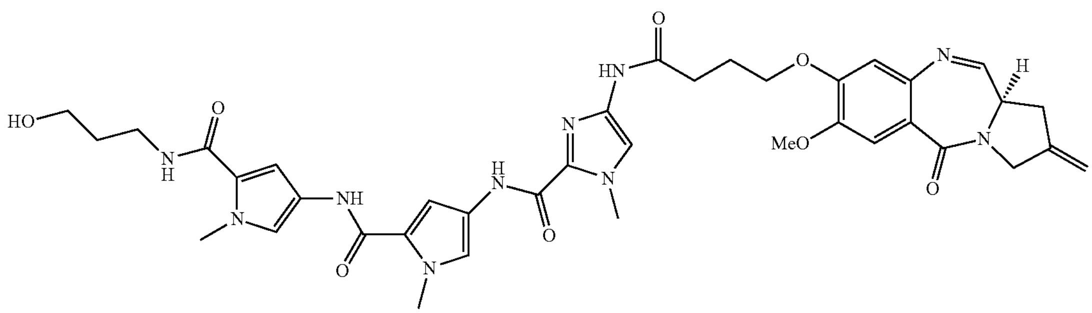 [SMILES: C=C1C[C@@H]2C=Nc3cc(OCCCC(=O)Nc4cn(C)c(C(=O)Nc5cc(C(=O)Nc6cc(C(=O)NCCCO)n(C)c6)n(C)c5)n4)c(OC)cc3C(=O)N2C1] |
| Compound No. 105 | 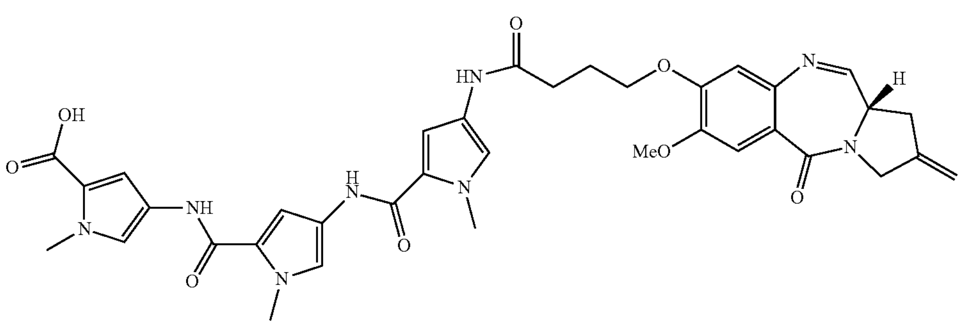 |
| Compound No. 66 (Example 32) | 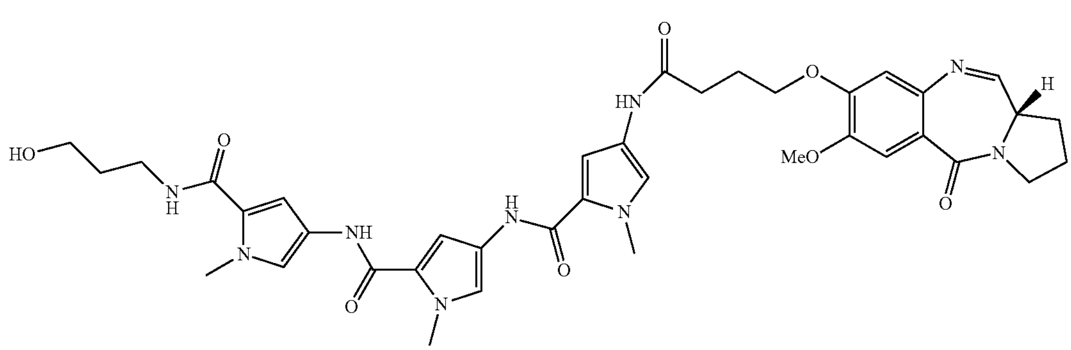 [SMILES: COc1cc2c(cc1OCCCC(=O)Nc1cc(C(=O)Nc3cc(C(=O)Nc4cc(C(=O)NCCCO)n(C)c4)n(C)c3)n(C)c1)N=C[C@@H]1CCCN1C2=O] |

TABLE 1-continued
| Compound No. | Structure |
|---|---|
| Compound No. 69 (Example 35) | 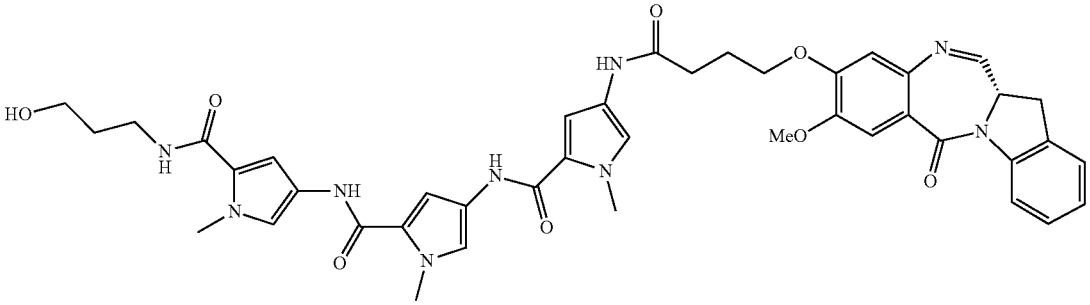 [SMILES: COc1cc2c(cc1OCCCC(=O)Nc1cc(C(=O)Nc3cc(C(=O)Nc4cc(C(=O)NCCCO)n(C)c4)n(C)c3)n(C)c1)N=C[C@@H]1Cc3ccccc3N1C2=O] |
| Compound No. 77 (Example 37) | 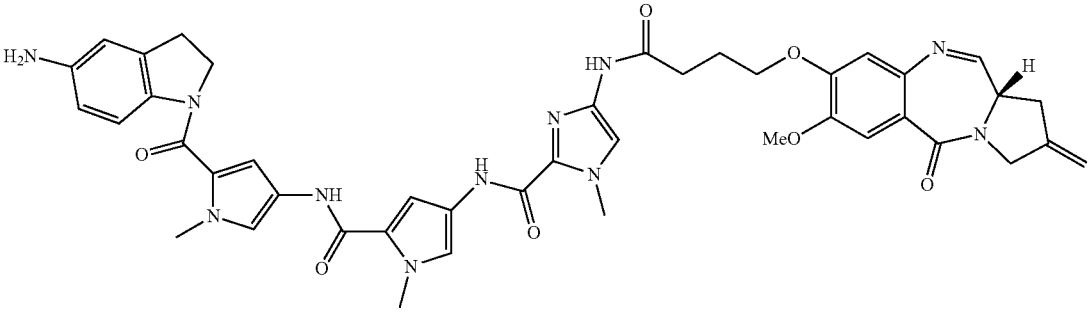 [SMILES: C=C1C[C@H]2C=Nc3cc(OCCCC(=O)Nc4cn(C)c(C(=O)Nc5cc(C(=O)Nc6cc(C(=O)N7CCc8cc(N)ccc87)n(C)c6)n(C)c5)n4)c(OC)cc3C(=O)N2C1] |
| Compound No. 78 (Example 38) | 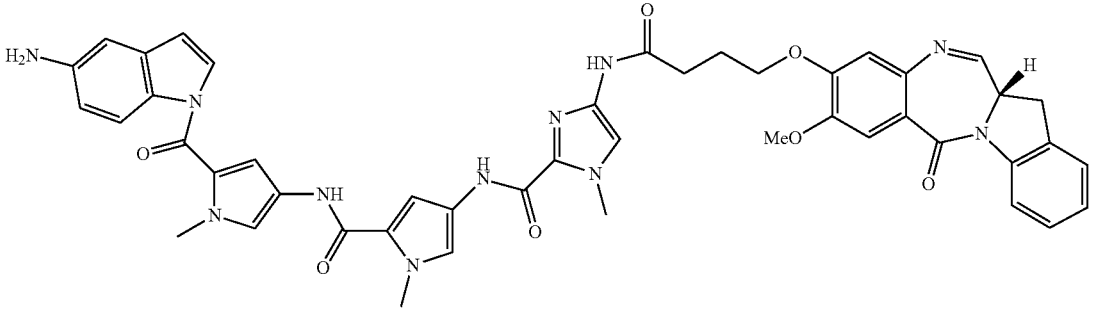 [SMILES: COc1cc2c(cc1OCCCC(=O)Nc1cn(C)c(C(=O)Nc3cc(C(=O)Nc4cc(C(=O)n5ccc6cc(N)ccc65)n(C)c4)n(C)c3)n1)N=C[C@@H]1Cc3ccccc3N1C2=O] |
| Compound No. 79 (Example 39) | 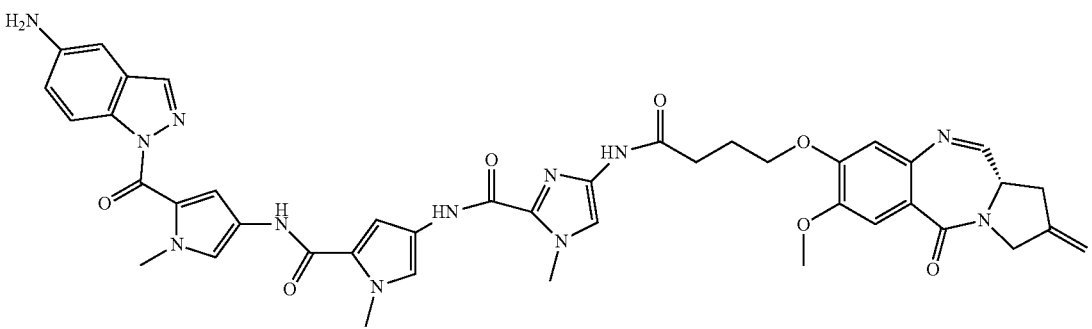 [SMILES: C=C1C[C@H]2C=Nc3cc(OCCCC(=O)Nc4cn(C)c(C(=O)Nc5cc(C(=O)Nc6cc(C(=O)n7ncc8cc(N)ccc87)n(C)c6)n(C)c5)n4)c(OC)cc3C(=O)N2C1] |

TABLE 1-continued

| Compound No. | Structure |
|---|---|
| Compound No. 82 (Example 40) | 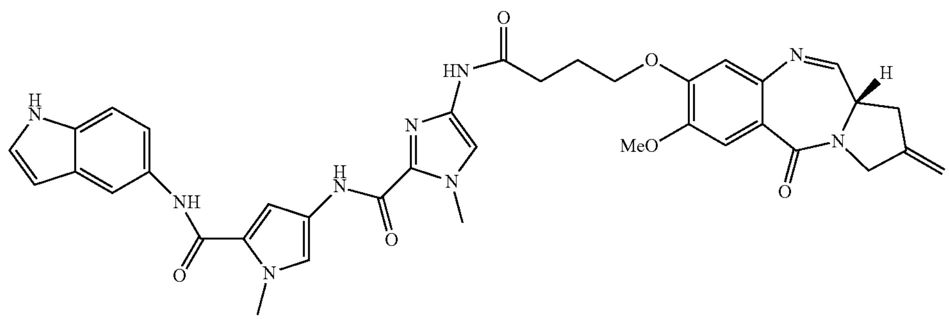 [SMILES: C=C1C[C@H]2C=Nc3cc(OCCCC(=O)Nc4cn(C)c(C(=O)Nc5cc(C(=O)Nc6ccc7[nH]ccc7c6)n(C)c5)n4)c(OC)cc3C(=O)N2C1] |
| Compound No. 83 (Example 41) | 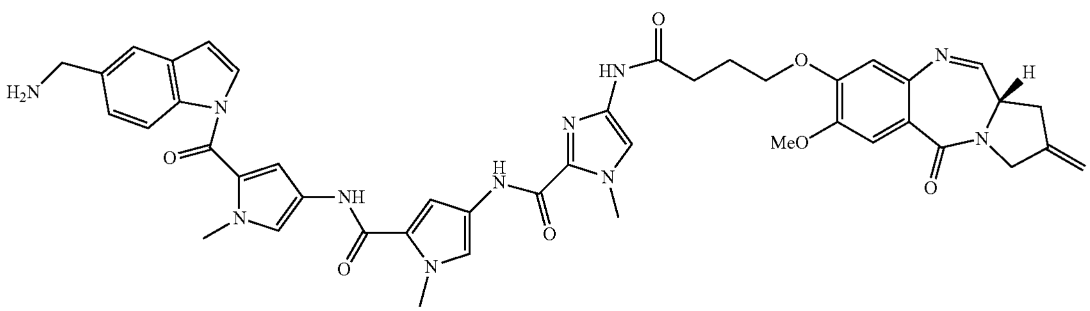 [SMILES: C=C1C[C@H]2C=Nc3cc(OCCCC(=O)Nc4cn(C)c(C(=O)Nc5cc(C(=O)Nc6cc(C(=O)n7ccc8cc(CN)ccc87)n(C)c6)n(C)c5)n4)c(OC)cc3C(=O)N2C1] |
| Compound No. 84 (Example 42) | 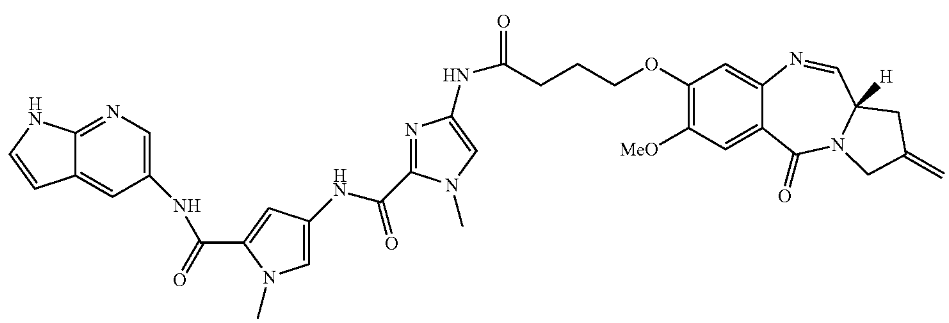 |
| Compound No. 85 (Example 43) | 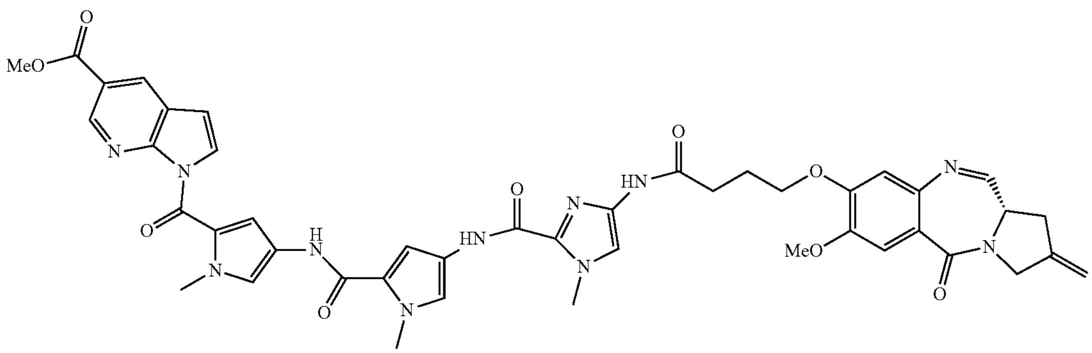 [SMILES: C=C1C[C@H]2C=Nc3cc(OCCCC(=O)Nc4cn(C)c(C(=O)Nc5cc(C(=O)Nc6cc(C(=O)n7ccc8cc(C(=O)OC)cnc87)n(C)c6)n(C)c5)n4)c(OC)cc3C(=O)N2C1] |

TABLE 1-continued

| Compound No. | Structure |
|---|---|
| Compound No. 86 | *(chemical structure)* |
| Compound No. 200 | *(chemical structure)* |
| Compound No. 201 | *(chemical structure)* |
| Compound No. 202 | *(chemical structure)* |
| Compound No. 203 | *(chemical structure)* |

TABLE 1-continued

| Compound No. | Structure |
|---|---|
| Compound No. 204 | 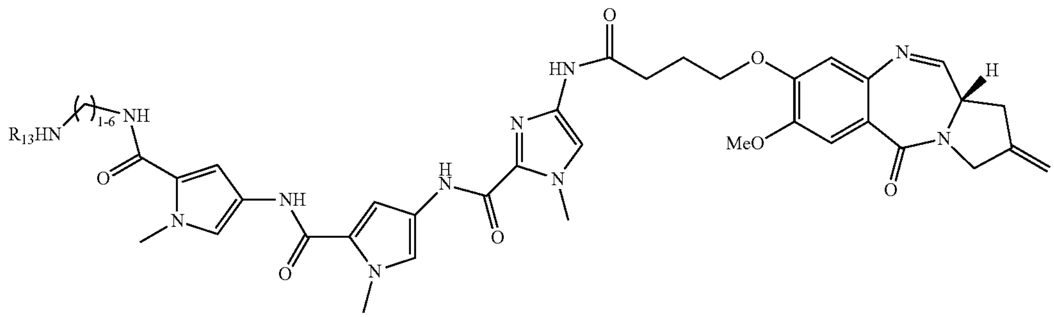 |
| Compound No. 205 | 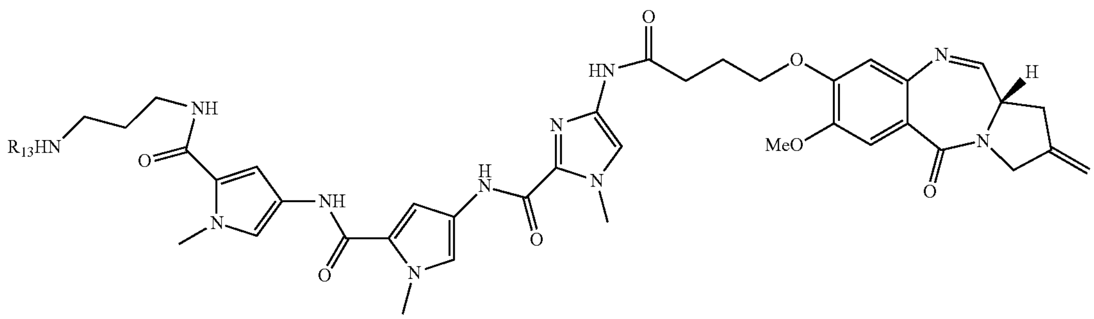 |
| Compound No. 206 | 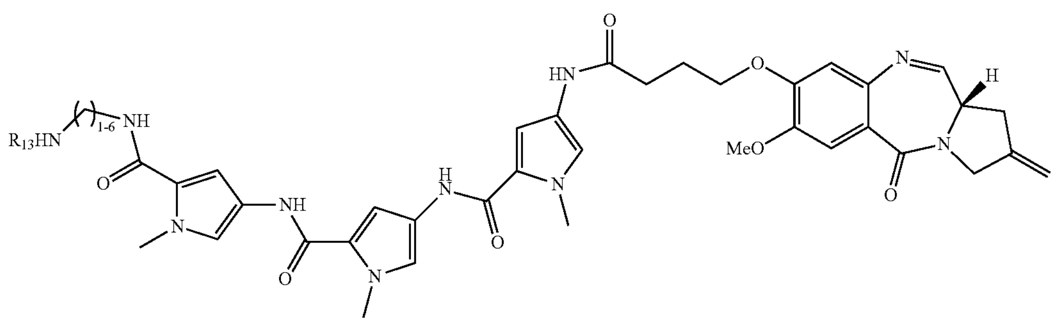 |
| Compound No. 207 | 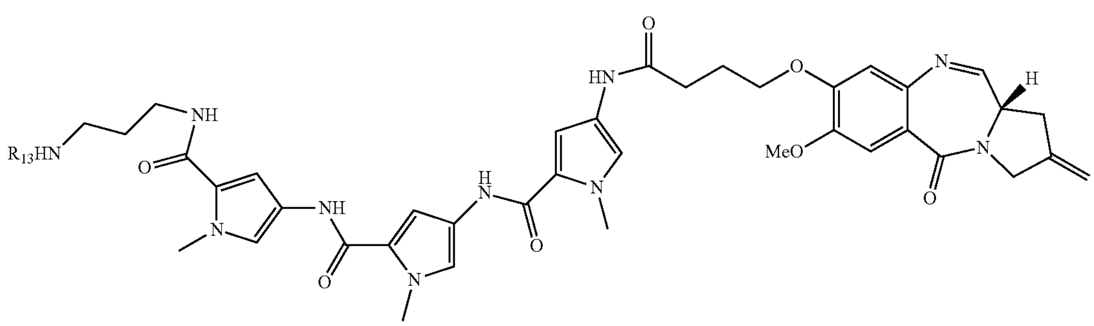 |

The present disclosure also features the modification of a compound of Formula (I) to include a linker. The compound of Formula (I) with a linker can be further modified so that it can be directly or indirectly connected to an antibody or antibody fragment to form a conjugate of the disclosure. The conjugate of the disclosure is also referred to as antibody-drug conjugate (ADC).

Representative examples of compounds of Formula (I) with a linker include those listed in Table 2, or a tautomer thereof, or a pharmaceutically acceptable salt or solvate of the compound or the tautomer.

TABLE 2
| Compound No. | Structure |
|---|---|
| Compound No. 37 (Example 14) | 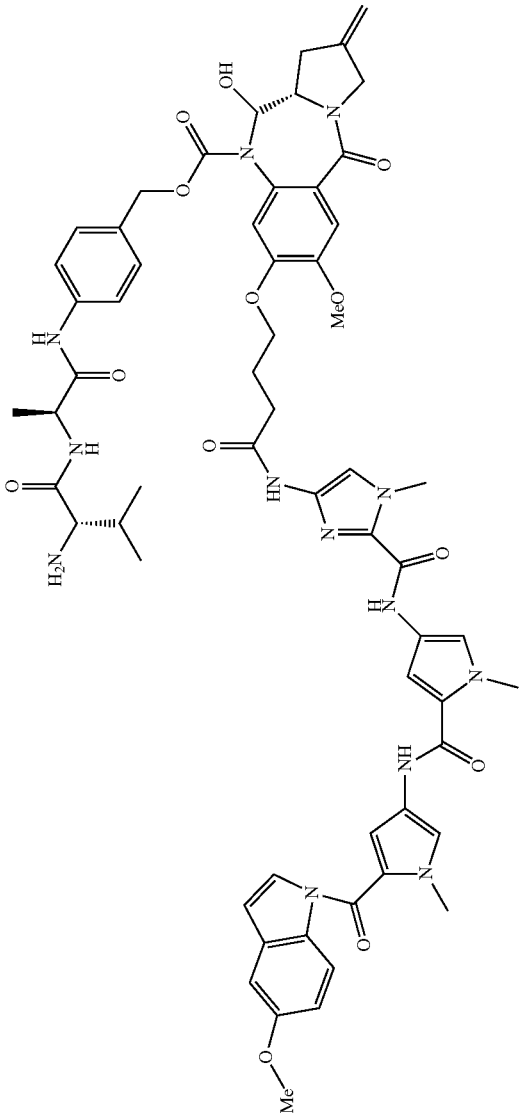 |

TABLE 2-continued

| Compound No. | Structure |
|---|---|
| Compound No. 38 (Example 14) | 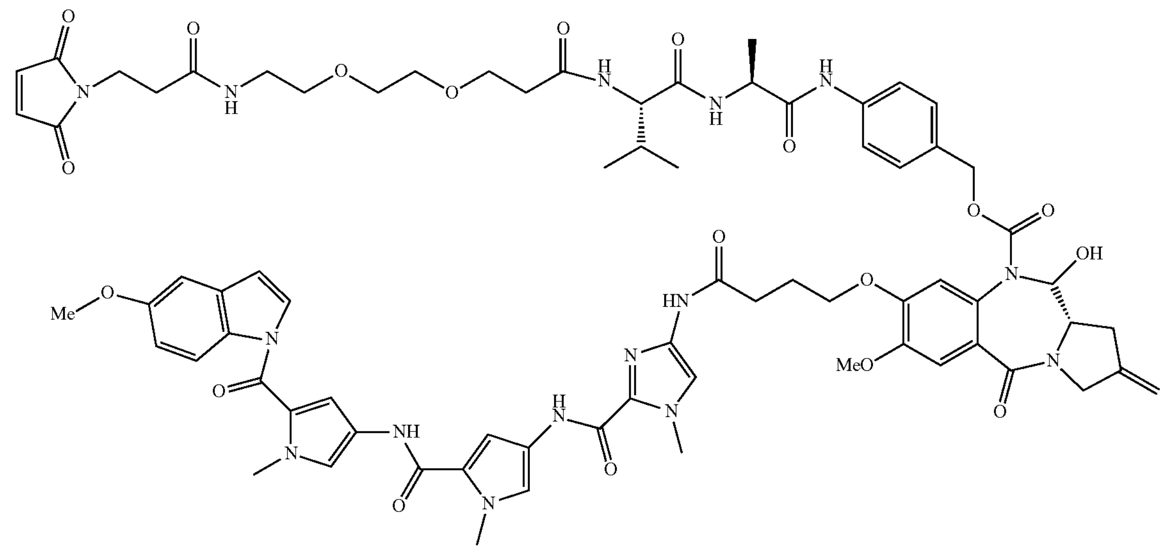 |

TABLE 2-continued
| Compound No. | Structure |
|---|---|
| Compound No. 40 (Example 16) | 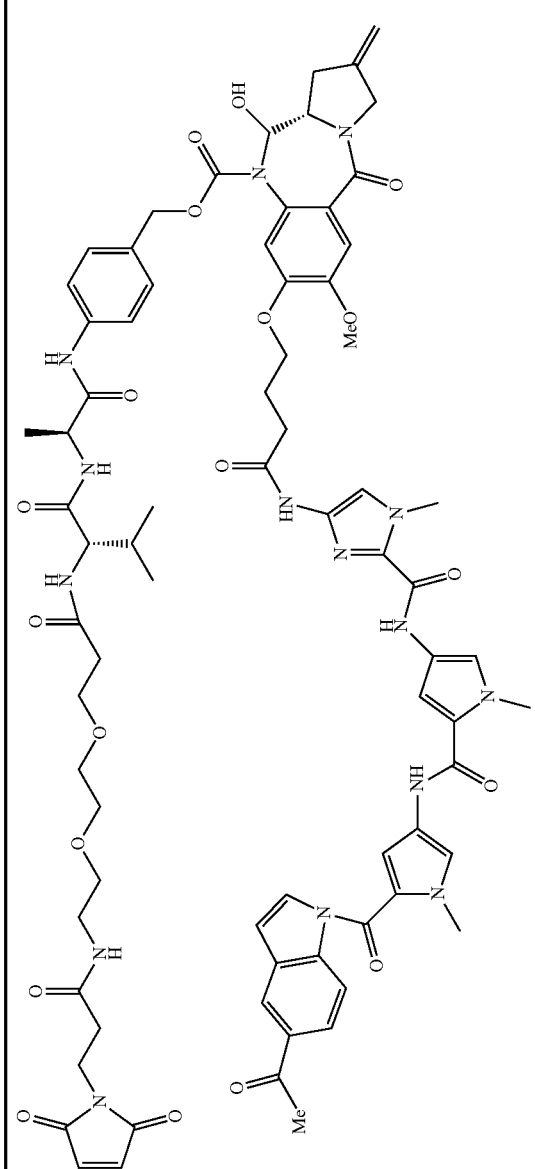 |
| Compound No. 42 (Example 18) | 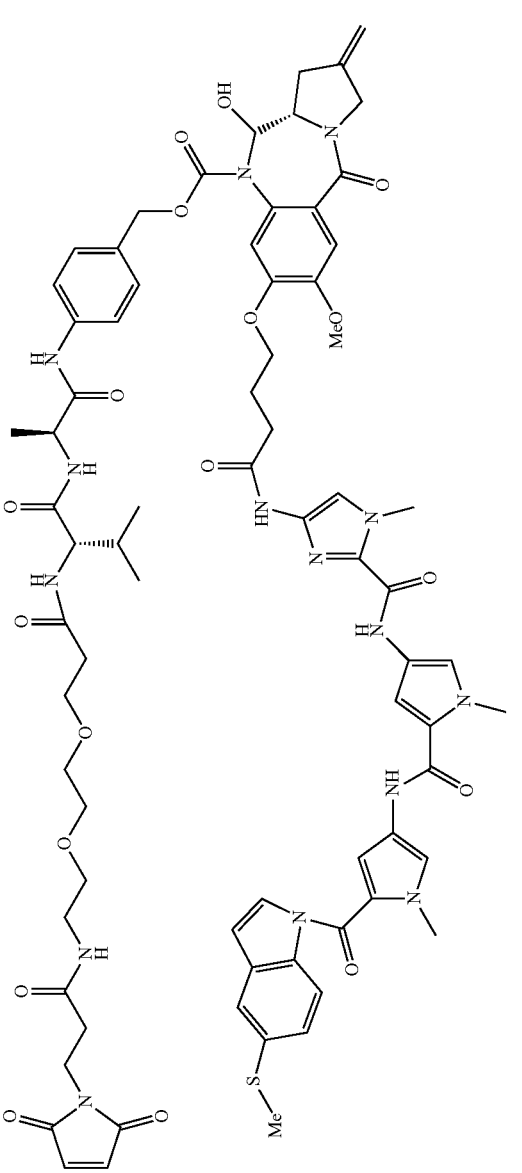 |

TABLE 2-continued
| Compound No. | Structure |
|---|---|
| Compound No. 45 (Example 20) | 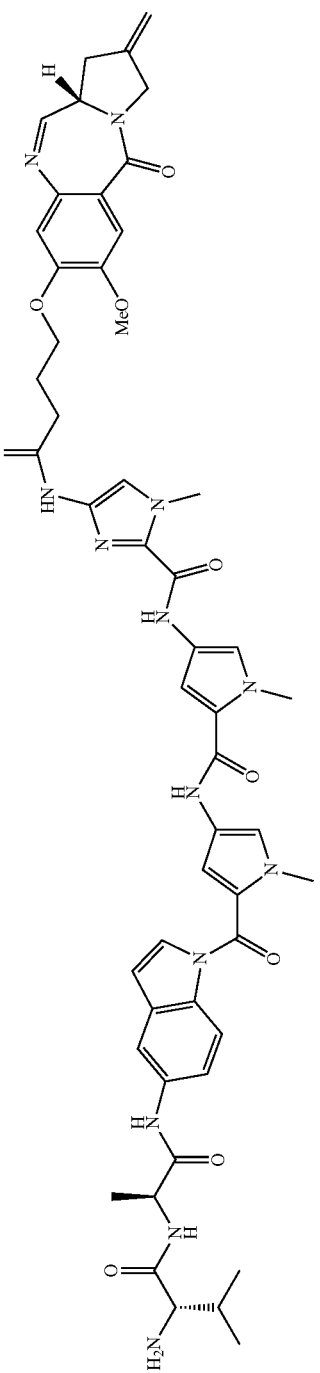 |
| Compound No. 46 (Example 20) | 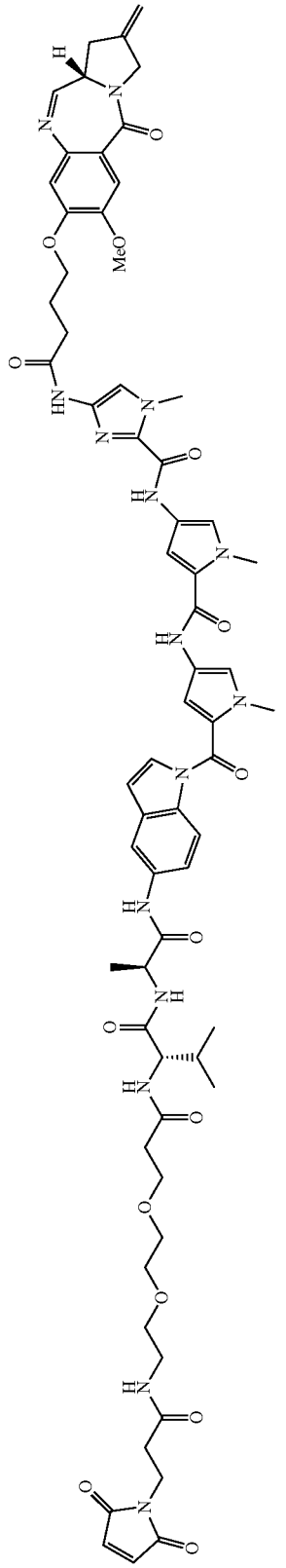 |
| Compound No. 59 (Example 26) | 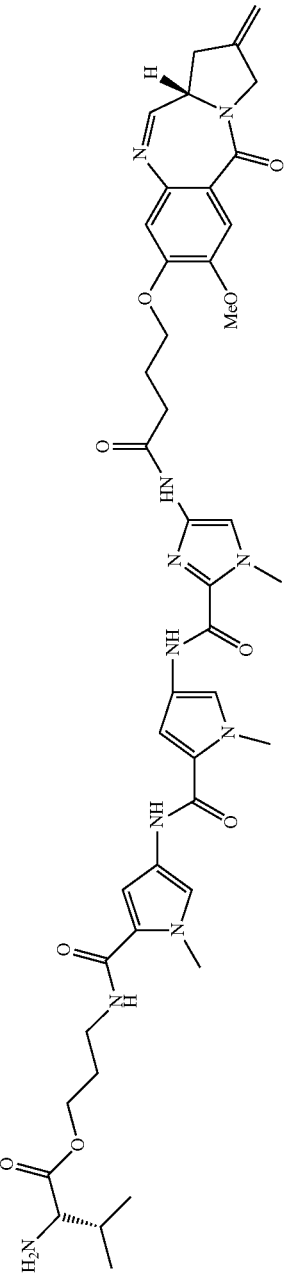 |

TABLE 2-continued

| Compound No. | Structure |
|---|---|
| Compound No. 60 (Example 26) | 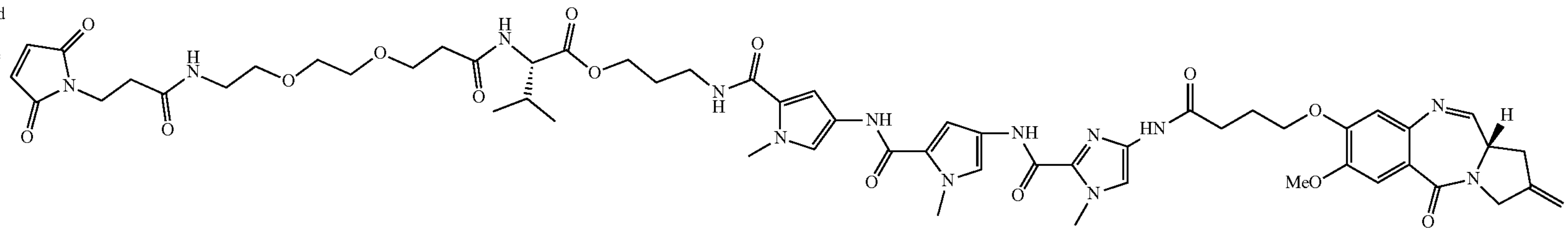 [SMILES: C=C1C[C@H]2C=Nc3cc(OCCCC(=O)Nc4cn(C)c(C(=O)Nc5cc(C(=O)Nc6cc(C(=O)NCCCOC(=O)[C@@H](NC(=O)CCOCCOCCNC(=O)CCN7C(=O)C=CC7=O)C(C)C)n(C)c6)n(C)c5)n4)c(OC)cc3C(=O)N2C1] |
| Compound No. 106 | 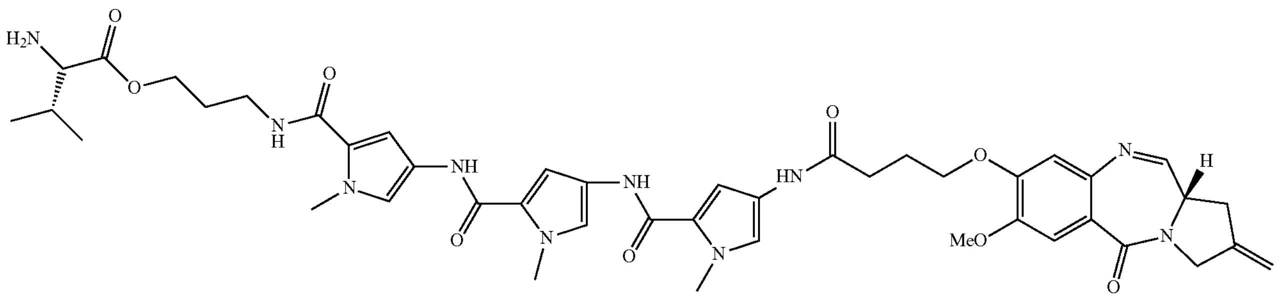 |
| Compound No. 107 | 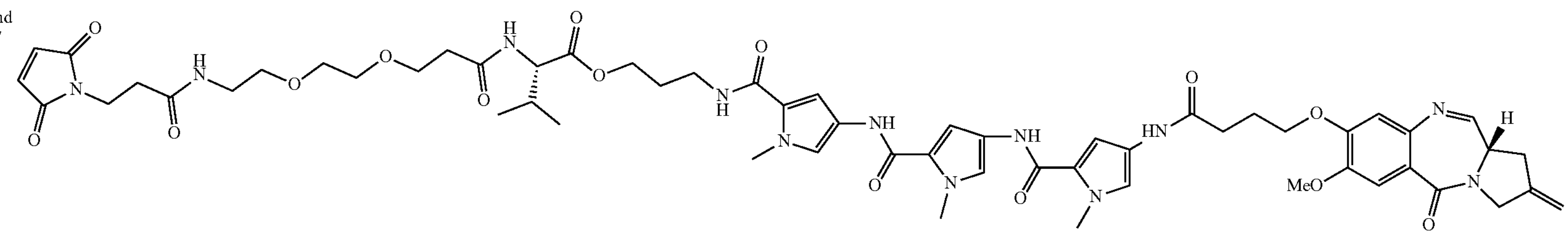 |

TABLE 2-continued

| Compound No. | Structure |
|---|---|
| Compound No. 62 (Example 28) | 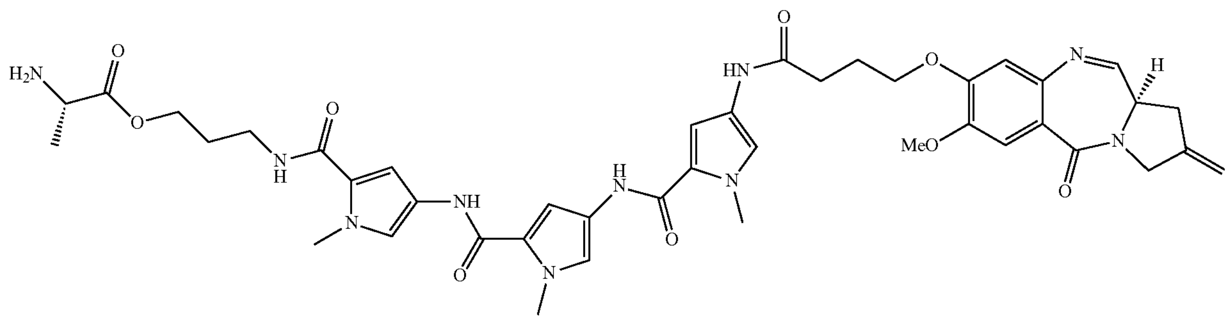 [SMILES: C=C1C[C@@H]2C=Nc3cc(OCCCC(=O)Nc4cc(C(=O)Nc5cc(C(=O)Nc6cc(C(=O)NCCCOC(=O)[C@H](C)N)n(C)c6)n(C)c5)n(C)c4)c(OC)cc3C(=O)N2C1] |
| Compound No. 63 (Example 28) | 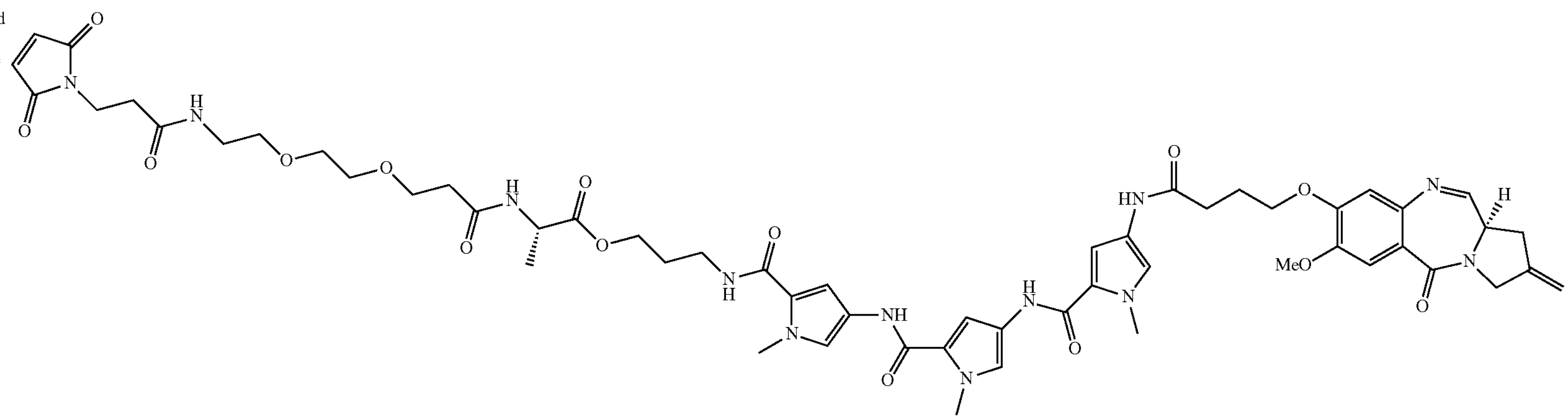 [SMILES: C=C1C[C@@H]2C=Nc3cc(OCCCC(=O)Nc4cc(C(=O)Nc5cc(C(=O)Nc6cc(C(=O)NCCCOC(=O)[C@H](C)NC(=O)CCOCCOCCNC(=O)CCN7C(=O)C=CC7=O)n(C)c6)n(C)c5)n(C)c4)c(OC)cc3C(=O)N2C1] |

TABLE 2-continued
| Compound No. | Structure |
|---|---|
| Compound No. 64 (Example 30) | 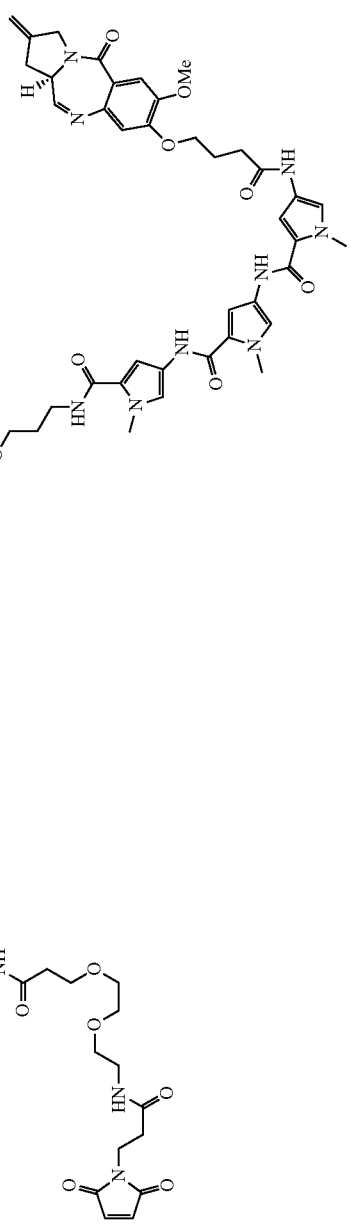 |
| Compound No. 67 (Example 33) | 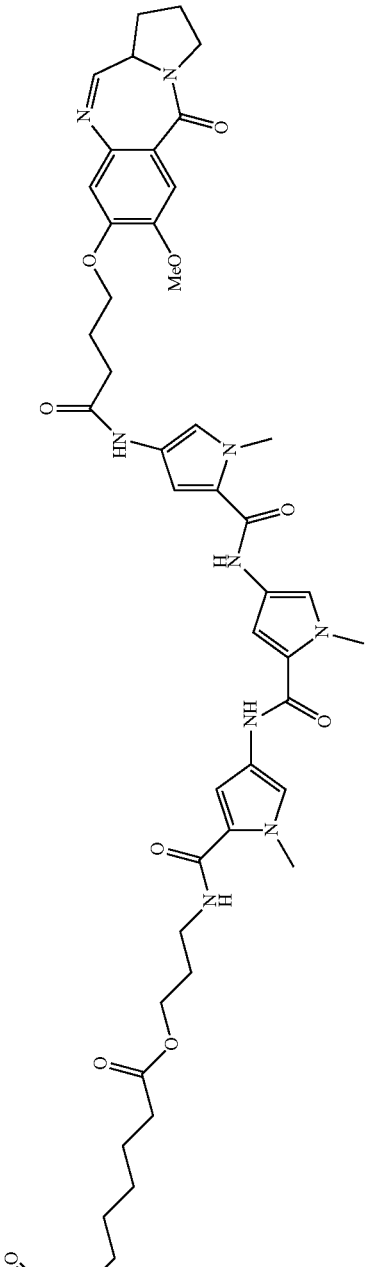 |

TABLE 2-continued

| Compound No. | Structure |
|---|---|
| Compound No. 71 (Example 35) | (chemical structure) |

The present disclosure also features a conjugate of a compound of Formula (I), wherein the conjugate comprising an antibody or antibody fragment that is directly or indirectly connected to the compound.

For example, the conjugates of compounds of Formula (I) further includes one or more polymeric scaffold, wherein the compound is connected to the antibody or antibody fragment via the one or more polymeric scaffold.

For example, the one or more polymeric scaffold comprises poly(1-hydroxymethylethylene hydroxymethyl-formal) (PHF).

For example, the PHF has a molecular weight ranging from about 2 kDa to about 300 kDa (e.g., about 2-40 kDa, about 6-20 kDa, about 8-15 kDa, 20-150 kDa, about 40-150 kDa, or about 50-100 kDa).

For example, for conjugating an antibody or antibody fragment having a molecular weight of 40 kDa or greater (e.g., 80 kDa or greater, 100 kDa or greater, 150 kDa or greater, 200 kDa or greater or 250 kDa or greater), the PHF used has a molecular weight (i.e., MW of the unmodified PHF) ranging from about 2 kDa to about 40 kDa (e.g., about 6-20 kDa or about 8-15 kDa).

For conjugating an antibody or antibody fragment having a molecular weight of 200 kDa or less (e.g., 150 kDa or less, 100 kDa or less, 80 kDa or less or 50 kDa or less), the PHF used has a molecular weight (i.e., MW of the unmodified PHF) ranging from about 20 kDa to about 300 kDa (e.g., about 20-150 kDa, about 40-150 kDa or about 50-100 kDa).

For example, the compound of Formula (I), upon conjugation with an antibody or antibody fragment, is of Formula (VI):

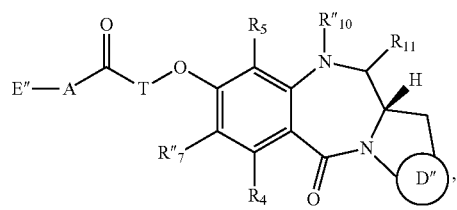

(VI)

or a tautomer thereof, or a pharmaceutically acceptable salt or solvate of the compound or the tautomer, wherein: the antibody or antibody fragment is directly or indirectly linked to the compound at the position of one of E", D", R"$_7$ or R"$_{10}$; and the remaining of E", D", R"$_7$ or R"$_{10}$ are respectively E, D, R$_7$, or R$_{10}$;

wherein:

E" is E or

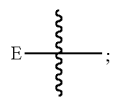

in which

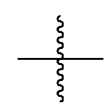

denotes direct or indirect linkage to the antibody or antibody fragment via a functional group of E;

D" is D or

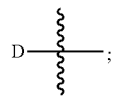

in which

denotes direct or indirect linkage to the antibody or antibody fragment via a functional group of D;

R"$_7$ is R$_7$ or

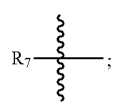

in which

denotes direct or indirect linkage to the antibody or antibody fragment via a functional group of R$_7$; and R"$_{10}$ is R$_{10}$ or

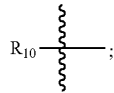

in which

denotes direct or indirect linkage to the antibody or antibody fragment via a functional group of R$_{10}$.

For example, E" is

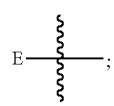

D" is D; R"$_7$ is R$_7$; and R"$_{10}$ is R$_{10}$.

For example, D" is

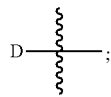

E" is E; R"$_7$ is R$_7$; and R"$_{10}$ is R$_{10}$.
For example, R"$_7$ is

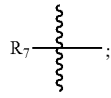

E" is E; D" is D; and R"$_{10}$ is R$_{10}$.
For example, R"$_{10}$

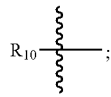

E" is E; D" is D; and R"$_7$ is R$_7$.

For example, the conjugates of Formula (VI) include those where each of the moieties defined for one of E", D", R"$_7$, R"$_{10}$, D, T, E, A, R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{31}$, R$_{32}$, R$_{33}$, R$_{34}$, R$_{35a}$, R$_{35b}$, R$_{36a}$, R$_{36b}$, R$_{36c}$, R$_{36d}$, R$_{37a}$, R$_{37b}$, R$_a$, R$^b$, R$^N$, R$^Q$, X$_0$, Y$_0$, Z$_0$, X$_1$, Y$_1$, Z$_1$, X$_2$, X$_3$, M, Q, m, n, r, s, t, and x, can be combined with any of the moieties defined for the others of E", D", R"$_7$, R"$_{10}$, D, T, E, A, R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{31}$, R$_{32}$, R$_{33}$, R$_{34}$, R$_{35a}$, R$_{35b}$, R$_{36a}$, R$_{36b}$, R$_{36c}$, R$_{36d}$, R$_{37a}$, R$_{37b}$, R$_a$, R$^b$, R$^N$, R$^Q$, X$_0$, Y$_0$, Z$_0$, X$_1$, Y$_1$, Z$_1$, X$_2$, X$_3$, M, Q, m, n, r, s, t, and x.

Representative examples of compound-antibody conjugates or compound-antibody fragment conjugates of the present disclosure include those listed in Table 3, or a tautomer thereof, or a pharmaceutically acceptable salt or solvate of the compound or the tautomer.

TABLE 3

| Conjugate No. | Structure |
|---|---|
| Conjugate No. 39 (Example 15) | 39 |

TABLE 3-continued
| Conjugate No. | Structure |
|---|---|
| Conjugate No. 41 (Example 17) | 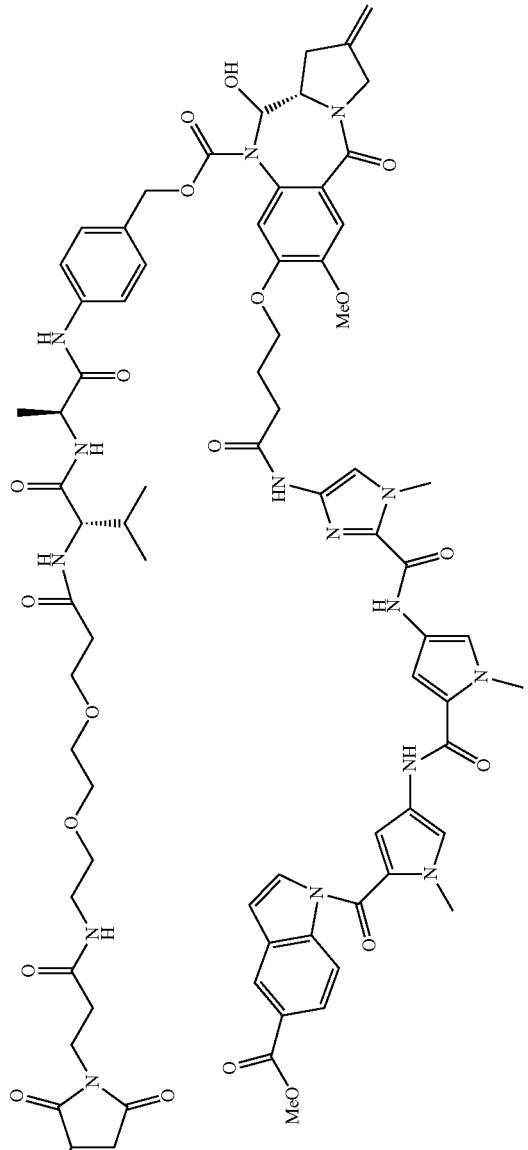 |
| Conjugate No. 43 (Example 19) | 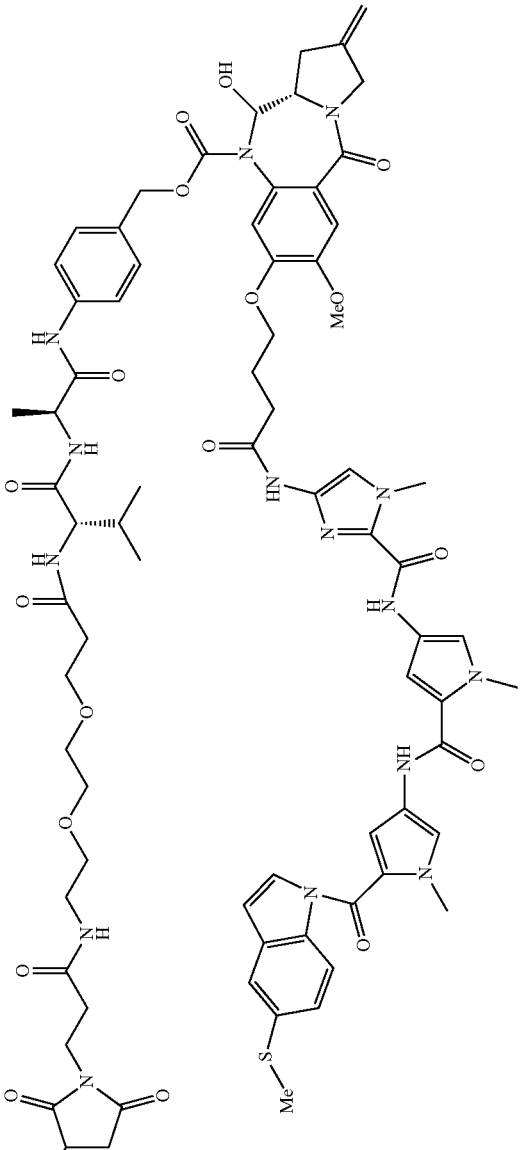 |

TABLE 3-continued

| Conjugate No. | Structure |
|---|---|
| Conjugate No. 47 (Example 21) | (chemical structure) |
| Conjugate No. 47A (Example 21A) | (chemical structure) |
| Conjugate No. 60A (Example 27) | (chemical structure) |

TABLE 3-continued
| Conjugate No. | Structure |
|---|---|
| Conjugate No. 63A (Example 29) | 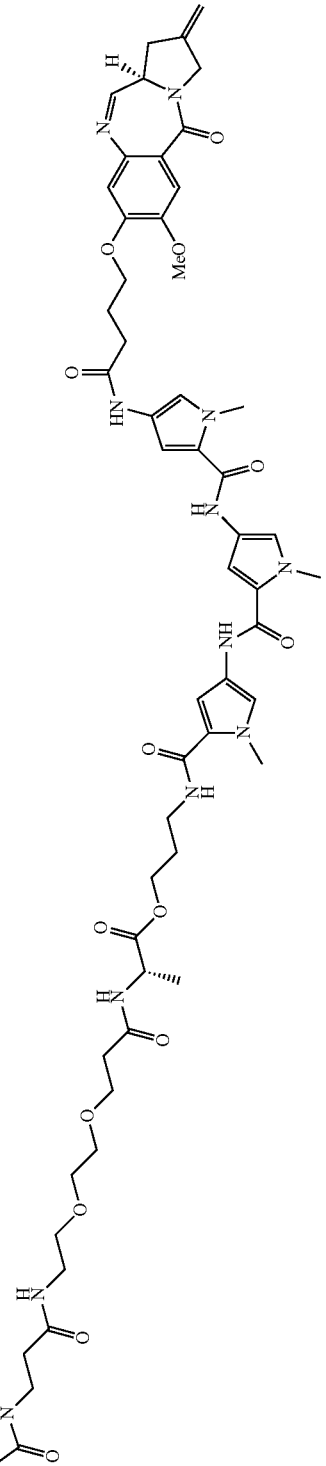 |
| Conjugate No. 65 (Example 31) | 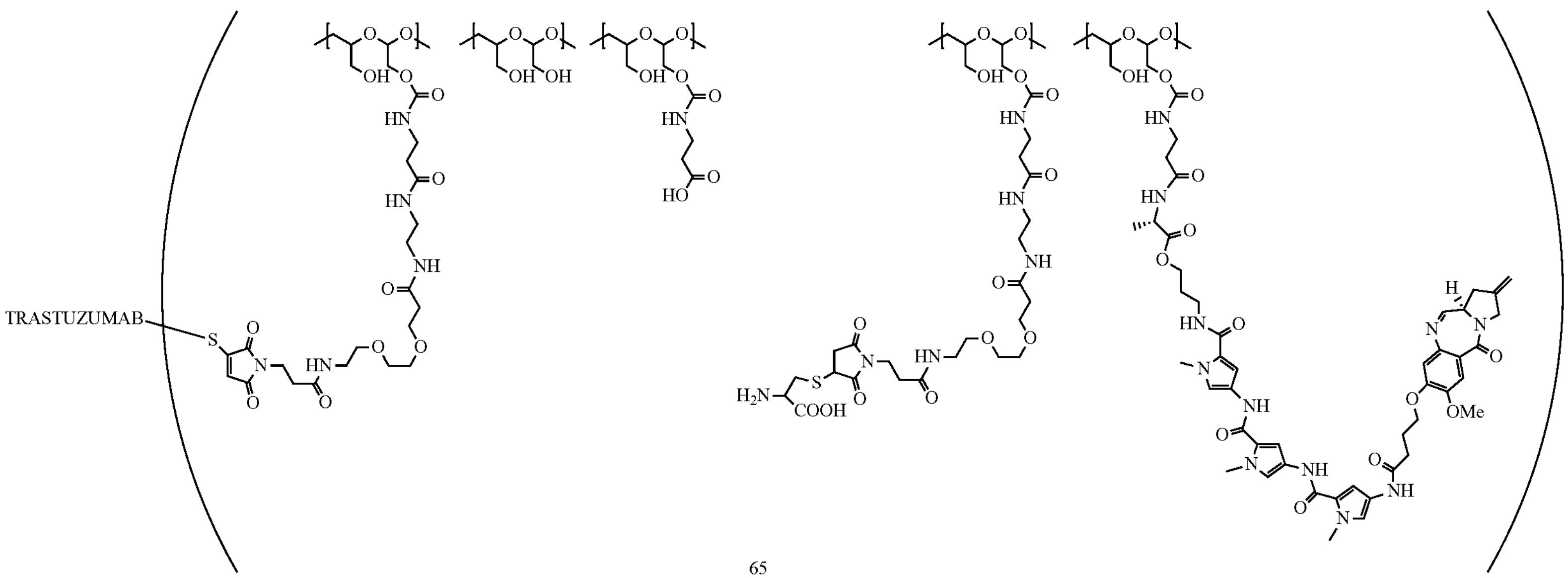 |

TABLE 3-continued
| Conjugate No. | Structure |
|---|---|
| Conjugate No. 68 (Example 34) | 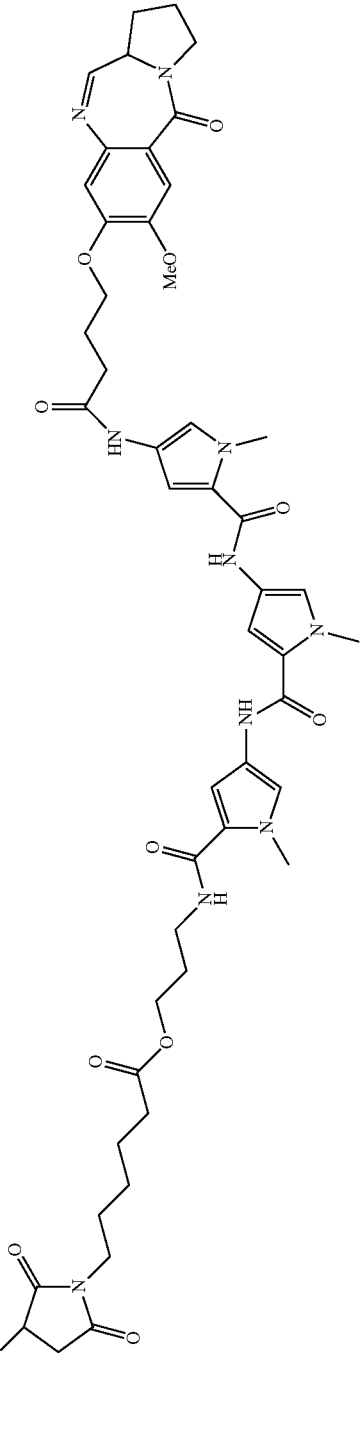 |
| Conjugate No. 72 (Example 36) | 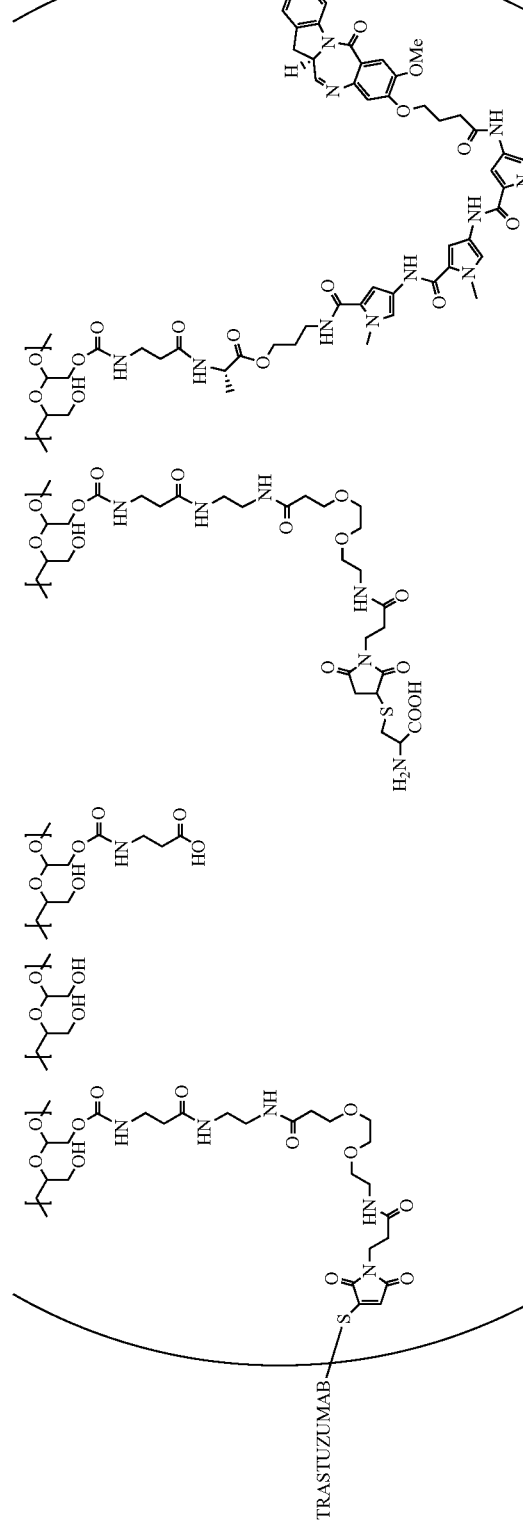 |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. The term "heterocycloalkyl" refers to a saturated or unsaturated nonaromatic ring system having one or more heteroatoms (such as O, N, S, P, or Se) as ring atoms, such as a 3-8 membered monocyclic, 7-12 membered bicyclic (fused, bridged, or spiro rings), or 11-14 membered tricyclic ring system (fused, bridged, or spiro rings) having, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, and the like. In the case of multicyclic non-aromatic rings, only one of the rings needs to be non-aromatic (e.g., 1,2,3,4-tetrahydronaphthalenyl or 2,3-dihydroindole). The terms "cycloalkylene" and "heterocycloalkylene" refer to the corresponding divalent groups, respectively.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, "alkyl linker" or "alkylene linker" is intended to include $C_1$, $C_2$, $C_3$, $C_4$, $C_5$ or $C_6$ straight chain (linear or branched) saturated divalent aliphatic hydrocarbon groups and $C_3$, $C_4$, $C_5$ or $C_6$ branched saturated aliphatic hydrocarbon groups. For example, $C_1$-$C_6$ alkylene linker is intended to include $C_1$, $C_2$, $C_3$, $C_4$, $C_5$ and $C_6$ alkylene linker groups. Examples of alkylene linker include, moieties having from one to six carbon atoms, such as, but not limited to, methyl ($-CH_2-$), ethyl ($-CH_2CH_2-$), n-propyl ($-CH_2CH_2CH_2-$), i-propyl ($-CHCH_3CH_2-$), n-butyl ($-CH_2CH_2CH_2CH_2-$), s-butyl ($-CHCH_3CH_2CH_2-$), i-butyl ($-C(CH_3)_2CH_2-$), n-pentyl ($-CH_2CH_2CH_2CH_2CH_2-$), s-pentyl ($-CHCH_3CH_2CH_2CH_2-$) or n-hexyl ($-CH_2CH_2CH_2CH_2CH_2CH_2-$).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups.

In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with one or more aromatic rings and do not contain any heteroatom in the ring structure. Examples include phenyl, naphthalenyl, etc. The term "arylene" refers to the corresponding divalent groups, such as phenylene.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable aromatic heterocyclic ring, such as a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like. The term "heteroarylene" refers to the corresponding divalent groups.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthyridine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, and [4.4.0] bicyclodecane and [2.2.2] bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., 1-4 heteroatoms selected from N, O and S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl (e.g., benzo[d][1,3]dioxole-5-yl), morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

The term "hydroxy" or "hydroxyl" includes groups with an —OH or —O-.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

As used herein, the term "bis-oxy-alkylene" refers —O-alkylene-O—, in which alkylene can be linear or branched, e.g., —CH$_2$—, —CH(CH$_3$)$_2$—, or —(CH$_2$)$_2$—.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its C$_1$-C$_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to —$NH_2$. "Alkylamino" includes groups of compounds wherein the nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to two alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present disclosure that contain nitrogens can be converted to N-oxides by treatment with an oxidizing agent (e.g., 3-chloroperoxybenzoic acid (m-CPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It should also be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

Furthermore, the structures and other compounds discussed in this disclosure include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any Formula described herein include the compounds themselves, as well as their salts, and their solvates, if applicable. A salt, for example, can be formed between an anion and a positively charged group (e.g., amino) on a compound of the disclosure. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of the disclosure. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. The compounds of the disclosure also include those salts containing quaternary nitrogen atoms.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Additionally, the compounds of the present disclosure, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hydrate refers to, for example, a mono-hydrate, a di-hydrate, a tri-hydrate, etc.

It may be convenient or desirable to prepare, purify, and/or handle a corresponding solvate of an active compound. Compounds of the disclosure include compounds where a nucleophilic solvent ($H_2O$, $R^4OH$, $R^4NH_2$, $R^4SH$) adds across the imine bond of the PBD moiety, which is illustrated below where the solvent is water or an alcohol ($R^4OH$, where $R^4$ is an ether substituent as described above):

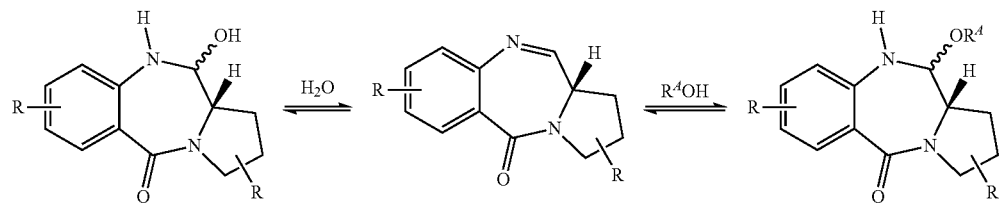

These forms can be called the carbinolamine and carbinolamine ether forms of the PBD. The balance of these equilibria depend on the conditions in which the compounds are found, as well as the nature of the moiety itself.

These compounds may be isolated in solid form, for example, by lyophilisation.

As defined herein, the term "derivative" refers to compounds that have a common core structure, and are substituted with various groups as described herein. For example, all of the compounds represented by Formula (I) are pyrrolo[2,1-c][1,4]benzodiazepines compounds(PBDs), and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present disclosure provides methods for the synthesis of the compounds of any of the Formulae and conjugates thereof described herein. The present disclosure also provides detailed methods for the synthesis of various disclosed compounds and conjugates of the present disclosure according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5$^{th}$ edition, John Wiley & Sons: New York, 2001; Greene, T. W., Wuts, P. G. M., *Protective Groups in Organic Synthesis*, 4$^{th}$ Edition, Wiley-Interscience, 2007; R. Larock, Comprehensive Organic Transformations, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

The compounds of this disclosure having any of the Formulae described herein may be prepared according to the procedures illustrated in Scheme 1 and the Examples, from commercially available starting materials or starting materials which can be prepared using literature procedures. The variables (such as m, t, $R_1$, $R_7$, $R_8$, $X_1$, $Y_1$, $Z_1$, $X_2$, $X_3$ etc.) in Scheme 1 and the Examples are as defined in any of the Formulae described herein, unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 4$^{th}$ Edition, Wiley-Interscience, 2007.

Preferred protecting groups include, but are not limited to:

For a hydroxyl moiety: TBS, benzyl, THP, Ac;

For carboxylic acids: benzyl ester, methyl ester, ethyl ester, allyl ester;

For amines: Cbz, BOC, DMB;

For diols: Ac (×2) TBS (×2), or when taken together acetonides;

For thiols: Ac;

For benzimidazoles: SEM, benzyl, PMB, DMB;

For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The compounds of Formula (I) may be prepared in a manner according to Scheme 1.

Scheme 1. General Procedure for Preparation of Compounds of Formula (I)

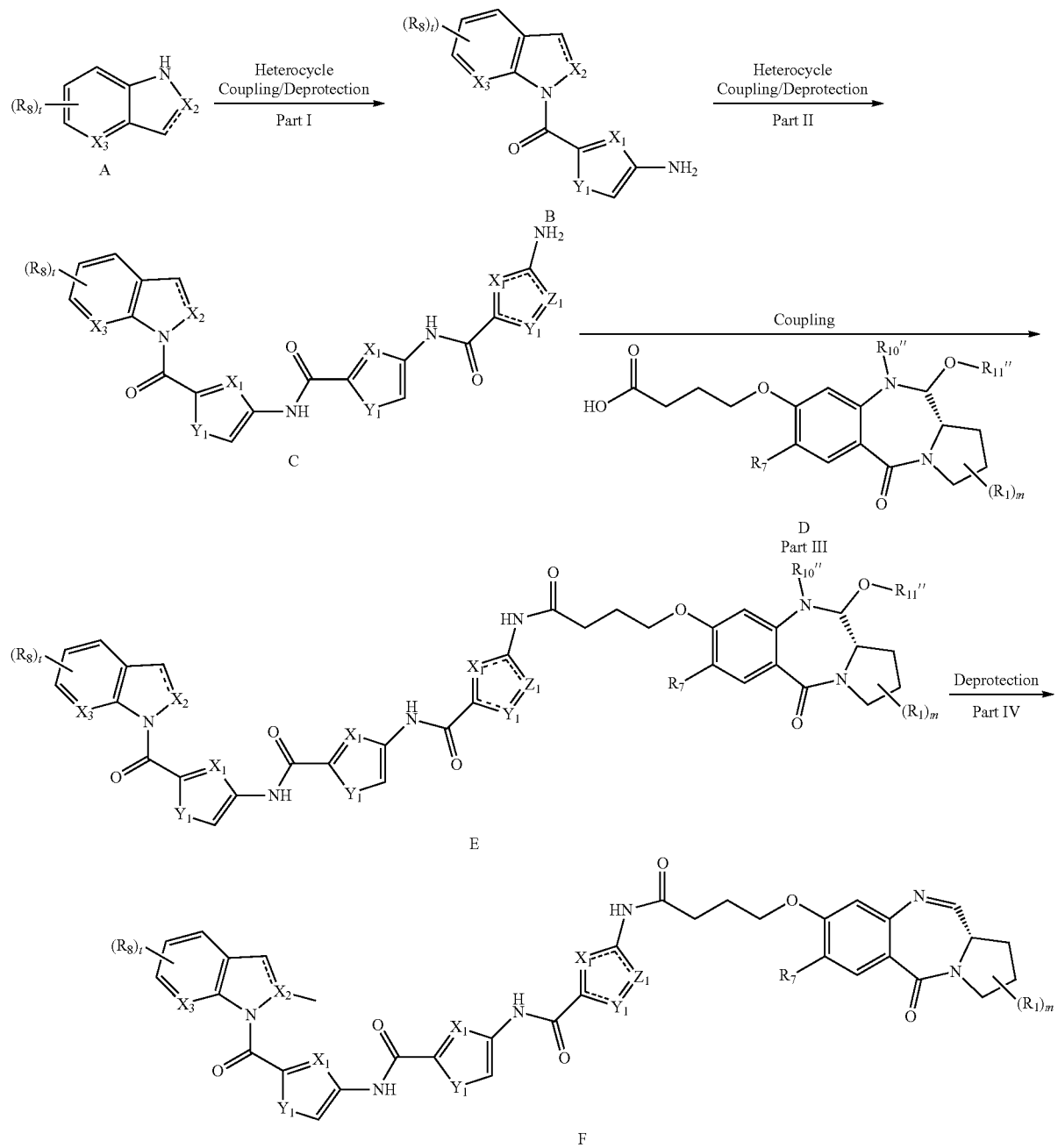

In one embodiment, as illustrated in Scheme 1 above, $R_8$ in compound A is protected using standard protecting groups. The next step in the synthesis, Part I, is the coupling of compound A to a protected heterocycle compound, followed by deprotection of the newly appended heterocycle compound to give compound B. An additional cycle of coupling and deprotection (Part II) gives compound C. The coupling and deprotection steps are carried out using standard amide-coupling and deprotection reagents.

Conjugation of compound C with compound D is conducted under standard amide bond formation conditions, e.g. in the presence of HOBt or DMAP and EDC.HCl or EDAC. In this step (Part III) in compound D, $R_{10}''$ is a nitrogen protecting group, such as, for example, allyloxycarbonyl (alloc), carbobenzyloxy (Cbz), p-methoxybenzyl carbonyl (Moz or MeOZ), acetyl (Ac), benzoyl (Bz), benzyl (Bn), trichloroethoxycarbonyl (Troc), t-butoxycarbonyl (BOC) or 9-fluorenylmethylenoxycarbonyl (Fmoc); and $R_{11}''$ is hydrogen or an oxygen protecting group such as for example, tetrahydropyranyl (THP), silyl ether, methyl ether, alkyl ether, benzyl ether, The final step in the synthesis (Part IV) involves deprotection of compound E and, simultaneous deprotection of the $R_8$ group to give compound F.

Methods for protection and deprotection of function groups are well known in the art and are described in, for example, Wuts, P. G. M. and Greene, T. W., Protective Groups in Organic Synthesis, 4$^{th}$ Edition, Wiley-Interscience, 2007. If both nitrogen and hydroxyl protecting groups are present, these are preferably selected to be removable by the same conditions.

If this deprotection is carried out in a solvent of Formula HQR$^Q$, then R$_{10}$ and R$_{11}$ will be H and QR$^Q$ respectively. Alternatively, these groups may be introduced by adding the compound to a different solvent to that in which the deprotection is carried out.

The conversion of compounds of Formula (I) as discussed above to those having R$_{11}$ as —SO$_x$M may be achieved by the addition of the appropriate bisulphite salt or sulphinate salt, followed by a purification step. Further methods are described in U.S. Pat. No. 4,309,437 and WO2012/128868, each of which is herein incorporated by reference.

Conjugates of the present disclosure can be prepared in a variety of ways using commercially available starting materials, compounds, antibodies, and antibody fragments each of which are known in the literature, or from readily prepared intermediates, by employing standard synthetic methods and procedures either known to those skilled in the art, or which will be apparent to the skilled artisan in light of the teachings herein. For example, for the synthesis of conjugates of compounds of Formula (I), where the antibody or antibody fragment is directly or indirectly linked to the compound at position E" or D" of Formula (VI), methods and linkers disclosed in WO2011/13063, WO2011/130616, WO2015/159076, WO2015/052535, WO2015/052534, WO2015/052321, WO2014/130879, WO2014/096365, WO2014/057122, WO2014/057073, WO2013/164593, WO2013/055993, WO2013/055990, WO2013/053873, WO2013/053871, WO2013/041606, WO2011/130616, and WO2011/130613 may be used. Each of these publications is incorporated herein by reference in its entirety.

As another example, for the synthesis of conjugates of compounds of Formula (I), where the antibody or antibody fragment is directly or indirectly linked to the compound at position R"$_7$, methods and linkers disclosed in WO2014140174(A1) and WO2016/037644 may be used. Each of these publications is incorporated herein by reference in its entirety.

As another example, for the synthesis of conjugates of compounds of Formula (I), where the antibody or antibody fragment is directly or indirectly linked to the compound at position R"$_{10}$, methods and linkers disclosed in WO 2013/055987, WO 2016/044560, WO 2016/044396, WO2015/159076, WO2015/095227, WO2015/095124, WO2015/052535, WO2015/052534, WO2015/052322, WO2014/174111, WO2014/096368, WO2014/057122, WO2014/057074, WO2014/022679, WO2014/011519, WO2014/011518, WO2013/177481, WO2013/055987, WO2011/130598, and WO2011/128650 may be used. Each of these publications is incorporated herein by reference in its entirety.

General Procedure A: Partial Selective Reduction of Protein (Antibody)

The partial selective reduction of the inter-chain disulfide groups or unpaired disulfide in the relevant antibody prior to conjugation with the polymer-drug conjugate is achieved by using a reducing agent, such as, for example, TCEP, DTT or β-mercaptoethanol. When the reduction is performed with an excess of the reducing agent, the reducing agent is removed prior to conjugation by SEC. The degree of conversion of the antibody disulfide groups into reactive sulfhydryl groups depends on the stoichiometry of antibody, reducing agent, pH, temperature and/or duration of the reaction. When some but not all of the disulfide groups in the antibody are reduced, the reduced antibody is a partially reduced antibody.

General Procedure B: Conjugation of Partially Reduced Antibody with Polymer Drug Conjugate The conjugation of the partially reduced antibody to the polymer-drug conjugate is conducted under neutral or slightly basic conditions (pH 6.5-8.5) at antibody concentrations of 1-10 mg/mL and polymer-drug conjugate concentrations of 0.5-10 mg/mL. The polymer-drug conjugate is typically used in 1-5.0 fold excess relative to the desired protein-polymer-drug conjugate stoichiometry. When the antibody is conjugated to the maleimido group of the polymer-drug conjugate, the conjugation is optionally terminated by the addition of a water-soluble maleimido blocking compound, such as, for example, N-acetyl cysteine, cysteine methyl ester, N-methyl cysteine, 2-mercaptoethanol, 3-mercaptopropanoic acid, 2-mercaptoacetic acid, mercaptomethanol (i.e., HOCH$_2$SH), benzyl thiol, and the like.

The resulting antibody-polymer-drug conjugate is typically purified by diafiltration to remove any unconjugated polymer-drug conjugate, unconjugated drug and small molecule impurities. Alternatively or additionally, appropriate chromatographic separation procedures such as, for example, size-exclusion chromatography, hydrophobic interaction chromatography, ion chromatography such as, for example, WCX chromatography; reversed phase chromatography, hydroxyl apatite chromatography, affinity chromatography or combinations thereof may be used to purify the antibody-polymer-drug conjugate. The resulting purified antibody-polymer-drug conjugate is typically formulated in a buffer at pH 5.0-6.5.

Other antibody-drug conjugates are synthesized with methods similar to the procedure described herein, involving other antibodies and/or antibody fragments. Also antibody-drug conjugates with varying ratios of drug to antibody are obtained by varying the number of antibody sulfhydryl groups and drug load.

Compounds and conjugates designed, selected and/or optimized by methods described above, once produced, can be characterized using a variety of assays known to those skilled in the art to determine whether the compounds or conjugates have biological activity. For example, the compounds or conjugates can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the conjugate molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

In certain embodiments, the activities of the compounds and conjugates disclosed herein can be characterized via in vitro studies (e.g., a DNA binding assay or CellTiter-Glo® Luminescent Cell Viability Assay) or in vivo studies (e.g., tumor xenograft studies in mice). The ability of the compounds of the disclosure to bind to DNA, and in particular oligonucleotides, can be measured using an Ion Pair Reversed-Phase HPLC assay, as described in Rahman, K. M., et al., *Journal of the American Chemical Society* 2009, 131, 13756-12766 and Narayanaswamy, M., et al., *Analyti-* cal *Biochemistry* 2008, 374, 173-181. The DNA binding affinity can also be evaluated by using a calf-thymus DNA thermal denaturation assay, as described in Wells, G., et al., *Journal of Medicinal Chemistry* 2006, 49, 5442-5461; Jenkins, T. C., et al., *Journal of Medicinal Chemistry* 1994, 37, 4529-4537; and Gregson, S. J., et al., *Journal of Medicinal Chemistry* 2001, 44, 737-748. The in vitro potency of antibody-drug conjugates can be measured by a cell proliferation assay. The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670).

Tumor growth inhibition (% TGI) is defined as the percent difference in median tumor volumes (MTVs) between treated and control groups. Treatment efficacy can be determined from the incidence and magnitude of regression responses of the tumor size observed during the study. Treatment may cause partial regression (PR) or complete regression (CR) of the tumor in an animal.

Also included are pharmaceutical compositions comprising one or more compounds and/or conjugates as disclosed herein in an acceptable carrier, such as a stabilizer, buffer, and the like. The conjugates can be administered and introduced into a subject by standard means, with or without stabilizers, buffers, and the like, to form a pharmaceutical composition. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral administration including intravenous, intraarterial, subcutaneous, intraperitoneal or intramuscular injection or infusion or intracranial, e.g., intrathecal or intraventricular, administration. The conjugates can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the drug is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of the modified polymer in the blood stream followed by distribution throughout the entire body. Administration routes that lead to systemic absorption include, without limitation: intravenous, subcutaneous, intraperitoneal, inhalation, oral, intrapulmonary, and intramuscular. Each of these administration routes exposes the compound or conjugate to an accessible diseased tissue. The rate of entry of an active agent into the circulation has been shown to be a function of molecular weight or size. The use of a conjugate of this disclosure can localize the drug delivery in certain cells, such as cancer cells via the specificity of antibodies.

A "pharmaceutically acceptable formulation" means a composition or formulation that allows for the effective distribution of the conjugates in the physical location most suitable for their desired activity. In one embodiment, effective delivery occurs before clearance by the reticuloendothelial system or the production of off-target binding which can result in reduced efficacy or toxicity. Non-limiting examples of agents suitable for formulation with the conjugates include: P-glycoprotein inhibitors (such as Pluronic P85), which can enhance entry of active agents into the CNS; biodegradable polymers, such as poly (DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

Also included herein are pharmaceutical compositions prepared for storage or administration, which include an effective amount of the desired compounds and/or conjugates in a pharmaceutically acceptable carrier or diluent. Acceptable carriers, diluents, and/or excipients for therapeutic use are well known in the pharmaceutical art. For example, buffers, preservatives, bulking agents, dispersants, stabilizers, dyes, can be provided. In addition, antioxidants and suspending agents can be used. Examples of suitable carriers, diluents and/or excipients include, but are not limited to: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The term "effective amount", as used herein, refers to an amount of a pharmaceutical agent to treat, ameliorate, or prevent an identified disease or condition, or to exhibit a detectable therapeutic or inhibitory effect. The effect can be detected by any assay or method known in the art. The precise effective amount for a subject will depend upon the subject's body weight, size, and health; the nature and extent of the condition; and the therapeutic or combination of therapeutics selected for administration. Effective amounts for a given situation can be determined by routine experimentation that is within the skill and judgment of the clinician. In a preferred aspect, the disease or condition to can be treated via gene silencing.

For any compound or conjugate, the effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

For example, a drug or its derivatives, drug-polymer conjugates or ADCs (including antibody-drug-polymer conjugates and antibody-drug conjugates) can be evaluated for their ability to inhibit tumor growth in several cell lines using CellTiter Glo®. Dose response curves can be generated using SoftMax Pro software and $IC_{50}$ values can be determined from four-parameter curve fitting. Cell lines employed can include those which are the targets of the antibody and a control cell line that is not the target of the antibody contained in the test conjugates.

In one embodiment, the PBD compounds and/or conjugates of the disclosure are formulated for parenteral administration by injection including using conventional catheterization techniques or infusion. Formulations for injection may be presented in unit dosage form, e.g., in ampules or in multi-dose containers, with an added preservative. The compounds and/or conjugates can be administered parenterally in a sterile medium. The compounds and/or conjugate, depending on the vehicle and concentration used, can either be suspended or dissolved in the vehicle. Advantageously, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. One or more of the compounds and/or conjugates can be present in association with one or more non-toxic pharmaceutically acceptable carriers and/or diluents and/or adjuvants, and if desired other active ingredients.

The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, a bland fixed oil can be employed including synthetic mono- or diglycerides. In addition, fatty acids such as oleic acid find use in the preparation of injectables.

The PBD compounds, conjugates and compositions described herein may be administered in appropriate form, preferably parenterally, more preferably intravenously. For parenteral administration, the compounds, conjugates or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

For PBD compounds disclosed herein, the appropriate dosage levels will depend on several factors, such as, for example, the type of disease to be treated, the severity and course of the disease, whether the compound is administered for preventing or therapeutic purposes, previous therapy, the patient's clinical history. Depending on the type and severity of the disease, about 100 ng to about 25 mg (e.g., about 1 µg/kg to 15 mg/kg, about 0.1-20 mg/kg) of the compound is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of compound to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of a compound. Other dosage regimens may be useful. The progress of this therapy is easily monitored by conventional techniques and assays. Ranges disclosed herein are expressed as amount administered based on the subject's weight, and one skilled in the art can easily express it as amount administered per body surface area of the subject. For example, 1 mg/kg body weight for a human adult is equivalent to about 37 mg/m$^2$ and 1 mg/kg body weight for a human child is equivalent to about 25 mg/m$^2$.

For PBD conjugates disclosed herein, dosage levels of the order of from between about 0.01 mg and about 200 mg per kilogram of body weight per day are useful in the treatment of the target conditions (between about 0.05 mg and about 7 g per subject per day). In some embodiments, the dosage administered to a patient is between about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight.

The amount of compound or conjugate that can be combined with the carrier materials to produce a single dosage form varies depending upon the host treated and the particular mode of administration. Dosage unit forms can generally contain from between about 0.01 mg and about 200 mg; between 0.01 mg and about 150 mg; between 0.01 mg and about 100 mg; between about 0.01 mg and about 75 mg; or between about 0.01 mg and about 50 mg; or between about 0.01 mg and about 25 mg; of a conjugate. For example, the PBD compound or conjugate of the disclosure can be administered to a subject in need thereof (e.g., a human patient) at a dose of about 100 mg, 3 times daily, or about 150 mg, 2 times daily, or about 200 mg, 2 times daily, or about 50-70 mg, 3-4 times daily, or about 100-125 mg, 2 times daily.

In some embodiments, the conjugates can be administered are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period.

In some embodiments about one to about four weeks after treatment, the patient can receive a second course of treatment. Specific clinical protocols with regard to route of administration, excipients, diluents, dosages, and times can be determined by the skilled artisan as the clinical situation warrants.

It is understood that the specific dose level for a particular subject depends upon a variety of factors including the activity of the specific compound or conjugate, the age, body weight, general health, sex, diet, time of administration, route of administration, and rate of excretion, combination with other active agents, and the severity of the particular disease undergoing therapy.

For administration to non-human animals, the compounds or conjugates can also be added to the animal feed or drinking water. It can be convenient to formulate the animal feed and drinking water so that the animal takes in a therapeutically appropriate quantity of the compounds or conjugates along with its diet. It can also be convenient to present the compounds or conjugates as a premix for addition to the feed or drinking water.

The PBD compounds and conjugates disclosed herein can also be administered to a subject in combination with other therapeutic compounds to increase the overall therapeutic effect. The use of multiple compounds to treat an indication can increase the beneficial effects while reducing the presence of side effects. In some embodiments, the compounds or conjugates are used in combination with chemotherapeutic agents, such as those disclosed in U.S. Pat. No. 7,303,749, U.S. 2016/0031887 and U.S. 2015/0133435, each of which is herein incorporated by reference by its entirety. In other embodiments, the chemotherapeutic agents, include, but are not limited to letrozole, oxaliplatin, docetaxel, 5-FU, lapatinib, capecitabine, leucovorin, erlotinib, pertuzumab, bevacizumab, and gemcitabine.

The present disclosure also provides pharmaceutical kits comprising one or more containers filled with one or more of the compounds, conjugates and/or compositions of the present disclosure, including, one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products.

In another aspect, the PBD compounds and conjugates of the disclosure are used in methods of treating animals (preferably mammals, most preferably humans and includes males, females, infants, children and adults).

The conjugates of the disclosure may be used to provide a PBD conjugate at a target location.

The target location is preferably a proliferative cell population. The antibody is an antibody for an antigen present in a proliferative cell population.

In one embodiment, the antigen is absent or present at a reduced level in a non-proliferative cell population compared to the amount of antigen present in the proliferative cell population, for example a tumor cell population.

The target location may be in vitro, in vivo or ex vivo.

The antibody-drug conjugate (ADC) of the disclosure include those with utility for anticancer activity. In particular, the ADC includes an antibody conjugated, i.e. covalently attached by a linker, to a PBD moiety.

At the target location the linker may not be cleaved. The ADC of the disclosure may have a cytotoxic effect without the cleavage of the linker to release a PBD drug moiety. The ADC of the disclosure selectively deliver cytotoxic agent to tumor tissue whereby greater selectivity, i.e., a lower efficacious dose, may be achieved.

In a further aspect, a conjugate as described herein is for use in the treatment of a proliferative disease. A second aspect of the present disclosure provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumors (e.g. histiocytoma, glioma, astrocytoma, osteoma), cancers (e.g. lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

In one embodiment, the treatment is of a pancreatic cancer.

In one embodiment, the treatment is of a tumor having $\alpha_v\beta_6$ integrin on the surface of the cell.

It is contemplated that the ADC of the present disclosure may be used to treat various diseases or disorders, e.g. characterized by the overexpression of a tumor antigen. Exemplary conditions or hyperproliferative disorders include benign or malignant tumors; leukemia, hematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition Treatment as a prophylactic measure (i.e., prophylaxis, prevention) is also included.

The subject/patient in need thereof may be an animal, mammal a placental mammal, a marsupial (e.g., kangaroo, wombat), a monotremre (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a fetus. In one preferred embodiment, the subject/patient is a human.

In one embodiment, the patient is a population where each patient has a tumor having αvβ6 integrin on the surface of the cell.

In certain embodiments, in practicing the method of the invention, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

Examples of diagnostic labels include, but are not limited to, diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include γ-emitting radionuclides, e.g., indium-111, technetium-99m and iodine-131, etc. Contrast agents for MRI (Magnetic Resonance Imaging) include magnetic compounds, e.g., paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves, e.g., emulsions, crystals, gas bubbles, etc. Still other examples include substances useful for neutron activation, such as boron and gadolinium. Further, labels can be employed which can reflect, refract, scatter, or otherwise affect X-rays, ultrasound, radiowaves, microwaves and other rays useful in diagnostic procedures. Fluorescent labels can be used for photoimaging. In certain embodiments a modifier comprises a paramagnetic ion or group.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following working examples are illustrative of the linkers, drug molecules and antibodies or antibody fragments, and methods for preparing same. These are not intended to be limiting and it will be readily understood by one of skill in the art that other reagents or methods may be utilized.

ABBREVIATIONS

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples Abbreviations:

ACN Acetonitrile
Alloc Allyloxycarbonyl
AcOH Acetic acid
BAIB (Diacetoxyiodo)benzene
BOC tert-butyloxycarbonyl
DIC N,N'-Diisopropylcarbodiimide
EEDQ Ethyl 2-ethoxy-1 (2H)-quinolinecarboxylate
EDTA Ethylenediaminetetraacetic acid
EtOH Ethanol DBU 1,5-Diazabicyclo(5.4.0)undec-5-ene
DABCO 1,4-Diazabicyclo[2.2.2]octane
DCM Dichloromethane
DIEA N,N-Diisopropylethylamine
DMAP N,N-Dimethylpyridin-4-amine
DMF Dimethylformamide
EDAC N1-((ethylimino)methylene)-N3,N3-dimethylpropane-1,3-diamine hydrochloride
EDC.HCl 1-Ethyl-3-[3-dimethylaminopropyl]carbodiimide hydrochloride
EG2 Diethylene glycol
EtOAc Ethyl acetate
HOAt 1-Hydroxy-7-azabenzotriazole
HOBt Hydroxybenzotriazole
Hex Hexanes
MES 2-(N-morpholino)ethanesulfonic acid
TEAA Triethylammonium acetate
TEMPO 2,2,6,6-Tetramethyl-1-piperidinyloxy
TCEP Tris[2-carboxyethyl] phosphine
THF Tetrahydrofuran
m-CPBA meta-Chloroperoxybenzoic acid
MI Maleimide or maleimido
PDI Polydispersity index
PHF poly(1-hydroxymethylethylene hydroxylmethylformal), or FLEXIMER®
RP-HPLC Reverse-phase high performance liquid chromatography
SEC Size exclusion chromatography
WCX Weak cation exchange chromatography General Information 4-((tert-butoxycarbonyl)amino)-1-methyl-1H-pyrrole-2-carboxylic acid was purchased from Oakwood Chemical, Estill, S.C.

4-((tert-butoxycarbonyl)amino)-1-methyl-1H-imidazole-2-carboxylic acid was purchased from Chem-Impex International, Inc., Wood Dale, Ill.

Tumor growth inhibition (% TGI) was defined as the percent difference in median tumor volumes (MTVs) between treated and control groups.

Treatment efficacy was determined from the incidence and magnitude of regression responses of the tumor size observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm$^3$ for one or more of these three measurements. In a CR response, the tumor volume was less than 13.5 mm3 for three consecutive measurements during the course of the study. An animal with a CR response at the termination of a study was additionally classified as a tumor-free survivor (TFS). Animals were monitored for regression responses.

HPLC purification was performed on a Phenomenex Gemini 5 m 110 Å, 250×10 mm, 5 micron, semi-preparation column.

Whenever possible the drug content of the conjugates was determined spectrophotometrically otherwise LC/MS or $^1$H-NMR was performed for quantitative determination of the drug content.

The protein content of the protein-polymer-drug conjugates was determined spectrophotometrically at 280 nm or by ELISA.

The drug-polymer-antibody conjugates, drug-polymer conjugates, drug carrying-polymeric scaffolds, or antibody-carrying polymer scaffolds described herein each typically have a polydispersity index (PDI) of ≤1.5, e.g., <1.2.

Antibody-polymer-drug conjugates, drug carrying-polymeric scaffolds, or antibody-carrying polymer scaffolds can be purified (i.e., removal of residual unreacted drug, antibody, or polymeric starting materials) by extensive diafiltration. If necessary, additional purification by size exclusion chromatography can be conducted to remove any aggregated antibody-polymer-drug conjugates. In general, the antibody-polymer-drug conjugates as purified typically contain less than 5% (e.g., <2% w/w) aggregated antibody-polymer-drug conjugates as determined by SEC; less than 0.5% (e.g., <0.1% w/w) free (unconjugated) drug as determined by RP-HPLC; less than 1% polymer-drug conjugate as determined by SEC and less than 2% (e.g., <1% w/w) unconjugated antibody or antibody fragment as determined by HIC-HPLC.

Example 1

Synthesis of (S,Z)—N-(5-((5-(5-amino-1H-indole-1-carbonyl)-1-methyl-1H-pyrrol-3-yl)carbamoyl)-1-methyl-1H-pyrrol-3-yl)-4-(4-((7-methoxy-2-methylene-5-oxo-2,3,5,11a-tetrahydro-1H-benzo[e]pyrrolo[1,2-a][1,4]diazepin-8-yl)oxy)butanamido)-1-methyl-1H-imidazole-2-carboxamide (8)

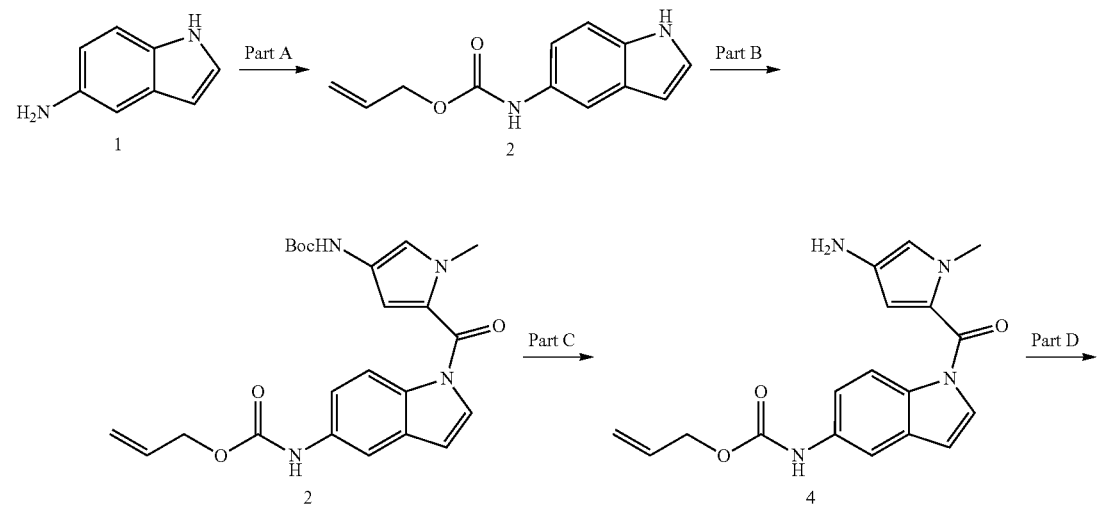

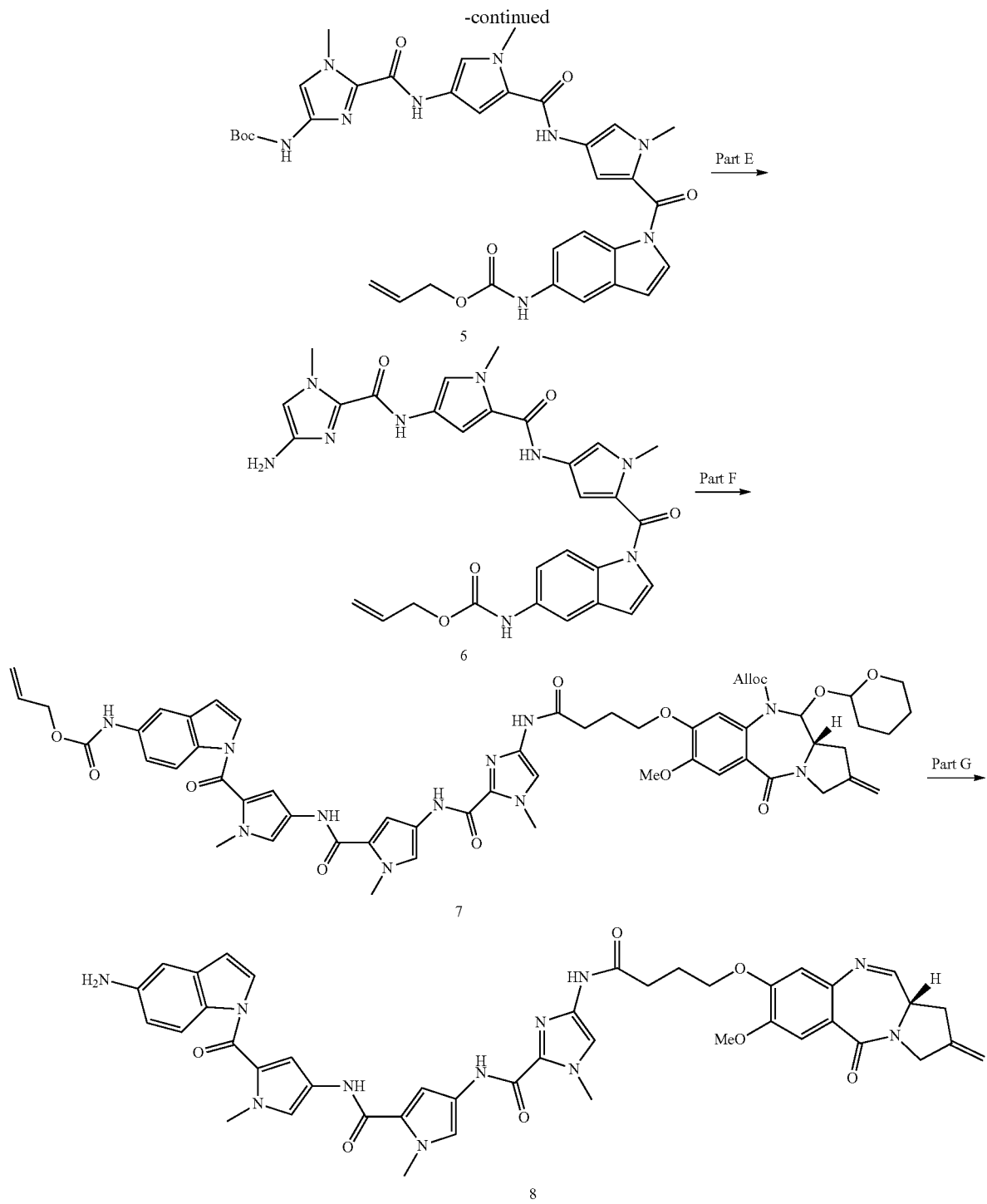

Part A:

To an ice-cold mixture of 1H-indol-5-amine and NaHCO$_3$ in a mixture of ACN (10 mL) and water (15 mL) was added a solution of allyl (2,5-dioxopyrrolidin-1-yl) carbonate in ACN (5 mL). The resulting mixture was stirred at room temp overnight, concentrated by rotary evaporation, and then EtOAc (60 mL) was added, the organic layer was washed with brine, dried over MgSO$_4$ and concentrated by rotary evaporation followed by purification on silica gel (0-80% Hex:EtOAc) to afford allyl 1H-indol-5-ylcarbamate (2). (1.54 g, 7.12 mmol, 94% yield).ESI MS: C$_{18}$H$_{19}$ClN$_4$O$_3$ (M+H) 217.2; found 217.1.

Part B:

To 4-((tert-butoxycarbonyl)amino)-1-methyl-1H-pyrrole-2-carboxylic acid (833 mg, 3.47 mmol) in THF (6 mL) was added 1,1'-di(1H-imidazol-1-yl)methanone (675 mg, 4.16 mmol). The mixture was stirred at room temperature for 18 h and the residual CO$_2$ byproduct was removed by rotary evaporation. The residue was dissolved in THF (6 mL) and then compound 2 (750 mg, 3.47 mmol) was added followed by DBU (256 µL, 1.73 mmol). The mixture was stirred at ~50° C. for 18 h. The solvent was removed by rotary evaporation, the residue dissolved in EtOAc (60 mL) and then washed successively with saturated NaHCO$_3$(20 mL), water (20 mL), and NH$_4$Cl (20 mL). The organic layer was dried over MgSO$_4$, and concentrated followed by purification on ISCO column (0-60% EtOAc/Hexanes) to yield allyl 1-(1-methyl-4-pivalamido-1H-pyrrole-2-carbonyl)-1H-indol-5-ylcarbamate (3) (0.87 g, 1.984 mmol, 57.2% yield).). $^1$H NMR (CD$_3$OD): δ 8.15 (1H, d, J=9.1 Hz), 7.78 (1H, s), 7.75 (1H, d, J=4.2 Hz), 7.28 (1H, D, J=8.9 Hz), 7.16 (1H, s), 6.61 (1H, s), 6.60 (1H, s), 6.09-5.96 (1H, m), 5.44-5.34 (1H, m), 5.29-5.20 (1H, m); 4.66 (2H, d, J=5.7 Hz), 3.90 (3H, s). ESI MS: C$_{23}$H$_{26}$N$_4$O$_5$ (M+H) 439.2; found 439.1.

Part C:

Compound 3 (360 mg, 0.821 mmol) was dissolved in dioxane (5 mL) and cooled to 0° C. under nitrogen followed by the addition of HCl in dioxane (5 mL, 32 mmol). The resulting mixture was allowed to slowly warm to room temperature over ~1 h then concentrated by rotary evaporation to yield allyl (1-(4-amino-1-methyl-1H-pyrrole-2-carbonyl)-1H-indol-5-yl)carbamate hydrochloride (4) (308 mg, 0.82 mmol, 100% yield). ESI MS: C$_{18}$H$_{19}$ClN$_4$O$_3$ (M+H) 339.1; found 339.2.

Part D:

To the solution of 4-(4-((tert-butoxycarbonyl)amino)-1-methyl-1H-imidazole-2-carboxamido)-1-methyl-1H-pyrrole-2-carboxylic acid (174 mg, 0.48 mmol, prepared from methyl 4-amino-1-methyl-1H-pyrrole-2-carboxylate and 4-(tert-butoxycarbonylamino)-1-methyl-1H-imidazole-2-carboxylic acid), compound 4 (180 mg, 0.48 mmol), N,N-dimethylpyridin-4-amine (106 mg, 0.864 mmol) and EDAC (184 mg, 0.96 mmol) in DCM (5 mL) was added DIEA (0.17 mL, 0.96 mmol) under N$_2$. The resulting solution was stirred at room temperature for 18 h. LC-MS showed the completion of the reaction. The reaction mixture was diluted with DCM, washed with water and brine. The organic layer was dried over Na$_2$SO$_4$ and concentrated. The residue was purified on an ISCO column (0-80% EtOAc/Hexanes) to give allyl 1-(1-methyl-4-(1-methyl-4-(1-methyl-4-pivalamido-1H-imidazole-2-carboxamido)-1H-pyrrole-2-carboxamido)-1H-pyrrole-2-carbonyl)-1H-indol-5-ylcarbamate (5) (220 mg, 0.32 mmol, 67% yield). ESI MS: C$_{34}$H$_{37}$N$_9$O$_7$ (M+H) 684.3; found 684.2.

Part E:

To compound 5 (220 mg, 0.322 mmol) dissolved in dioxane (2 mL) at 0° C. under nitrogen, was added HCl in dioxane (2 mL, 8 mmol). The resulting mixture was allowed to slowly warm to room temperature over ~1 h, then concentrated by rotary evaporation to yield allyl (1-(4-(4-(4-amino-1-methyl-1H-imidazole-2-carboxamido)-1-methyl-1H-pyrrole-2-carboxamido)-1-methyl-1H-pyrrole-2-carbonyl)-1H-indol-5-yl)carbamate hydrochloride (6) (200 mg, 0.322 mmol, 100% yield). ESI MS: C$_{29}$H$_{30}$ClN$_9$O$_5$ (M+H) 584.2; found 584.2.

Part F:

To the solution of 4-((11 aS)-10-(allyloxycarbonyl)-7-methoxy-2-methylene-5-oxo-11-(tetrahydro-2H-pyran-2-yloxy)-2,3,5,10,11,11a-hexahydro-1H-benzo[e]pyrrolo[1,2-a][1,4]diazepin-8-yloxy)butanoic acid (prepared by a modification of the procedure described in US20150133435 (A1)) (86 mg, 0.16 mmol), compound 6 (100 mg, 0.161 mmol), N,N-dimethylpyridin-4-amine (49.3 mg, 0.403 mmol) and EDAC (61.8 mg, 0.323 mmol) in DCM (3 mL) was added DIEA (0.085 mL, 0.484 mmol) under N$_2$. The resulting solution was stirred at room temperature for 18 h. LC-MS showed the completion of the reaction. The solution was diluted by DCM, washed by water and brine. The organic layer was dried over Na$_2$SO$_4$ and concentrated. The residue was purified on ISCO column (0-20% MeOH/DCM) to yield (11aS)-allyl-8-(4-((2-((5-((5-(5-(((allyloxy)carbonyl)amino)-1H-indole-1-carbonyl)-1-methyl-1H-pyrrol-3-yl)carbamoyl)-1-methyl-1H-pyrrol-3-yl)carbamoyl)-1-methyl-1H-imidazol-4-yl)amino)-4-oxobutoxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (7) (100 mg, 0.09 mmol, 57% yield). ESI MS: C$_{56}$H$_{61}$N$_{11}$O$_{13}$ (M+H) 1096.4; found 1096.0.

Part G:

To a solution of compound 7 (100 mg, 0.091 mmol) in DCM (3 mL) was added triphenylphosphine (5.98 mg, 0.023 mmol) and pyrrolidine (9.43 µl, 0.114 mmol), stirred at room temperature for 10 min, was added tetrakis(triphenylphosphine)palladium(0) (5.27 mg, 4.56 µmol). The resulting mixture was stirred at room temperature for 2 h. LC-MS showed the completion of the reaction. The solvent was removed by rotary evaporation and the residue purified on ISCO column (0-20% MeOH/DCM) to yield (S,Z)—N-(5-((5-(5-amino-1H-indole-1-carbonyl)-1-methyl-1H-pyrrol-3-yl)carbamoyl)-1-methyl-1H-pyrrol-3-yl)-4-(4-((7-methoxy-2-methylene-5-oxo-2,3,5,11a-tetrahydro-1H-benzo[e]pyrrolo[1,2-a][1,4]diazepin-8-yl)oxy)butanamido)-1-methyl-1H-imidazole-2-carboxamide (8) (39 mg, 0.047 mmol, 51.8% yield). ESI MS: C$_{43}$H$_{43}$N$_{11}$O$_7$ (M+H) 825.3; found 826.2. $^1$H NMR (400 MHz, DMSO-d$_6$) δ 2.16 (2H, bs), 2.65 (2H, d), 3.48 (3H, s), 3.67 (6H, bs), 3.90 (8H, m), 5.03 (1H, s), 5.29 (1H, s), 6.42 (1H, d), 6.82 (4H, m), 7.29 (2H, m), 7.62 (3H, m), 8.13 (1H, d), 8.54 (1H, s).

Example 2

Synthesis of (S,Z)—N-(5-(5-amino-1H-indole-1-carbonyl)-1-methyl-1H-pyrrol-3-yl)-4-(4-((7-methoxy-2-methylene-5-oxo-2,3,5,11a-tetrahydro-1H-benzo[e]pyrrolo[1,2-a][1,4]diazepin-8-yl)oxy) butanamido)-1-methyl-1H-imidazole-2-carboxamide (12)

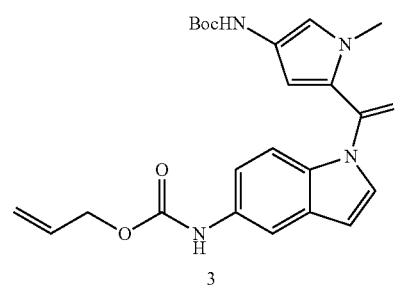

3

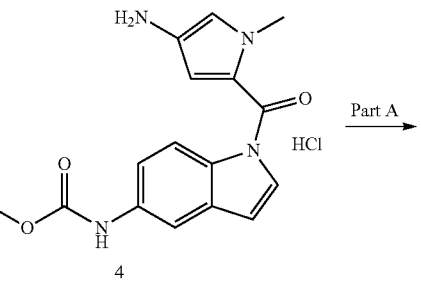

4

Part A

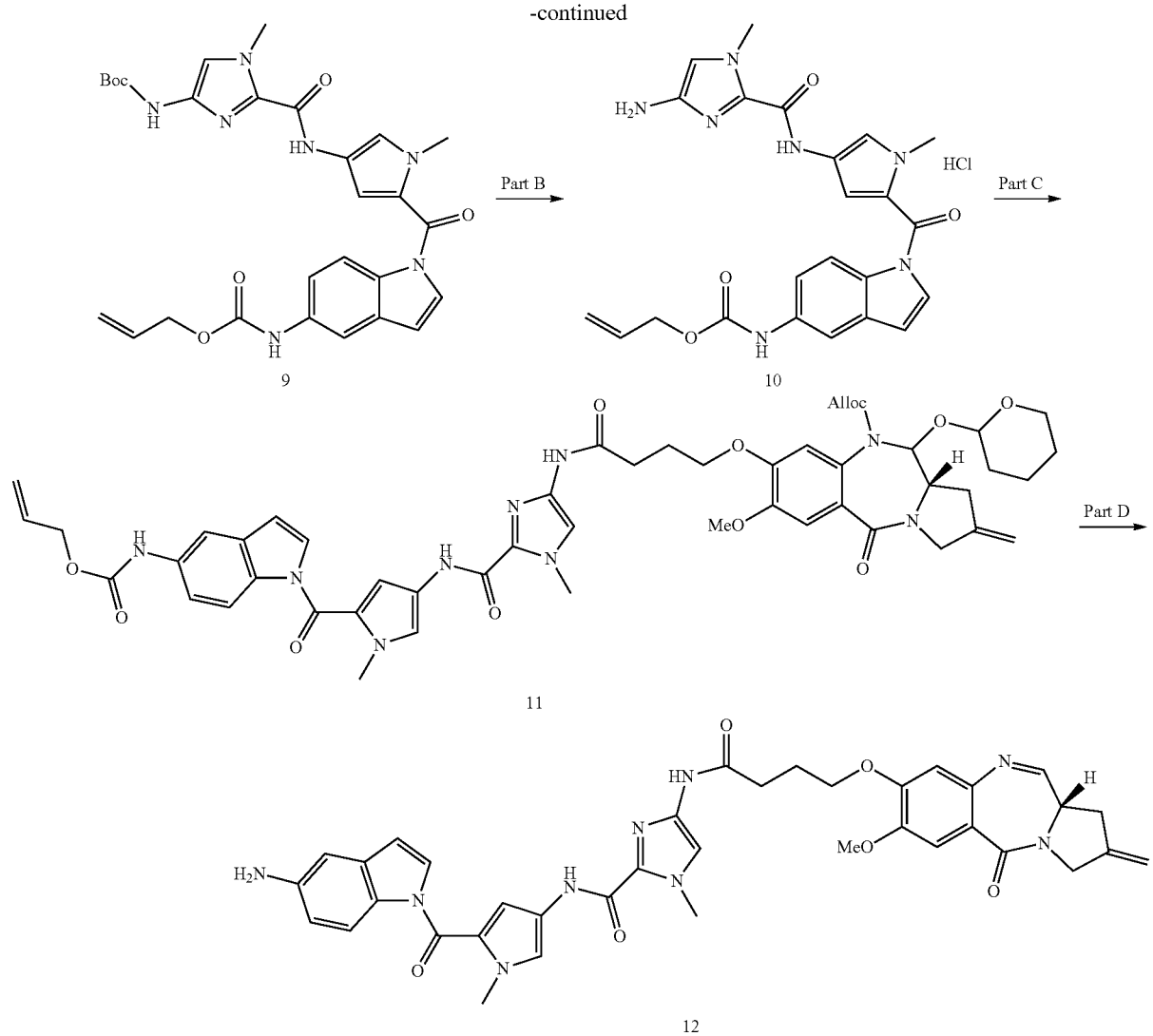

Part A:

To the solution of compound 4, prepared as described in Example 1 (100 mg, 0.267 mmol)), 4-((tert-butoxycarbonyl)amino)-1-methyl-1H-imidazole-2-carboxylic acid (64.4 mg, 0.267 mmol), EDAC (92 mg, 0.48 mmol and N,N-dimethylpyridin-4-amine (65.2 mg, 0.53 mmol) in DCM (6 mL) was added N-ethyl-N-isopropylpropan-2-amine (69 mg, 0.53 mmol). The resulting solution was stirred at room temperature for 18 h. LC-MS showed the completion of the reaction. The reaction mixture was diluted by DCM and washed with water and brine. The organic layer was dried over $Na_2SO_4$ and concentrated. The residue was purified on ISCO column (0-80% EtOAc/Hexanes) to yield allyl (1-(4-(4-((tert-butoxycarbonyl)amino)-1-methyl-1H-imidazole-2-carboxamido)-1-methyl-1H-pyrrole-2-carbonyl)-1H-indol-5-yl)carbamate (9) (130 mg, 0.231 mmol, 87% yield). ESI MS: $C_{28}H_{31}N_7O_6$ (M+H) 562.2; found 562.2.

Part B:

To a solution of compound 9 (130 mg, 0.231 mmol) in dioxane (2 mL) at 0° C. under nitrogen was added HCl in dioxane (2 mL, 8 mmol) and the resulting mixture was slowly warmed to room temperature over ~1 h and then concentrated by rotary evaporation to yield allyl (1-(4-(4-amino-1-methyl-1H-imidazole-2-carboxamido)-1-methyl-1H-pyrrole-2-carbonyl)-1H-indol-5-yl)carbamate hydrochloride (10) (115 mg, 0.231 mmol, 100% yield). ESI MS: $C_{23}H_{24}ClN_7O_4$ (M+H) 462.2; found 462.1.

Part C:

To a solution of 4-((11aS)-10-(allyloxycarbonyl)-7-methoxy-2-methylene-5-oxo-11-(tetrahydro-2H-pyran-2-yloxy)-2,3,5,10,11,11a-hexahydro-1H-benzo[e]pyrrolo[1,2-a][1,4]diazepin-8-yloxy)butanoic acid, (80 mg, 0.151 mmol), prepared by a modification of the procedure described in US2015/0133435, compound 10 (75 mg, 0.151 mmol), N,N-dimethylpyridin-4-amine (46.1 mg, 0.377 mmol) and EDAC (57.8 mg, 0.302 mmol) in DCM (3 mL) under argon was added DIEA (0.079 mL, 0.452 mmol). The resulting solution was stirred at room temperature for 18 h. LC-MS showed the completion of the reaction. The solution was diluted by DCM and washed with water and brine. The organic layer was dried over $Na_2SO_4$ and concentrated. The residue was purified on ISCO column (0-20% MeOH/DCM) to yield (11aS)-allyl 8-(4-((2-((5-(5-(((allyloxy)carbonyl)amino)-1H-indole-1-carbonyl)-1-methyl-1H-pyrrol-3-yl)carbamoyl)-1-methyl-1H-imidazol-4-yl)amino)-4-oxobutoxy)-7-methoxy-2-methylene-5-oxo-11-((tetrahydro-2H- pyran-2-yl)oxy)-2,3,11,11a-tetrahydro-1H-benzo[e]pyrrolo[1,2-a][1,4]diazepine-10(5H)-carboxylate (11) (60 mg, 0.062 mmol, 40.9% yield) ESI MS: $C_{50}H_{55}N_9O_{12}$ (M+H) 974.4; found 974.2.

Part D:

To a solution of compound 11 (60 mg, 0.062 mmol) in DCM (3 mL) at room temperature under argon was added triphenylphosphine (4.04 mg, 0.015 mmol) and pyrrolidine (6.37 μl, 0.077 mmol) and stirred at room temperature for 10 min. To this was added tetrakis(triphenylphosphine)palladium(0) (3.56 mg, 3.08 μmol) and the solution was allowed to stir at room temperature for 2 h. LC-MS showed the completion of the reaction. The solvent was removed by rotary evaporation and the residue purified on ISCO column (0-20% MeOH/DCM) to yield (S)—N-(5-(5-amino-1H-indole-1-carbonyl)-1-methyl-1H-pyrrol-3-yl)-4-(4-((7-methoxy-2-methylene-5-oxo-2,3,5,11a-tetrahydro-1H-benzo[e]pyrrolo[1,2-a][1,4]diazepin-8-yl)oxy)butanamido)-1-methyl-1H-imidazole-2-carboxamide (12) (21 mg, 0.03 mmol, 48.4% yield). ESI MS: $C_{37}H_{37}N_9O_6$ (M+H) 704.3; found 704.1. $^1$H NMR (400 MHz, DMSO-d6) δ 2.02 (2H, bs), 3.01 (2H, bs), 3.80 (3H, s), 3.85 (4H, bs), 3.94 (3H, s), 4.11 (3H, bs), 4.94 (1H, s), 5.12 (1H, s), 6.50 (1H, s), 6.73 (1H, m), 6.81 (1H, s), 6.88 (1H, s), 7.31 (1H, s), 7.45 (1H, s), 7.60 (2H, m), 7.74 (1H, m), 7.90 (2H, d), 10.11 (1H, s), 10.26 (1H, s).

Example 3

Synthesis of (S,Z)—N-(5-(4-aminobenzylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (3A)

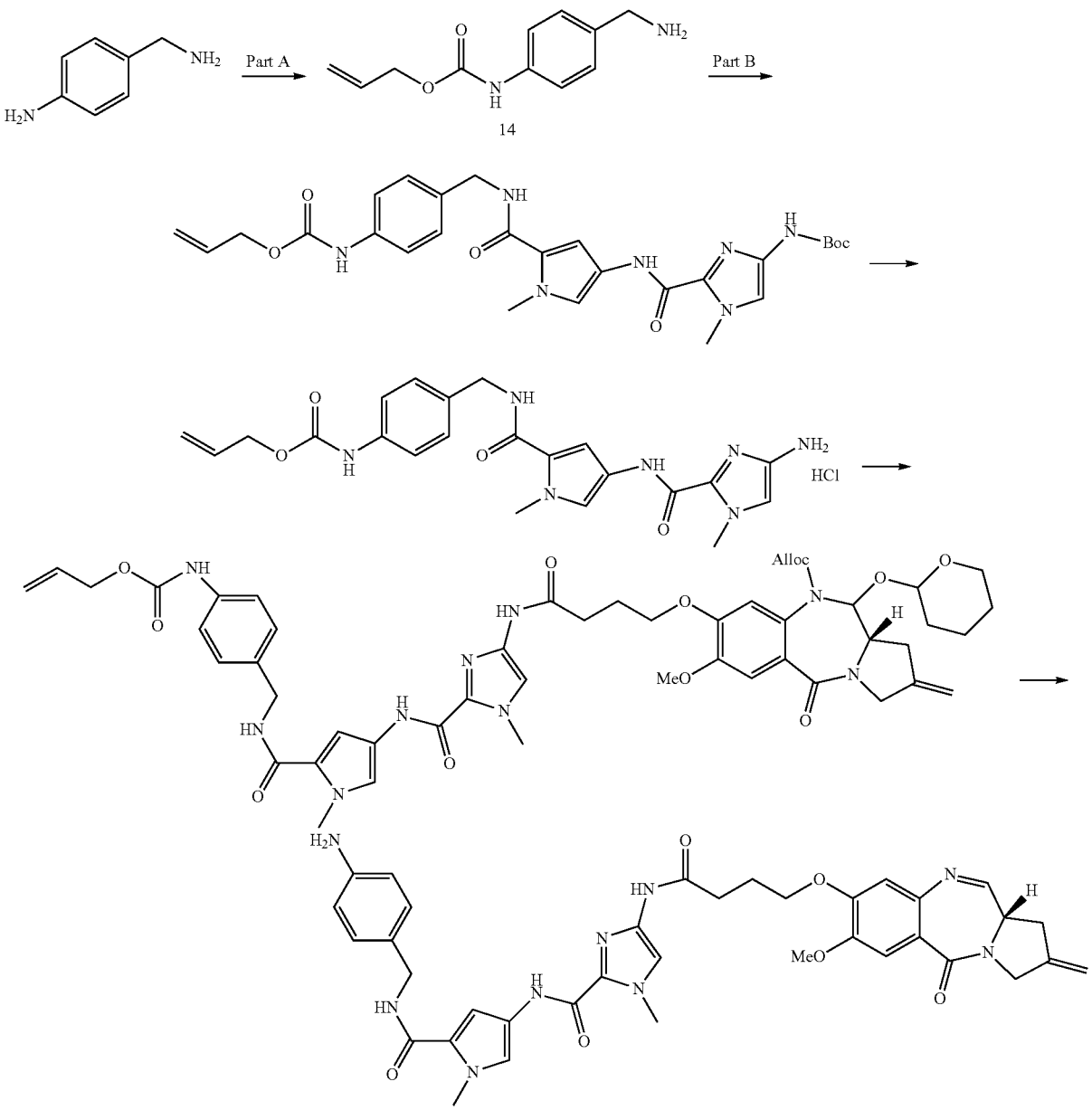

3A

Part A:

To a solution of 4-(aminomethyl)aniline (0.926 mL, 8.19 mmol) (13) in AcOH (3 mL) and water (27 mL) was added a solution of allyl carbonochloridate (0.917 mL, 8.59 mmol) in dioxane (30 mL). The color of the mixture changed from yellow to colorless during the addition of allyl carbonochloridate. The mixture was stirred at room temp for 16 h, concentrated to yield allyl 4-(aminomethyl)phenylcarbamate (14) (1.6 g, 7.65 mmol, 93% yield). $^1$H NMR (400 MHz, DMSO-$d_6$) δ 3.90 (2H, s), 4.6 (2H, d), 5.21 (2H, d), 5.24 (2H, d), 5.95 (1H, m), 7.44 (4H, m), 8.49 (2H, s), 9.85 (2H, s).

Part B:
The title compound 3A was prepared from compound 14 using the procedure described for compound 4 to compound 12 in Example 2. ESI MS: $C_{36}H_{39}N_9O_6$ 694.3; found 694.2.

Example 4

Synthesis of (S,Z)—N-(5-(5-(4-aminobenzylcarbamoyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (4A)

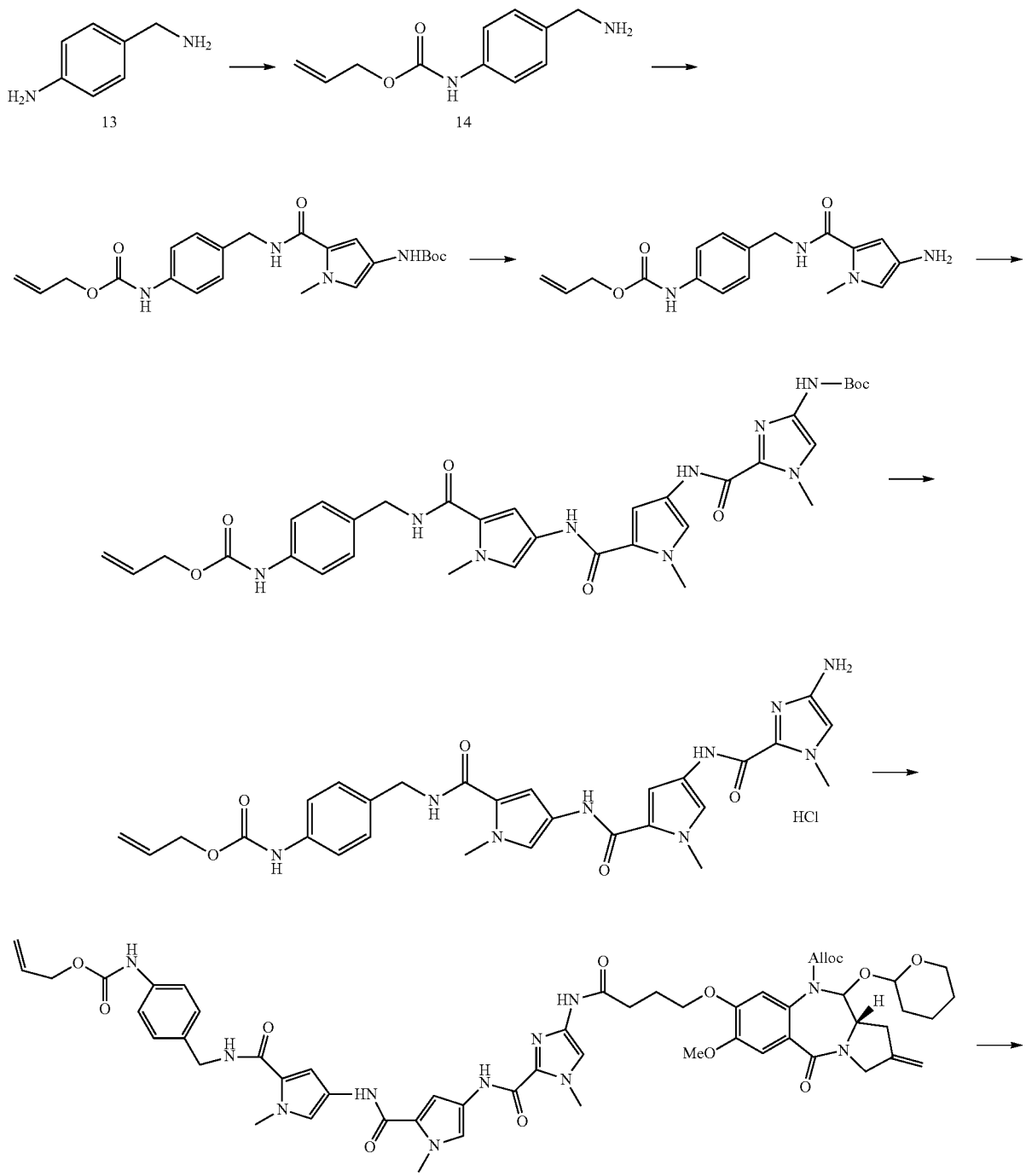

125 126
-continued
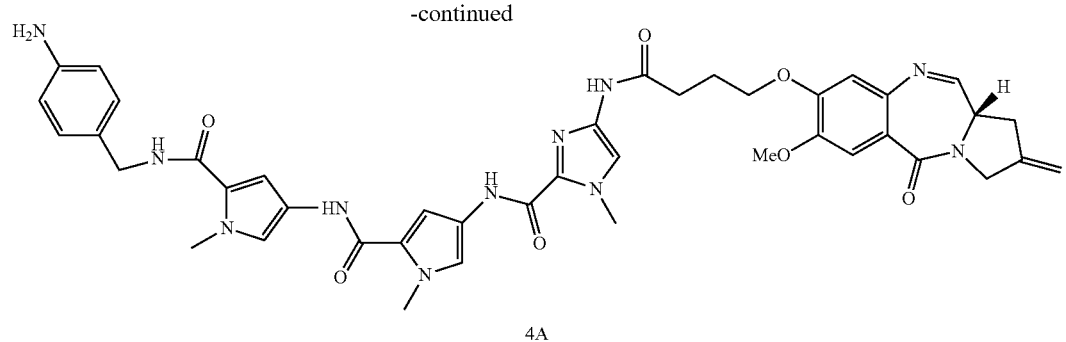
4A
Example 5
Synthesis of (S,Z)—N-(5-(5-aminoisoindoline-2-carbonyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (5A)
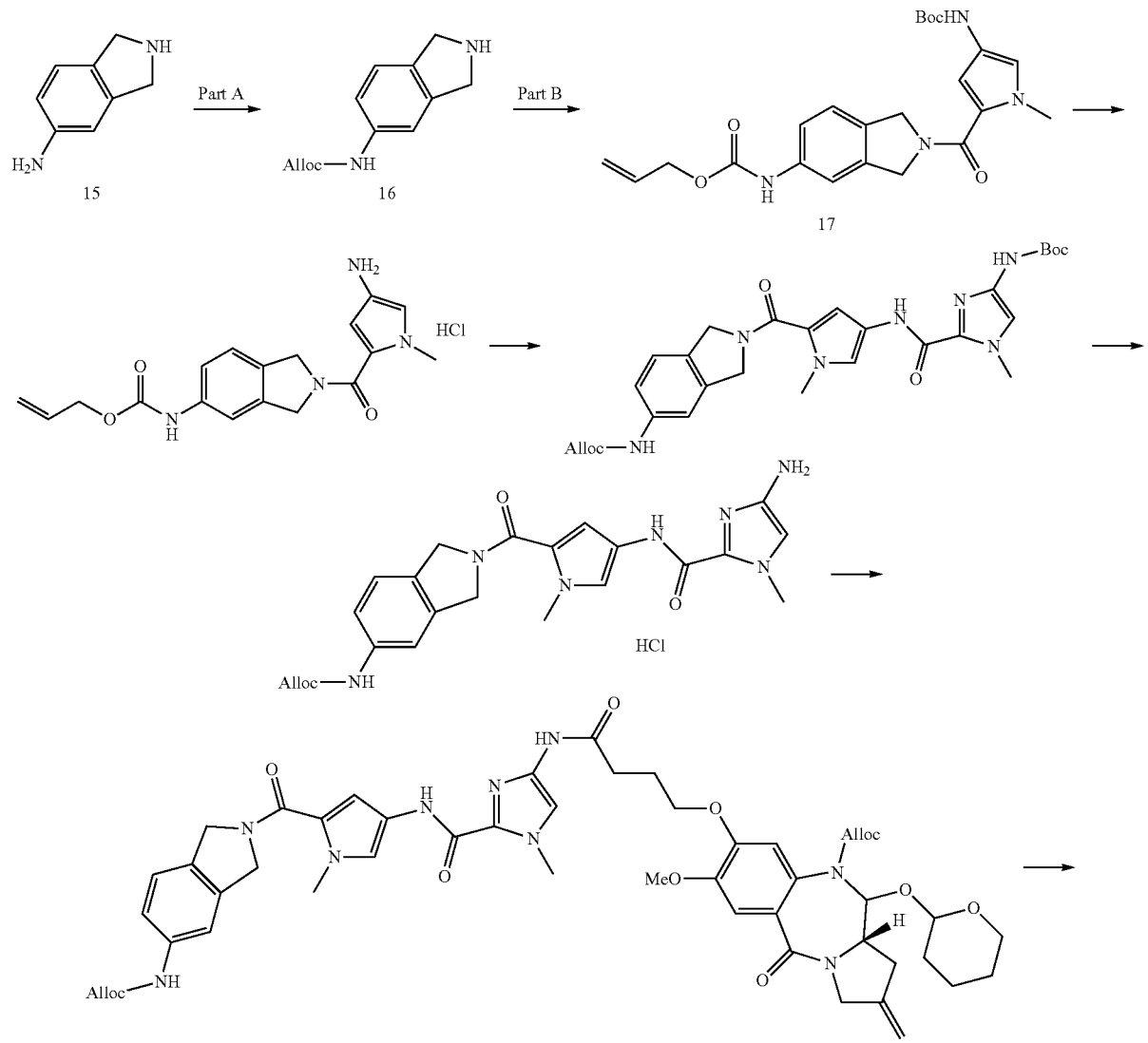

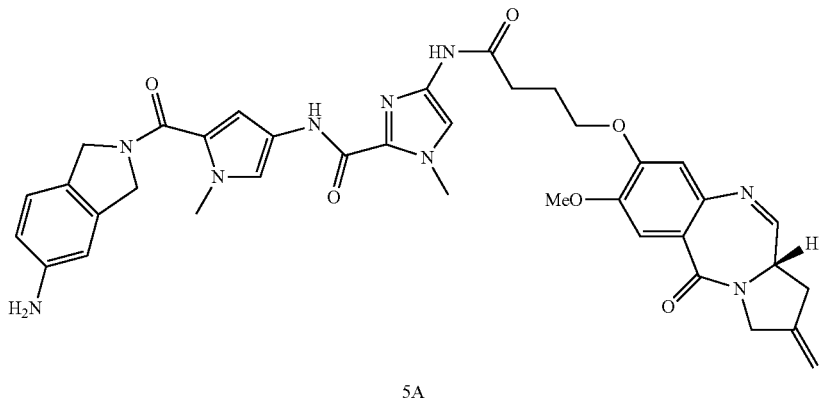

5A

Part A:

To a solution of isoindolin-5-amine (15) (1 g, 7.45 mmol) in AcOH (3 mL) and water (27 mL) was added a solution of allyl carbonochoridate (0.835 mL, 7.83 mmol) in dioxane (30 mL). The color of the mixture changed from brown to colorless during the addition of allyl carbonochloridate. The mixture was stirred at room temperature for 16 h, concentrated to dryness rotary evaporation to give allyl isoindolin-5-ylcarbamate (16) (1.545 g, 7.08 mmol, 95% yield). $^1$H NMR (400 MHz, DMSO-$d_6$) δ 4.67 (4H, m), 5.24 (1H, q), 5.31 (1H, q), 5.95 (1H, m), 6.83 (1H, s), 7.16 (1H, m), 7.44 (1H, s).

Part B:

A solution of compound 16 (300 mg, 1.375 mmol), 4-((tert-butoxycarbonyl)amino)-1-methyl-1H-pyrrole-2-carboxylic acid (330 mg, 1.375 mmol), DMAP (336 mg, 2.75 mmol), EDC.HCl (474 mg, 2.474 mmol) and DIEA (0.479 mL, 2.75 mmol) in ACN (4 mL) and DMF (5 mL) was stirred at room temperature for 16 h. The reaction mixture was diluted with EtOAc (150 mL) and washed with saturated NH$_4$Cl (50 mL). The organic layer was washed with sat NaHCO$_3$ and brine, dried over MgSO$_4$ and concentrated to give a dark oil. The crude product was purified on ISCO column (50-80% EtOAc/Hexanes) to yield allyl (2-(4-((tert-butoxycarbonyl)amino)-1-methyl-1H-pyrrole-2-carbonyl)isoindolin-5-yl)carbamate (17). (350 mg, 0.795 mmol, 57.8% yield). ESI MS: $C_{23}H_{28}N_4O_5$ (M+H) 441.2; found 441.2.

The title compound 5A was prepared from compound 17 using the procedure described for compound 3 to compound 12 in Example 2. ESI MS: $C_{37}H_{39}N_9O_6$ 706.3; found 706.2.

Example 6

Synthesis of (S,Z)—N-(5-(5-(5-aminoisoindoline-2-carbonyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (6A)

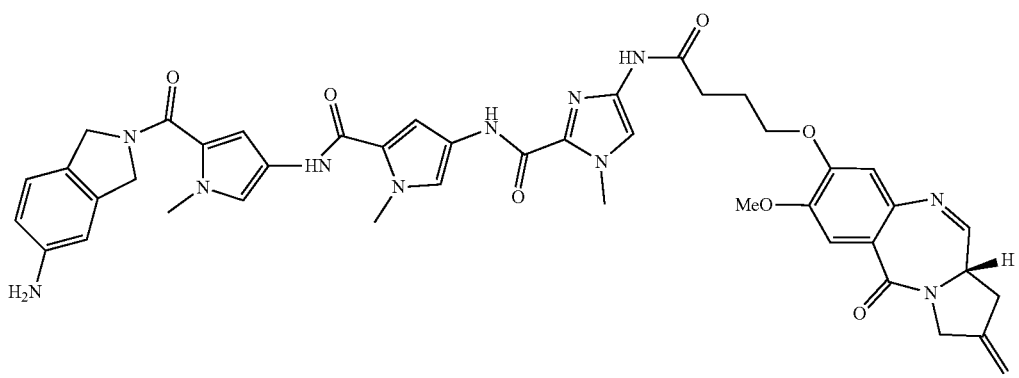

6A

The title compound 6A was prepared from compound 17 using the procedure described for compound 3 to compound 8 in Example 1. ESI MS: $C_{43}H_{45}N_{11}O_7$ 828.4; found 828.2.

Example 7

Synthesis of (S,Z)—N-(5-(5-methoxy-1H-indole-1-carbonyl)-1-methyl-1H-pyrrol-3-yl)-4-(4-(7-methoxy-2-methylene-5-oxo-2,3,5,111a-tetrahydro-1H-benzo[e]pyrrolo[1,2-a][1,4]diazepin-8-yloxy)butanamido)-1-methyl-1H-imidazole-2-carboxamide (7A)

3.12 mmol) in THF (10 mL) at 0° C. was added sodium hydride (125 mg, 3.12 mmol) and the solution stir for 10 min. This reaction mixture was added into the initial reaction mixture and the stirring continued for 15 h at 50° C. EtOAc was added and the mixture was washed successively with water and brine. The organic layer was dried over $Na_2SO_4$, and concentrated followed by purification on ISCO column (0-50% EtOAc/Hexanes) to give tert-butyl 5-(5-methoxy-

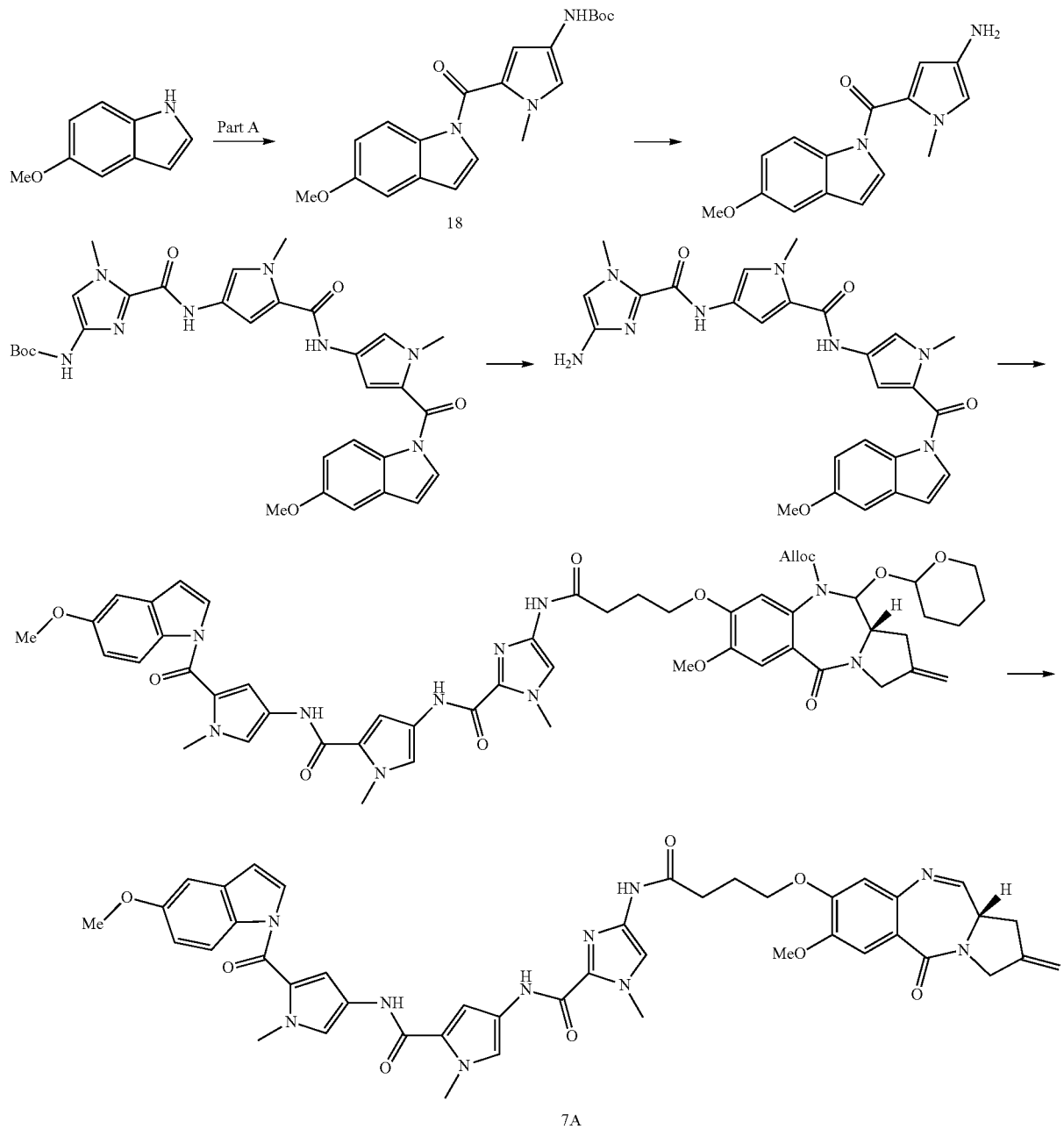

Part A:

To 4-((tert-butoxycarbonyl)amino)-1-methyl-1H-pyrrole-2-carboxylic acid (750 mg, 3.12 mmol) in THF (10 mL) was added 1,1'-di(1H-imidazol-1-yl)methanone (607 mg, 3.75 mmol). The mixture was stirred for at room temperature for 18 h and the residual $CO_2$ byproduct was removed by rotary evaporation. Separately to 5-methoxy-1H-indole (459 mg, 1H-indole-1-carbonyl)-1-methyl-1H-pyrrol-3-ylcarbamate (18) (565 mg, 1.53 mmol, 49.0% yield)) ESI MS: $C_{20}H_{23}N_3O_4$ (M+H) 370.2 found 370.2.

The title compound 7A was prepared from compound 18 using the procedure described for compound 3 to compound 8 in Example 1. ESI MS: $C_{44}H_{44}N_{10}O_8$ 841.3; found 841.2.

Example 8

Synthesis of (S,Z)-methyl 1-(4-(4-(4-(4-(7-methoxy-2-methylene-5-oxo-2,3,5,11a-tetrahydro-1H-benzo[e]pyrrolo[1,2-a][1,4]diazepin-8-yloxy) butanamido)-1-methyl-1H-imidazole-2-carboxamido)-1-methyl-1H-pyrrole-2-carboxamido)-1-methyl-1H-pyrrole-2-carbonyl)-1H-indole-5-carboxylate (8A)

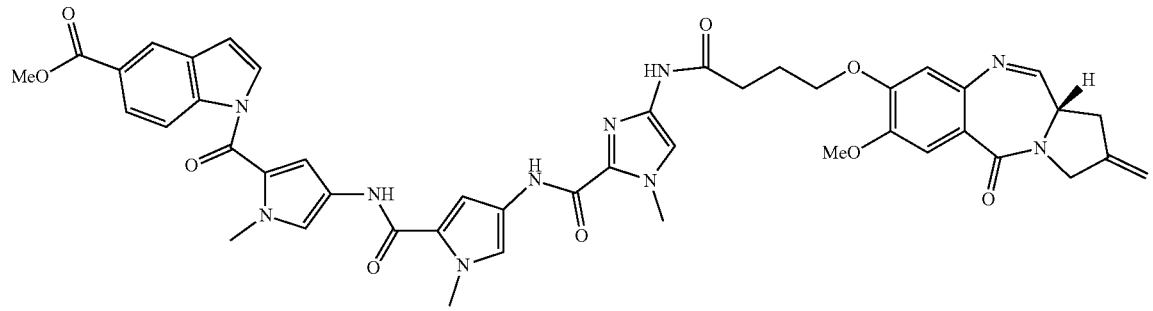

8A

The title compound 8A was prepared using the procedure described in Example 1, except methyl 1H-indole-5-carboxylate (547 mg, 3.12 mmol) was used instead of 1H-indol-5-amine. ESI MS: $C_{45}H_{44}N_{10}O_9$ 869.3; found 869.2.

Example 9

Synthesis of (S,Z)-4-(4-(7-methoxy-2-methylene-5-oxo-2,3,5,11a-tetrahydro-1H-benzo[e]pyrrolo[1,2-a] [1,4]diazepin-8-yloxy)butanamido)-1-methyl-N-(1-methyl-5-(1-methyl-5-(5-(methylthio)-1H-indole-1-carbonyl)-1H-pyrrol-3-ylcarbamoyl)-1H-pyrrol-3-yl)-1H-imidazole-2-carboxamide (19)

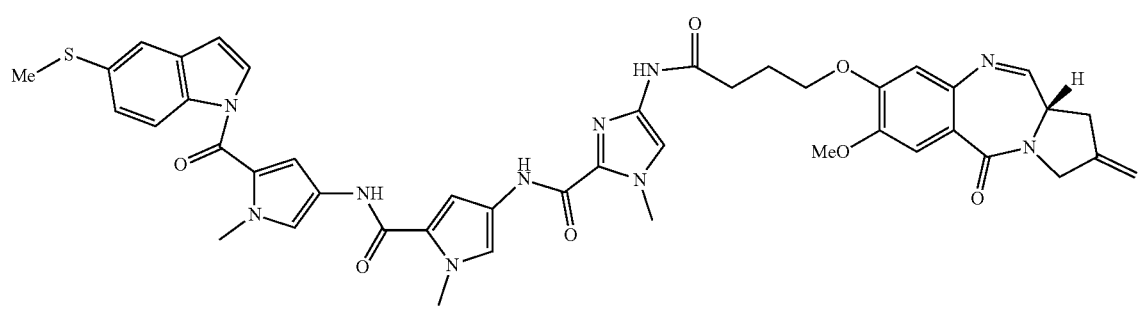

19

The title compound was prepared using the procedure described in Example 7, except methyl 5-(methylthio)-1H-indole (510 mg, 3.12 mmol) was used instead of 5-methoxy-1H-indole. ESI MS: $C_{56}H_{61}N_{11}O_{13}$ 825.3; found 826.2.

Example 10

Synthesis of (S,Z)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-N-(1-methyl-5-(1-methyl-5-(5-(methylsulfonyl)-1H-indole-1-carbonyl)-1H-pyrrol-3-ylcarbamoyl)-1H-pyrrol-3-yl)-1H-imidazole-2-carboxamide (20)

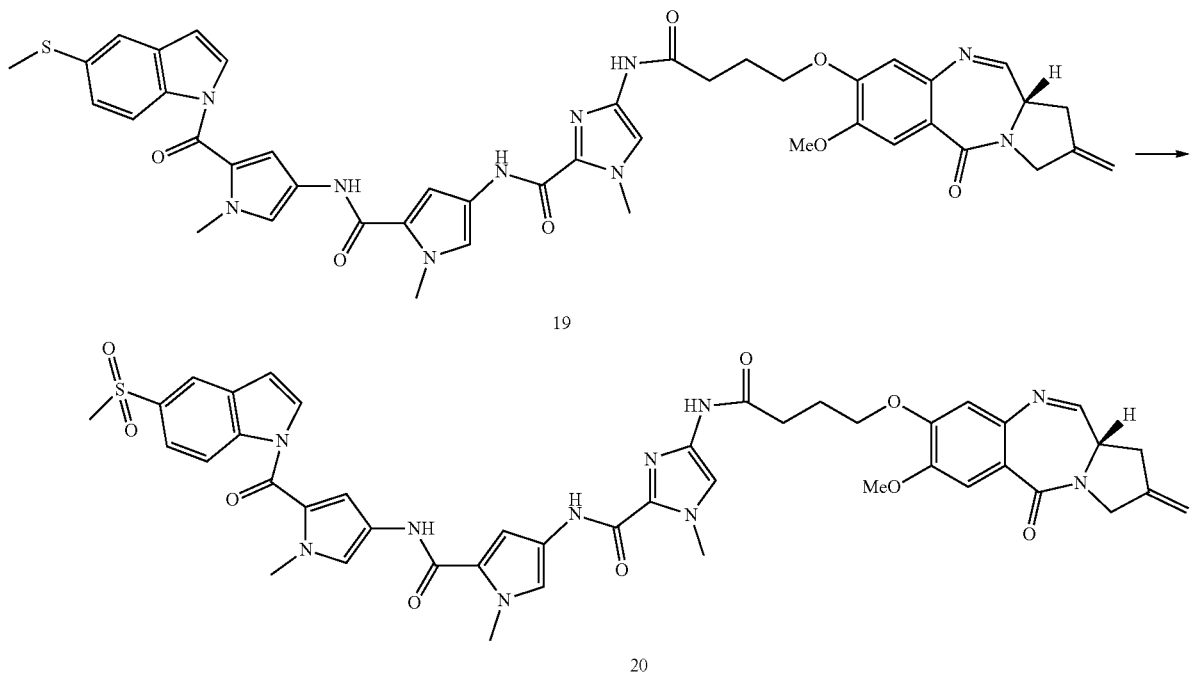

To a solution of compound 19 (6 mg, 7.00 μmol) in DCM (1 mL) at −40° C. was added m-CPBA (1.21 mg, 7 μmol). The resulting solution was stirred for 1 h. LC-MS showed completion of the reaction. A solution of Na$_2$S$_2$O$_3$ and NaHCO$_3$ was added to the reaction mixture, diluted with DCM, washed with brine and the organic layer was dried and concentrated. The crude product was purified on ISCO column (0-20% MeOH/DCM) to yielded (S)-4-(4-((7-methoxy-2-methylene-5-oxo-2,3,5,11a-tetrahydro-1H-benzo[e]pyrrolo[1,2-a][1,4]diazepin-8-yl)oxy)butanamido)-1-methyl-N-(1-methyl-5-((1-methyl-5-(5-(methyl sulfonyl)-1H-indole-1-carbonyl)-1H-pyrrol-3-yl)carbamoyl)-1H-pyrrol-3-yl)-1H-imidazole-2-carboxamide (20) (3 mg, 3.37 μmol, 48.2% yield). ESI MS: C$_{44}$H$_{44}$N$_{10}$O$_9$S (M+H) 889.3; found 889.2.

Example 11

Synthesis of (S,Z)—N-(5-(5-(4-amino-1H-indole-1-carbonyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (11A)

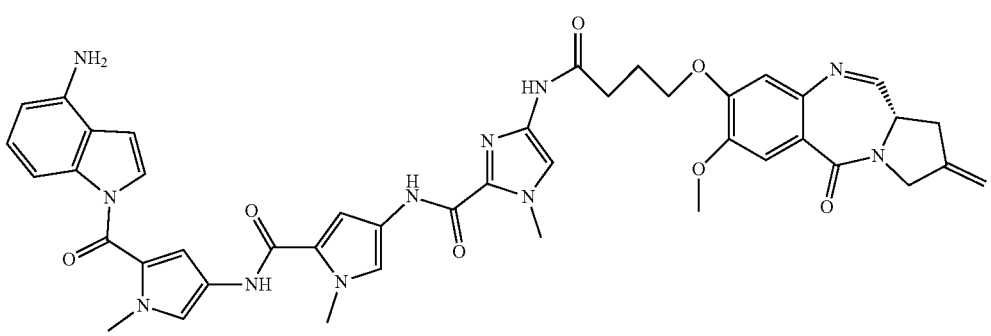

The title compound 11A was prepared using the procedure described in Example 1, except 1H-indol-4-amine (1 g, 7.57 mmol) was used instead of 1H-indol-5-amine. ESI MS: $C_{56}H_{61}N_{11}O_{13}$ 825.3; found 826.2.

Example 12

Synthesis of (S,Z)—N-(5-(5-(6-amino-1H-indazole-1-carbonyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (28)

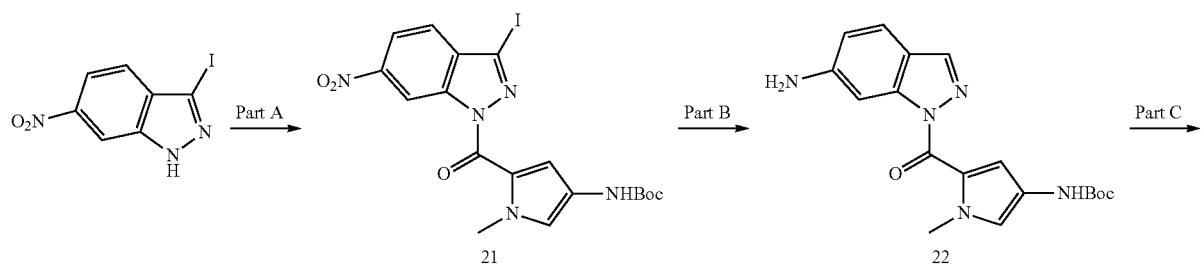

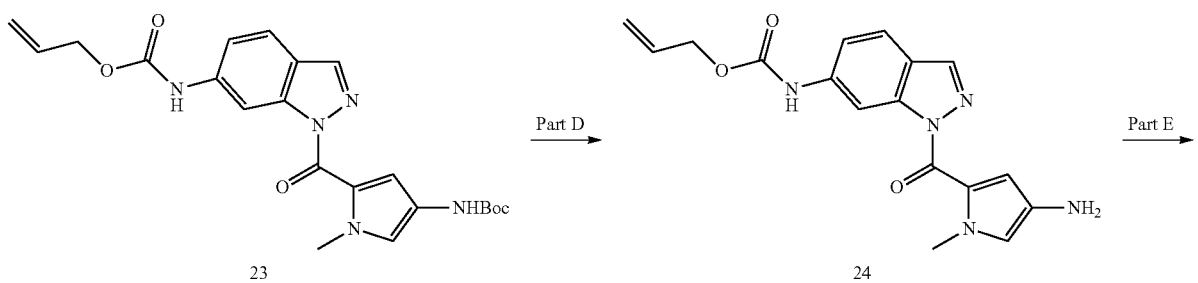

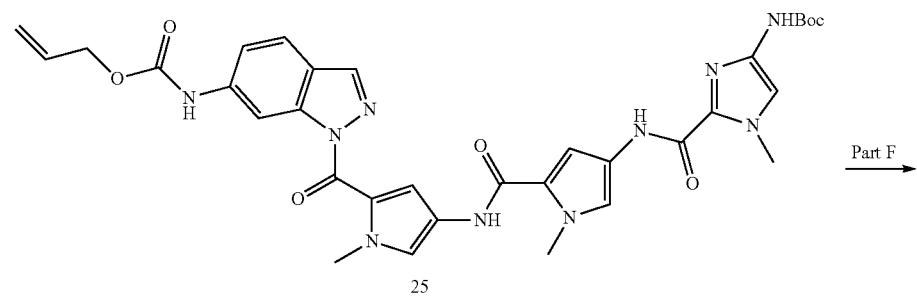

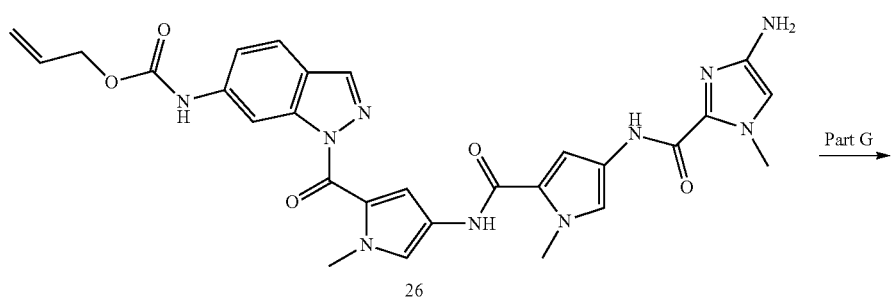

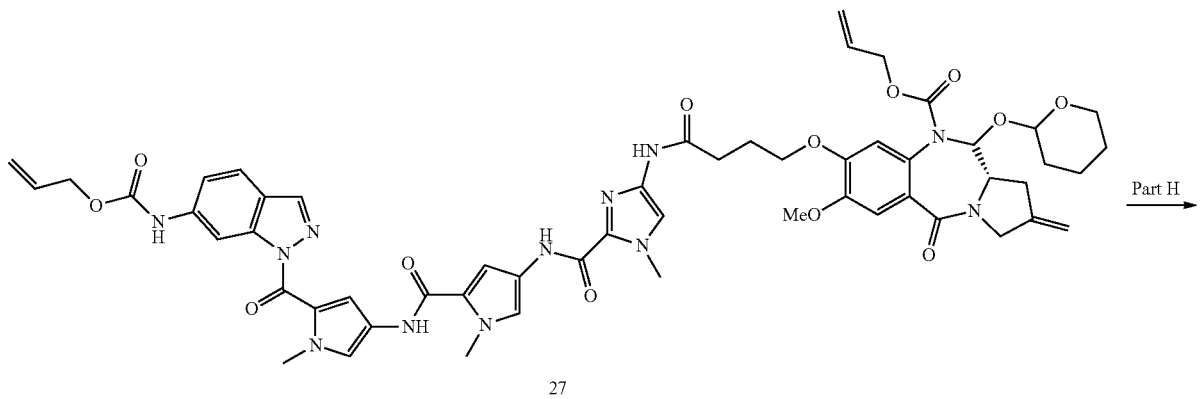

27

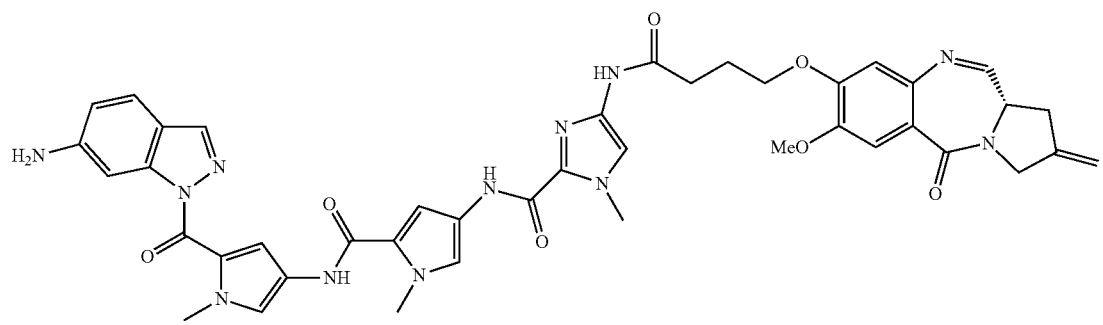

28

A mixture of 4-((tert-butoxycarbonyl)amino)-1-methyl-1H-pyrrole-2-carboxylic acid (499 mg, 2.1 mmol), EDCI.HCl (531 mg, 2.76 mmol), DMAP (507 mg, 4.14 mmol), DIEA (482 μL, 2.76 mmol) and DCM (16 mL) was stirred at room temperature for 15 minutes, then 3-iodo-6-nitro-1H-indazole (400 mg, 1.38 mmol) was added and the stirring continued for 16 h. The reaction mixture was diluted with DCM, then washed with saturated NaHCO$_3$ and water. The organic layer were then dried over Na$_2$SO$_4$ and concentrated to yield a crude yellow product that was purified by chromatography on ISCO column (20% EtOAc/Hexanes), to yield tert-butyl 5-(3-iodo-6-nitro-1H-indazole-1-carbonyl)-1-methyl-1H-pyrrol-3-ylcarbamate (21) as a yellow solid (443 mg, 866 μmol, 63% yield).

Part B:

A mixture of compound 21(443 mg, 867 μmol), zinc powder (1.7 g 26 mmol), EtOH (22 mL) and AcOH (5.5 mL) was heated at 80° C. for 3.5 h. The reaction mixture was filtered, the solids were rinsed with MeOH and the filtrate evaporated. The residue was chromatographed on ISCO column (5% MeOH/DCM) to give tert-butyl 5-(6-amino-1H-indazole-1-carbonyl)-1-methyl-1H-pyrrol-3-ylcarbamate (22) was as a tan foam (147 mg, 48% yield).

Part C:

To a solution of compound 22 (147 mg, 334 μmol) and pyridine (42 μL, 417 μmol) in THF (3 mL) at −40° C. was added dropwise, over a period of 5 minutes, a solution of allyl chloroformate (46 μL, 350 μmol) in THF (3 mL). The reaction mixture was allowed warm to room temperature with stirring overnight followed by dilution with DCM and then washed with water, 5% aqueous HCl and brine. The organic layer was dried over Na$_2$SO$_4$ and evaporated to yield an off-white solid that was used in the next step (Part D) without further purification. (141 mg, 321 μmol, 78% yield). $^1$H NMR (400 MHz, DMSO-d$_6$) δ 10.25 (s, 1H), 10.03 (s, 1H), 9.15 (s, 1H), 7.72 (s, 1H), 7.68 (s, 1H), 7.40 (dd, 1H), 6.96 (d, 2H), 5.92-6.03 (m, 1H), 5.30 (dd, 2H), 4.63 (d, 2H), 3.79 (s, 3H), 1.45 (s, 9H).

Part D:

To a solution of compound 23 (141 mg, 397 μmol) in dioxane (2 mL) at room temperature was added 4M HCl/dioxane (2 mL). The resulting mixture was stirred at room temperature for 20 h and then concentrated by rotary evaporation to yield allyl 1-(4-amino-1-methyl-1H-pyrrole-2-carbonyl)-1H-indazol-6-ylcarbamate (24) as a tan powder (121 mg, 100% yield).

Part E:

A mixture of 4-(4-((tert-butoxycarbonyl)amino)-1-methyl-1H-imidazole-2-carboxamido)-1-methyl-1H-pyrrole-2-carboxylic acid (173 mg, 476 μmol), EDCI.HCl (152 mg, 0.74 mmol), DMAP (146 mg, 1.2 mmol), DIEA (70 μL, 397 μmol) and DCM (5 mL) was stirred at room temperature for 15 minutes, then compound 24 (121 mg, 397 μmol), and DIEA (210 μL, 1.2 mmol) in DCM (2 mL) were added and the stirring continued for 15.5 h. The reaction mixture was diluted with DCM, then washed with saturated NaHCO$_3$ and water. The organic layer was then dried over Na$_2$SO$_4$ and concentrated to yield a yellow foam that was purified by chromatography on ISCO column (10% MeOH/DCM) to yield compound 25, (128 mg, 187 μmol, 46% yield). $^1$H NMR (400 MHz, DMSO-d$_6$) δ 10.27 (s, 1H), 10.06 (s, 1H), 10.01 (s, 1H), 9.93 (s, 1H), 9.32 (s, 1H), 7.77 (d, 1H), 7.70 (d, 1H), 7.42 (dd, 1H), 7.35 (d, 1H), 7.28 (d, 1H), 7.20 (br s, 1H), 7.17 (dd, 2H), 5.93-6.03 (m, 1H), 5.30 (dd, 2H), 4.63 (d, 2H), 3.93 (s, 3H), 3.85 (s, 3H), 3.83 (s, 3H), 1.45 (s, 9H).

Part F:

To a solution of compound 25 (128 mg, 187 μmol) in dioxane (2 mL) was added a solution of 4M HCl in dioxane (2 mL). The reaction mixture was stirred at room temperature for 15.5 h followed by concentration and drying under high vacuum to yield compound 26 as a tan solid (120 mg, 100% yield).

Part G:

A mixture of 4-((11aS)-10-(allyloxycarbonyl)-7-methoxy-2-methylene-5-oxo-11-(tetrahydro-2H-pyran-2-yloxy)-2,3,5,10,11,11a-hexahydro-1H-benzo[e]pyrrolo[1,2-a][1,4]diazepin-8-yloxy)butanoic acid prepared by a modification of the procedure described in US20150133435 (A1) (164 mg, 309 μmol), EDCI.HCl (79 mg, 412 μmol), DMAP (75 mg, 618 mol), DIEA (36 μL, 206 μmol) and DCM (10 mL) was stirred at room temperature for 15 minutes. Then a solution of compound 26 (120 mg, 206 mol) and DIEA (108 μL, 618 μmol) in DCM (2 mL) was added and the resulting mixture stirred at room temperature for 14.5 h. LC-MS showed the completion of the reaction. The reaction mixture was diluted with DCM, then washed with water and saturated NaHCO$_3$ solution. The organic layer was dried over Na$_2$SO$_4$ and concentrated. This crude product was purified on ISCO column (5% MeOH/DCM) to yield (11S,11aS)-allyl 8-(4-(2-(5-(5-(6-(allyloxycarbonylamino)-1H-indazole-1-carbonyl)-1-methyl-1H-pyrrol-3-ylcarbamoyl)-1-methyl-1H-pyrrol-3-ylcarbamoyl)-1-methyl-1H-imidazol-4-ylamino)-4-oxobutoxy)-7-methoxy-2-methylene-5-oxo-11-(tetrahydro-2H-pyran-2-yloxy)-2,3,11,11a-tetrahydro-1H-benzo[e]pyrrolo[1,2-a][1,4]diazepine-10(5H)-carboxylate (27) as a yellow foam (60 mg, 55 mol 28% yield). $^1$H NMR (400 MHz, DMSO-d$_6$) δ 10.31 (s, 1H), 10.18 (s, 1H), 10.01 (s, 1H), 9.95 (s, 1H), 7.98 (d, 1H), 7.83 (d, 1H), 7.40-7.46 (m, 3H), 7.28 (d, 1H), 7.16 (d, 1H), 7.08 (d, 1H), 6.92 (s, 1H), 6.82 (s, 1H), 5.93-6.06 (m, 2H), 5.75 (s, 1H), 5.62 (dd, 2H), 5.38 (dd, 2H), 5.25 (dd, 2H), 5.12 (m, 2H), 5.02 (d, 2H), 4.65 (d, 2H), 4.63 (d, 1H), 4.32-4.60 (m, 2H), 4.10 (m, 2H), 3.76-4.02 (m, 14H), 3.50 (m, 2H), 3.16 (d, 1H), 2.91 (m, 1H), 2.02 (m, 2H), 1.63 (br s, 2H), 1.30-1.55 (m, 4H).

Part H:

A solution of compound 27 (49 mg, 45 μmol), DCM (5 mL), DABCO (50 mg, 0.45 mmol), tetrakis(triphenylphosphine)palladium(IV) (10 mg, 9 μmol) was stirred at room temperature for 0.5 h. The solvent was removed by rotary evaporation and the residue purified on ISCO column (5% MeOH/DCM) to give (S,Z)—N-(5-(5-(6-amino-1H-indazole-1-carbonyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (28) as a clear oil (20 mg, 24 μmol, 54% yield). $^1$H NMR (400 MHz, CDCl$_3$) δ9.10 (s, 1H), 8.53 (s, 1H), 8.42 (s, 1H), 7.75 (s, 2H), 7.61 (d, 1H), 7.51 (s, 1H), 7.33 (s, 1H), 7.25-7.30 (m, 3H), 7.02 (d, 1H), 6.86 (s, 1H), 6.73 (d, 1H), 5.30 (s, 2H), 5.12 (s, 1H), 5.05 (s, 1H), 4.24 (m, 1H), 4.12 (s, 2H), 3.92-4.03 (m, 10H), 3.79 (s, 3H), 3.70 (m, 1H), 2.65-2.98 (m, 4H), 2.27 (m, 2H).

Example 13

Synthesis of (S,Z)—N-(5-(5-(6-amino-1H-indole-1-carbonyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (13A)

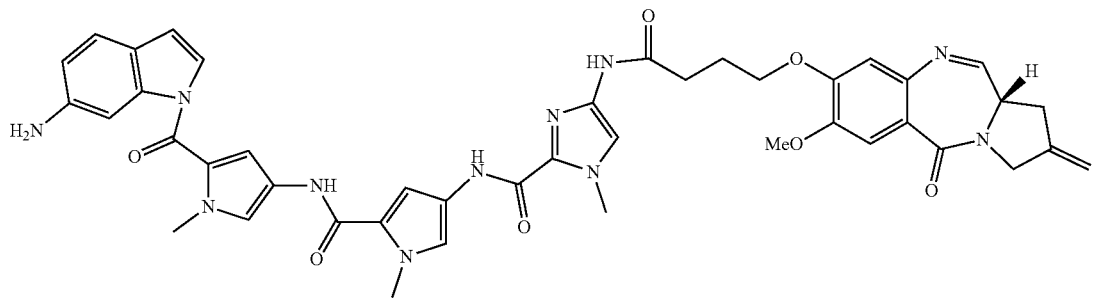

13A

The title compound 13A was prepared as described in Example 1 except 1H-indol-6-amine (1 g, 7.57 mmol) was used instead of 1H-indol-5-amine. ESI MS: C$_{43}$H$_{43}$N$_{11}$O$_7$ (M+H) 826.3; found 825.8.

Example 14
Synthesis of (11S,11aS)-4-((2S,5S)-19-(2,5-dioxo-2,5-dihydro-1H-pyrrol-1-yl)-5-isopropyl-2-methyl-4,7,17-trioxo-10,13-dioxa-3,6,16-triazanonadecanamido)benzyl 11-hydroxy-7-methoxy-8-(4-(2-(5-(5-(5-methoxy-1H-indole-1-carbonyl)-1-methyl-1H-pyrrol-3-ylcarbamoyl)-1-methyl-1H-pyrrol-3-ylcarbamoyl)-1-methyl-1H-imidazol-4-ylamino)-4-oxobutoxy)-2-methylene-5-oxo-2,3,11,11a-tetrahydro-1H-benzo[e]pyrrolo[1,2-a][1,4]diazepine-10(5H)-carboxylate (38)
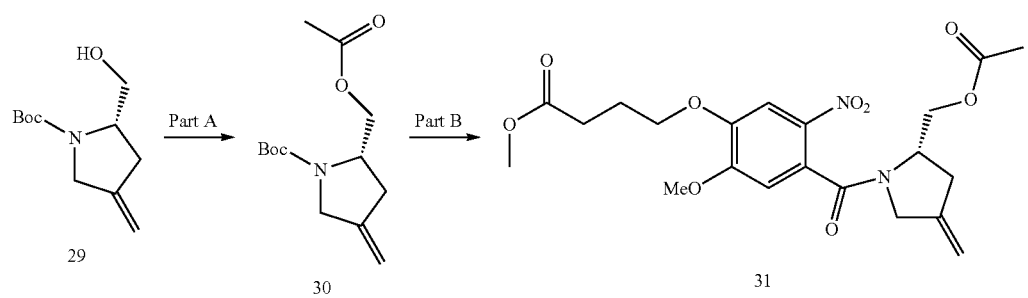
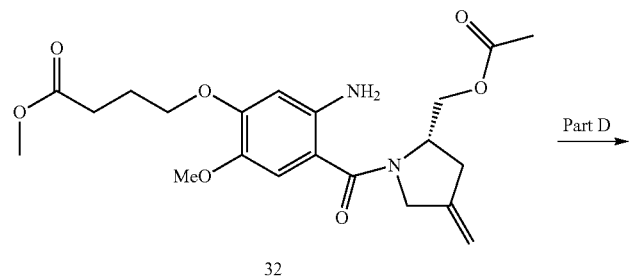
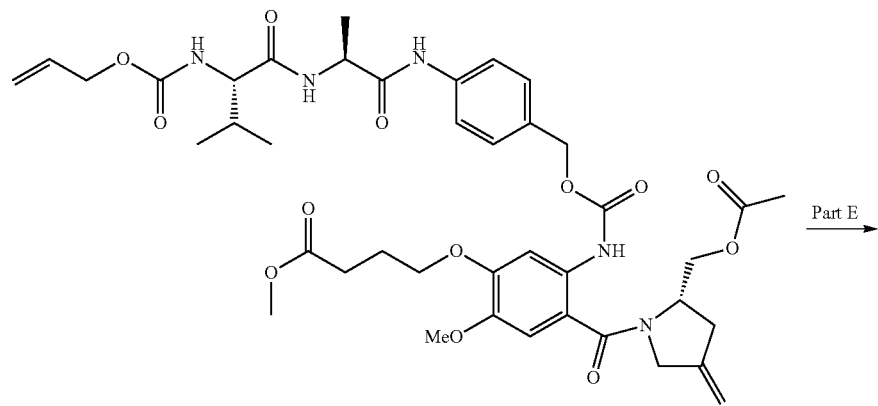

-continued
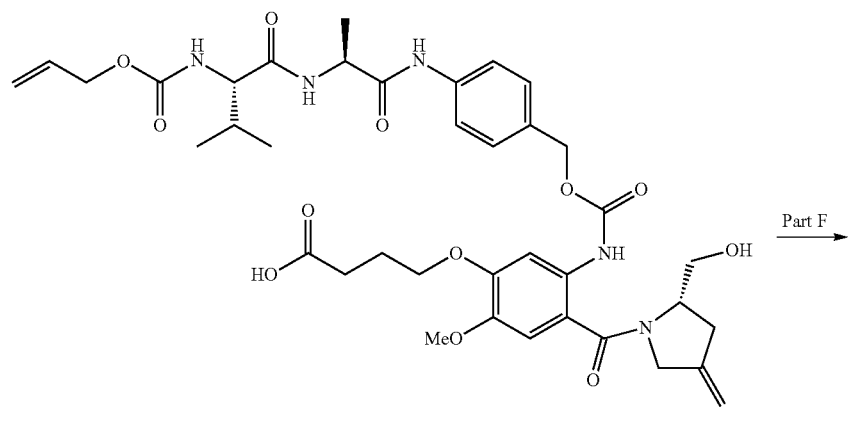
34
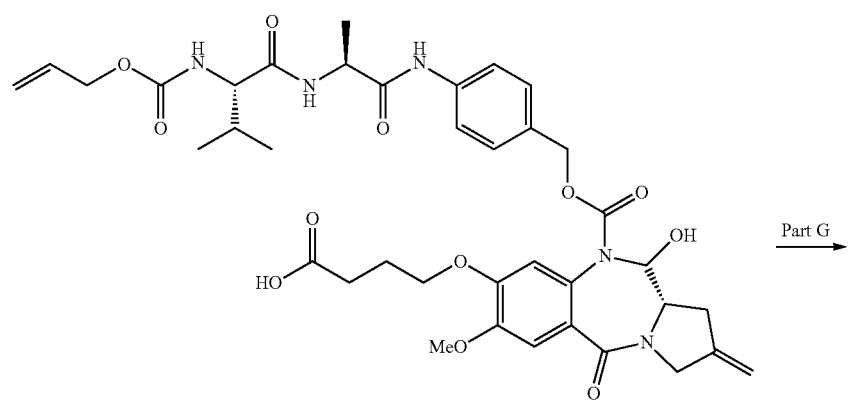
35
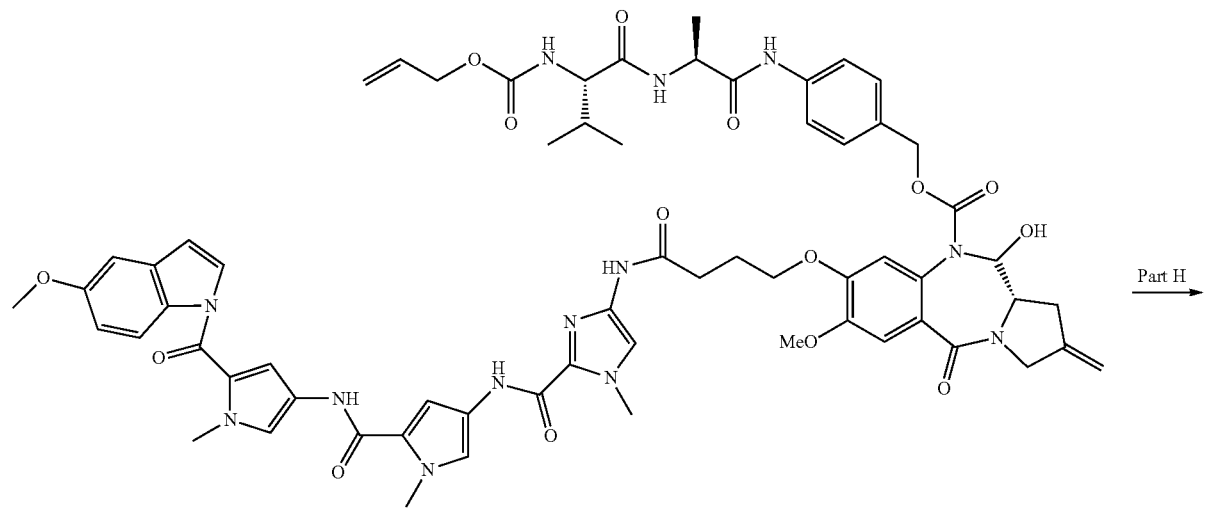
36

-continued

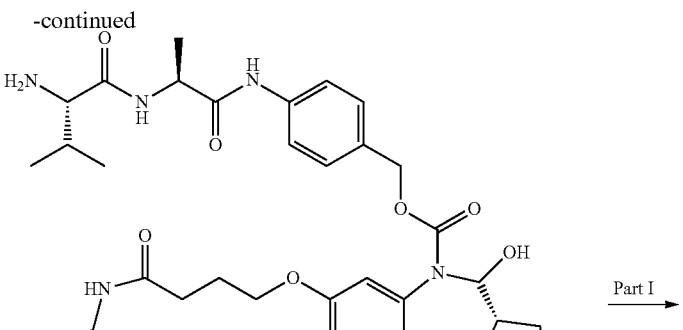
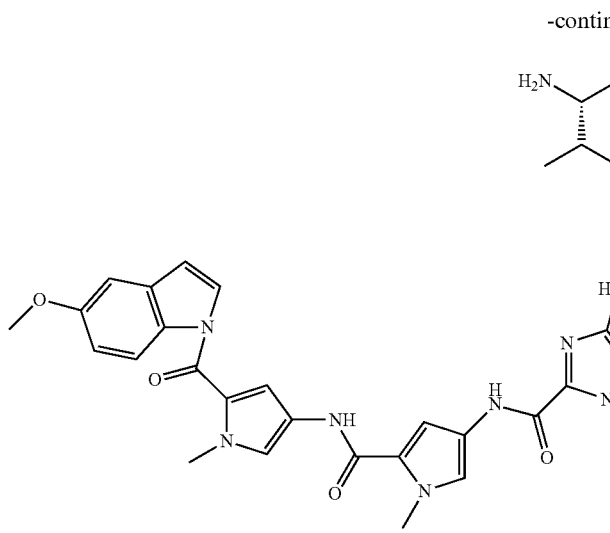

37

Part I →

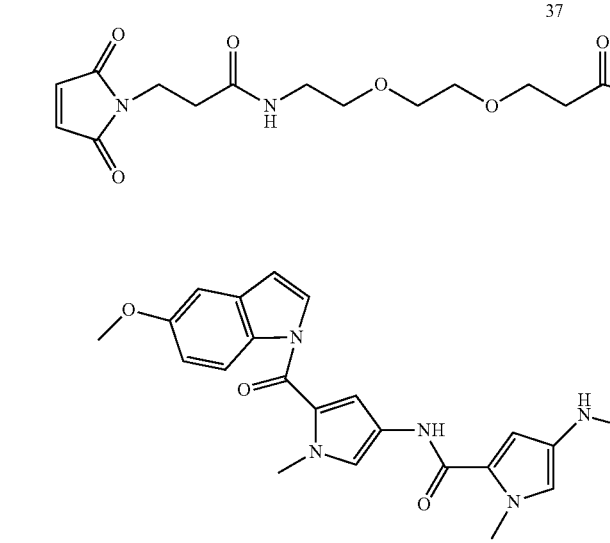
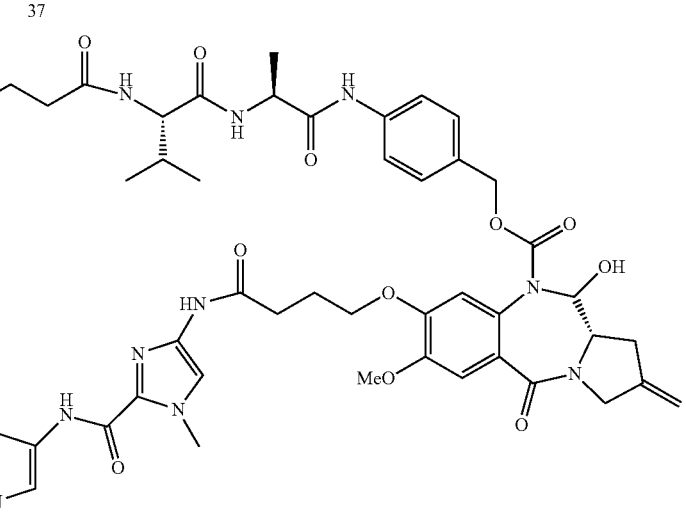

38

Part A:

To an ice-cold solution of tert-butyl (S)-2-(hydroxymethyl)-4-methylenepyrrolidine-1-carboxylate (1.24 g, 5.81 mmol; prepared as described in WO 2014/058538) and TEA (0.97 mL, 6.98 mmol) in dry DCM (10 mL) was slowly added a solution of acetyl chloride (0.498 mL, 6.98 mmol) in dry DCM (2 mL). The ice bath was removed and the mixture was stirred at room temperature for ~5 h until TLC indicated the reaction was complete. The reaction mixture was diluted to 30 mL with DCM and washed successively with 0.1 M HCl and brine. The organic phase was dried over MgSO$_4$, concentrated by rotary evaporation, followed by purified on silica gel (Hex:EtOAc, 0-40% B) to give tert-butyl (S)-2-(acetoxymethyl)-4-methylenepyrrolidine-1-carboxylate (30) as a colorless oil (1.24 g, 84% yield). $^1$H NMR (CDCl$_3$): δ 4.99 (2H, s), δ 4.28 (1H, bs), 4.16 (2H, dd), 4.11-3.90 (2, mH), 3.86 (1H, d), 2.73 (1H, bs), 2.55-2.28 (1H, m), 2.04 (3H, s), 1,47 (9H, s).

Part B:

To an ice-cold solution of compound 30 (1.2 g, 4.7 mmol) in dry DCM (5 mL) was added TFA (5 mL) under argon. The mixture was stirred at 0° C. for 3-4 hours and then concentrated by rotary evaporation. The oily residue was dissolved in acetonitrile and concentrated. The residue was resuspended in toluene and concentrated. The crude TFA salt was dried overnight under high vacuum and used without further purification in the next step.

In a separate flask, oxalyl chloride (2M in DCM, 3 mL, 6.13 mmol) was slowly added to an ice-cold solution a solution of 5-methoxy-4-(4-methoxy-4-oxobutoxy)-2-nitrobenzoic acid (1.48 g, 4.72 mmol; prepared according to procedure in *J. Med. Chem.*2006, 49, 5442-5461) in dry DCM (14 mL) followed by a few drops of dry DMF. The mixture was allowed to slowly reach room temperature while the reaction was monitored by quenching aliquots in MeOH and analyzing by LCMS. The crude reaction was stirred overnight at room temperature. Solvent was removed under vacuum and the residue was subjected to several cycles of dissolution/concentration in THF or toluene followed by final concentration under high vacuum (~45 min) to remove residual oxalyl chloride. The crude acid chloride was then dissolved in dry THF (14 mL) and added dropwise under argon to an ice-cold mixture of DIEA (2.44 g, 18.9 mmol) and the previously prepared crude TFA salt in dry THF (10 mL). The ice bath was removed and the mixture was allowed to reach room temperature. After 2 h LCMS indicated the reaction was complete. The reaction mixture was diluted with EtOAc (60 mL) and washed successively with water, 0.1 M HCl and brine. The organic phase was dried over MgSO$_4$ and concentrated under vacuum. The crude material was purified on silica gel (Hex:EtOAc, 0-90% B) to give methyl (S)-4-(4-(2-(acetoxymethyl)-4-methylenepyrrolidine-1-carbonyl)-2-methoxy-5-nitrophenoxy)butanoate (31) as a yellow oil (1.76 g, 83% yield). $^1$H NMR (CDCl$_3$): δ 7.70 (1H, s), 6.81 (1H, s), 5.13 (1H, d, J=11.4 Hz), 5.03 (1H, s), 4.90 (1H, s), 4.85-4.76 (1H, m), 4.62 (1H, d, J=16.8 Hz), 4.15 (2H, t, J=5.7 Hz), 3.97 (3H, s), 3.71 (3H, s), 2.92-2.76 (1H, m), 2.57 (2H, t, J=6.8 Hz), 2.27-2.18 (2H, m), 2.07 (3H, s). ESI-MS Calcd for C$_{21}$H$_{27}$N$_2$O$_9$, 451.17 (M+H); found, 451.1.

Part C:

To a solution of compound 31 in dry MeOH (35 mL) was added SnCl$_2$ and the mixture was stirred at reflux for ~3.5 h at which point TLC indicated the reaction was complete. The crude reaction mixture was added to ice-cold saturated aqueous solution of NaHCO$_3$ while stirring. After ~20 min EtOAc was added and the mixture was stirred ~40 min. The slurry was filtered through diatomaceous earth and the filtrate was allowed to separate into phases. The organic phase was dried over MgSO$_4$ and then concentrated by rotary evaporation. The crude residue was purified on silica gel (DCM:MeOH, 0-5% B) to give methyl (S)-4-(4-(2-(acetoxymethyl)-4-methylenepyrrolidine-1-carbonyl)-5-amino-2-methoxyphenoxy)butanoate (32) as a yellow oil (862 mg, 53% yield). $^1$H NMR (CDCl$_3$): δ 6.74 (1H, s), 6.27 (1H, s), 5.02 (1H, s), 4.97 (1H, s) 4.81 (1H, s), 4.29-4.08 (4H, m), 4.03 (3H, t, J=6.31 Hz), 3.79 (3H, s), 3.69 (3H, s), 2.84-2.72 (1H, m), 2.54 (2H, t, J=7.1 Hz), 2.46 (1H, d, J=15.8 Hz), 2.2-2.11 (2H, m), 2.04 (3H, s). ESI-MS Calcd for C$_{21}$H$_{29}$N$_2$O$_7$ 421.2 (M+H); found 421.2.

Part D:

To a solution of compound 32 (0.862 g, 2.1 mmol), DIEA (0.357 mL, 2.1 mmol), and HOAt (0.140 g, 1 mmol) in dry NMP (2 mL) was added allyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate (prepared by a modification of the procedure described in WO 2016038383A1) in ~4 mL NMP (~4 L). The mixture was stirred ~8.5 h at 50° C. and then overnight at room temperature. Additional allyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate was added (0.417 g) and the mixture was stirred at 50° C. for ~6 h. The reaction mixture was diluted with EtOAc (150 mL) and washed successively with 50 mL each of saturated aqueous NH$_4$Cl, water, saturated NaHCO$_3$ and brine. The organic layer was dried over MgSO$_4$ and concentrated. The crude material was purified on silica gel (DCM:MeOH, 0-7% B) to give methyl 4-(4-((S)-2-(acetoxymethyl)-4-methylenepyrrolidine-1-carbonyl)-5-(((((4-((S)-2-((S)-2-(((allyloxy)carbonyl)amino)-3-methylbutanamido)propanamido)benzyl)oxy)carbonyl)amino)-2-methoxyphenoxy)butanoate (33) as a semi-pure (~80%) colorless solid (1.41 g, 63% yield). ESI-MS Calcd for C$_{41}$H$_{54}$N$_5$O$_{13}$ 824.4 (M+H); found 824.2.

Part E:

To a solution of compound 33 in MeOH (13 mL) was added a solution of potassium carbonate in water (2 mL). The mixture was stirred 7.5 h at room temperature and then the solvent was removed under vacuum and the residue diluted with 0.1 M HCl (60 mL). The pH was adjusted to 1-2 with 1 M HCl and the mixture was extracted with EtOAc. The organic layer was dried over MgSO4 and concentrated. The crude product was purified by silica gel chromatography to give 4-(5-(((((4-((S)-2-((S)-2-(((allyloxy)carbonyl) amino)-3-methylbutanamido)propanamido)benzyl)oxy)carbonyl)amino)-4-((S)-2-(hydroxymethyl)-4-methylenepyrrolidine-1-carbonyl)-2-methoxyphenoxy)butanoic acid (34) as a colorless solid (0.540 g, 56% yield). $^1$H NMR (CD$_3$OD): δ 7.58 (2H, d, J=8.3 Hz), 7.34 (2H, d, 8.6 Hz), 7.18 (1H, s), 6.99 (1H, s), 6.0-5.86 (1H, m), 5.3 (H, d, J=17 Hz), 5.17 (1H, d, J=10.9 Hz), 5.09 (2H, s), 4.99 (H, bs), 4.9-4.87 (1H, bs, partially buried beneath solvent peak), 4.87-4.82 (1H buried beneath solvent peak), 4.63-4.53 (2H, m), 4.53-4.43 (2H, m), 4.12-4.0 (3H, m), 4.0-3.91 (2H, m), 3.83 (3H, s), 3.74-3.56 (1H, m), 2.79-2.54 (2H, m), 2.51 (2H, t, J=6.8 Hz), 2.13-2.0 (3H, m), 1.44 (3H, d, J=6.8 Hz), 1.0-0.91 (m, 6H, m). ESI-MS Calcd for C$_{38}$H50N$_5$O$_{12}$ 768.4 (M+H). Found 768.2.

Part F:

To a suspension of compound 34 (462 mg, 60.2 μmol) in DCM (5 mL) was added TEMPO (9.4 mg, 60 μmol), followed by BAIB (213 mg, 66.2 μmol). The reaction mixture quickly became homogenous and was stirred under argon overnight. The crude reaction mixture was adsorbed onto silica gel and purified on silica gel (DCM:MeOH, 0-15% B) to give 4-(((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)butanoic acid (35) as a colorless solid (355 mg, 77% yield). $^1$H NMR (DMSO-d$_6$): 12.17 (1H, s), 10.0 (1H, s), 8.16 (1H, t, J=7.1 Hz), 7.53 (2H, d, J=7.2 Hz), 7.31 (1H, bs), 7.27-7.21 (1H, m), 7.17 (2H, d, J=7.9 Hz), 7.05 (1H, s), 6.72 (1H, s), 6.60 (1H, bs), 5.99-5.82 (1H, m), 5.44-5.34 (1H, m), 5.30 (1H, d, J=16 Hz), 5.21-4.98 (4H, m), 4.83 (1H, d, J=11.9 Hz), 4.56-4.45 (2H, m), 4.45-4.34 (1H, m), 4.16-4.05 (1H, m), 4.02-3.85 (3H, m), 3.79 (3H, s), 3.45 (1H, t, J=8.5 Hz), 2.95-2.81 (1H, m), 2.58-2.50 (1H, m, partially buried in solvent peak), 2.44-2.30 (2H, m), 2.04-1.85 (3H, m), 1.30 (3H, d, J=6.9 Hz), 0.93-0.79 (6H, m). ESI-MS Calcd for C$_{38}$H$_{48}$N$_5$O$_{12}$ 766.3 (M+H); found 766.2.

Part G:

To a solution of compound 35 (40 mg, 0.052 mmol) in THF (04 mL) was added NMP (0.1 mL) followed by EDC (9.73 mg, 0.063 mmol). The mixture was stirred ~5 min before the addition of a mixture of 4-amino-N-(5-(5-(5-methoxy-1H-indole-1-carbonyl)-1-methyl-1H-pyrrol-3-yl-carbamoyl)-1-methyl-1H-pyrrol-3-yl)-1-methyl-1H-imidazole-2-carboxamide (28.8 mg, 0.052 mmol, prepared as described in Example 7), DIEA (19 μL, 0.125 mmol), and DMAP (6.4 mg, 0.052 mmol) in NMP (0.2 mL). The reaction mixture was stirred overnight at room temperature. The reaction mixture was diluted with EtOAc (90 mL) and then washed successively with 30 mL each of saturated NH$_4$Cl, water, and brine. The organic phase was dried over MgSO$_4$, concentrated and purified on silica gel (DCM:MeOH, 0-15% B) to give 4-((S)-2-((S)-2-(((allyloxy)carbonyl)amino)-3-methylbutanamido)propanamido)benzyl (11S,11aS)-11-hydroxy-7-methoxy-8-(4-((2-((5-((5-(5-methoxy-1H-indole-1-carbonyl)-1-methyl-1H-pyrrol-3-yl)carbamoyl)-1-methyl-1H-pyrrol-3-yl)carbamoyl)-1-methyl-1H-imidazol-4-yl)amino)-4-oxobutoxy)-2-methylene-5-oxo-2,3,11,11a-tetrahydro-1H-benzo[e]pyrrolo[1,2-a][1,4]diazepine-10(5H)-carboxylate (36) as a yellow solid (17.4 mg, 57%). ESI-MS Calcd for C$_{64}$H$_{72}$N$_{13}$O$_{15}$ 1262.5 (M+H); found 1262.0.

Part H:

To a solution of compound 36 (17 mg, 0.013 mmol) in dry THF (0.75 mL, previously degassed by bubbling argon through the THF for 5-10 min) was added triphenylphosphine (0.88 mg, 3 µmol) and pyrrolidine (1.2 mg, 17 µmol) and the mixture was stirred for ~5 min. To this mixture was added tetrakistriphenylphosphine palladium (0.8 mg, 0.7 µmol) and the reaction mixture was stir at room temperature under argon while monitoring by LCMS. After ~2 h more triphenylphosphine (0.25 equiv), pyrrolidine (1.25 equiv), and tetrakistriphenylphosphine palladium (0.05 equiv) were added. After 5 h the reaction mixture was concentrated under vacuum followed by purified by silica gel chromatography (DCM:MeOH containing 0.5% TEA in both mobile phase A and B (gradient=0-10% B)) to give 4-((S)-2-((S)-2-amino-3-methylbutanamido)propanamido)benzyl (11S,11aS)-11-hydroxy-7-methoxy-8-(4-((2-((5-((5-(5-methoxy-1H-indole-1-carbonyl)-1-methyl-1H-pyrrol-3-ylcarbamoyl)-1-methyl-1H-pyrrol-3-ylcarbamoyl)-1-methyl-1H-imidazol-4-ylamino)-4-oxobutoxy)-2-methylene-5-oxo-2,3,11,11a-tetrahydro-1H-benzo[e]pyrrolo[1,2-a][1,4]diazepine-10 (5H)-carboxylate (38) as a colorless solid (3.2 mg, 15% yield for two steps starting from compound 37). ESI-MS Calcd for $C_{74}H_{86}N_{15}O_{19}$ $_{1488.6}$ (M+H); found 1487.8.

Example 15

Preparation of Trastuzumab Conjugate of Compound 38 (39)

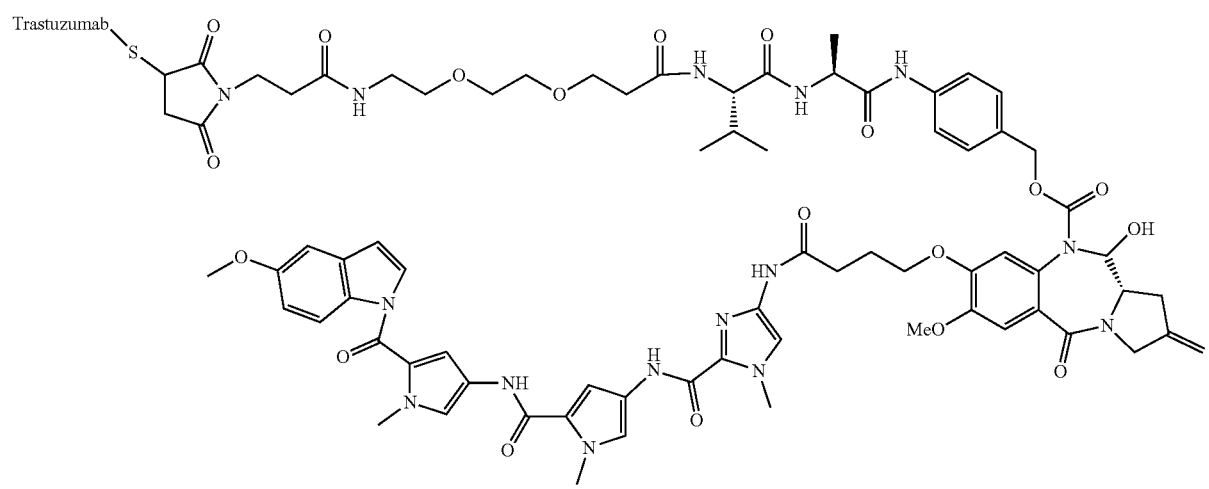

39 dole-1-carbonyl)-1-methyl-1H-pyrrol-3-yl)carbamoyl)-1-methyl-1H-pyrrol-3-yl)carbamoyl)-1-methyl-1H-imidazol-4-yl)amino)-4-oxobutoxy)-2-methylene-5-oxo-2,3,11,11a-tetrahydro-1H-benzo[e]pyrrolo[1,2-a][1,4]diazepine-10 (5H)-carboxylate (37) in a semi-pure form. This material was used in the next step (see Part I) without further purification. ESI-MS Calcd for $C_{60}H_{68}N_{13}O_{13}$ 1178.5 (M+H); found 1178.0.

Part I:

To a solution of compound 37 (~16 mg, 14 µmol) in dry (~1 mL) was added HOBt (3.7 mg, 27 µmol), 2,5-dioxopyrrolidin-1-yl 3-(2-(2-(3-(2,5-dioxo-2,5-dihydro-1H-pyrrol-1-yl)propanamido)ethoxy)ethoxy)propanoate (11.6 mg, 27 µmol) and triethylamine (2.1 µL, 15 mol). The mixture was stirred for ~1.5 h at room temperature at which point LCMS indicated that the reaction was complete. The reaction mixture was then purified by preparative HPLC (water:ACN both containing 0.1% formic acid; gradient: 10-90% over 25

To a solution of Trastuzumab (20 mg, 0.135 µmol), in TEAA buffer (50 mM, 1 mM EDTA, pH 7, 2 mL) was added a solution of TCEP (0.087 mg, 0.304 µmol) and the resulting mixture was incubated for 1 h at 37° C. The reaction mixture was allowed to cool to room temperature and then diluted with TEAA buffer (1 mL) and propylene glycol (0.7 mL). A solution of compound 38 (prepared as described in Example 13) in 0.435 mL ACN/propylene glycol (7:3) was then slowly added while vigorous stirring the reaction mixture. The reaction mixture was stirred at room temperature for ~1 h before quenching with cysteine (0.344 mg, 2.84 mol, 21.5 µL of 16.4 mg/mL stock in TEAA buffer) over ~1 h. The crude product was purified by SEC (Biosep SEC 3000, pH 5.5, 50 mM sodium phosphate, 300 mM NaCl) followed by buffer exchange into formulation buffer (25 mM citrate, 75 mM NaCl, 50 mg/mL trehalose, pH 5.5) to give the conjugate (8.1 mg, 41% yield). The purified conjugate had a PBD to trastuzumab ratio was of 4.9 (by UV-Vis using molar extinction $\varepsilon_{320\ nm}$=28,013 cm$^{-1}$M$^{-1}$ and $\varepsilon_{280\ nm}$=24,217 cm$^{-1}$M$^{-1}$ for compound 38 and $\varepsilon_{280\ nm}$=226,107 cm$^{-1}$M$^{-1}$ for trastuzumab.

Example 16

Synthesis of (11S,11aS)-4-((2S,5S)-19-(2,5-dioxo-2,5-dihydro-1H-pyrrol-1-yl)-5-isopropyl-2-methyl-4,7,17-trioxo-10,13-dioxa-3,6,16-triazanonadecanamido)benzyl 11-hydroxy-7-methoxy-8-(4-(2-(5-(5-(methoxycarbonyl)-1H-indole-1-carbonyl)-1-methyl-1H-pyrrol-3-ylcarbamoyl)-1-methyl-1H-pyrrol-3-ylcarbamoyl)-1-methyl-1H-imidazol-4-ylamino)-4-oxobutoxy)-2-methylene-5-oxo-2,3,11,11a-tetrahydro-1H-benzo[e]pyrrolo[1,2-a][1,4]diazepine-10(5H)-carboxylate (40)

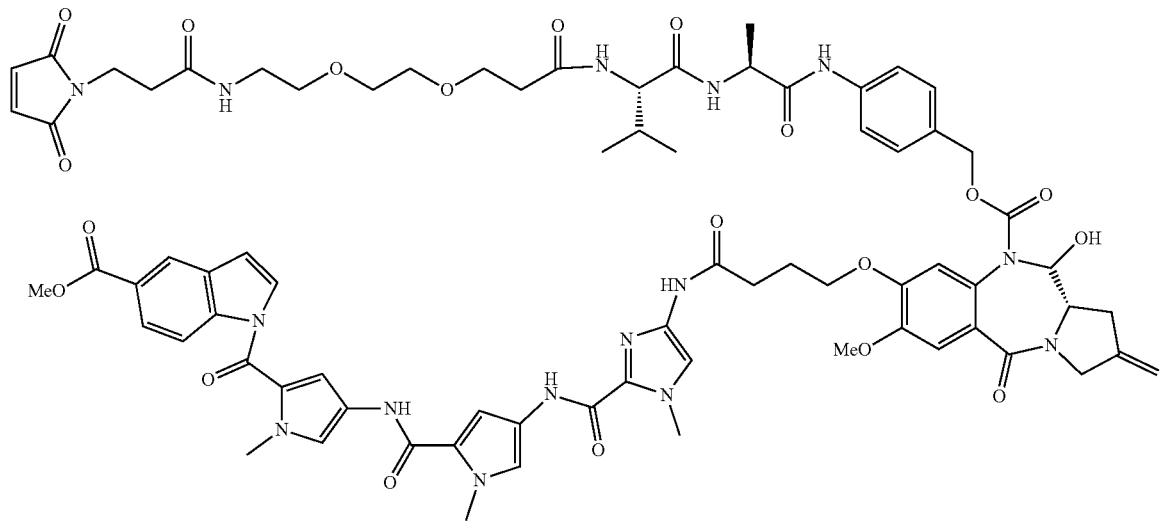

40

The title compound was prepared using the procedure described in Example 14 except that 2-(5-(5-(5-(methoxycarbonyl)-1H-indole-1-carbonyl)-1-methyl-1H-pyrrol-3-ylcarbamoyl)-1-methyl-1H-pyrrol-3-ylcarbamoyl)-1-methyl-1H-imidazole-2-carboxamide (prepared as described in Example 8) was used instead of 4-amino-N-(5-(5-(5-methoxy-1H-indole-1-carbnoyl)-1-methyl-H-pyrrol-3-yl-carbamoyl)-1-methyl-1H-pyrrol-3-y)-1-methyl-1H-imidazole-2-carboxamide in Part G.

Example 17

Preparation of Trastuzumab Conjugate of Compound 40 (41)

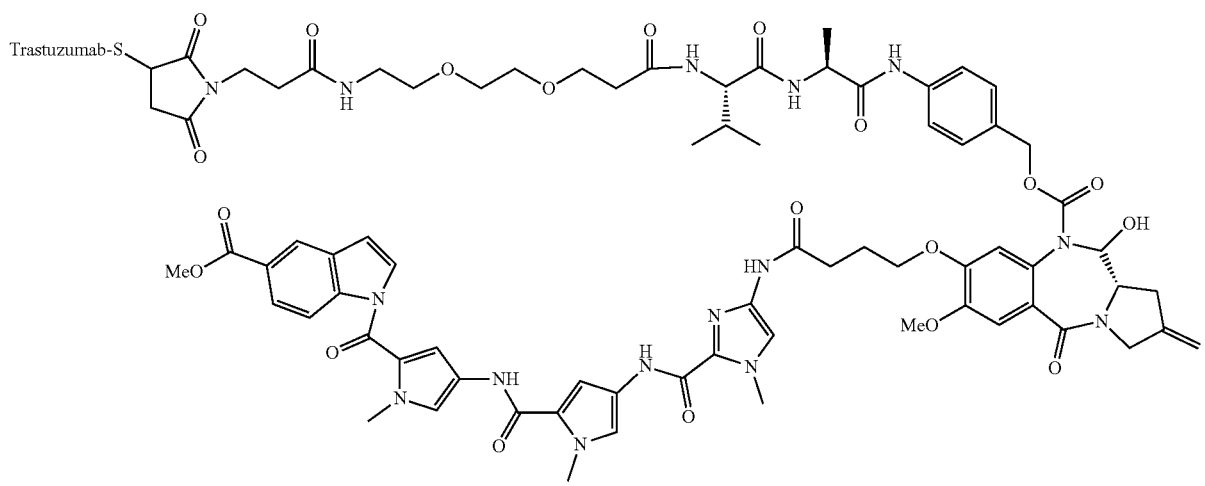

41

The title conjugate was prepared using the procedure described in Example 15 except that compound 40 was used instead of compound 38. The purified conjugate had a PBD to trastuzumab ratio was of 5.8 (by UV-Vis using molar extinction $\varepsilon_{320\ nm}$=37,404 cm$^{-1}$M$^{-1}$ and $\varepsilon_{280\ nm}$=37,028 cm$^{-1}$M$^{-1}$ for compound 38 and $\varepsilon_{280\ nm}$=226,107 cm$^{-1}$M$^{-1}$ for trastuzumab).

Example 18

Synthesis of (11S,11aS)-4-((2S,5S)-19-(2,5-dioxo-2,5-dihydro-1H-pyrrol-1-yl)-5-isopropyl-2-methyl-4,7,17-trioxo-10,13-dioxa-3,6,16-triazanonadecanamido)benzyl 11-hydroxy-7-methoxy-8-(4-(1-methyl-2-(1-methyl-5-(1-methyl-5-(5-(methylthio)-1H-indole-1-carbonyl)-1H-pyrrol-3-ylcarbamoyl)-1H-pyrrol-3-ylcarbamoyl)-1H-imidazol-4-ylamino)-4-oxobutoxy)-2-methylene-5-oxo-2,3,11,11a-tetrahydro-1H-benzo[e]pyrrolo[1,2-a][1,4]diazepine-10(5H)-carboxylate (42)

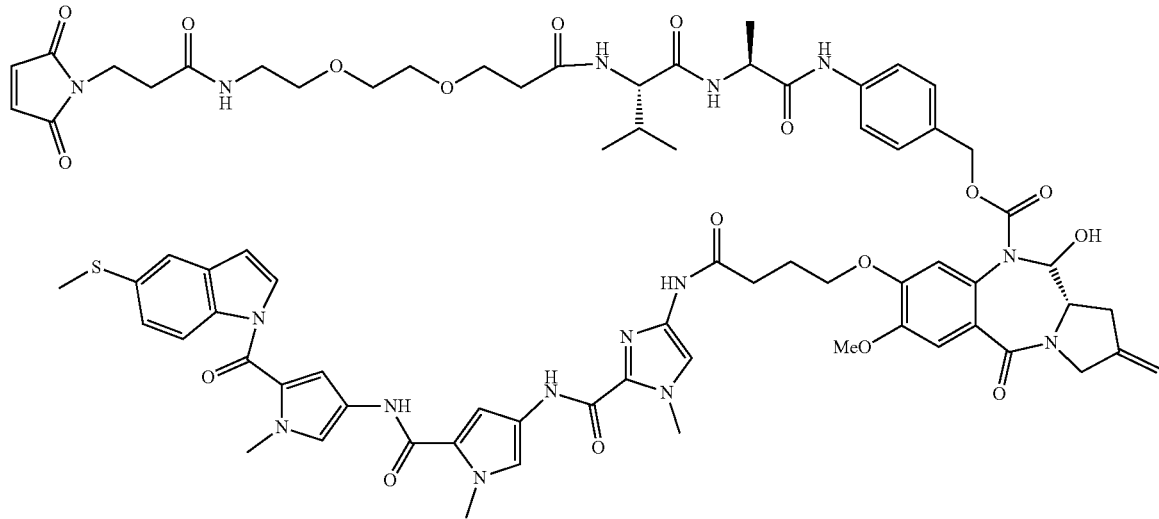

42

The title compound was prepared using the procedure described in Example 14 except that 1-methyl-2-(1-methyl-5-(1-methyl-5-(5-(methylthio)-1H-indole-1-carbonyl)-1H-pyrrol-3-ylcarbamoyl)-1H-pyrrol-3-ylcarbamoyl)-1H-imidazole-2-carboxamide (prepared as described in Example 9) was used instead of 4-amino-N-(5-(5-(5-methoxy-1H-indole-1-carbonyl)-1-methyl-1H-pyrrol-3-ylcarbamoyl)-1-methyl-1H-pyrrol-3-yl)-1-methyl-1H-imidazole-2-carboxamide in Part G.

Example 19

Preparation of Trastuzumab Conjugate of Compound 42 (43)

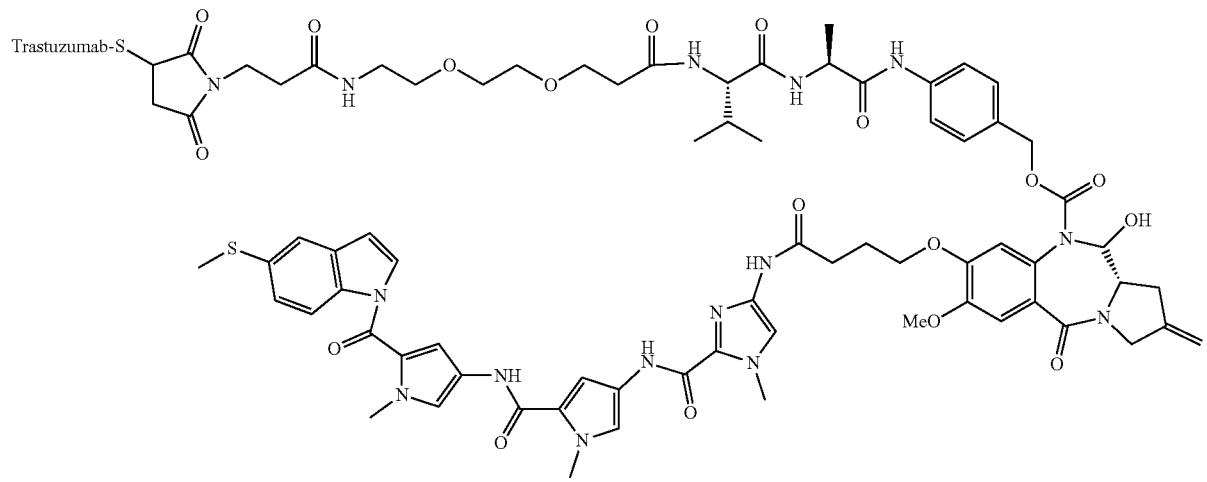

43

The title conjugate was prepared using the procedure described in Example 15 except that compound 42 was used instead of compound 38. The purified conjugate had a PBD to trastuzumab ratio was of 4.3 (by UV-Vis using molar extinction $\varepsilon_{320\ nm}=38,978$ cm$^{-1}$M$^{-1}$ and $\varepsilon_{280\ nm}=34,095$ cm$^{-1}$M$^{-1}$ for compound 42 and $\varepsilon_{8280\ nm}=226,107$ cm$^{-1}$M$^{-1}$ for trastuzumab).

Example 20

Synthesis of N-(5-((5-(5-((2S,5S)-19-(2,5-dioxo-2,5-dihydro-1H-pyrrol-1-yl)-5-isopropyl-2-methyl-4,7,17-trioxo-10,13-dioxa-3,6,16-triazanonadecanamido)-1H-indole-1-carbonyl)-1-methyl-1H-pyrrol-3-yl)carbamoyl)-1-methyl-1H-pyrrol-3-yl)-4-(4-(((S)-7-methoxy-2-methylene-5-oxo-2,3,5,11a-tetrahydro-1H-benzo[e]pyrrolo[1,2-a][1,4]diazepin-8-yl)oxy)butanamido)-1-methyl-1H-imidazole-2-carboxamide (46)

Part A:
To the solution of compound 8 (21.23 mg, 0.026 mmol, prepared as described in Example 1) in THF (1 mL) and DMA (0.2 ml) were added (S)-2-((S)-2-(allyloxycarbonylamino)-3-methylbutanamido)propanoic acid (7 mg, 0.026 mmol) and EEDQ (7.63 mg, 0.031 mmol). The resulting solution was stirred at room temperature for 18 h. LC-MS showed the completion of the reaction. The crude product was purified on Silica Gel (0-15% MeOH/DCM) to give allyl ((S)-1-(((S)-1-((1-(4-(4-(4-(4-(((S)-7-methoxy-2-methylene-5-oxo-2,3,5,11a-tetrahydro-1H-benzo[e]pyrrolo[1,2-a][1,4]diazepin-8-yl)oxy)butanamido)-1-methyl-1H-imidazole-2-carboxamido)-1-methyl-1H-pyrrole-2-carboxamido)-1-methyl-1H-pyrrole-2-carbonyl)-1H-indol-5-yl)amino)-1-oxopropan-2-yl)amino)-3-methyl-1-oxobutan-2-yl)carbamate (44) (22 mg, 0.02 mmol, 79% yield). ESI MS: C$_{55}$H$_{61}$N$_{13}$O$_{11}$ (M+H) 1080.5; found 1080.2.

Part B:
To the solution of compound 44 (22 mg, 0.02 mmol) in DCM (1 mL) was added tetrakis(triphenylphosphine)palla-

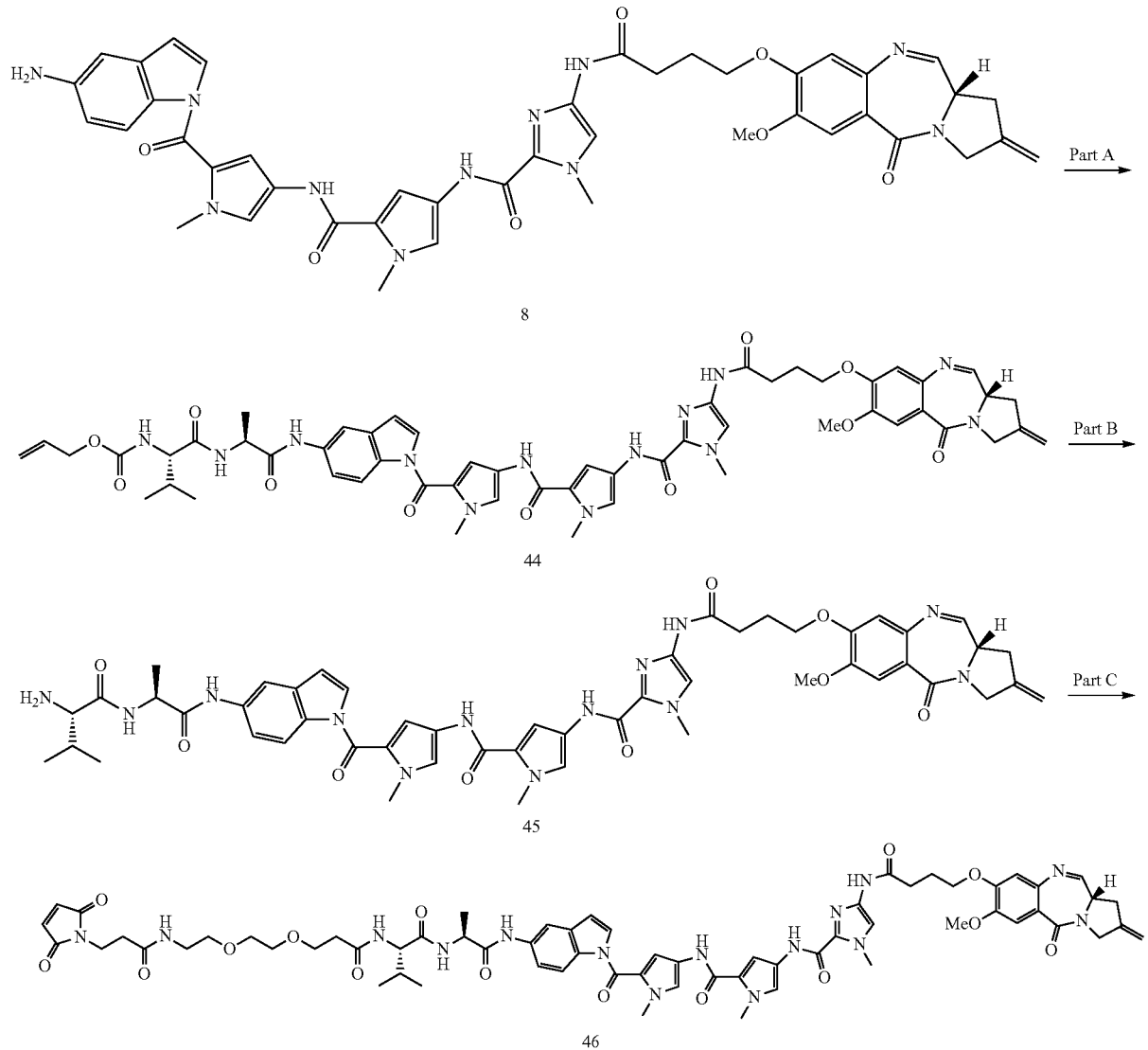

dium(0) (23.54 mg, 0.02 mmol) and 1,4-diazabicyclo[2.2.2]octane (11.42 mg, 0.102 mmol). The resulting solution was stirred at room temperature for 1 h under argon. The reaction mixture was concentrated and the crude product purified on Silica Gel (0-15% MeOH/DCM) to give N-(5-((5-(5-((S)-2-((S)-2-amino-3-methylbutanamido)propanamido)-1H-indole-1-carbonyl)-1-methyl-1H-pyrrol-3-yl)carbamoyl)-1-methyl-1H-pyrrol-3-yl)-4-(4-(((S)-7-methoxy-2-methylene-5-oxo-2,3,5,11a-tetrahydro-1H-benzo[e]pyrrolo[1,2-a][1,4]diazepin-8-yl)oxy)butanamido)-1-methyl-1H-imidazole-2-carboxamide (45) (6 mg, 6.02 µmol, 29.6% yield). ESI MS: $C_{51}H_{57}N_{13}O_9$ (M+H) 996.4; found 996.2.

Part C:

To a solution of compound 45 (6 mg, 6.02 µmol) in DMF (0.5 ml) was added HOBt (0.298 mg, 2.209 µmol), 2,5-dioxopyrrolidin-1-yl 3-(2-(2-(3-(2,5-dioxo-2,5-dihydro-1H-pyrrol-1-yl)propanamido)ethoxy)ethoxy)propanoate (0.940 mg, 2.209 µmol) and triethylamine (0.308 µl, 2.209 µmol). The mixture was stirred 16 hr at room temp. LC-MS showed the completion of the reaction. The solvent was removed and the crude product purified by HPLC (0.1 N formic Acid 10-90% ACN/Water) to give N-(5-((5-(5-((2S,5S)-19-(2,5-dioxo-2,5-dihydro-1H-pyrrol-1-yl)-5-isopropyl-2-methyl-4,7,17-trioxo-10,13-dioxa-3,6,16-triazanonadecanamido)-1H-indole-1-carbonyl)-1-methyl-1H-pyrrol-3-yl)carbamoyl)-1-methyl-1H-pyrrol-3-yl)-4-(4-(((S)-7-methoxy-2-methylene-5-oxo-2,3,5,11a-tetrahydro-1H-benzo[e]pyrrolo[1,2-a][1,4]diazepin-8-yl)oxy)butanamido)-1-methyl-1H-imidazole-2-carboxamide (46) (1 mg, 0.765 µmol, 38.1% yield). ESI MS: $C_{65}H_{75}N_{15}O_{15}$ (M+H) 1306.6; found 1306.6.

Example 21

Preparation of Trastuzumab Conjugate of Compound 46 (47)

47

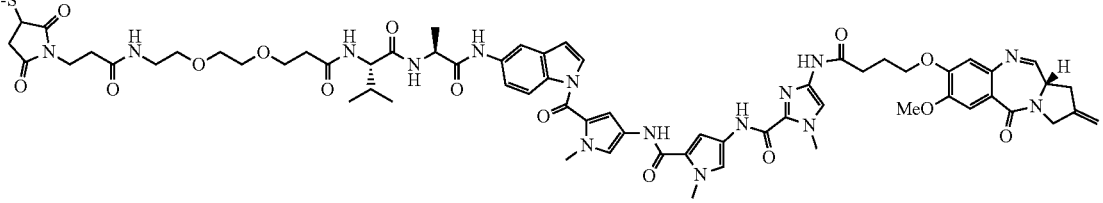

The title conjugate was prepared using the procedure described in Example 15 except that compound 46 was used instead of compound 38. The purified conjugate had a PBD to trastuzumab ratio of 3.3 (by UV-Vis using molar extinction $\varepsilon_{322\ nm}=38{,}072\ cm^{-1}M^{-1}$ and $\varepsilon_{280\ nm}=34{,}191\ cm^{-1}M^{-1}$ for compound 46 and $\varepsilon_{280\ nm}=226{,}107\ cm^{-1}M^{-1}$ for trastuzumab).

Example 21A

Preparation of Sulfite Derivative of Conjugate 47 (47A)

47A

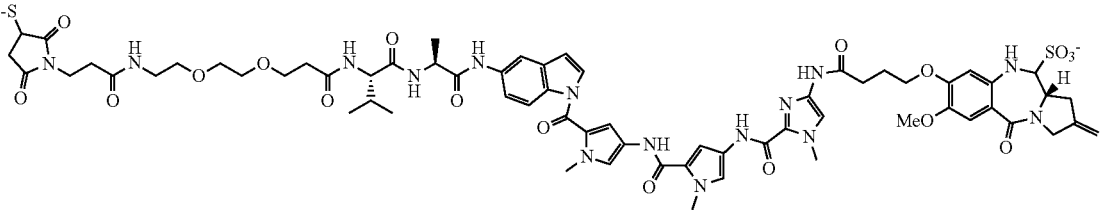

The title conjugate was prepared using the procedure described in Example 15 except that after 1 h reaction with the reduced protein, the crude conjugate was treated with sodium bisulfite (5 equiv per drug) over ~2 h. The crude reaction mixture was centrifuged to precipitate insoluble material, decanted and then purified by WCX (Mobile phase A: 20 mM MES, pH 5.8; Mobile phase B: 20 mM MES, 300 mM NaCl, pH 5.8; gradient: 20-50% B over 32 min). The purified conjugate was buffer exchanged into bisulfite formulation buffer (50 µM sodium bisulfite, 25 mM citrate, 75 mM NaCl, 50 mg/mL trehalose, pH 5.5). The purified conjugate had a PBD to trastuzumab ratio of 4.7 (by UV-Vis using molar extinction $\varepsilon_{322\ nm}$=38,072 cm$^{-1}$M$^{-1}$ and $\varepsilon_{280\ nm}$=34,191 cm$^{-1}$M$^{-1}$ for compound 46 and $\varepsilon_{280\ nm}$=226,107 cm$^{-1}$M$^{-1}$ for trastuzumab).

Example 22

Synthesis of (S,Z)—N-(5-(5-(6-amino-1H-indole-1-carbonyl)-1-methyl-1H-pyrrol-3-ylcarbamoyl)-1-methyl-1H-pyrrol-3-yl)-2-(4-(7-methoxy-2-methylene-5-oxo-2,3,5,11a-tetrahydro-1H-benzo[e]pyrrolo[1,2-a][1,4]diazepin-8-yloxy)butanamido)thiazole-4-carboxamide (48)

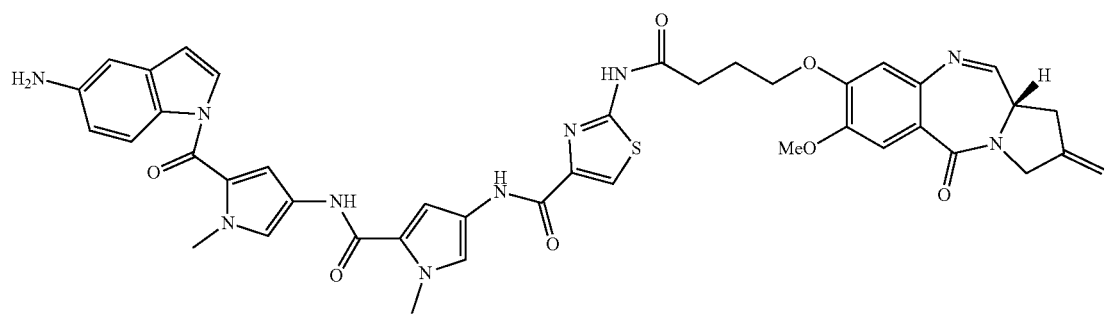

48

The title compound (48) was prepared as described in Example 1 except 4-(2-(tert-butoxycarbonylamino)thiazole-4-carboxamido)-1-methyl-1H-pyrrole-2-carboxylic acid (100 mg, 0.273 mmol) was used instead of 4-(4-(tert-butoxycarbonylamino)-1-methyl-1H-imidazole-2-carboxamido)-1-methyl-1H-pyrrole-2-carboxylic acid. ESI MS: C42H40N10O7S (M+H) 829.3; found 828.7.

Example 23

Synthesis of (S,Z)-4-(4-(4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamido)-1-methyl-1H-pyrrole-2-carboxamido)-1-methyl-1H-pyrrole-2-carboxylic Acid (51)

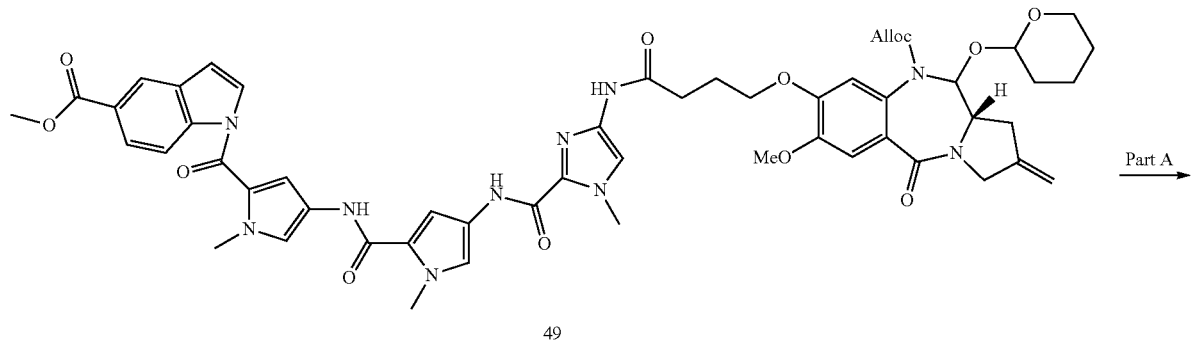

49

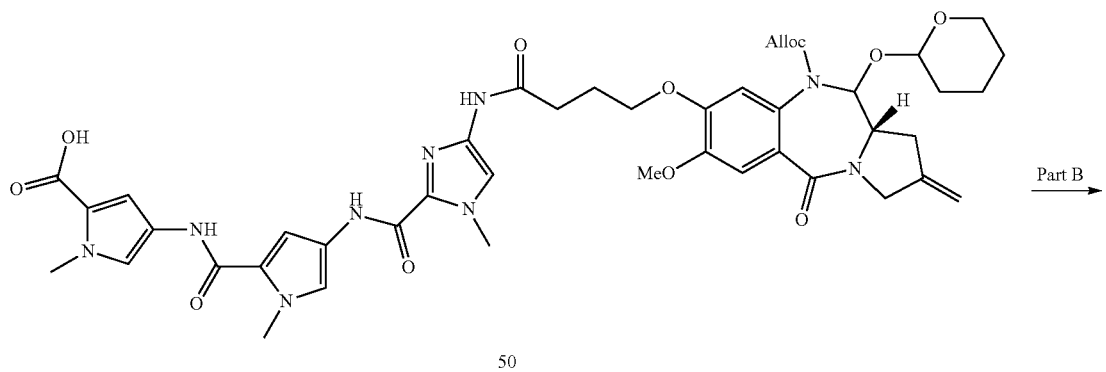

50

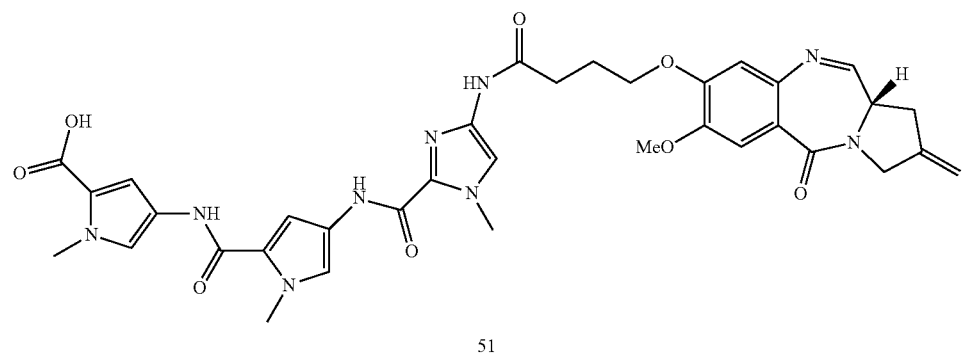

51

Part A:

To a solution of compound 49 (10 mg, 9.48 µmol) in 1,4-dioxane (1 mL) was added sodium hydroxide (0.095 ml, 0.095 mmol). The resulting solution was stirred at room temperature for 2 h. LC-MS showed the completion of the reaction. The crude product was purified on ISCO column (0-15% MeOH/DCM) to give 4-(4-(4-(4-(((11 aS)-10-((allyloxy)carbonyl)-7-methoxy-2-methylene-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)butanamido)-1-methyl-1H-imidazole-2-carboxamido)-1-methyl-1H-pyrrole-2-carboxamido)-1-methyl-1H-pyrrole-2-carboxylic acid (50) (4.6 mg, 5.12 µmol, 53.9% yield). ESI MS: $C_{44}H_{51}N_9O_{12}$ (M+H) 898.4 found 898.2

Part B:

The title compound (51) was prepared using the procedure described in Part G in Example 1. ESI MS: $C_{35}H_{37}N_9O_6$ (M+H) 712.3; found 711.9.

Example 24

(R,Z)-N-(3-hydroxypropyl)-4-(4-(4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-pyrrole-2-carboxamido)-1-methyl-1H-pyrrole-2-carboxamido)-1-methyl-1H-pyrrole-2-carboxamide (55)

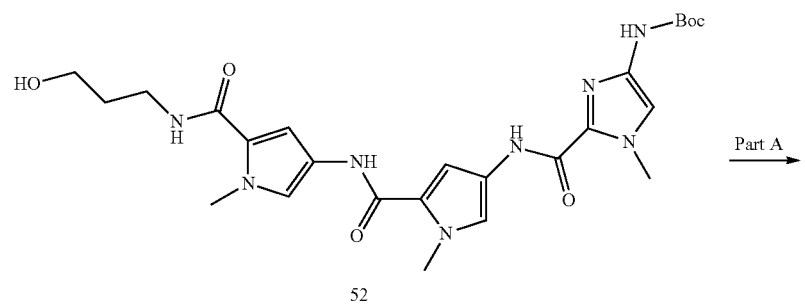

52

-continued

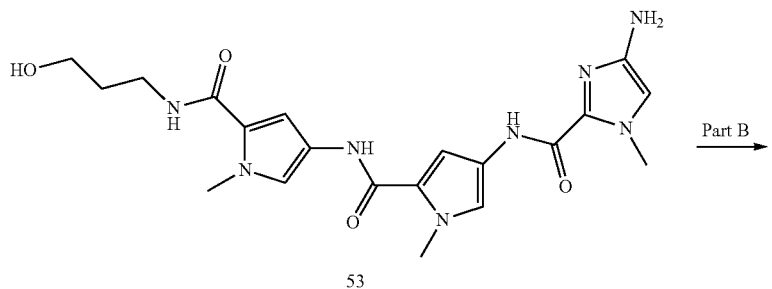

53

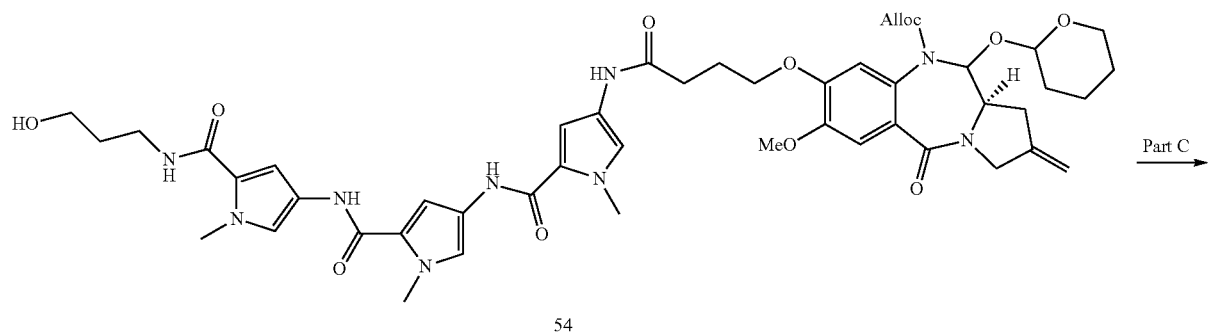

54

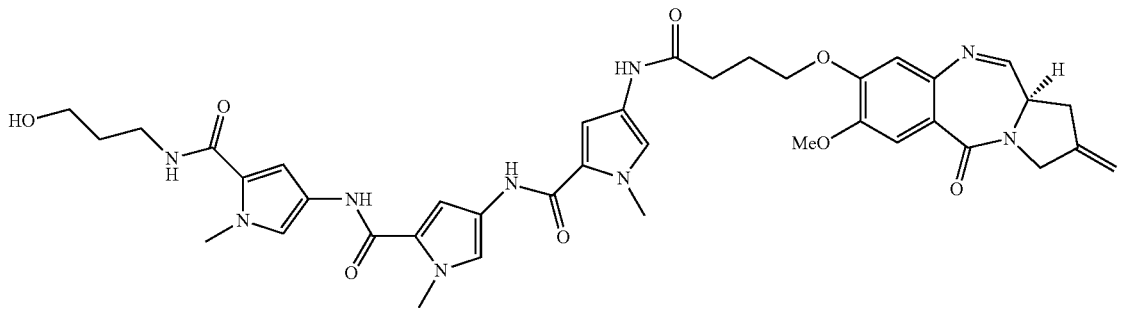

55

Part A:

To solution of compound 52 (140 mg, 0.258 mmol) in MeOH (3 ml) at 0° C. was added 4N HCl in dioxane (3 mL, 12 mmol) and the resulting mixture was stirred for 1 h then allowed to warm to room temperature. The reaction was monitored by LC/MS and was complete after 16 h. The reaction mixture was concentrated by rotary evaporation followed by high vacuum pumping to obtain compound 53 as a HCl salt in quantitative yield. ESI MS: $C_{21}H_{27}N_7O_4$ (M=H) 442.5; found 442.1.

Part B:

4-(((11aR)-10-((allyloxy)carbonyl)-7-methoxy-2-methylene-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)butanoic acid (132 mg, 0.249 mmol), EDC (95 mg, 0.498 mmol) and DMAP (76 mg, 0.622 mmol) in DMF (2 ml) were stirred for 30 minute at room temperature. To the resulting mixture was added compound 53 (110 mg, 0.249 mmol). The reaction was monitored by LC/MS. After 2 h the reaction was complete and the mixture was poured into ice water, the organic layer was washed with EtOAc, dilute NaHCO$_3$, dried over Na$_2$SO$_4$ and concentrated. The residue was purified by silica gel chromatography using DCM/MeOH as mobile phase with a 5-20% MeOH gradient to give the title compound (54) as an amber glassy solid (121 mg, 51% yield). ESI MS: $C_{48}H_{59}N_9O_{12}$ (M+H) 955; found 954.2.

Part C:

To a solution of compound 54 (60 mg, 0.063 mmol) in DCM (5 mL) at room temperature under argon was added triphenylphosphine (4.12 mg, 0.016 mmol) and pyrrolidine (6.24 µl, 0.075 mmol) and stirred at room temperature for 10 min. To this was added tetrakis(triphenylphosphine)palladium(0) (3.63 mg, 3.14 µmol) and the solution was allowed to stir at room temperature for 2 h. LC-MS showed the completion of the reaction. The solvent was removed by rotary evaporation and the residue purified by reversed phase chromatography using an acetonitrile/water gradient buffered with 0.1% formic acid to give the title compound (55) as an amorphous solid (22 mg, 45% yield). ESI MS: $C_{39}H_{45}N_9O_8$ (M+H) 767.8; found 768.1.

Example 25

Synthesis of (S,Z)—N-(5-(5-(3-hydroxypropylcarbamoyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (56)

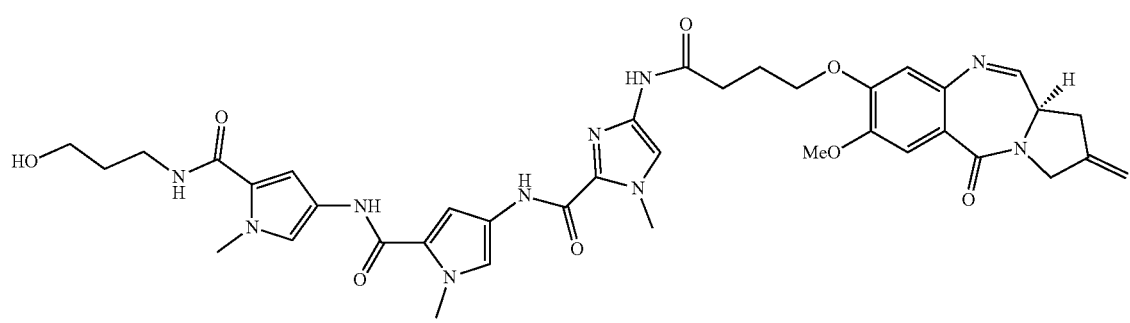

56

The title compound was prepared using the procedure in Example 24 except tert-butyl (2-((5-((5-((3-hydroxypropyl)carbamoyl)-1-methyl-1H-pyrrol-3-yl)carbamoyl)-1-methyl-1H-pyrrol-3-yl)carbamoyl)-1-methyl-1H-imidazol-4-yl)carbamate was used instead of tert-butyl (5-((5-((5-((3-hydroxypropyl)carbamoyl)-1-methyl-1H-pyrrol-3-yl)carbamoyl)-1-methyl-1H-pyrrol-3-yl)carbamoyl)-1-methyl-1H-pyrrol-3-yl)carbamate to give 21 mg, 74.5% yield ESI MS: $C_{38}H_{44}N_{10}O_8$ (M+H) 769.8; found 769.2.

Example 26

(R)-3-(4-(4-(4-(4-((S,Z)-7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamido)phenyl)-1-methyl-1H-pyrrole-2-carboxamido)propyl 16-(2,5-dioxo-2,5-dihydro-1H-pyrrol-1-yl)-2-isopropyl-4,14-dioxo-7,10-dioxa-3,13-diazahexadecan-1-oate

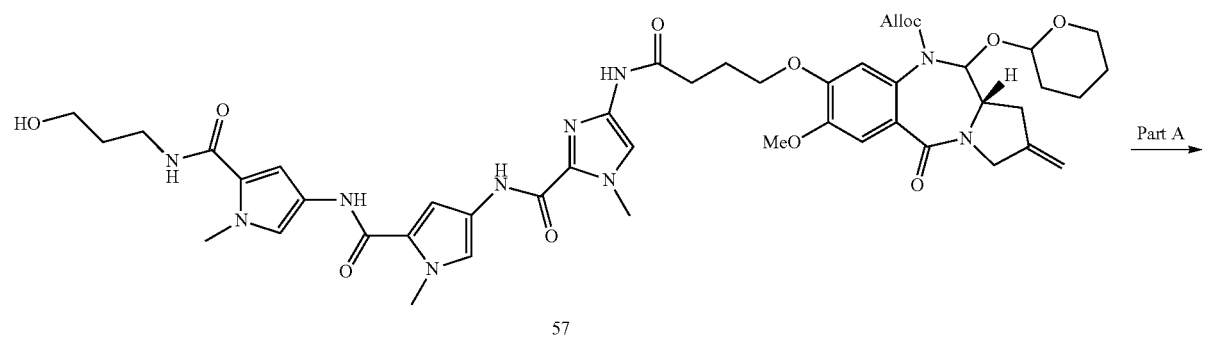

57

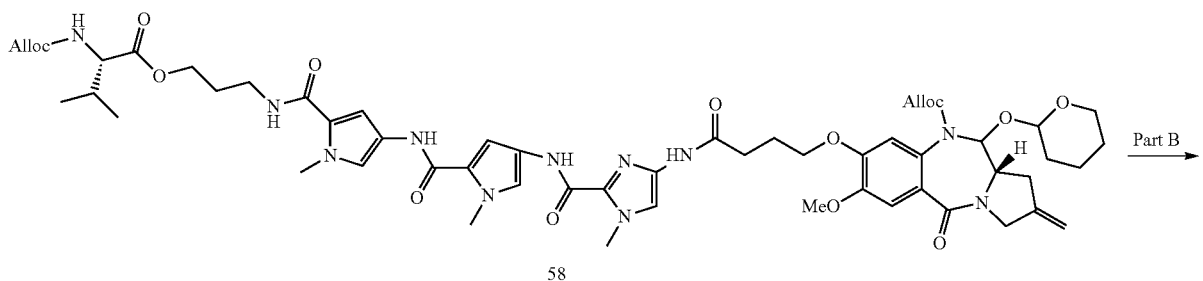

58

-continued

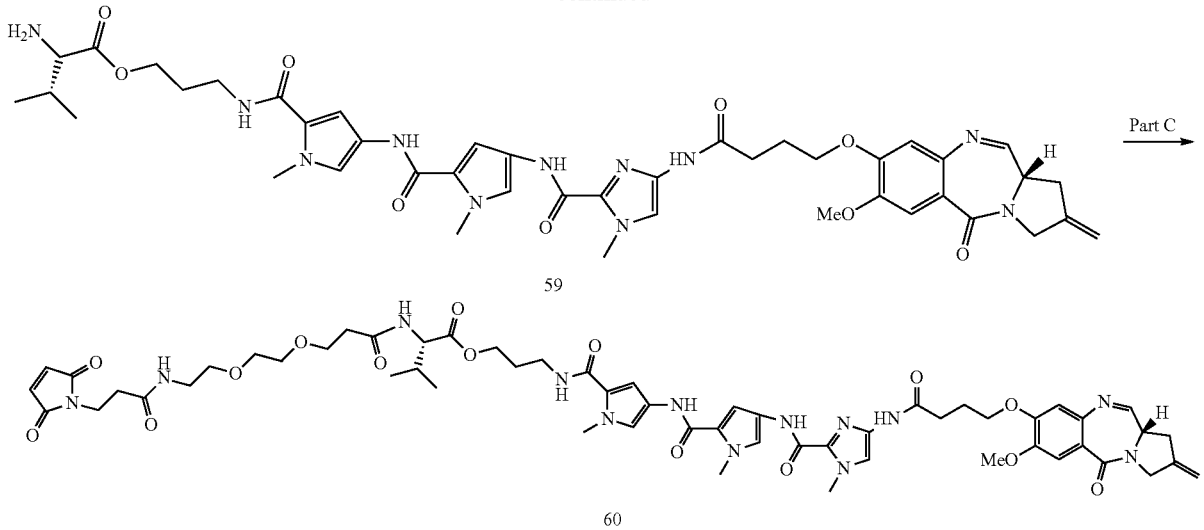

59

60

Part A:

To a solution of (R)-2-(((allyloxy)carbonyl)amino)-3-methylbutanoic acid (33.2 mg, 0.165 mmol) in DCM (2 mL) at 0° C. was added DIC (0.051 mL, 0.33 mmol) and the resulting mixture was stirred for 15 minutes and then added to compound 57 (150 mg, 0.165 mmol) and DMAP (60.5 mg, 0.495 mmol). The resulting mixture was stirred to room temperature for 2 h. A second aliquot of (R)-2-(((allyloxy)carbonyl)amino)-3-methylbutanoic acid was added and the stirring continued for an additional 2 h. LC/MS showed the reaction was essentially complete. The reaction mixture was diluted with EtOAc, the organic layer was washed with NaHCO$_3$, brine, dried over Na$_2$SO$_4$ and concentrated. The residue was purified by silica gel chromatography using 0-10% MeOH in DCM as eluent to give (11aS)-allyl 8-(4-((2-((5-((5-(((R)-2-(((allyloxy)carbonyl)amino)-3-methylbutanoyl)oxy)propyl)carbamoyl)-1-methyl-1H-pyrrol-3-yl)carbamoyl)-1-methyl-1H-pyrrol-3-yl)carbamoyl)-1-methyl-1H-imidazol-4-yl)amino)-4-oxobutoxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate (58) as a solid (40 mg, 67% yield). ESI MS: C$_{56}$H$_{71}$N$_{11}$O$_{15}$ (M+H) 1139.2; found 1139.8.

Part B:

The title compound was prepared from compound 58 using the procedure described in Example 24, Part C to give compound 59 (22 mg, 72% yield). ESI MS: C$_{43}$H$_{53}$N$_{11}$O$_9$ (M+H) 868.9; found 868.3.

Part C:

The title compound was prepared from compound 59 using the procedure described in Example 14, Part I to give compound 60 (R)-3-(4-(4-(4-(4-(((S)-7-methoxy-2-methylene-5-oxo-2,3,5,11a-tetrahydro-1H-benzo[e]pyrrolo[1,2-a][1,4]diazepin-8-yl)oxy)butanamido)-1-methyl-1H-imidazole-2-carboxamido)-1-methyl-1H-pyrrole-2-carboxamido)-1-methyl-1H-pyrrole-2-carboxamido)propyl 16-(2,5-dioxo-2,5-dihydro-1H-pyrrol-1-yl)-2-isopropyl-4,14-dioxo-7,10-dioxa-3,13-diazahexadecan-1-oat (18 mg, 60% yield). ESI MS; C$_{57}$H71N$_{13}$O$_{15}$ (M+H) 1179.2; found 1178.4.

Example 27

Preparation of Trastuzumab Conjugate of Compound 60 (60A)

60A

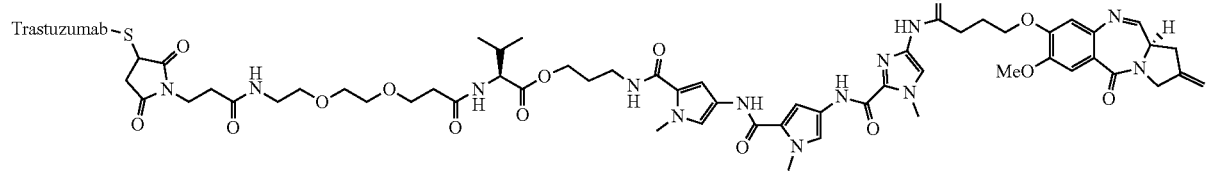

The title conjugate was prepared using the procedure described in Example 15 except that compound 60 was used instead of compound 38. The purified conjugate had a PBD to trastuzumab ratio was of 4.1 by UV-Vis using molar extinction $\varepsilon_{10\ nm}$=37,500 cm$^{-1}$M$^{-1}$ and $\varepsilon_{280\ nm}$=25,394 cm$^{-1}$M$^{-1}$ for compound 60 and $\varepsilon_{280\ nm}$=226,107 cm$^{-1}$M$^{-1}$ for trastuzumab).

Example 28

Synthesis of (R)-3-(4-(4-(4-(4-((R,Z)-7-methoxy-2-methylene-5-oxo-2,3,5,11a-tetrahydro-1H-benzo[e]pyrrolo[1,2-a][1,4]diazepin-8-yloxy)butanamido)-1-methyl-1H-pyrrole-2-carboxamido)-1-methyl-1H-pyrrole-2-carboxamido)-1-methyl-1H-pyrrole-2-carboxamido)propyl 16-(2,5-dioxo-2,5-dihydro-1H-pyrrol-1-yl)-2-methyl-4,14-dioxo-7,10-dioxa-3,13-diazahexadecan-1-oate (63)

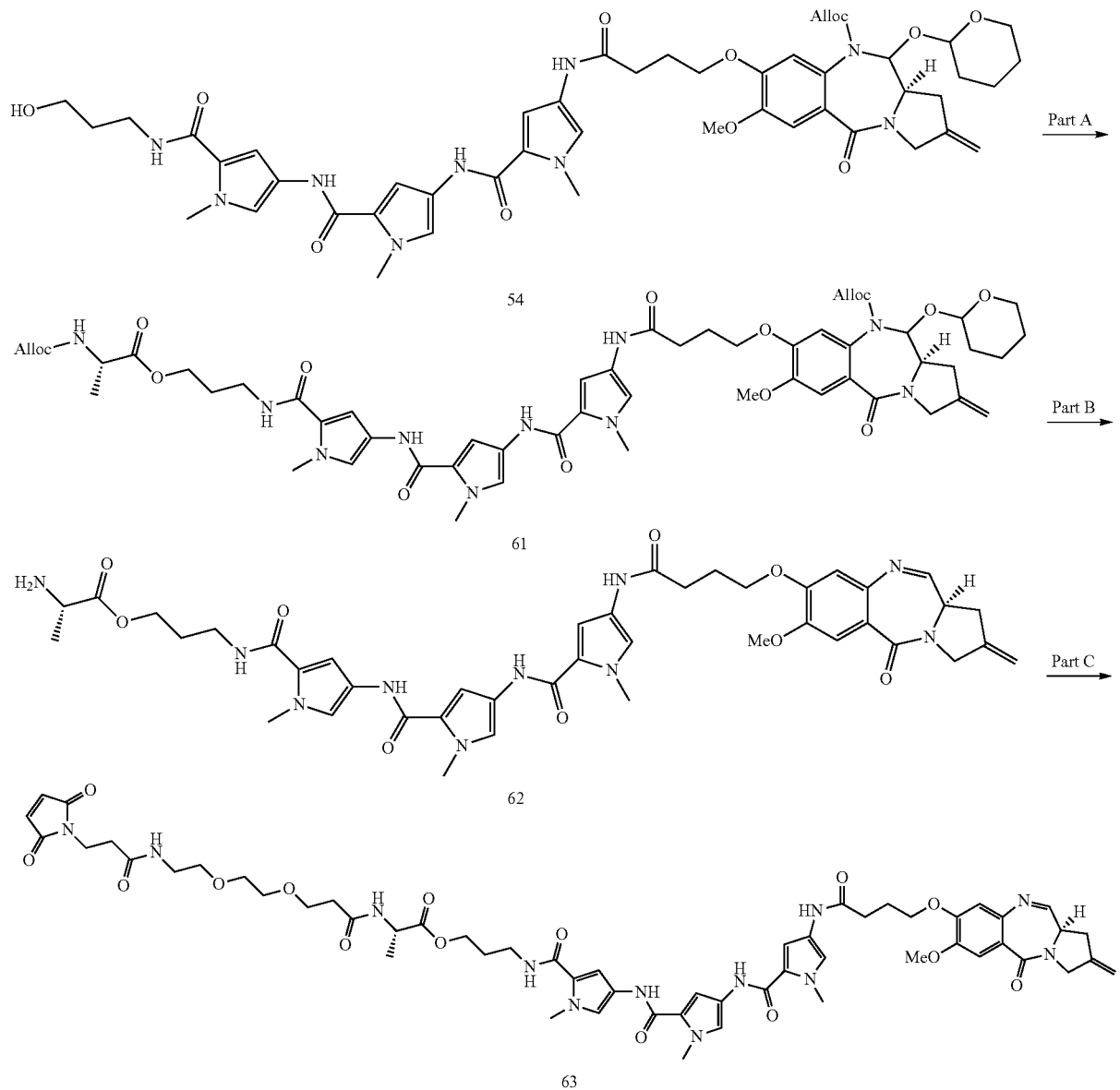

Part A:

To a solution of (R)-2-(((allyloxy)carbonyl)amino)propanoic acid (8.35 mg, 0.048 mmol) in DCM (2 mL) at 0° C. was added DIC (0.051 mL, 0.33 mmol) and the resulting mixture was stirred for 15 minutes and then added to compound 54 (46 mg, 0.048 mmol) and DMAP (17.67 mg, 0.145 mmol). The resulting mixture was stirred to room temperature for 1 h. A second aliquot of (R)-2-(((allyloxy)carbonyl)amino)-3-methylbutanoic acid was added and the stirring continued for an additional 1 h. LC/MS showed the reaction was essentially complete. The reaction mixture was diluted with EtOAc, the organic layer was washed with NaHCO$_3$, brine, dried over Na$_2$SO$_4$ and concentrated. The residue was purified by silica gel chromatography using 0-10% MeOH in DCM as eluent to give compound 61 as a solid (26.5 mg, 50% yield). ESI MS: C$_{56}$H$_{71}$N$_{10}$O$_{15}$ (M+H) 1109.2, found 1109.1.

Part B:

The title compound was prepared from compound 61 using the procedure described in Example 24, Part C to give compound 62 (16.2 mg, 81% yield). ESI MS; C$_{42}$H$_{50}$N$_{10}$O$_9$ (M+H) 838.9, found 839.1.

Part C:

The title compound was prepared from compound 62 using the procedure described in Example 14, Part I to give compound 63 (R)-3-(4-(4-(4-(4-(((R)-7-methoxy-2-methylene-5-oxo-2,3,5,11a-tetrahydro-1H-benzo[e]pyrrolo[1,2-a][1,4]diazepin-8-yl)oxy)butanamido)-1-methyl-1H-pyrrole-2-carboxamido)-1-methyl-1H-pyrrole-2-carboxamido)-1- methyl-1H-pyrrole-2-carboxamido)propyl 16-(2,5-dioxo-2,5-dihydro-1H-pyrrol-1-yl)-2-methyl-4,14-dioxo-7,10-dioxa-3,13-diazahexadecan-1-oate (2.5 mg, 48% yield). ESI MS; $C_{56}H_{68}N_{12}O_{15}$ (M+H) 1149.2, found 1149.1.

Example 29

Preparation of Trastuzumab Conjugate of Compound 63 (63A)

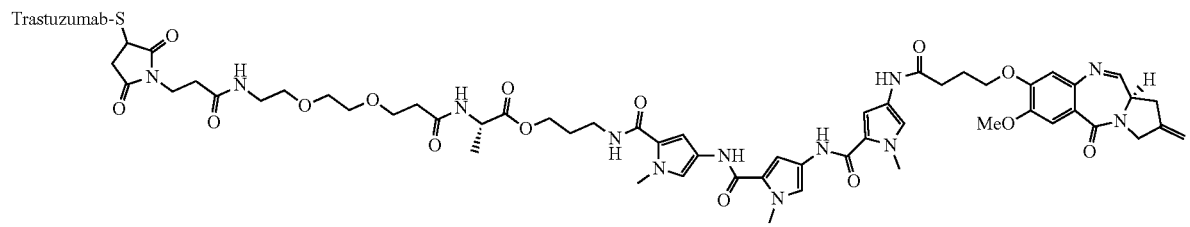

63A

The title conjugate was prepared using the procedure described in Example 15 except that compound 63 was used instead of compound 38. The purified conjugate had a PBD to trastuzumab ratio was of 3.4 by UV-Vis using molar extinction $_{310\ nm}$=37,500 cm$^{-1}$M$^{-1}$ and $\varepsilon_{280\ nm}$=25,394 cm$^{-1}$M$^{-1}$ for compound 60 and $\varepsilon_{280\ nm}$=226,107 cm$^{-1}$M$^{-1}$ for trastuzumab).

Example 30

Synthesis of 6K PHF-BA (22%)-PEG2-MI (3%)Compound 62 (64)

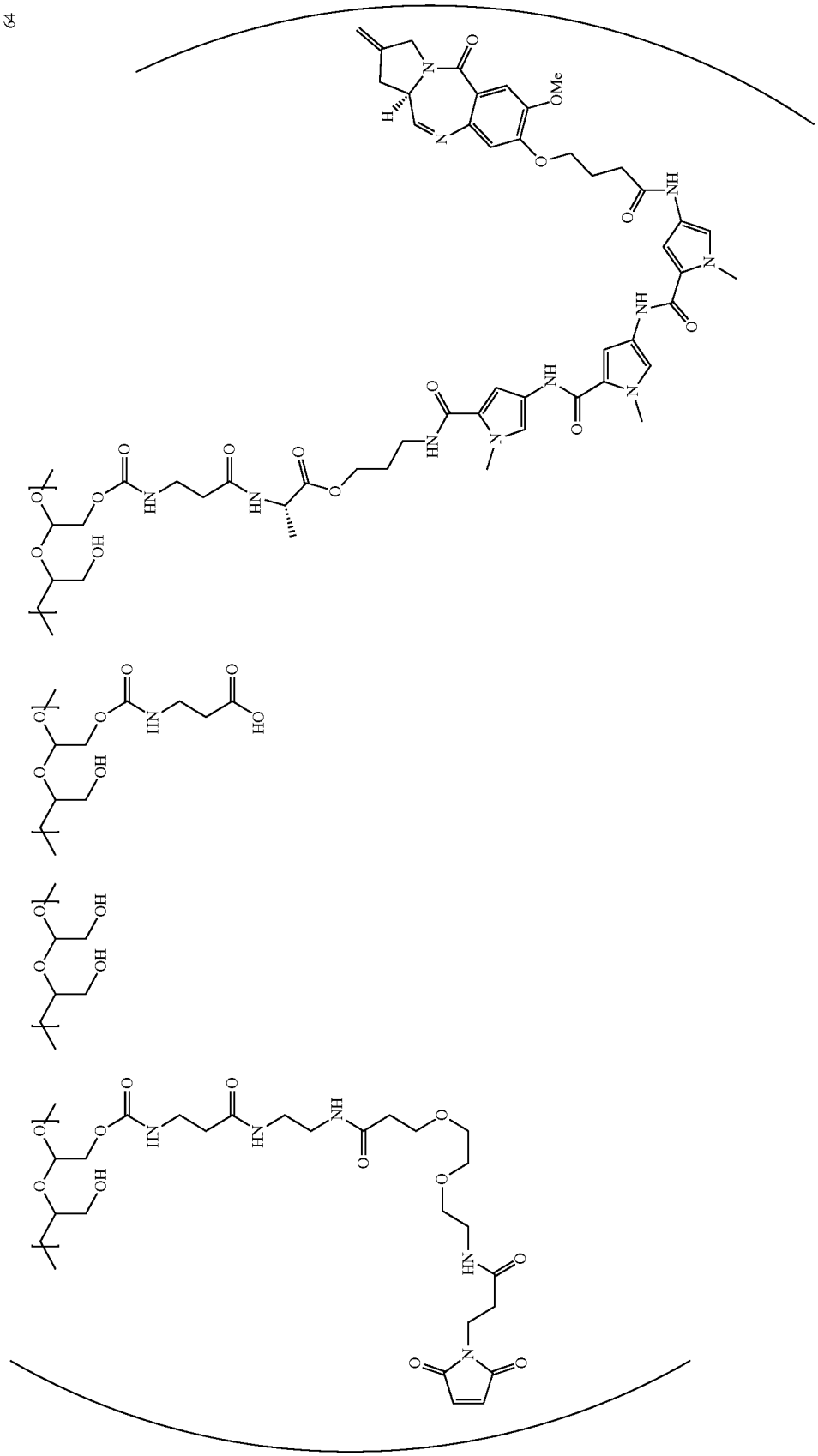

To a solution of 6K PHF-BA (22%)-EG2-MI (3.5%) (47.8 mg, prepared as described in US2015010440, Example 2) in MES buffer (10 mM, pH 5.8, 2.54 mL) was added a solution of compound 62 (7.71 mg, 8.7 μmol) in NMP (0.632 mL) followed by NHS (1.6 mg). To this mixture was added EDC in 3 portions (3×1.7 mg) over 2 h and the mixture was stirred overnight at room temperature. The crude product was purified directly on C-18 RP HPLC (Mobile phase A: 20 mM MES, pH 6.0; Mobile phase B: acetonitrile; gradient: 10-70% over 23 min). The purified conjugate was concentrated first under vacuum to remove acetonitrile and then concentrated further on a 1 K MWCO stir cell membrane to afford the title compound (64) as an aqueous solution (3.7 mL, 3.85 mg/mL, 14.25 mg; molecular weight of 7.3 kDa,); the trastuzumab to compound 64 ratio was 1.5.

Example 31

Preparation of Trastuzumab Conjugate of Compound 64 (65)

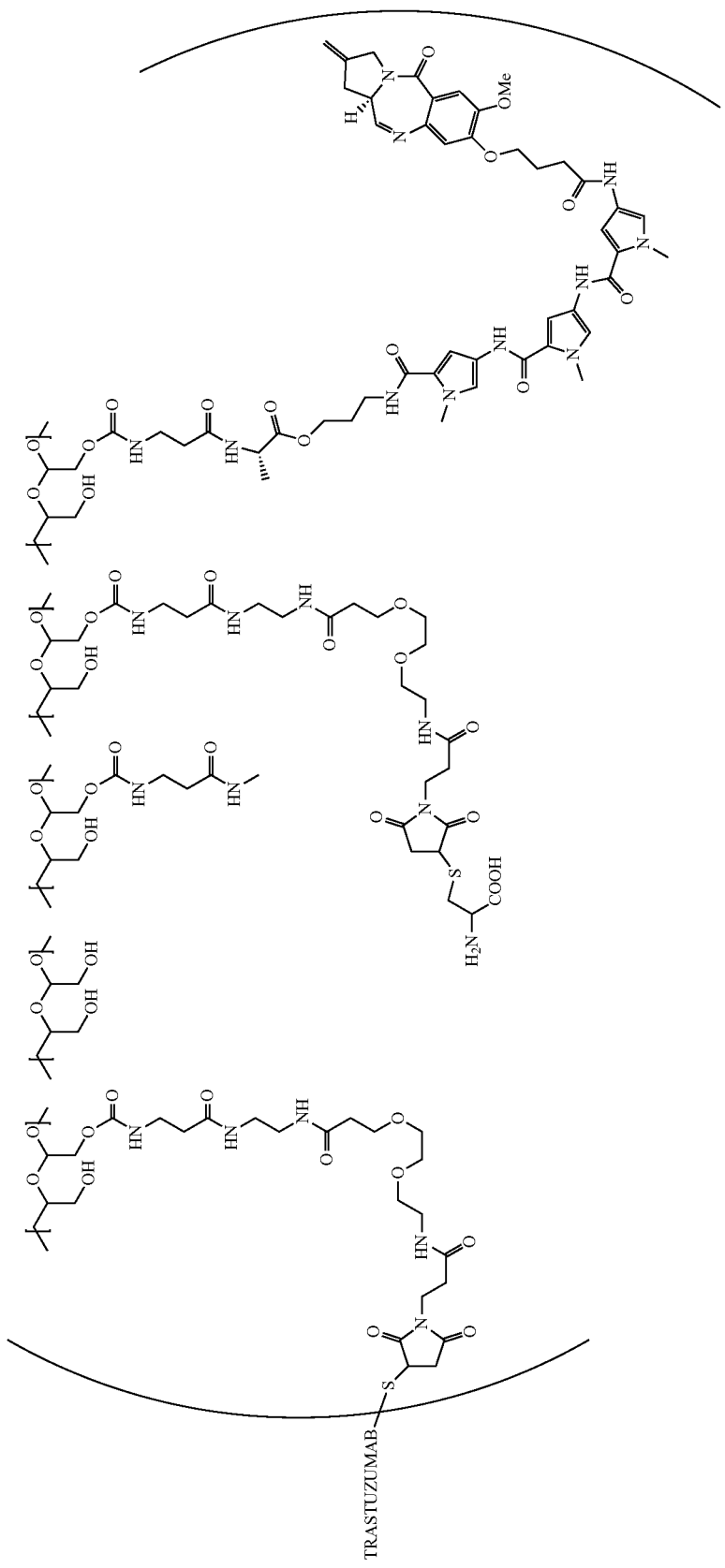

To a solution of trastuzumab (21 mg, 0.142 μmol) in 2.1 TEAA buffer (pH 7, 50 mM containing 1 mM EDTA) was added a solution of TCEP (27.3 μL of 0.112 mg, 0.390 μmol). The mixture was agitated for 90 minutes at 37° C., then cooled to room temperature and added slowly to a solution of compound 64 (1.9 mL, 7.3 mg) in TEAA buffer, pH 7. The mixture was stirred for 45 minutes at room temp and then quenched by reacting with cysteine (0.145 mL, 4.8 mg) over ~60 min at room temperature. The crude mixture was centrifuged and the supernatant was purified by WCX (Mobile phase A: 20 mM MES, pH 5.8; Mobile phase B: 20 mM MES, 300 mM NaCl; gradient: 10-65% over 35 min-utes) to afford the title conjugate as an aqueous solution (14.5 mg, 4 mL, 3.63 mg/mL); the trastuzumab to compound 65 ratio was 3.4.

Example 32

Synthesis of (S,Z)—N-(3-hydroxypropyl)-4-(4-(4-(4-(7-methoxy-5-oxo-2,3,5,11a-tetrahydro-1H-benzo[e]pyrrolo[1,2-a][1,4]diazepin-8-yloxy)butanamido)-1-methyl-1H-pyrrole-2-carboxamido)-1-methyl-1H-pyrrole-2-carboxamido)-1-methyl-1H-pyrrole-2-carboxamide (66)

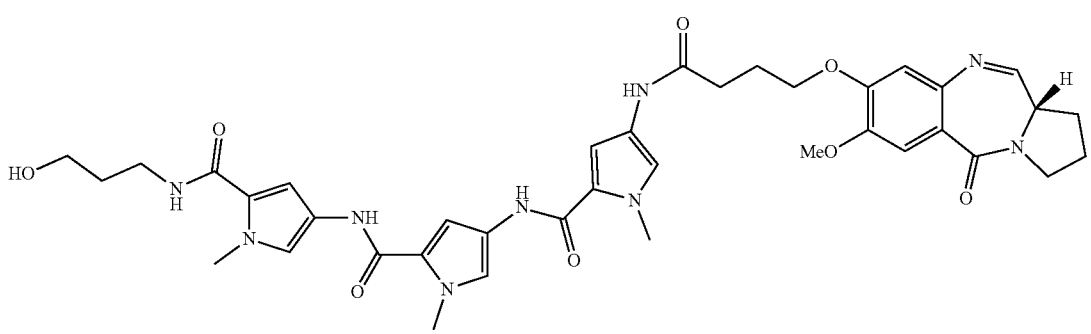

The title compound was prepared using the procedure in Example 24, Part B except 4-((11aR)-10-(allyloxycarbonyl)-11-hydroxy-7-methoxy-5-oxo-2,3,5,10,11,11a-hexahydro-1H-benzo[e]pyrrolo[1,2-a][1,4]diazepin-8-yloxy)butanoic acid was used instead 4-((11aR)-10-((allyloxy)carbonyl)-7-methoxy-2-methylene-5-oxo-11-((tetrahydro-2H-pyran-2-yl)oxy)-2,3,5,10,11,11a-hexahydro-1H-benzo[e]pyrrolo[1,2-a][1,4]diazepin-8-yl)oxy)butanoic acid to give compound 66 (15 mg, 68% yield) ESI MS: $C_{38}H_{45}N_9O_8$ (M+H) 755.8; found 756.2.

Example 33

Synthesis of (Z)-3-(4-(4-(4-(4-(7-methoxy-5-oxo-2,3,5,11a-tetrahydro-1H-benzo[e]pyrrolo[1,2-a][1,4]diazepin-8-yloxy)butanamido)-1-methyl-1H-pyrrole-2-carboxamido)-1-methyl-1H-pyrrole-2-carboxamido)-1-methyl-1H-pyrrole-2-carboxamido)propyl 6-(2,5-dioxo-2,5-dihydro-1H-pyrrol-1-yl)hexanoate (67)

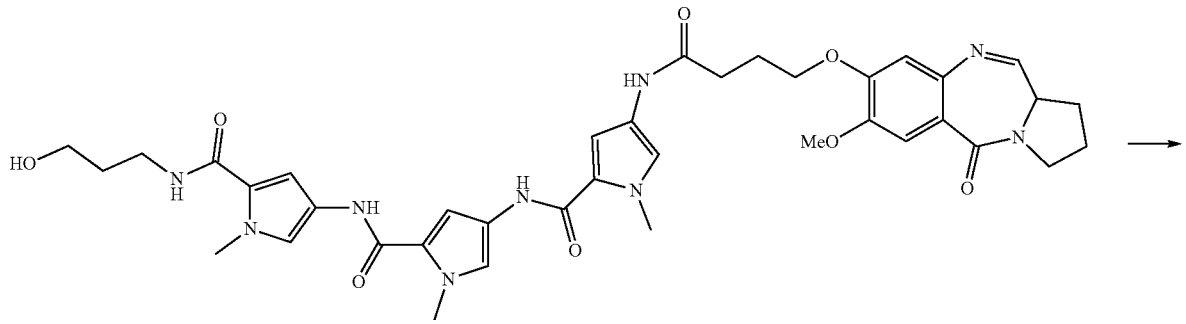

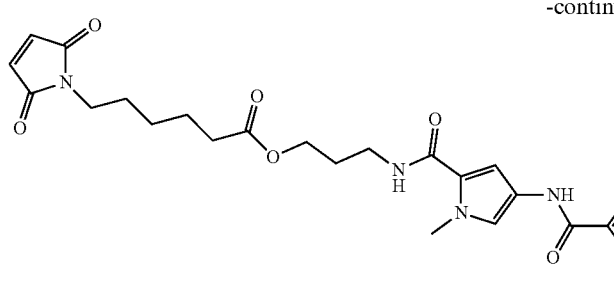
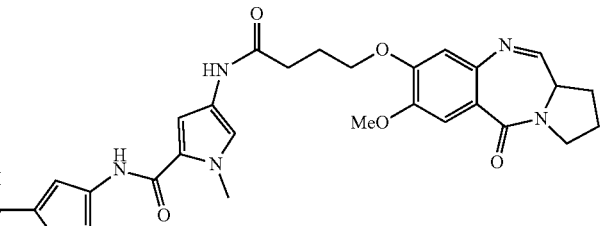

67

To a solution of 6-(2,5-dioxo-2,5-dihydro-1H-pyrrol-1-yl)hexanoic acid (4.19 mg, 0.02 mmol) in DCM (0.5 mL) at 0° C. was added DIC (6.18 µl, 0.04 mmol) and the resulting mixture was stirred for 10 minutes and then added to compound 66 (15 mg, 0.02 mmol), DMAP (7.27 mg, 0.06 mmol) and DCM (0.5 ml). The resulting mixture was stirred to room temperature for 1 h. A second aliquot of 6-(2,5-dioxo-2,5-dihydro-1H-pyrrol-1-yl)hexanoic acid (4.19 mg, 0.02 mmol), DIC (6.18 µl, 0.04 mmol) and DCM (0.5 ml) was added and stirring overnight. LC/MS showed the reaction was essentially complete. The reaction mixture was diluted with EtOAc, the organic layer was washed with NaHCO$_3$, brine, dried over Na$_2$SO$_4$ and concentrated. The residue was purified by C18 reverse phase chromatography using CH3CN to water buffered with 0.1% formic acid as eluent to give compound 67 as an amorphous solid (8 mg, 42% yield). ESI MS: C$_{48}$H$_{56}$N$_{10}$O$_{11}$ (M+H) 949.0, found 949.3.

Example 34

Preparation of Trastuzumab Conjugate of Compound 67 (68)

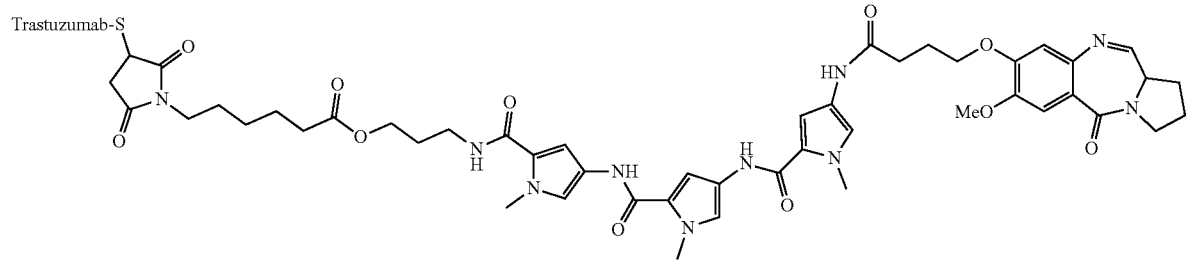

68

The title conjugate was prepared using the procedure described in Example 15 except that compound 67 was used instead of compound 38. The purified conjugate had a PBD to trastuzumab ratio was of 5.6 by UV-Vis using molar extinction $\varepsilon_{10\ nm}$=37,500 cm$^{-1}$M$^{-1}$ and $\varepsilon_{280\ nm}$=25,394 cm$^{-1}$M$^{-1}$ for compound 67 and $\varepsilon_{280\ nm}$=226,107 cm$^{-1}$M$^{-1}$ for trastuzumab).

Example 35

Synthesis of (R)-3-(4-(4-(4-(4-(((S)-8-methoxy-6-oxo-12a,13-dihydro-6H-benzo[5,6][1,4]diazepino[1,2-a]indol-9-yl)oxy)butanamido)-1-methyl-1H-pyrrole-2-carboxamido)-1-methyl-1H-pyrrole-2-carboxamido)-1-methyl-1H-pyrrole-2-carboxamido)propyl 2-aminopropanoate (71)

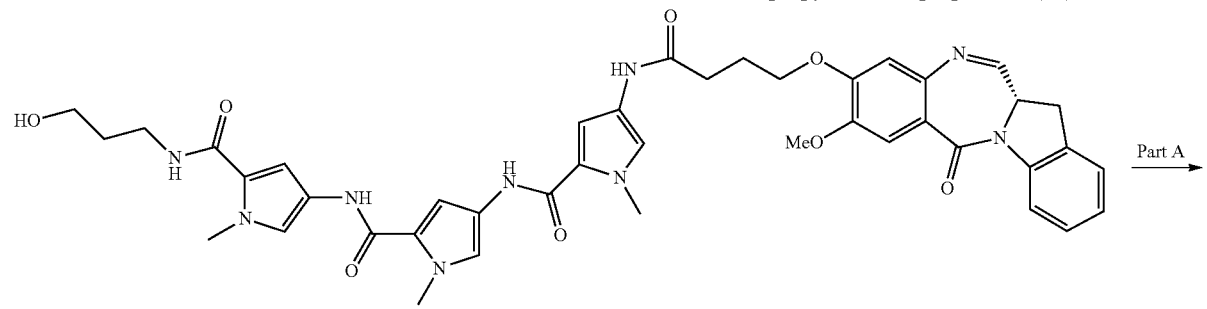

69

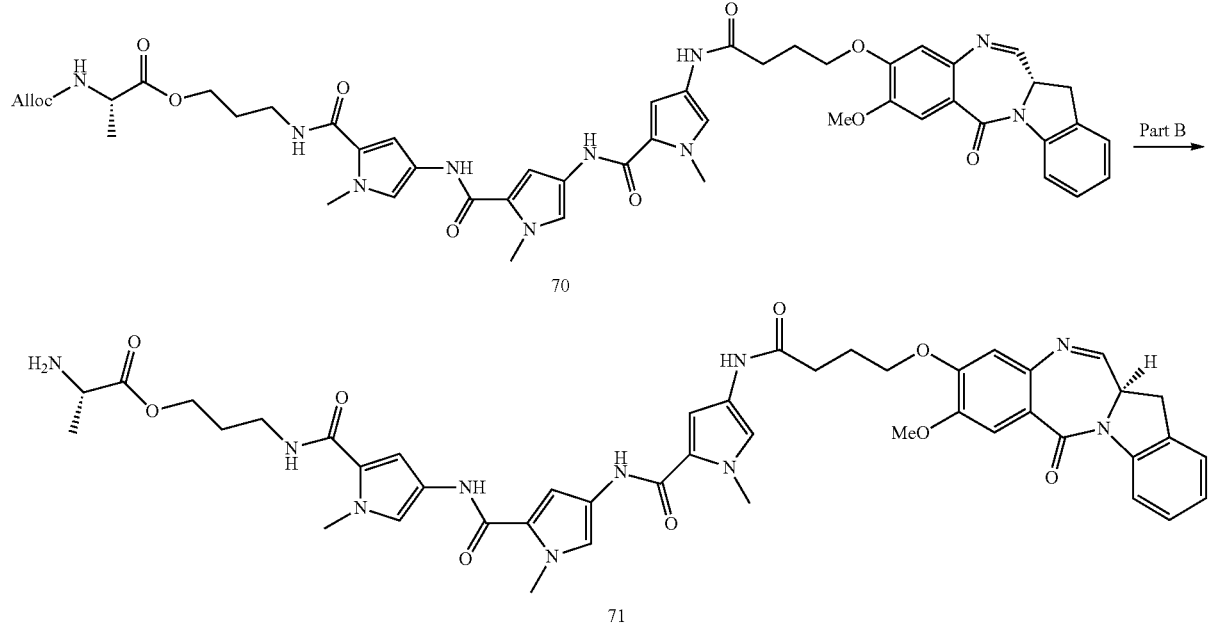

Part A:

Compound 69 (prepared as described in Example 24, except 4-(((12S,12aS)-11-((allyloxy)carbonyl)-8-methoxy-6-oxo-12-((tetrahydro-2H-pyran-2-yl)oxy)-11,12,12a,13-tetrahydro-6H-benzo[5,6][1,4]diazepino[1,2-a]indol-9-yl)oxy)butanoic acid was used instead of 4-((11aR)-10-(allyloxycarbonyl)-7-methoxy-2-methylene-5-oxo-11-(tetrahydro-2H-pyran-2-yloxy)-2,3,5,10,11,11a-hexahydro-1H-benzo[e]pyrrolo[1,2-a][1,4]diazepin-8-yloxy)butanoic acid) was used to prepare compound 70 using the procedure described in Example 26, Part B, except (R)-2-(((allyloxy)carbonyl)amino)propanoic acid (3.88 mg, 0.022 mmol) was used instead of (R)-2-(((allyloxy)carbonyl)amino)-3-methylbutanoic acid. (19 mg, 88% yield). ESI MS: $C_{49}H_{54}N_{10}O_{11}$ (M+H) 959.4; found 959.0.

Part B:

The title compound was prepared from compound 70 using the procedure described in Example 24, Part C to give compound 71 (5.8 mg, 33.5% yield). ESI MS: $C_{45}H_{50}N_{10}O_9$ (M+H) 875.4; found 875.1

Example 36

Preparation of Trastuzumab Conjugate of 6K PHF-BA (22%)-PEG2-MI (3.5%)-Compound 71 (72)

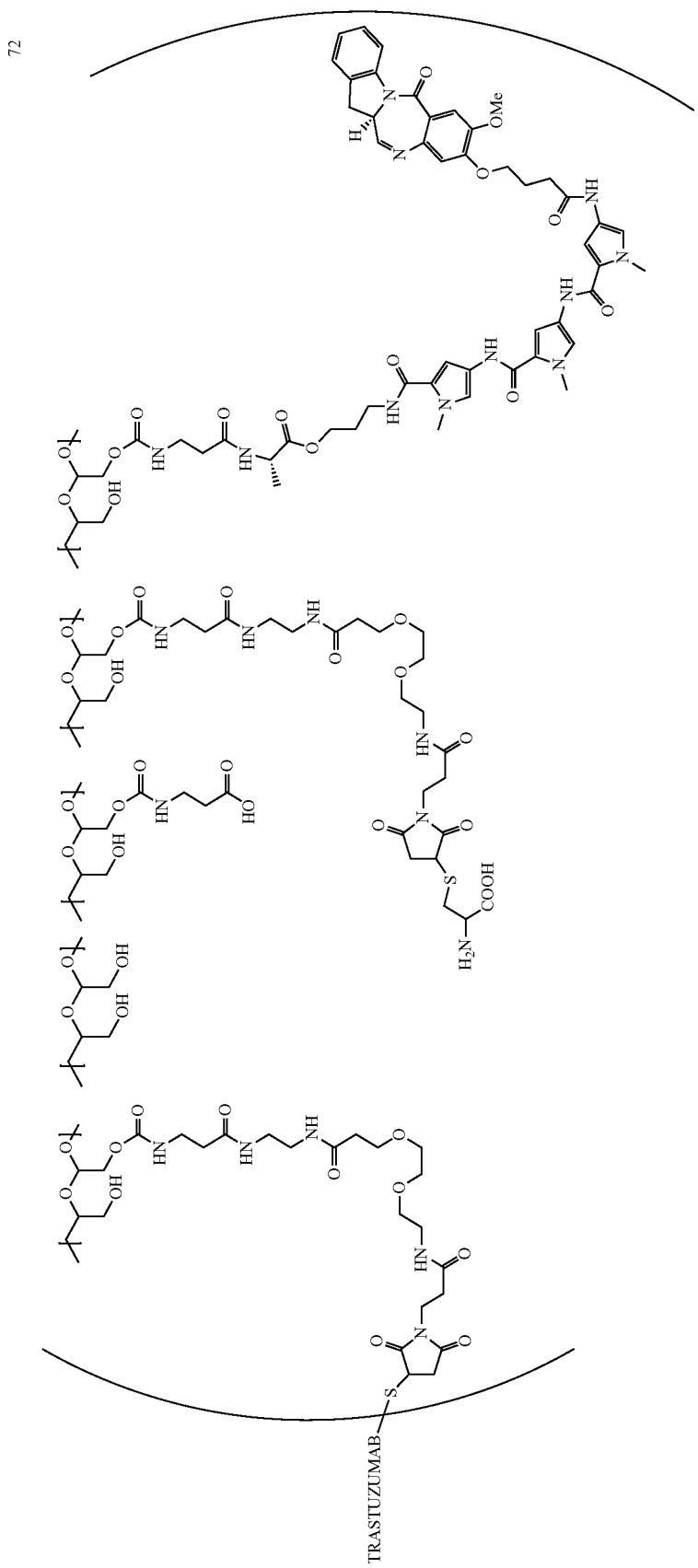

The title conjugate was prepared as described in Example 31, except 6K PHF-BA (22%)-EG2-MI (3.5%) Compound 71 (5%) was used instead of 6K PHF-BA (22%)-PEG2-MI (3%)-Compound 62 (3%). The purified conjugate had a PBD to trastuzumab ratio of 6.7.

Example 37

Synthesis of (S,Z)—N-(5-(5-(5-aminoindoline-1-carbonyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (77)

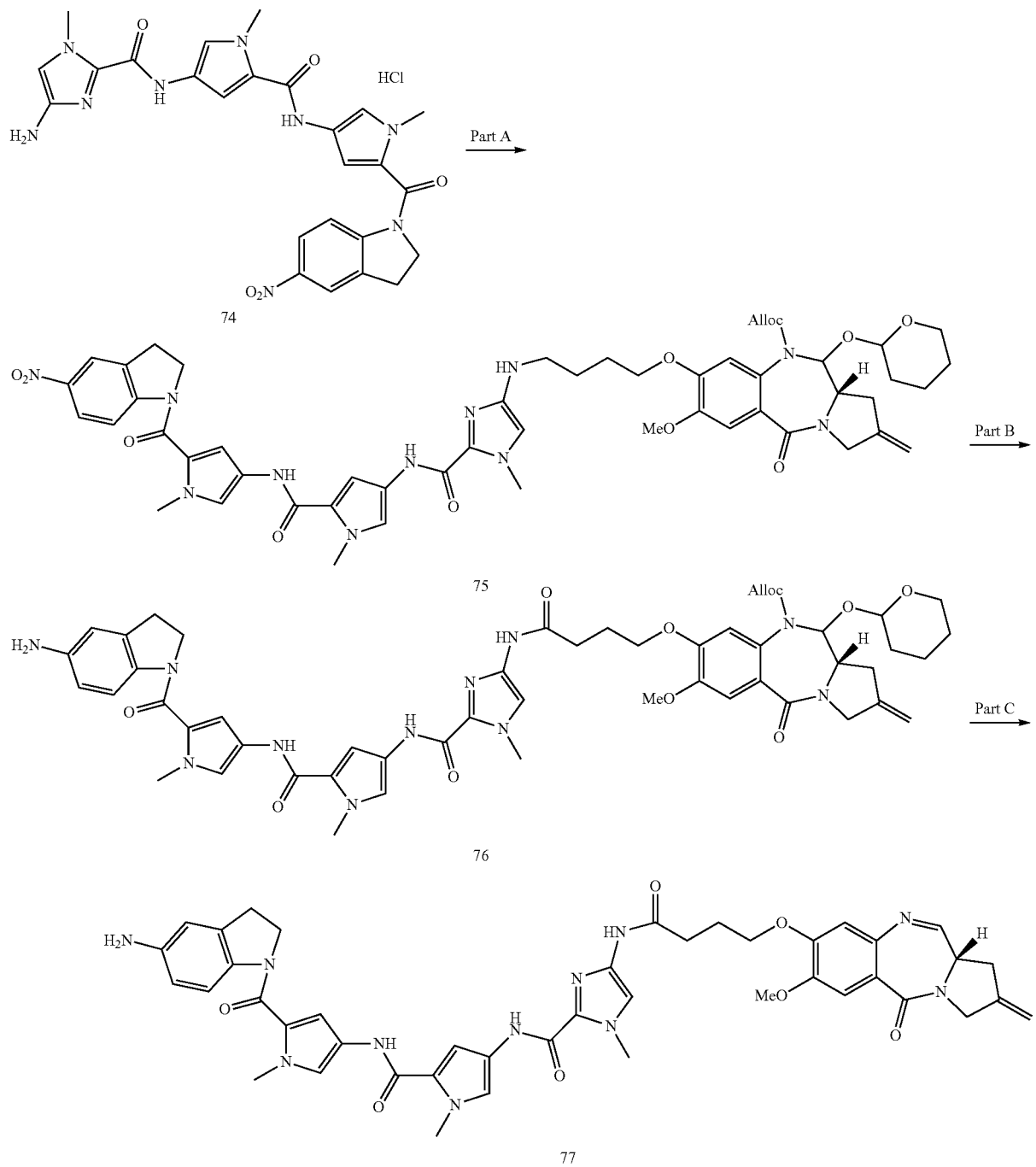

Part A:

Compound 75 was prepared as described in Example 1, Part F, except 4-amino-1-methyl-N-(1-methyl-5-(1-methyl-5-(5-nitroindoline-1-carbonyl)-1H-pyrrol-3-ylcarbamoyl)-1H-pyrrol-3-yl)-1H-imidazole-2-carboxamide hydrochloride (119 mg, 0.210 mmol, prepared from (4-amino-1-methyl-1H-pyrrol-2-yl)(5-nitroindolin-1-yl)methanone hydrochloride as described in Example 1, Part C) was used instead of Compound 6. ESI MS: $C_{52}H_{58}N_{11}O_{13}$ 1044.4 (M+H); found 1043.6.

Part B and Part C:

Compound 75 (100 mg, 0.096 mmol) was combined with iron (16.05 mg, 0.287 mmol) in EtOH (3.0 ml), Saturated aqueous ammonium chloride (1 mL) and distilled water (1 mL) were added, and the heterogeneous mixture was heated to 80° C. with stirring. After 2 h, mixture was diluted in EtOAc and washed with water and brine. The organic phase was dried with $MgSO_4$, filtered, and concentrated under reduced pressure and then purified to give compound 76 (36 mg, 37.1% yield). ESI MS: $C_{52}H_{60}N_{11}O_{11}$ 1014.5 (M+H); found 1013.7. The title compound was prepared from compound 76 using the procedure in Example 1, Part H to give 1.1 mg, 3.74% yield. ESI MS: $C_{43}H_{46}NO_{11}O_7$ (M+H) 828.4; found 827.8.

Example 38

Synthesis of (S)—N-(5-((5-(5-amino-1H-indole-1-carbonyl)-1-methyl-1H-pyrrol-3-yl)carbamoyl)-1-methyl-1H-pyrrol-3-yl)-4-(4-((8-methoxy-6-oxo-2a,13-dihydro-6H-benzo[5,6][1,4]diazepino[1,2-a]indol-9-yl)oxy)butanamido)-1-methyl-1H-imidazole-2-carboxamide (78)

78

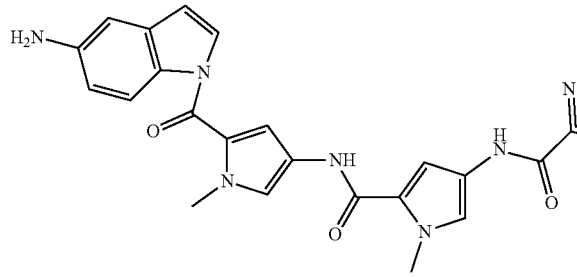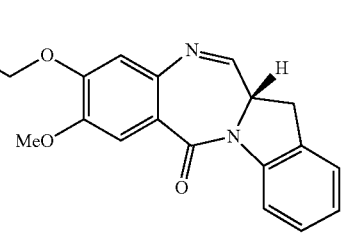

The title compound was prepared using the procedure in Example 1, Parts F and G except 4-(((12 S, 12aS)-11-((allyloxy)carbonyl)-8-methoxy-6-oxo-12-((tetrahydro-2H-pyran-2-yl)oxy)-11,12,12a,13-tetrahydro-6H-benzo[5,6][1,4]diazepino[1,2-a]indol-9-yl)oxy)butanoic acid was used instead 4-((11aR)-10-(allyloxycarbonyl)-11-hydroxy-7-methoxy-5-oxo-2,3,5,10,11,11a-hexahydro-1H-benzo[e]pyrrolo[1,2-a][1,4]diazepin-8-yloxy)butanoic acid in Part F to give compound 78 (12.5 mg, 23.13% yield). ESI MS: $C_{46}H_{44}N_{11}O_7$ (M+H) 862.3; found 861.7.

Example 39

Synthesis of (S,Z)—N-(5-(5-(5-amino-1H-indazole-1-carbonyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (79)

79

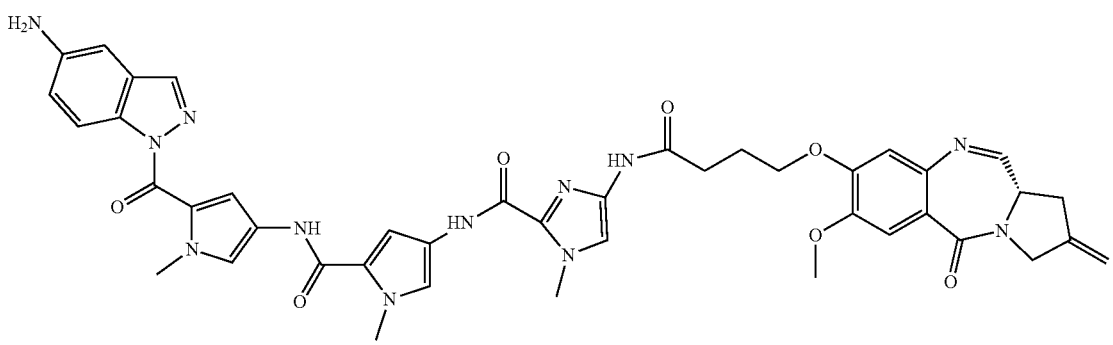

The title compound was prepared using the procedure describe in Example 1, except allyl 1-(4-(4-amino-1-methyl-1H-pyrrole-2-carboxamido)-1-methyl-1H-pyrrole-2-carbonyl)-1H-indazol-5-ylcarbamate hydrochloride (61 mg, 0.132 mmol) was used instead of allyl 1-(4-(4-amino-1-methyl-1H-pyrrole-2-carboxamido)-1-methyl-1H-pyrrole-2-carbonyl)-1H-indol-5-ylcarbamate hydrochloride in Part A. ESI MS: $C_{42}H_{42}N_{12}O_7$ (M+H) 827.9; found 826.

Example 40

Synthesis of (S,Z)—N-(5-(5-(1H-indol-5-ylcarbamoyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (82)

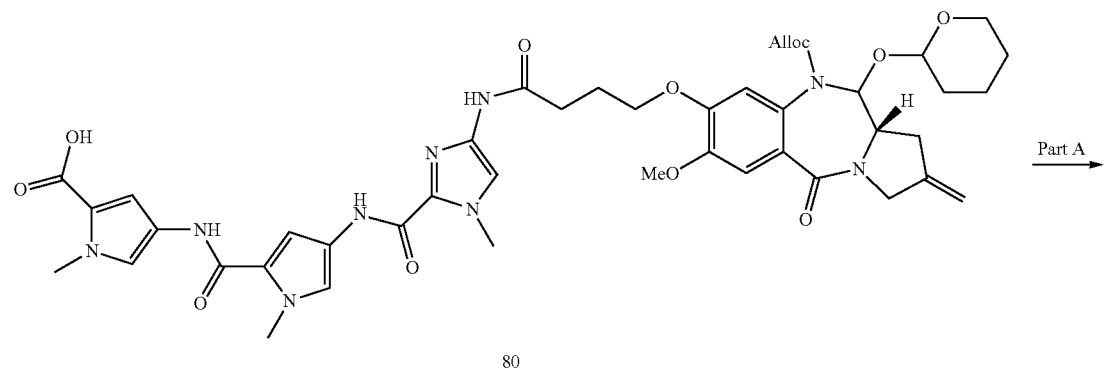

80

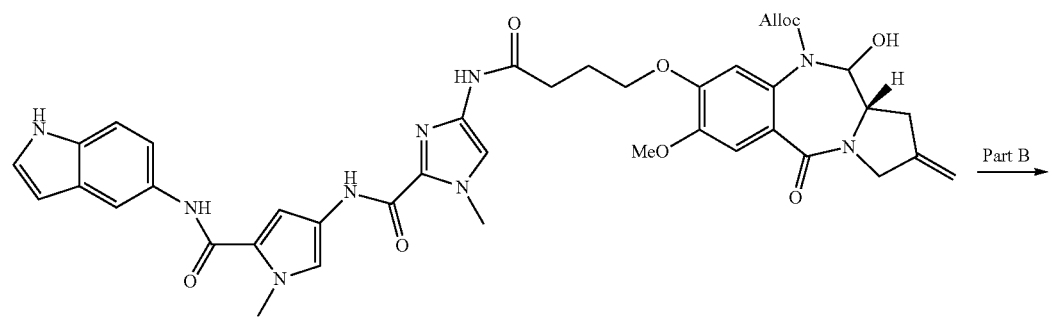

81

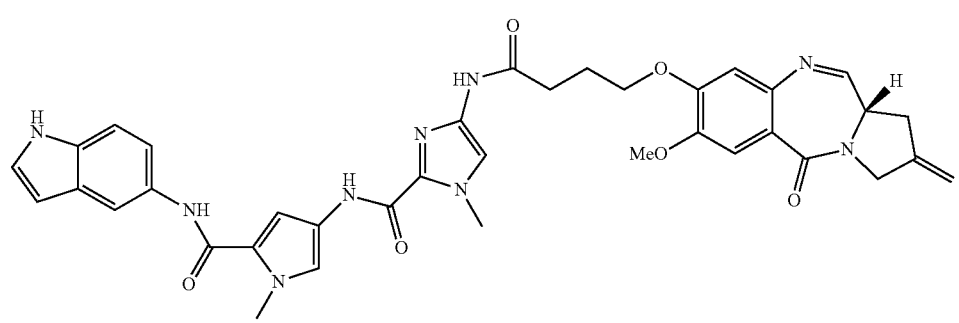

82

Part A and Part B:

Compound 80 (37 mg, 0.045 mmol) was reacted with 1H-indol-5-amine (5 mg, 0.038 mmol) using the procedure described in Example 1, Part A, to give compound 81 which was used without further purification to give the title compound 82 using the procedure in Example 1, Part H resulting in 3 mg, 10% yield. ESI MS: $C_{43}H_{43}NO_{11}O_7$ (M+H) 826.8; found 825.9.

Example 41

Synthesis of (S,Z)—N-(5-(5-(5-(aminomethyl)-1H-indole-1-carbonyl)-1-methyl-1H-pyrrol-3-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (83)

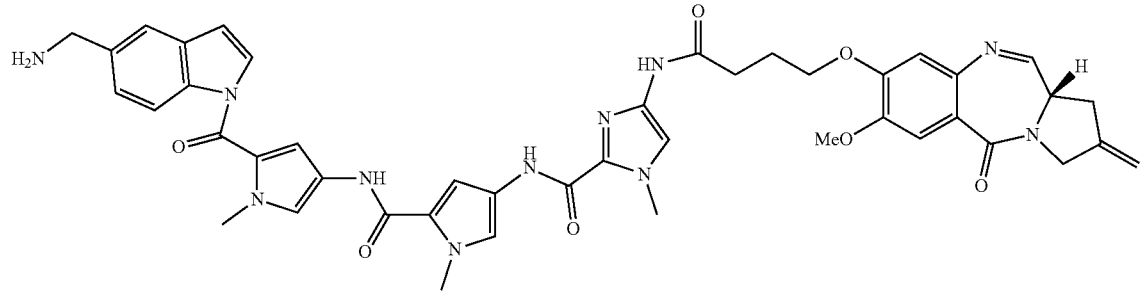

83

The title compound 83 was prepared as described in Example 12 except allyl (1-(4-(4-(4-amino-1-methyl-1H-imidazole-2-carboxamido)-1-methyl-1H-pyrrole-2-carboxamido)-1-methyl-1H-pyrrole-2-carbonyl)-1H-indol-5-yl)methylcarbamate hydrochloride (127 mg, 0.2 mmol) was used instead of compound 26. ESI MS: $C_{44}H46N_{11}O_7$ (M+H) 840.4; found 839.7.

Example 42

Synthesis of (S,Z)—N-(5-(1H-pyrrolo[2,3-b]pyridin-5-ylcarbamoyl)-1-methyl-1H-pyrrol-3-yl)-4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamide (84)

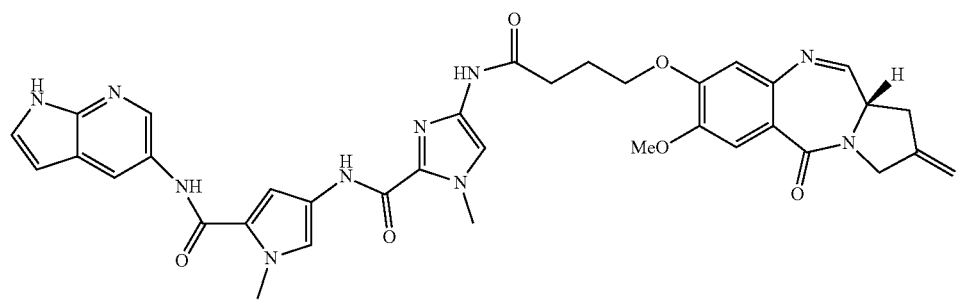

84

The title compound was prepared as described in Example 40 except 1H-pyrrolo[2,3-b]pyridin-5-amine (4.3 mg, 0.032 mmol) was used instead of 1H-indol-5-amine. ESI MS: $C_{42}H_{42}N_{12}O_7$ (M+H) 827.9; found 826.9.

Example 43

Synthesis of (S,Z)-methyl 1-(4-(4-(4-(4-(7-methoxy-2-methylene-5-oxo-2,3,5,11a-tetrahydro-1H-benzo[e]pyrrolo[1,2-a][1,4]diazepin-8-yloxy)butanamido)-1-methyl-1H-imidazole-2-carboxamido)-1-methyl-1H-pyrrole-2-carboxamido)-1-methyl-1H-pyrrole-2-carbonyl)-1H-pyrrolo[2,3-b]pyridine-5-carboxylate (85)

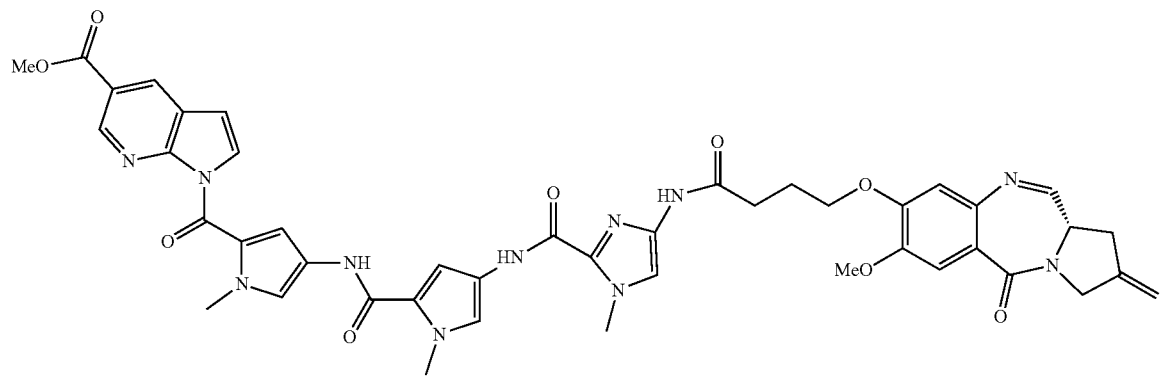

The title compound 85 was prepared using the procedure described in Example 1, except methyl 1H-indole-5-carboxylate (5.72 mg, 0.032 mmol) was used instead of 1H-indol-5-amine. $C_{44}H_{43}N_{11}O_9$ (M+H) 870.9; found 869.8

Example 44

Cell Viability Assay for Antibody-Polymer-Drug Conjugates

PBD compounds and conjugates thereof were evaluated for their antiproliferation properties in tumor cell lines in vitro using CellTiter-Glo® (Promega Corp). Cells were plated in black walled 96-well plate and allowed to adhere overnight at 37° C. in a humidified atmosphere of 5% $CO_2$. BT474, SKBR3, NCI-$N_{87}$ cells (HER2 expressing cells), JIMT1 cells (HER2 medium expression level cells) and MCF7 cells (HER2 low expressing levels cells) and were plated at a density of 5,000 cells per well. The next day the medium was replaced with 50 μL fresh medium and 50 μL of 2× stocks of PBD compounds or antibody-PBD conjugate were added to appropriate wells, mixed and incubated for 72 h. CellTiter-Glo® reagent was added to the wells at room temperature and the luminescent signal was measured after 10 min using a SpectraMax M5 plate reader (Molecular Devices). Dose response curves were generated using Soft-Max Pro software. $IC_{50}$ values were determined from four-parameter curve fitting.

Table I and Table II give illustrative results for the antiproliferation properties of the PBD compounds and conjugates thereof respectively.

TABLE I

| Compound No. | BT474 $IC_{50}$ (nmol/L) | SKBR3 $IC_{50}$ (nmol/L) | N87 $IC_{50}$ (nmol/L) | JIMT1 $IC_{50}$ (nmol/L) | MCF7 $IC_{50}$ (nmol/L) |
|---|---|---|---|---|---|
| 8 | 0.84 | 0.15 | 0.43 | 2.2 | 4 |
| 12 | 2 | 0.4 | 7 | 4.4 | 13.9 |
| 3A | 69 | 9.0 | 14 | 91 | 214 |
| 4A | 26.8 | 9.4 | 24.1 | 11.4 | 1000 |
| 5A | 2.9 | 0.97 | 5.3 | 16 | 24.2 |
| 6A | 5.3 | 1.5 | 4.2 | 8.9 | 17.1 |
| 7A | 0.6 | 0.15 | 0.3 | 1.1 | 2.7 |
| 8A | 0.83 | 0.14 | 2.9 | 0.55 | 3.7 |
| 19 | 0.59 | 0.2 | 0.35 | 1.34 | 2.1 |
| 20 | 126 | 5.5 | 26 | 19.9 | 202 |
| 11A | 4 | 0.67 | 1.5 | 11.3 | 14.8 |
| 28 | 2.9 | 0.16 | 1.02 | 0.6 | 2.6 |
| 13A | 2.5 | 0.28 | 0.73 | 3.6 | 4.4 |
| 48 | 4 | 0.3 | 0.7 | 4.5 | 7.6 |
| 51 | 300 | 260 | 300 | 300 | 300 |
| 55 | 7.5 | 2.5 | 5 | 2 | 47 |
| 56 | 23.3 | 7.9 | 13.6 | 9 | 54.5 |
| 66 | 86 | 16 | 27 | 15 | 121 |
| 69 | 4.7 | 1.5 | 3 | 1.5 | 69 |
| 77 | 37.1 | 1.4 | 6.4 | 8.6 | 14.9 |
| 78 | 0.63 | 0.06 | 0.29 | 1.1 | 1.9 |
| 79 | 0.66 | 0.09 | 0.31 | 2.1 | 2.6 |
| 82 | 32 | 3.6 | 7.9 | 10.8 | 27 |
| 83 | 2.5 | 0.18 | 0.81 | 1.2 | 2.4 |
| 84 | 5.4 | 0.66 | 1.5 | 3.6 | 3.8 |
| 85 | 6.3 | 0.58 | 0.97 | 14.2 | 8.0 |

TABLE II

| Conjugate No. | BT474 $IC_{50}$ (nmol/L) | SKBR3 $IC_{50}$ (nmol/L) | N87 $IC_{50}$ (nmol/L) | JIMT1 $IC_{50}$ (nmol/L) | MCF7 $IC_{50}$ (nmol/L) |
|---|---|---|---|---|---|
| 47 | 32.3 | 0.10 | 0.16 | 20 | 300 |
| 47A | 0.44 | 0.04 | 0.11 | 300 | 300 |
| 60A | 300 | 0.09 | 6.1 | 192 | 300 |
| 63A | 0.9 | 0.03 | 0.17 | 0.9 | 300 |
| 65 | 0.8 | 0.03 | 0.15 | 1.1 | 300 |

As shown in Tables I and II, the compounds and antibody-drug conjugates show efficacy in the tested cell lines.

Example 45

Tumor Growth Response to Administration of Antibody-Polymer-Drug Conjugates

Female CB-17 SCID mice were inoculated subcutaneously with NCI-N$_{87}$ cells (n=10 for each group). Test compound or vehicle were dosed IV as a single dose on day 1. Tumor size was measured at the times indicated in the FIGURE using digital calipers. Tumor volume was calculated and was used to determine the delay in tumor growth. Mice were sacrificed when tumors reached a size of 800 mm$^3$. Tumor volumes are reported as the mean±SEM for each group.

The FIGURE provides the results for the tumor response in mice inoculated subcutaneously with NCI-N$_{87}$ cells (n=10 for each group) after IV administration as a single dose on day 1 of vehicle, Trastuzumab-drug conjugate, Conjugate 47, Example 21, or Conjugate 60A, Example 27 each at 3 mg/kg. The results show that on day 78 at 3 mg/kg conjugate 47 resulted in 5 partial responses, 5 complete responses and 2 tumor free at day 78.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula (I),

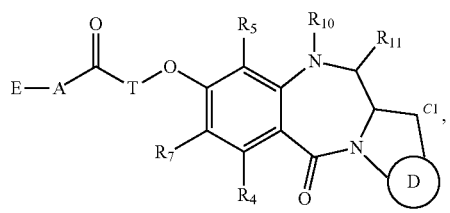

(I)

or a tautomer thereof, or a pharmaceutically acceptable salt or solvate of the compound or the tautomer, wherein:

D is D2:

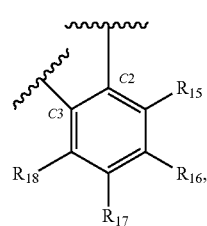

(D2)

T is C$_{1-10}$ alkylene linker;

A is

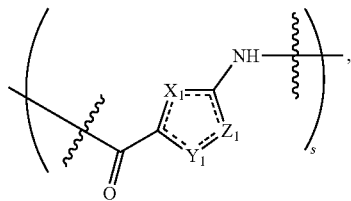

wherein the —NH group of A is connected to the —C(O)-T-moiety of Formula (I) and the C═O moiety of A is connected to E; and each

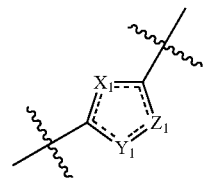

independently is

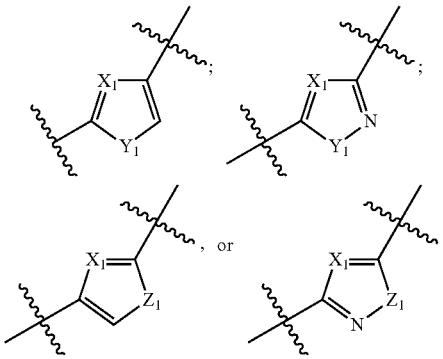

E is —OH, —NH—(C$_{1-6}$ alkylene)-R$_{13a}$, E1, E2, E3, or E4:

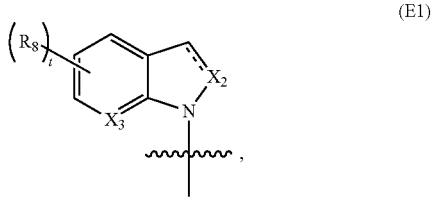

(E1)

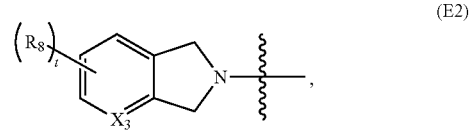

(E2)

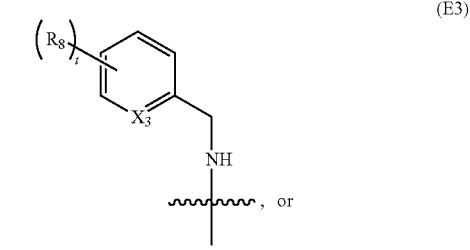

(E3)

-continued

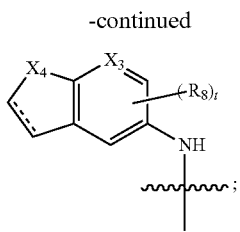
(E4)

wherein the dotted line in E1 or E4 indicates the presence of a single or double bond;

$R_4$, $R_5$ and $R_7$ are each independently —H, —$R_2$, —OH, —$OR_2$, —SH, —$SR_2$, —$NH_2$, —$NHR_2$, —$NR_2R_3$, —$NO_2$, —$SnMe_3$, halo, or a polyethylene glycol unit —$(OCH_2CH_2)_r$—$OR_a$; or $R_4$ and $R_7$ together form bis-oxy-$C_{1-3}$ alkylene;

each occurrence of $R_2$ and $R_3$ independently is an optionally substituted $C_{1-8}$ alkyl, optionally substituted $C_{2-8}$ alkenyl, optionally substituted $C_{2-8}$ alkynyl, optionally substituted $C_{3-8}$ cycloalkyl, optionally substituted 3- to 20-membered heterocycloalkyl, optionally substituted $C_{6-20}$ aryl, or optionally substituted 5- to 20-membered heteroaryl, and, optionally in relation to the group $NR_2R_3$, $R_2$ and $R_3$ together with the nitrogen atom to which they are attached form an optionally substituted 4-, 5-, 6- or 7-membered heterocycloalkyl or an optionally substituted 5- or 6-membered heteroaryl;

each $R_8$ independently is —OH, halo, —$NO_2$, —CN, —$N_3$, —$OR_2$, —COOH, —$COOR_2$, —$COR_2$, —$OCONR_{13}R_{14}$, —$CONR_{13}R_{14}$, $C_{1-10}$ alkyl, —CO—NH—($C_{1-6}$ alkylene)-$R_{3a}$, $C_{3-10}$ cycloalkyl, $C_{2-10}$ alkenyl, $C_{2-10}$ alkynyl, a polyethylene glycol unit —$(OCH_2CH_2)_r$—$OR_a$, 3- to 14-membered heterocycloalkyl, 5- to 12-membered heteroaryl, —$S(=O)_2R_{12}$, —$S(=O)_2NR_{13}R_{14}$, —$SR_{12}$, —$SO_xM$, —$OSO_xM$, —$NR_9COR_{19}$, —NH(C=NH)NH$_2$, or —$R_{20}$—$R_{21}$—$NR_{13}R_{14}$;

each $R_9$ independently is $C_{1-10}$ alkyl, $C_{3-10}$ cycloalkyl, $C_{2-10}$ alkenyl, or $C_{2-10}$ alkynyl;

$R_{10}$ is —H or a nitrogen protecting group;

$R_{11}$ is -$QR^Q$ or —$SO_xM$;

or $R_{10}$ and $R_{11}$ taken together with the nitrogen atom and carbon atom to which they are respectively attached, form a N=C double bond;

each $R_{12}$ independently is $C_{1-7}$ alkyl, 3- to 20-membered heterocycloalkyl, 5- to 20-membered heteroaryl, or $C_{6-20}$ aryl;

each occurrence of $R_{13}$ and $R_{14}$ are each independently H, $C_{1-10}$ alkyl, 3- to 20-membered heterocycloalkyl, 5- to 20-membered heteroaryl, or $C_{6-20}$ aryl;

each $R_{13a}$ independently is —OH or —$NR_{13}R_{14}$;

$R_{15}$, $R_{16}$, $R_{17}$, and $R_{18}$ are each independently —H, —OH, halo, —$NO_2$, —CN, —$N_3$, —$OR_2$, —COOH, —$COOR_2$, —$COR_2$, —$OCONR_{13}R_{14}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3-14 membered heterocycloalkyl, 5- to 12-membered heteroaryl, —$NR_{13}R_{14}$, —$S(=O)_2R_{12}$, —$S(=O)_2NR_{13}R_{14}$, —$SR_{12}$, —$SO_xM$, —$OSO_xM$, —$NR_9COR_{19}$, or —NH(C=NH)NH$_2$;

each $R_{19}$ independently is $C_{1-10}$ alkyl, $C_{3-10}$ cycloalkyl, $C_{2-10}$ alkenyl, or $C_{2-10}$ alkynyl;

each $R_{20}$ independently is a bond, $C_{6-10}$ arylene, 3-14 membered heterocycloalkylene, or 5- to 12-membered heteroarylene;

each $R_{21}$ independently is a bond or $C_{1-10}$ alkylene;

each $X_1$ independently is $CR_b$ or N;

each $Y_1$ independently is CH, $NR_a$, O or S, wherein when

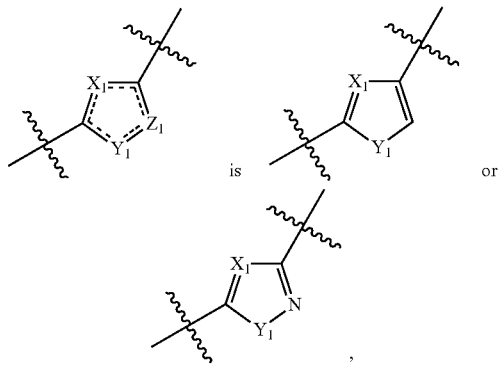

then $Y_1$ is $NR_a$, O, or S;

each $Z_1$ independently is CH, $NR_a$, O or S, wherein when

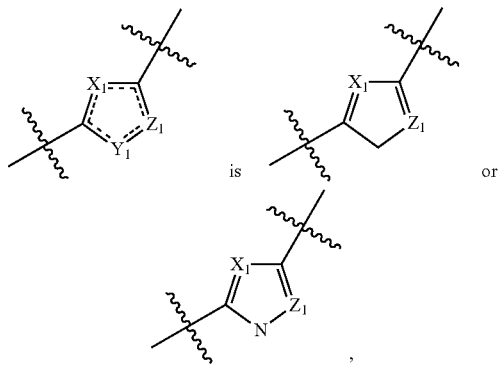

then Z1 is $NR_a$, O, or S;

each $R_a$ independently is H or $C_{1-4}$ alkyl;

each $R_b$ independently is H, OH, $C_{1-4}$ alkyl, or $C_{1-4}$ alkoxyl;

$X_2$ is CH, CH$_2$, or N;

$X_3$ is CH or N;

$X_4$ is NH, O, or S;

Q is O, S, or NH;

when Q is S or NH, then $R^Q$ is —H or optionally substituted $C_{1-7}$ alkyl; or when Q is O, then $R^Q$ is —H or optionally substituted $C_{1-7}$ alkyl or —$SO_xM$;

each M independently is H or a monovalent pharmaceutically acceptable cation;

each r independently is an integer from 1 to 200;

s is 1, 2, 3, 4, 5, or 6;

t is 0, 1, or 2;

each x independently is 2 or 3, and when E is E4, the dotted line indicates the presence of a double bond, $X_3$ is CH, and $X_4$ is O or S, then s is 2, 3, 4, 5, or 6.

2. The compound of claim 1, wherein T is $C_{2-6}$ alkylene linker.

3. The compound of claim 1, wherein T is $C_{2-4}$ alkylene linker.

4. The compound of claim 1, wherein T is propylene.

5. The compound of claim 1, wherein the compound is of Formula (III):

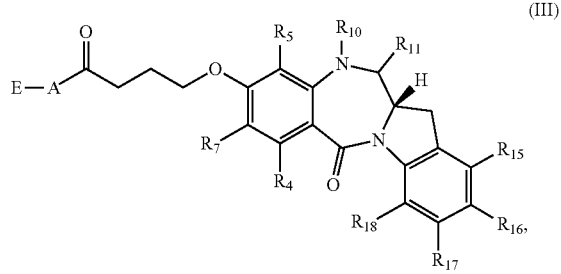
(III)
or a tautomer thereof, or a pharmaceutically acceptable salt or solvate of the compound or the tautomer.
6. The compound of claim 1, wherein each
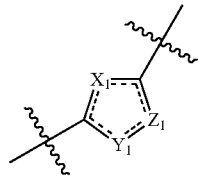
independently is
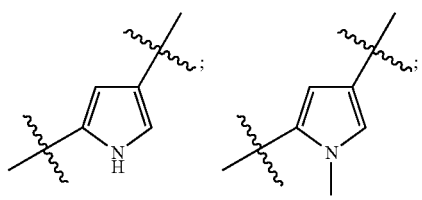
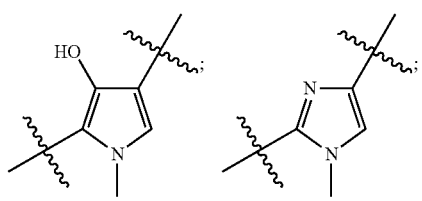
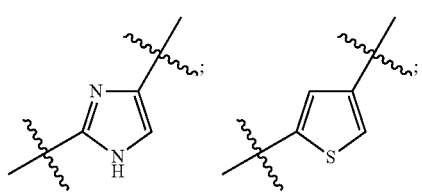
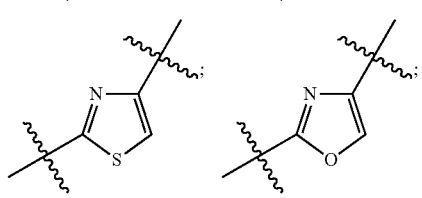
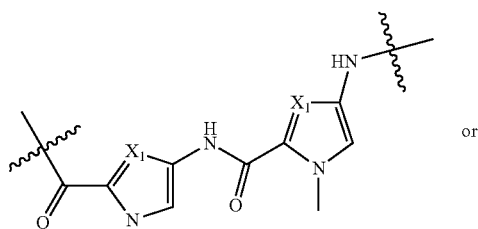
7. The compound of claim 1, wherein A is:
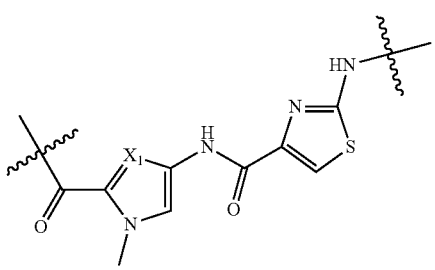
wherein each $X_1$ independently is CH or N.
8. The compound of claim 1, wherein A is:
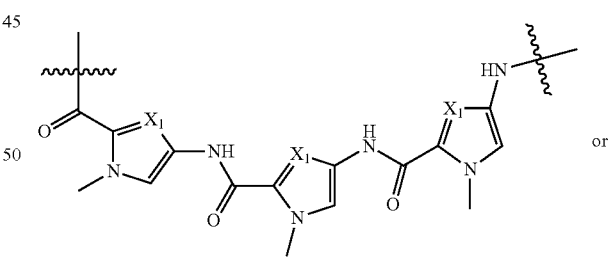
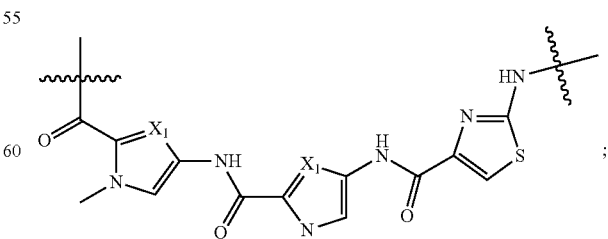
wherein each $X_1$ independently is CH or N.

9. The compound of claim 1, wherein A is

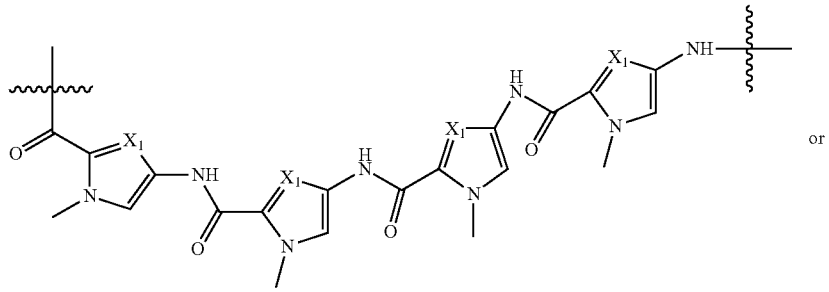

or

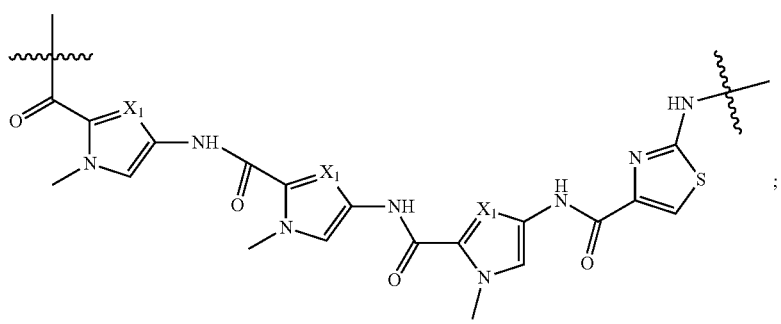

;

wherein each $X_1$ independently is CH or N.

10. The compound of claim 1, wherein E is:

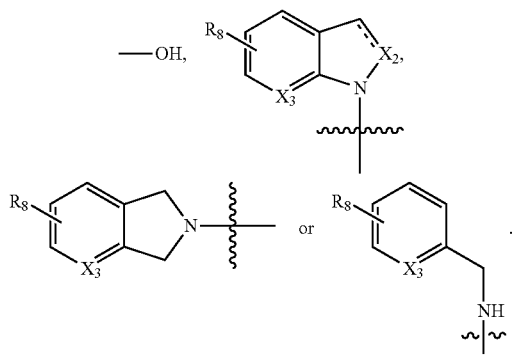

11. The compound of claim 1, wherein $R_4$, $R_5$ and $R_7$ are each independently —H, —$R_2$, —OH, —$OR_2$, —SH, —$SR_2$, —$NH_2$, —$NHR_2$, —$NR_2R_3$, —$NO_2$, halo, or a polyethylene glycol unit —$(OCH_2CH_2)_r$—$OR_a$.

12. The compound claim 1, wherein $R_4$ and $R_7$ together form bis-oxy-$C_{1-3}$ alkylene.

13. The compound of claim 1, wherein each $R_8$ independently is —OH, halo, —$NO_2$, —CN, —$N_3$, —$OR_2$, —COOH, —$COOR_2$, —$COR_2$, —$OCONR_{13}R_{14}$, —$CONR_{13}R_{14}$, —CO—NH—($C_{1-6}$ alkylene)-$R_{13a}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3- to 14-membered heterocycloalkyl, 5- to 12-membered heteroaryl, —$S(=O)_2R_{12}$, —$S(=O)_2NR_{13}R_{14}$, —$SR_{12}$, —NH(C=NH)$NH_2$, or —$R_{20}$—$R_{21}$—$NR_{13}R_{14}$.

14. The compound of claim 1, wherein each of $R_{20}$ and $R_{21}$ is a bond.

15. The compound of claim 1, wherein one of $R_{20}$ and $R_{21}$ is a bond and the other is not a bond.

16. The compound of claim 1, wherein $R_{20}$ is a bond and $R_{21}$ is $C_{1-10}$ alkylene.

17. The compound of claim 1, wherein $R_{21}$ is a bond and $R_{20}$ is $C_{6-10}$ arylene, 3-14 membered heterocycloalkylene or 5- to 12-membered heteroarylene.

18. The compound of claim 1, wherein each $R_8$ independently is —OH, —$OR_2$, —COOH, —$COOR_2$, —$COR_2$, —$OCONR_{13}R_{14}$, —$CONR_{13}R_{14}$, —CO—NH—($C_{1-6}$ alkylene)-$R_{13a}$, a polyethylene glycol unit —$(OCH_2CH_2)_r$—$OR_a$, 3- to 7-membered heterocycloalkyl, 5- to 6-membered heteroaryl, $S(=O)_2R_{12}$, —$S(=O)_2NR_{13}R_{14}$, —$SR_{12}$, or —$R_{20}$—$R_{21}$—$NR_{13}R_{14}$;

wherein $R_{13}$ and $R_{14}$ are each independently —H or $C_{1-10}$ alkyl;

each $R_{20}$ is phenylene; and each $R_{21}$ independently is $C_{1-4}$ alkylene.

19. The compound of claim 1, wherein $R_{10}$ and $R_{11}$ taken together with the nitrogen atom and carbon atom to which they are respectively attached, form a N=C double bond.

20. The compound of claim 1, wherein $R_{10}$ is —H or a nitrogen protecting group, and $R_{11}$ is -$QR^Q$.

21. The compound of claim 1, wherein $R_{15}$, $R_{16}$, $R_{17}$, and $R_{18}$ are each independently —H, —OH, halo, —$NO_2$, —CN, —$N_3$, —$OR_2$, —COOH, —$COOR_2$, —$COR_2$, —$OCONR_{13}R_{14}$, $C_{1-10}$ alkyl, $C_{3-10}$ cycloalkyl, $C_{2-10}$ alkenyl, $C_{2-10}$ alkynyl, a polyethylene glycol unit —$(OCH_2CH_2)_r$—$OR_a$, 3-14 membered heterocycloalkyl, 5- to 12-membered heteroaryl, —$NR_{13}R_{14}$, —$S(=O)_2R_{12}$, —$S(=O)_2NR_{13}R_{14}$, —$SR_{12}$, or —NH(C=NH)$NH_2$.

22. The compound of claim 5, wherein the compound is of any of Formulae (III-a)-(III-c):

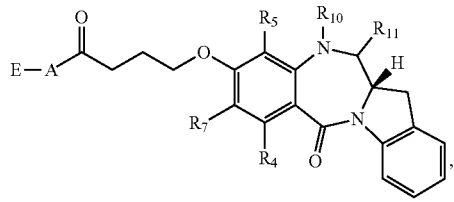

(III-a)

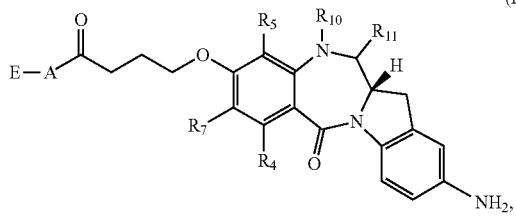

(III-b)

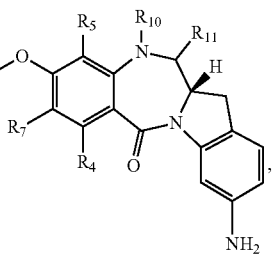

(III-c)

or a tautomer thereof, or a A pharmaceutically acceptable salt or solvate of the compound or the tautomer.

23. The compound of claim 1, wherein the compound contains at most one —SO$_x$M or —OSO$_x$M.

24. The compound of claim 1, wherein R$_{11}$ is —OSO$_x$M or —SO$_x$M.

25. The compound of claim 22, wherein the compound is:

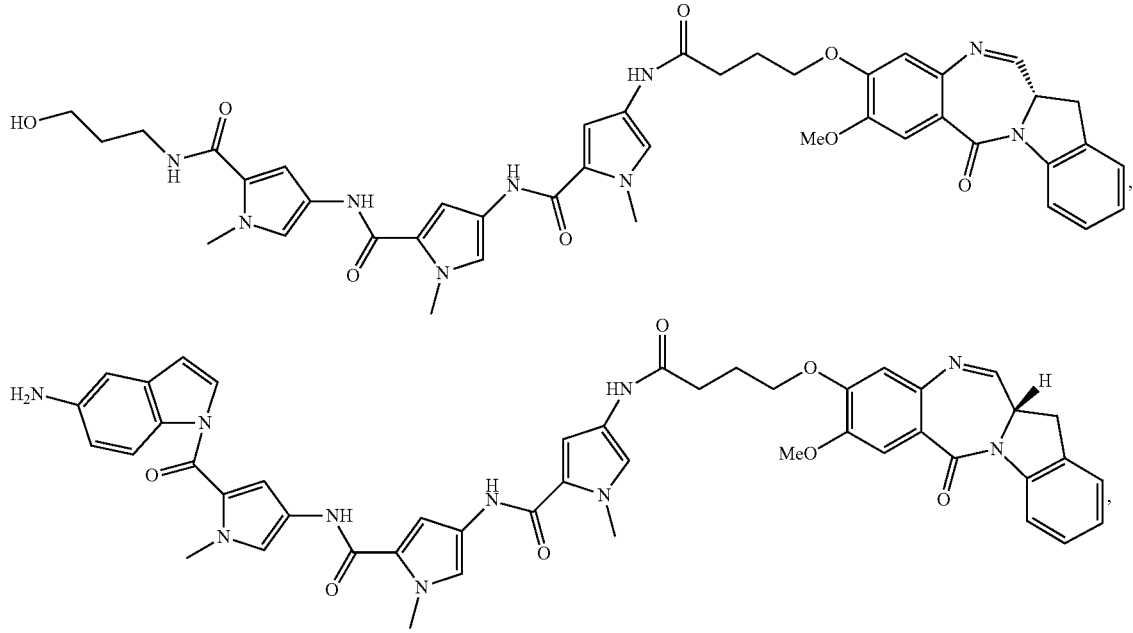

or a tautomer thereof, or a pharmaceutically acceptable salt or solvate of the compound or the tautomer.

* * * * *

UNITED STATES PATENT AND TRADEMARK OFFICE
CERTIFICATE OF CORRECTION

PATENT NO. : 10,660,901 B2
APPLICATION NO. : 16/181867
DATED : May 26, 2020
INVENTOR(S) : Mao Yin et al.

It is certified that error appears in the above-identified patent and that said Letters Patent is hereby corrected as shown below:

In the Claims

At Column 198, Claim number 1, Line numbers 25-33, first structure:

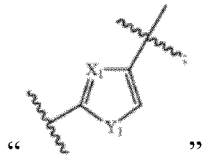

Should read:

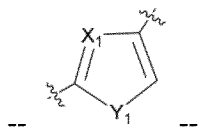

At Column 199, Claim number 1, Line number 33:
"NH-($C_{1-6}$ alkylene)-$R_{3a}$, $C_{3-10}$ cycloalkyl, $C_{2-10}$ alk-"
Should read:
-- NH-($C_{1-6}$ alkylene)-$R_{13a}$, $C_{3-10}$ cycloalkyl, $C_{2-10}$ alk- --

At Column 200, Claim number 1, Line numbers 24-32, second structure:

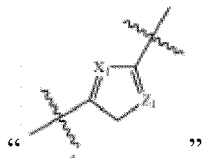

Should read:

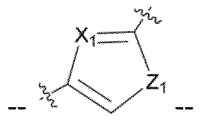

Signed and Sealed this
Twenty-eighth Day of July, 2020

Andrei Iancu
*Director of the United States Patent and Trademark Office*

At Column 200, Claim number 1, Line numbers 33-38:

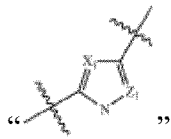

Should read:

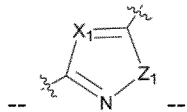

At Column 200, Claim number 1, Line number 40:
"then Z1 is NR$_a$, O, or S;"
Should read:
-- then $Z_1$ is NR$_a$, O, or S; --

At Column 202, Claim number 6, Line numbers 1-8, second structure:

Should read:

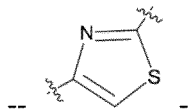

At Column 204, Claim number 18, Line number 43:
"lene)-R$_{13a}$, a polyethylene glycol unit -(OCH$_2$CH$_2$)$_r$-"
Should read:
-- lene)-R$_{13a}$, a polyethylene glycol unit -(OCH$_2$CH$_2$)$_r$- --

At Column 206, Claim number 22, Line number 14:
"or a tautomer thereof, or a A pharmaceutically acceptable"
Should read:
-- or a tautomer thereof, or a pharmaceutically acceptable --

At Column 205 and 206, Claim number 25, last compound:

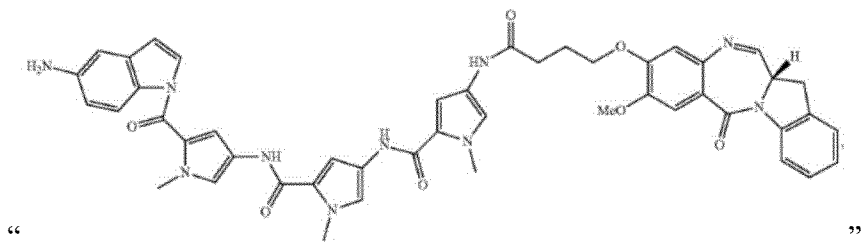

CERTIFICATE OF CORRECTION (continued)
U.S. Pat. No. 10,660,901 B2

Should read:

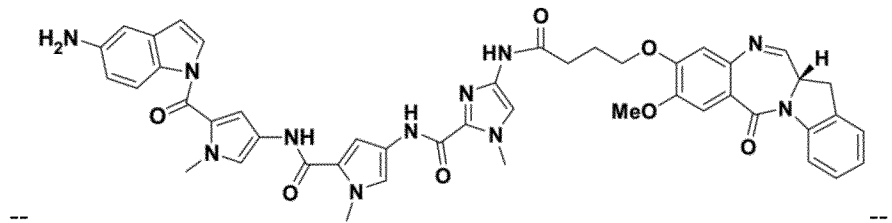

-- --